United States Patent
Fowler et al.

(10) Patent No.: US 10,160,808 B2
(45) Date of Patent: *Dec. 25, 2018

(54) ANTI-VLA1 (CD49A) ANTIBODY PHARMACEUTICAL COMPOSITIONS

(71) Applicant: SANTARUS, INC., San Diego, CA (US)

(72) Inventors: Adam Jeremy Fowler, Encinitas, CA (US); Craig Michael Bowe, Encinitas, CA (US); Wayne Curtis Yount, Franklinton, NC (US); Nathan Jeremy Cobb, Durham, NC (US); Timothy Martin Kelly, Raleigh, NC (US)

(73) Assignee: Santarus, Inc., Bridgewater, NJ (US)

( * ) Notice: Subject to any disclaimer, the term of this patent is extended or adjusted under 35 U.S.C. 154(b) by 380 days.

This patent is subject to a terminal disclaimer.

(21) Appl. No.: 14/379,095

(22) PCT Filed: Feb. 14, 2013

(86) PCT No.: PCT/US2013/026034
§ 371 (c)(1),
(2) Date: Aug. 15, 2014

(87) PCT Pub. No.: WO2013/123114
PCT Pub. Date: Aug. 22, 2013

(65) Prior Publication Data
US 2016/0017043 A1    Jan. 21, 2016

Related U.S. Application Data

(60) Provisional application No. 61/599,827, filed on Feb. 16, 2012.

(51) Int. Cl.
| C07K 16/28 | (2006.01) |
| A61K 39/395 | (2006.01) |
| A61K 9/00 | (2006.01) |
| A61K 47/18 | (2017.01) |
| A61K 47/26 | (2006.01) |

(52) U.S. Cl.
CPC ........ *C07K 16/2842* (2013.01); *A61K 9/0019* (2013.01); *A61K 39/3955* (2013.01); *A61K 39/39591* (2013.01); *A61K 47/183* (2013.01); *A61K 47/26* (2013.01); *C07K 2317/56* (2013.01); *C07K 2317/94* (2013.01)

(58) Field of Classification Search
None
See application file for complete search history.

(56) References Cited

U.S. PATENT DOCUMENTS

| 4,683,195 A | 7/1987 | Mullis et al. |
| 5,391,481 A | 2/1995 | Chess et al. |
| 5,530,101 A | 6/1996 | Queen et al. |
| 5,565,332 A | 10/1996 | Hoogenboom et al. |
| 5,585,089 A | 12/1996 | Queen et al. |
| 5,648,260 A | 7/1997 | Winter et al. |
| 5,693,761 A | 12/1997 | Queen et al. |
| 5,693,762 A | 12/1997 | Queen et al. |
| 5,733,743 A | 3/1998 | Johnson et al. |
| 5,773,743 A | 6/1998 | Ogawa et al. |
| 5,788,966 A | 8/1998 | Chess et al. |
| 5,789,650 A | 8/1998 | Lonberg et al. |
| 5,798,230 A | 8/1998 | Bornkamm et al. |
| 5,827,690 A | 10/1998 | Meade et al. |
| 5,849,992 A | 12/1998 | Meade et al. |
| 5,855,888 A | 1/1999 | Nishida et al. |
| 5,859,205 A | 1/1999 | Adair et al. |
| 6,001,961 A | 12/1999 | Jonczyk et al. |
| 6,016,159 A | 1/2000 | Faris |
| 6,075,181 A | 6/2000 | Kucherlapati et al. |
| 6,127,524 A | 10/2000 | Casipit et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,291,650 B1 | 9/2001 | Winter et al. |
| 6,300,064 B1 | 10/2001 | Knappik et al. |
| 6,303,313 B1 | 10/2001 | Wigler et al. |
| 6,307,026 B1 | 10/2001 | King et al. |
| 6,326,403 B1 | 12/2001 | Holzemann et al. |
| 6,407,213 B1 | 6/2002 | Carter et al. |
| 6,602,503 B1 | 8/2003 | Lobb et al. |
| 6,632,927 B2 | 10/2003 | Adair et al. |
| 6,652,856 B2 | 11/2003 | Gotwals et al. |
| 6,955,810 B2 | 10/2005 | Gotwals et al. |
| 7,358,054 B2 | 4/2008 | Lyne et al. |
| 7,462,353 B2 | 12/2008 | Gotwals et al. |
| 7,612,181 B2 | 11/2009 | Wu et al. |
| 7,723,073 B2 | 5/2010 | Karpusas et al. |
| 7,745,396 B2 | 6/2010 | Lucas |
| 7,910,099 B2 | 3/2011 | Karpusas et al. |

(Continued)

FOREIGN PATENT DOCUMENTS

| EP | 239400 A2 | 9/1987 |
| EP | 0843691 A1 | 5/1998 |

(Continued)

OTHER PUBLICATIONS

Diffuse Connective Tissue Disease: Rheumatoid Arthritis, The Merk Manual, 17th Edition, 1999, pp. 416-423.
Extended European Search Report for EP 12742734.2 dated Apr. 20, 2015.
Morand et al.: "Continuation of long term treatment with hydroxychloroquine in systemic lupus erythematosus and rheumatoid arthritis", Annals of the Rheumatic Diseases, 1992, 51: 1318-1321.
Patient Information on Etanercept, Australian Rheumatology Association, Revised May 2009—next review May 2010, pp. 1-3.
Rubbert-Roth et al.: "Treatment options in patients with rheumatoid arthritis failing intial TNF inhibitor therapy: a critical review", Arthritis Research & Therapy, 2009, 11 (Suppl 1): S1, pp. 1-12.

(Continued)

*Primary Examiner* — Yunsoo Kim
(74) *Attorney, Agent, or Firm* — McCarter & English, LLP; Jonathan M. Sparks; Marcie B. Clarke

(57) ABSTRACT

Formulations of anti-VLA-1 antibodies are described.

7 Claims, 9 Drawing Sheets
Specification includes a Sequence Listing.

(56) References Cited

U.S. PATENT DOCUMENTS

| | | |
|---|---|---|
| 8,084,028 B2 | 12/2011 | Karpusas et al. |
| 8,084,029 B2 | 12/2011 | Hansen et al. |
| 8,084,031 B2 | 12/2011 | Gotwals et al. |
| 8,557,240 B2 | 10/2013 | Gotwals et al. |
| 2003/0070185 A1 | 4/2003 | Jakobovits et al. |
| 2003/0232333 A1 | 12/2003 | Ladner et al. |
| 2004/0081651 A1 | 4/2004 | Karpusas et al. |
| 2004/0208870 A1 | 10/2004 | Allan |
| 2005/0226877 A1 | 10/2005 | Gotwals et al. |
| 2006/0286112 A1 | 12/2006 | Kellermann et al. |
| 2007/0071675 A1 | 3/2007 | Wu et al. |
| 2008/0118496 A1 | 5/2008 | Medich et al. |
| 2009/0238762 A1 | 9/2009 | Totoritis et al. |
| 2010/0027216 A1 | 2/2010 | Matsushima et al. |
| 2010/0233159 A1 | 9/2010 | Relton et al. |
| 2010/0272716 A1 | 10/2010 | Karpusas et al. |
| 2012/0087925 A1 | 4/2012 | Gotwals et al. |
| 2012/0177638 A1 | 7/2012 | Karpusas et al. |
| 2013/0216556 A1 | 8/2013 | Fowler et al. |
| 2014/0017261 A1 | 1/2014 | Totoritis |
| 2014/0110827 A1 | 4/2014 | Tsukahara et al. |
| 2014/0154259 A1 | 6/2014 | De Fougerolles et al. |
| 2016/0017043 A1 | 1/2016 | Fowler et al. |

FOREIGN PATENT DOCUMENTS

| | | |
|---|---|---|
| EP | 843961 A1 | 5/1998 |
| JP | 08131185 A | 5/1996 |
| JP | 2005-507639 A | 3/2005 |
| WO | 9007861 A1 | 7/1990 |
| WO | 9313798 A1 | 7/1993 |
| WO | 199417828 A2 | 8/1994 |
| WO | 9519790 A1 | 7/1995 |
| WO | 9634096 A1 | 10/1996 |
| WO | 9711718 A1 | 4/1997 |
| WO | 9718838 A1 | 5/1997 |
| WO | 9856418 A1 | 12/1998 |
| WO | 99/61040 A2 | 12/1999 |
| WO | 00/20459 A1 | 4/2000 |
| WO | 00/72881 A1 | 12/2000 |
| WO | 0078221 A1 | 12/2000 |
| WO | 01/73444 A2 | 10/2001 |
| WO | 01/96365 A1 | 12/2001 |
| WO | 02072030 A2 | 9/2002 |
| WO | 2002/083854 A2 | 10/2002 |
| WO | 03/068262 A1 | 8/2003 |
| WO | 2005/016883 A2 | 2/2005 |
| WO | 2005/019177 A1 | 3/2005 |
| WO | 2005/019200 A2 | 3/2005 |
| WO | 2006/124269 A2 | 11/2006 |
| WO | 2006133286 A2 | 12/2006 |
| WO | 2007124090 A2 | 11/2007 |
| WO | 07/140249 A1 | 12/2007 |
| WO | 2010102241 A1 | 9/2010 |
| WO | 2011084750 A1 | 7/2011 |
| WO | 2012106497 A2 | 8/2012 |
| WO | 2013123114 A2 | 8/2013 |

OTHER PUBLICATIONS

U.S. Appl. No. 11/108,581, Granted, filed Apr. 18, 2005, U.S. Pat. No. 7,462,353, Dec. 9, 2008.
U.S. Appl. No. 12/268,459, Granted, filed Nov. 11, 2008, U.S. Pat. No. 8,084,031, Dec. 27, 2011.
U.S. Appl. No. 13/296,778, Granted, filed Nov. 15, 2011, U.S. Pat. No. 8,557,240, Oct. 15, 2013.
U.S. Appl. No. 14/021,547, Published, filed Sep. 9, 2013, 2014-0154259.
U.S. Appl. No. 09/996,768, Granted, filed Jun. 1, 2000, U.S. Pat. No. 6,955,810, Oct. 18, 2005.
U.S. Appl. No. 12/015,213, Granted, filed Jan. 16, 2008, U.S. Pat. No. 7,723,073, May 25, 2010.
U.S. Appl. No. 13/017,919, Granted, filed Jan. 31, 2011, U.S. Pat. No. 8,084,028, Dec. 27, 2011.
U.S. Appl. No. 13/297,124, Published, filed Nov. 15, 2011, 2012-0177638.
U.S. Appl. No. 12/727,965, Granted, filed Mar. 19, 2010, U.S. Pat. No. 7,910,099, Mar. 22, 2011.
U.S. Appl. No. 14/597,262, Pending, filed Jan. 15, 2015.
U.S. Appl. No. 10/474,865, Granted, filed Apr. 12, 2002, U.S. Pat. No. 7,358,054, Apr. 15, 2008.
U.S. Appl. No. 12/301,988, Published, filed May 24, 2007, 2010-0233159.
U.S. Appl. No. 13/981,699, Published, filed Feb. 2, 2012, 2014-0017261.
U.S. Appl. No. 13/766,966, Published, filed Feb. 14, 2013, 2013-0216556.
U.S. Appl. No. 14/015,039, Abandoned, filed Aug. 30, 2013, 2014-0110827.
Gotwals et al., "Divalent Cations Stabilize the alpha 1 beta 1 Integrin I Domain" Biochemistry 38:8280-8288 (1999).
Gotwals et al., "The alpha 1 beta 1 Integrin is expressed during Neointima Formation in Rat Arteries and Mediates Collagen Matrix Reorganization" J. Clin. Invest 97:2469-2477 (1996).
Grayson et al., "alpha d beta 2 Integrin Is Expressed on Human Eosinophils and Functions as an Alternative Ligand for Vascular Cell Adhesion Molecule 1 (VCAM-I)" J. Exp. Med. 188:2187-2191 (1984).
Green et al., "Antigen-specific Human Monoclonal Antibodies From Mice Engineered with Human Heavy and Light Chain YACs" Nature Genetics 7:13-21 (1994).
Hemler et al. "Characterization of the Cell Surface Heterodimer VLA-4 and Related Peptides" J.Immunol. 262:11478-11485 (1987).
Hemler et al., "Glycoproteins of 210,000 and 130,000 M.W. on Activated T Cells: Cell Distribution and Antigenic Relation to Components on Resting Cells and T Cell Lines" J. Imunnol. 132:3011-3018 (1984).
Hemler et al., "Very Late Activation Antigens on Rheumatoid Synovial Fluid T Lymphocytes: Association with Stages of T Cell Activation" J. Clin. Invest. 78:696-702 (1986).
Hemler et al., "VLA-I:A T Cell Surface Antigen which Defines a Novel Late Stage of Human T Cell Activation" Eur. J. Immunol. 15:502-508 (1985).
Hessle et al., "Basement membrane diversity detected by monoclonal antibodies" Differentiation 26:49-54 (1984).
Hokibara et al., "Effects of monoclonal antibodies to adhesion molecules on eosinophilic myocarditis in Toxocara canis-infected CBA/J mice", Clin. Exp. Imrnunol. 114, 236-244, 1998.
Holmes et al., "Conformational Correction Mechanisms Aiding Antigen Recognition by a Humanized Antibody" J. Exp. Med. 187:479-485 (1998).
Holt et al., "Domain antibodies: proteins for therapy", Trends Biotechnol. 2003; 21(11):484-490. (Abstract Only).
Hoogenboom et al. "Antibody phage display technology and its applications" (1998) Immunotechnology 4:1-20.
Hoogenboom et al. "Natural and designer binding sites made by phage display technology" (2000) Immunol Today 2:371-8.
Huang and Stollar "Construction of representative immunoglobulin variable region cDNA libraries from human peripheral blood lymphocytes without in vitro stimulation." (1991) J. Immunol. Methods 141:227-236.
Huang et al., "A Majority of Ig H Chain cDNA of Normal Human Adult Blood Lymphocytes Resembles cDNA for Fetal Ig and Natural Autoantibodies" J. Immunol. 151:5290-5300 (1993).
Hurtrel et al., "Different Time Course Patterns of Local Expression of Delayed-Typed Hypersensitivity to Sheep Red Blood Cells in Mice" Cell. Irnmunol. 142:252-263 (1992).
Huth et al., "NMR and Mutagenesis Evidence for an I Domain Allosteric Site that Regulates Lymphocyte Function-Associated Antigen 1 Ligand Binding" Proc. Natl. Acad. Sci. USA 97:5231-5236 (2000).
Ianaro et al., "Anti-Very Late Antigen-1 Monoclonal Antibody Modulates the Development of Secondary Lesion and T-Cell Response in Experimental Arthritis" Lab. Invest. 80:73-80 (2000).

(56) References Cited

OTHER PUBLICATIONS

Ignatius et al., "Molecular Cloning of the Rat Integrin alpha1 Subunit: A Receptor for Laminin and Collagen" J.Cell Biology 111:709-720 (1990).
International Preliminary Examination Report for PCT/US00/15004 dated Jul. 17, 2001.
International Preliminary Examination Report for PCT/US02/11521 dated Apr. 28, 2004.
International Preliminary Report on Patentability & Written Opinion for PCT/US2007/069654 dated Oct. 10, 2007.
International Preliminary Report on Patentability and Written Opinion for PCT/US12/23590 dated Aug. 6, 2013.
International Search Report and Written Opinion, International Application No. PCT/US2013/026034, dated Oct. 21, 2013.
International Search Report dated Feb. 24, 2004 from International Application No. PCT/US02/11521.
International Search Report dated Nov. 13, 2000 from International Application No. PCT/US00/15004.
International Search Report for PCT/07/69654 dated Oct. 23, 2007.
International Search Report for PCT/US12/023590 dated Jul. 23, 2012.
Jones et al., "Principles of Protein-Protein Interactions" Proc. Natl. Acad. Sci. USA 93: 13-20 (1996).
Jones et al., "Replacing the Complementarity-Determining Regions in a Human Antibody with Those from a Mouse" Nature 321:522-525 (1986).
Jordi, "Integrin-collagen complex: a metal glutamate handshake" Structure 8(6):R121-R126—2000.
Kakimoto et al., "The Effect of Anti-adhesion Molecule Antibody on the Development of Collagen-Induced Arthritis" Cell Immunol. 142:326-337 (1992).
Kamata et al., "Critical Threonine and Aspartic Acid Residues within the I Domains of beta 2 Integrins for Interactions with Intercellular Adhesion Molecule 1 (ICAM-1) and C3bi" J. Biological Chem. 270:12531-12535 (1995).
Karpusas et al., "Crystal Structure of the alpha 1 beta 1 Integrin I Domain in Complex with an Antibody Fab Fragment" J. Mol. Biol. 327:1031-1041 (2003).
Keely et al., "Alteration of collagen-dependent adhesion, motility, and morphogenesis by the expression of antisense alpha2 integrin mRNA in mammary cells" J. Cell Science 108:595-607 1995.
Kern et al., "The Role of the I Domain in Ligand Binding of the Human Integrin alpha 1 beta 1" J. Biol. Chem. 269:22811-55816 (1994).
Kim et al. "A novel binding site in collagen type III for integrins alpha1beta1 and alpha2beta1." (2005) J. Biol. Chem. 280:32512-32520.
Kinashi et al., "Adhesion Molecules in Hematopoietic Cells" Blood Cells 20:25-44 (1994).
King et al., "Echovirus 1 Interaction with the Human Very Late Antigen-2 (Integrin) Domain" J. Biol. Chem. 272:28518-28522 (1997).
Knight et al., "The Collagen-binding A-domains of Integrins and Recognize the Same Specific Amino Acid Sequence, GFOGER, in Native (Triple-helical) Collagens" J. Biol. Chem. 275:35-40 2000.
Kolbinger et al., "Humanization of a Mouse Anti-human IgE Antibody: A Potential Therapeutic for IgE-mediated Allergies" Protein Eng. 6:971-980 (1993).
Krieglstein, C.F., et al., "Collagen-Binding Integrin alphalbetal Regulates Intestinal Inflammation in Experimental Colitis," J. Clin. Invest., 110:1173-1782 (2002).
Laffon et al., Very Late Activation Antigen of Synovial Fluid T cells from Patients with Rheumatoid Arthritis and other Rheumatic Diseases Arthritis and Rheumatism 32:386-392 (1989).
Langholz et al., "Collagen and Collagenase Gene Expression in Three-dimensional Collagen Lattices Are Differentially Regulated by alpha 1 beta 1 and alpha 2 beta 1 Integrins" J. Cell Biol. 131:1903-1915 (1995).

Larson et al., "Primary Structure of the Leukocyte Function-associated Molecule-1 alpha Subunit: an Integrin with an Embedded Domain Defining a Protein Superfamily" J. Cell Biol. 108:703-712 (1989).
Lee et al., "Crystal Structure of the A Domain from the Subunit of Integrin CR3 (CD11b/CD18)" Cell 80:631-638 (1995).
Lee et al., "Two conformations of the integrin A-domain (I-domain): a pathway for activation" Structure 3:1333-1340 (1995).
Lees et al. "NXY-059 for acute ischemic stroke." (2006) N. Engl. J. Med. 354:588-600.
Leibiger et al., "Variable domain-linked oligosaccharides of a human monoclonal IgG: structure and influence on antigen binding", Biochem. J. (1999) 338:529-538.
Seiffge, "Protective Effects of Monoclonal Antibody to VLA-4 on Leukocyte Adhesion and Course of Disease in Adjuvant Arthritis in Rats" J. Rheurnatol. 23:2086-2091 (1996).
Senger, D.R., et al., "The alpha1beta1 and alpha2beta1 Integrins Provide Critical Support for Vascular Endothelial Growth Factor Signaling, Endothelial Cell Migration, and Tumor Angiogenesis," American Journal of Pathology, 160(1):195 (2002).
Shakin-Eshleman et al., "The Amino Acid at the X Position of an Asn-X-Ser Sequon Is an Important Determinant of N-Linked Core-glycosylation Efficiency", J. Biol. Chem. (1996), 271(11), 6363-6366.
Shaw et al., "Molecular Cloning of the Human Mucosal Lymphocyte Integrin alphaE Subunit" J. Biol. Chem. 269:6016-6025 (1994).
Shimaoka, "Computational design of an integrin I domain stabilized in the open high affinity conformation." Nature Structural Biol. 7(8):674-678 (2000).
Snyder et al. "The binding conformation of Taxol in beta-tubulin: A model based on electron crystallographic density" PNAS, 2001; 98(9) 5312-5316.
Solenski et al., "Transient Ischemic Attacks: Part II. Treatment" American Family Physician, 69(7):1681-1688 (2004).
Sonnenberg et al., "A Complex of Platelet Glycoproteins Ic and IIa Identified by a Rat Monoclonal Antibody" J. Biol. Chem. 262:10376-10383 (1987).
Springer et al., "Adhesion receptors of the immune system" Nature 346:425-434 (1990).
Stacker et al., "Leukocyte integrin P150,95 (CD11c/CD18) functions as an adhesion molecule binding to a counter-receptor on stimulated endothelium" J. Immunol., 146:648-655 (1991).
Supplemental European Search Report and Opinion for EP 07 78 4108 dated Nov. 18, 2010.
Suzuki, K. et al., "Semaphorin 7A initiates T-cell-mediated inflammatory responses through alpha 1 beta 1 integrin", Nature, 446:680-684, 2007.
Takada et al., "The primary structure of the VLA-2/Collagen receptor alpha 2 subunit (platelet GPla): homology to other integrins and the presence of a possible collagen-binding domain" J. Cell Biol. 109:397-407 (1989).
Takeuchi, et al. Upregulated Expression and Function of Integrin Adhesive Receptors in Systemic Lupus Erythematosus Patients with Vasculitis. J. Clin. Invest. 92:3008-3016, 1993.
Tawil, et al., "Alpha 1 beta 1 integrin heterodimer functions as a dual laminin/collagen receptor in neural cells." Biochemistry. Jul. 10, 1990;29(27):6540-4.
Taylor et al., "Transfer of Type II Collagen-Induced Arthritis From DBAII to Severe Combined Immunodeficiency Mice Can Be Prevented by Blockage of Mac-I" Immunology 88: 315-321 (1996).
Tedder et al., "L-Selectin-deficient Mice Have Impaired Leukocyte Recruitment into Inflammatory Sites" J. Exp. Med. 181:2259-2264 (1995).
Tempest et al. "Reshaping a human monoclonal antibody to inhibit human respiratory syncytial virus infection in vivo" (1991) Biotechnology 9:266-271.
Tempest et al., "Reshaping a Human Monoclonal Antibody to Inhibit Human Respiratory Syncytical Virus Infection In Vivo" Bio. Tech. 9:266-271 (1991).
Terashita et al., "Enhancement of Delayed-Type Hypersensitivity to Sheep Red Blood Cells in Miche by Granulocyte Colony-Stimulating Factor Administration at the Elicitation Phase" J. Immunol. 156:4638-4643 (1996).

(56) References Cited

OTHER PUBLICATIONS

Terato et al., "Collagen-Induced Arthritis in Mice: Synergistic Effect of E. coli Lipopolysaccharide Bypasses Epitope Specificity in the Induction of Arthritis with Monoclonal Antibodies to Type II Collagen" Autoimmunity 22: 137-147 (1995).
Terato et al., "Induction of Arthritis with Monoclonal Antibodies to Collagen" J. Immunol. 148:2103-2108 (1992).
Tomizuka et al., "Functional Expression of Germline Transmission of a Human Chromosome Fragment in Chimaeric Mice" Nature Genetics 16:133-143 (1997).
Tsunoda, I. et al., "Modulation of Experimental Autoimmune Encephalomyelitis by VLA-2 Blockade", Brain Pathol., 17:45-55, 2007.
Van der Vieren et al., A Novel Leukointegrin alpha d beta 2, Binds Preferentially to ICAM-3 Immunity 3:683-690 (1995).
Verhoeyen et al., "Reshaping Human Antibodies: Grafting an Antilysozyme Activity" Science 239:1534:1536 (1987).
Wang et al., "Differential regulation of airway epithelial integrins by growth factors" Am. J. Respir.Cell Mol. Biol. 15:664-672 (1996).
Ward et al., "Binding activities of a repertoire of single immunoglobulin variable domains secreted from Escherichia coli" Nature 341:544-546 (1989).
Watts, G.M., et al., "Manifestations of Inflammatory Arthritis Are Critically Dependent on LFA-1", J. Immunology, 174:3668-3675, 2005.
Wayner et al., "The function of multiple extracellular matrix receptors in mediating cell adhesion to extracellular matrix: preparation of monoclonal antibodies to the fibronectin receptor that specifically inhibit cell adhesion to fibronectin and react with platelet glycoproteins Ic-IIa" J. Cell Biol. 107:1881-1891 (1988).
Weinacker et al., "Role of the Integrin alpha v beta 6 in Cell Attachment to Fibronectin" J. Biol.Chem. 269:6940-6948 (1993).
Weitz-Schmidt et al. "Statins selectively inhibit leukocyte function antigen-1 by binding to a novel regulatory integrin site." (2001) Nat. Med. 7:687-692.
Welschof et al., "Amino Acid Sequence based PCR Primers for Amplification of Rearranged Human Heavy and Light Chain Immunoglobulin Variable Region Genes" J. Immuno. Meth. 179:203-214 (1995).
Woessner et al., "The determination of hydroxyproline in tissue and protein samples containing small proportions of this imino acid" Arch. Biochem. Biophys. 93:440-447 (1961).
Wright, A. and Morrison, S.L., Effect of Altered CH2-associated Carbohydrate Structure on the Functional Properties and In Vivo Fate of Chimeric Mouse-Human Immunoglobulin G1, J. Exp. Med. (1994), 180:1087-1096.
Written Opinion European Patent Office for European application No. 04018151.3 dated Mar. 22, 2012.
Written Opinion for PCT/US00/15004 and European Application No. 00942654.5 dated Mar. 9, 2001.
Yao et al., "Laminins promote the locomotion of skeletal myoblasts via the alpha 7 integrin receptor" J. Cell Science 109:3139-3150 (1996).
Yednock, T.A. et al., "Prevention of experimental autoimmune encephalomyelitis by antibodies against alpha4 beta1 integrin", Nature, 356:63-66, 1992.
Bank I et al., "A novel monoclonal antibody, 1B3.1, binds to a new epitope of the VLA-1 molecule", Cellular Immunology, 122:416-423 (1989).
Edmundson et al. "Binding of peptides to proteins: an exercise in molecular design." Ciba Found Symp. 158: 213-25, (1991), Abstract.
International Preliminary Report on Patentability for International Application No. PCT/US2013/026034 dated Aug. 19, 2014.
Nienaber VL et al., "Discovering novel ligands for macromolecules using X-ray crytallographic screening", Nature Biotechnology, 18; 1105-1108, (2000).
Van Regenmortel, Mapping Epitope Structure and Activity: From One-Dimensional Prediction to Four-Dimensional Description of Antigenic Specificity, Methods: A Comparaion to Methods in Enzymology, 9, 465-472 (1996).

Weinachter et al., "Group Report 8: Models of Hypoxia and Cerebral Ischemia", Pharmacopsychiat, 23, 94-98, (1990).
Li et al., "Three-Dimensional Structures of the Free and Antigen-Bound Fab from Monoclonal Antilysozyme Antibody HyHEL-63" Biochemistry 39:6296-6309 (2000).
Lin et al., "Very late antigen 4 (VLA4) antagonists as anti-inflammatory agents", Current Opinion in Chem. Biology, 2, 453-457, 1998.
Little, et al., "Of mice and Men: hybridoma and recombant antibodies", Review Immunology Today, vol. 21, No. 8, pp. 364-370, 2000.
Lobb et al., "The Pathophysiologic Role of alpha4 Integrins In Vivo", J. Clin. Invest., 94, 1722-1728, 1994.
Lobb et al., "The role of alpha 4 Integrins in lung pathophysiology", European Resp. Journ. Supp., 9(22), 1996.
Lowry et al., "Protein Measurement with the folin phenol reagent" Dept. of Pharma., Washington Univ. School of Med. 265-275 (1951).
Luque et al., "Functional regulation of the human integrin VLA-1 (CD49a/CD29) by divalent cations and stimulatory beta 1 antibodies", FEBS Letters 346 (1994) 278-284.
Mackay et al., "Lymphotoxin Receptor Triggering Induces Activation of the Nuclear Factor B Transcription Factor in Some Cell Types" J. Biol. Chem. 271:24934-24938 (1996).
Mendez et al., "Functional Transplant of Megabase Human Immunoglobulin Loci Recapitulates Human Antibody Response in Mice" Nature Genetics 15:146-156 (1997).
Mendrick et al., "Glomerular Epithelial and Mesangial Cells Differentially Modulate the Binding Specificities ofVLA-I and VLA-2" Laboratory Investigation 72:367-375 (1995).
Mendrick et al., "Temporal Expression of VLA-2 and Modulation of its ligand Specificity by Rat Glomerular Epithelial Cells in vitro" Lab. Invest. 69:690-702 (1993).
Michishita et al., "A Novel Divalent Cation-Binding Site in the A Domain of the Beta2 Integrin CR3 (CD11b/CDI8) Is Essential for Ligand Binding" Cell Press 72:857-867 (1993).
Miyake et al., "Evidence for a Role of the Integrin VLA-4 in Lympho-hemapoiesis" J. Exp. Med. 173:599-607 (1991).
Miyake et al., "Integrin-mediated interaction with Extracellular Matrix Proteins Regulates Cytokine Gene Expression in Synovial Fluid Cells of Rheumatoid Arthritis Patients" J. Exp. Med. 177:863-868 (1993).
Mombaerts et al., "RAG-I-Deficient Mice Have No Mature Band T Lymphocytes" Cell 68:869-877—1992.
Mod et al., "Attenuation of Collagen-Induced Arthritis in 55-kDa TNF Receptor Type 1 (TNFRI)-IgGI-Treated and TNFRI-Deficient Mice" J. Immunol. 157:3178-3182 (1996).
Muller et al., "VEGF and the Fab Fragment of a Humanized Neutralizing Antibody: Crystal Structure of the Complex at 2.4 A Resolution and Mutational Analysis of the Interface" Structure 6:1153-1167 (1998).
Nagler et al., "Reduction in Pulmonary Fibrosis In Vivo by Halofuginone" A.m. J. Respir. Crit.Care Med. 154:-1082-1086 (1996).
Nishimura et al., "Integrin alpha v beta 8" J. Biol. Chem. 269:28708-28715 (1994).
Nolte et al., "Crystal Structure of the Integrin I-Domain: Insights into Integrin I-Domain Function" FEBS Lett. 452:379-385 (1999).
Noto et al., "Identification and Functional Characterization of Mouse CD29 with a mAB" Int. Immunol. 7:835-842 (1995).
Odum, N. et al., "Prevalence of late stage T cell activation antigen (VLA-1) in active juvenile chronic arthritis", Ann. Rheumatic Diseases, 46:846-852, 1987.
Orlandi, "Cloning immunoglobulin variable domains for expression by the polymerase chain reaction" Proc. Natl., Acad. Sci. USA 86:3833-3837 (1989).
Padlan, E.A., "Anatomy of the antibody molecule", Mol Immunol. (1994), 31(3):169-217.
Panka et al., "Variable region framework differences result in decreased or increased affinity of variant anti-digoxin antibodies" Proc. Natl. Acad. Sci. USA 85(9):3080-3084 (1988).

(56) References Cited

OTHER PUBLICATIONS

Papadopoulos et al., "Expression of Integrins in Alveolar Epithelia of Fetal and Adult Lung Tissue and in Interstitial Lung Diseases", Verh. Dtsch. Ges. Path., 77, 292-295 (1993). Abstract Only.
Partial European Search Report for EP 02 72 8745 dated Feb. 16, 2005.
Partial European Search Report for EP 02 72 8745 dated Dec. 13, 2004.
Persson et al., "Generation of diverse high-affinity human monoclonal antibodies by repertoire cloning" Proc. Natl. Acad. Sci. USA 88:2432-2436 (1991).
Pfaff et al. "Binding of purified collagen receptors (alpha 1 beta 1, alpha 2 beta 1) and RGD-dependent integrins to laminins and laminin fragments." (1994) Eur. J. Biochem. 225:975-84.
Pischel et al., "Use of the monoclonal antibody 12F1 to Characterize the Differentiation Antigen VLA-21" J. Immunol. 138:226-233 (1987).
Plows et al., "Mice Lacking Mature T and B Lymphocytes Develop Arthritic Lesions After Immunization with Type II Collagen" J. Innmunol. 162:1018-1023 (1999).
Portolano et al., "Lack of promiscuity in autoantigen-specific H and L chain combinations as revealed by human H and L chain Roulette", J. Immunol. (1993), 150(3):880-887.
Powers et al. "Expression of single-chain Fv-Fc fusions in Pichia pastoris." (2001) J. Immunol. Methods 251:123-35.
Pozzi et al., "Integrin alpha 1 beta 1 Mediates a Unique Collagen-Dependent Proliferation Pathway In Vivo", Journal of Cell Biology, 142(2), 587-594, 1998.
Qu et al., "The role of the divalent cation in the structure of the I domain from the CDIIA/CD18 integrin" Structure 4:931-942 (1996).
Qu et al., Crystal structure of the 1-domain form the CDIIa1CDI8 (LFA-I, aLbeta2) integrin Proc. Natl. Acad. Sci. USA 92:10277-10281 (1995).
Queen et al., "A humanized antibody that binds to the interleukin 2 receptor" Proc. Natl. Acad. Sci.USA 86:10029-10033 (1989).
Rich et al., "Trench-shaped Binding Sites Promote Multiple Classes of Interactions between Collagen and the Adherence Receptors, 1 Integrin and *Staphylococcus aureus* Can MSCRAMM" J. Biol. Chem. 274:24906-24913 (1999).
Riechmann et al., "Reshaping human antibodies for therapy" Nature 332:323-327 (1988).
Riikonen et al., "Antibody against human alpha 1 beta 1 integrin inhibits HeLa cell adhesion to laminin and to type I, IV, and V collagens" Biochem. Biophys. Res. Commun. 209:205-212 (1995).
Riikonen et al., "Transforming growth factor-beta regulates collagen gel contraction by increasing alpha 2 beta 1 integrin expression in osteogenic cells" J. Biol. Chem. 270:376-382 (1994).
Roy-Chaudhury et al., "Adhesion molecule interactions in human glomerulonephritis: Importance of the tubulointerstitium", Kidney International, 49, 127-134, 1996.
Sampson et al., "Global Gene Expression Analysis Reveals a Role for the Integrin in Renal Pathogenesis" J. Biol. Chem. 276:34182-34188 (2001).
Sanchez-Madrid et al., "Three distinct antigens associated with human T-lymphocyte-mediated cytolysis: LFA-1, LFA-2, and LFA-3." Immunol. 79:7489-7493 (1982).
Santarus: "Santarus Initiates Phase I Clinical Study with SAN-300," http://ir.santarus.com/releasedetail.cfm?releaseid+555930, XP002696720, Mar. 11, 2011 [retrieved on May 8, 2012].
Schapira, K., et al., "Genetic Deletion or Antibody Blockade of alpha1beta1 Integrin Induces a Stable Plaque Phenotype in ApoE-/-Mice," Arteriosclerosis, Thrombosis, and Vascular Biology, 25:1917-1924 (2005).
Scheynius et al., "Reduced Contact Sensitivity Reactions in Mice Treated with Monoclonal Antibodies to Leukocyte Function-Associated Molecule-I and intercellular Adhesion Molecule-I" J. Immunol. 150:655-663 (1993).
Schiro et al., "Integrin alpha 2 beta 1 (VLA-2) Mediates Reorganization and Contraction of Collagen Matrices by Human Cells" Cell 67:403-410 (1991).

Schwartz, B.R. et al., "Identification of Surface Proteins Mediating Adherence of CD11/CD18-deficient Lymphoblastoid Cells to Cultured Human Endothelium", J. Clin. Invest., 85:2019-2022, 1990.
Abraham, W.M., et al. "A Monoclonal Antibody to alpha1beta1 Blocks Antigen-Induced Airway Responses in Sheep," American Journal of Respiratory and Critical Care Medicine, 169:97-104 (2004).
Adams et al., "Coronary Risk Evaluation in Patients with Transient Ischemic Attack and Ischemic Stroke" Circulation, 108(9):1278-1290 (2003).
Alcocer-Varela, J., et al., "Interleukin-1 and Interleukin-6 Activities are Increased in the Cerebrospinal Fluid of Patients with CNS Lupus Erythematosus and Correlate with Local Late T-Cell Acitvation Markers," Lupus, 1:111-117 (1992).
Baker, et al., "Developmental and injury-induced expression of alpha1beta1 and alpha6beta1 integrins in the rat spinal cord", Brain Res. Jan. 26, 2007; 1130(1): 54-66.
Baldwin et al., "Cation binding to the integrin CDII b I domain and activation model assessment" Structure 6:923-935 (1998).
Bank et al. Lymphocytes Expressing alpha1beta1 integrin (Very Late Antigen-1) in peripheral blood of patients with arthritis are a subset of CD45RO(+) T-cells primed for rapid adhesion to collagen IV. Clin Immunol. Dec. 2002;105(3):247-58.
Bank, I. et al., Analysis of recombinant human alpha1 integrin I-domain with a function-blocking monoclonal antibody, 1B3.1, IMAJ, vol. 2, Supplement 2, pp. 19-20, Dec. 2000.
Bank, I. et al., "Expression and Functions of Very Late Antigen 1 in Inflammatory Joint Diseases", J. Clin. Immunol. 11(1):29-38, 1991.
Bennett et al., "Inhibition of fibrinogen binding to stimulated human platelets by a monoclonal antibody" Proc. Natl. Acad. Sci.USA 80:2417-2421 (1983).
Boerner et al., " Production of Antigen-Specific Human Monoclonal Antibodies From In Vitro-Primed Human Splenocytes" J. Immunol. 147:86-95 (1991).
Border et al., "Transforming Growth Factor Beta in Tissue Fibrosis" New England J. Medicine 331:1286-1292 (1994).
Bossy et al., " Characterization of the Integrin Alpha8 subunit: A new integrin beta1-associated subunit, which is prominently expressed on axons and on cells in contact with basal laminae in chick embryos" EMBO J. 10:2375-2385 (1991).
Brezinsky et al., "A Simple Method of Enriching Populations of Transfected CHO Cells for Cells of Higher Specific Productivity" J. Immunol. Methods 277:141-155 (2003).
Bridges et al., "Variable Region cDNA Sequences and Characterization of Murine Anti-Human Interferon gamma Receptor Monoclonal Antibodies that Inhibit Receptor Binding by Interferon gamma" Mol. Immunol. 32:1329-2989 (1995).
Briesewitz, et al., "Expression of Native and Truncated Forms of the Human Integrin alpha 1 Subunit," Journal of Biological Chemistry, 268(4):2989-2996 (1993).
Camper et al., "Isolation, Cloning, and Sequence Analysis of the Integrin Subunit alpha 10, a beta 1-associated Collagen Binding integrin Expressed on Chondrocytes" J. Biol. Chem. 273:20383-20389 (1998).
Carter et al., "Humanization of an Anti-p185 HER2 Antibody for Human Cancer Therapy" Proc. Natl. Acad. Sci. USA 89:4285-4289 (1992).
Cerf-Bensussan et al., "The human intraepithelial lymphocyte marker HML-1 is an integrin consisting of a Beta7 subunit associated with a distinctive alpha chain" Eur. J. Immunol. 22:273-277 (1992).
Chapman, et al., "Leukocyte adhesion molecules", British Medical Bulletin, 51(2):296-311, 1995.
Chothia et al., "Conformations of Immunoglobulin Hypervariable Regions" Nature 342:877-883 (1989).
Clackson et al., "Making antibody fragments using phage display libraries" Proc. Natl. Acad. Sci.USA 352:624-628 (1991).
Co et al., "Humanized antibodies for antiviral therapy" Proc. Natl. Acad. Sci. USA 88:2869-2873 (1991).
Colbert et al., "The effect of fluorescein labels on the affinity of antisera to small haptens" J. Imunol. Methods 140:227-233 (1991).
Colognato et al. "The Laminin alpha 2-Chain Short Arm Mediates Cell Adhesion through Both the alpha 1 beta 1 and alpha 2 beta 1 Integrins" (1997) J. Biol. Chem. 272:29330-29336.

(56) References Cited

OTHER PUBLICATIONS

Colognato-Pyke et al. "Mapping of network-forming, heparin-binding, and alpha 1 beta 1 integrin-recognition sites within the alpha-chain short arm of laminin-1" (1995) J. Biol. Chem. 270:9398-9406.
Cook et al., "Treatment with an Antibody to VLA-1 Integrin Reduces Glomerular and Tubulointerstitial Scarring in a Rat Model of Crescentic Glomerulonaphritis" Am. J. Pathol. 161:1265-1272 (2002).
Corbi et al., "cDNA cloning and complete primary structure for the alpha subunit of a leukocyte adhesion glycoprotein, p150,95" EMBO Journal, vol. 6, No. 13, p. 4023-4028, 1987.
Corbi et al., The Human Leukocyte Adhesion Glycoprotein Mac-I (Complement Receptor Type 3, CDIIb) alpha Subunit J. Biol. Chem. 263:12403-12411, 1988.
Cosgrove et al., "Integrin and Transforming Growth Factor-I Play Distinct Roles in Alport Glomerular Pathogenesis and Serve as Dual Targets for Metabolic Therapy" Am. J. Path. 157:16498-1659 (2000).
Davies et al., "Interactions of Protein Antigens with Antibodies" Proc. Natl. Acad. Sci. USA 93:7-12 (1996).
Davies, "The osteoclast Functional Antigen, Implicated in the Regulation of Bone Resorption, Is Biochemically Related to the Vitronectin Receptor" J. Cell Biology 109:1817-1826 (1989).
De Fougerolles et al., "Global Expression Analysis of Extracellular Matrix-Integrin interactions in Monocytes" Immunity 13:749-758 (2000).
De Fougerolles et al., "Regulation of Inflammation by Collagen-Binding Integrins and integrins alpha 1 beta 1 and alpha 2 beta 1 in Models of Hypersensitivity and Arthritis" J. Clin. Invest. 105:721-729 (2000).
Diamond et al., "The I Domain Is a Major Recognition Site on the Luekocyte Integrin Mac-1 (CD-11b/CD18) for Four distinct Adhesion Ligands", J. Cell Biology 120:1031-1043 (1993).
Edwards et al., "Identification of Amino Acids in the CDIIa I-domain Important for Binding of the DA Leukocyte Function-associated Antigen-I (LFA-I) to Intercellular Adhesion Molecules-I (ICAM-1)" J. Biol. Chem. 270:12635-12640 (1995).
Eigenbrot et al., "X-ray Structures of the Antigen-binding Domains from Three Variants of Humanized anti-p185 HER2 Antibody 4D5 and Comparison with Molecular Modeling" J. Mol. Biol. 229:969-995 (1993).
Elices, M.J. et al., "VCAM-1 on Activated Endothelium Interacts with the Leukocyte Integrin VLA-4 at a Site Distinct from the VLA-4/Fibronectin Binding Site", Cell, 60:577-584, 1990.
Emsley et al., "Crystal Structure of the I Domain from Integrin" J. Biol. Chem. 272:28512-28517 (1997).
Emsley et al., "Structural Basis of Collagen Recognition by Integrin" Cell 100:47-56 (2000).
European Search Report & Opinion for EP 10 185 467.7 dated Mar. 2, 2011.
European Search Report for European Application Serial No. 04 01 8151.3 dated Feb. 28, 2011.
Extended European Search Report for EP 14178388.6 dated Jan. 27, 2015.
Fabbri et al., "A functional monoclonal antibody recognizing the human alpha1-integrin I-domain" Tissue Antigens 48:47-51 (1996).
Fiorucci et al., "Importance of Innate Immunity and Collagen Binding Integrin alpha 1 beta 1 in TNBS-Induced Colitis", Immunity, 17, 769-780, 2002.
Fischmann et al., "Crystallographic Refinement of the Three-Dimensional Structure of the FabD1.3-Lysozyme Complex at 2.5-Å Resolution" J. Biol. Chem. 266:12915-12920 (1991).
Foote et al., "Antibody Framework Residues Affecting the Conformation of the Hypervariable Loops" J. Mol. Biol. 224:487-499 (1992).
Gardner et al., "Absence of integrin alpha 1 beta 1 in the mouse causes loss of feedback regulation of collagen synthesis in normal and wounded dermis", J. Cell Science, 112, 263-272, 1999.
Gardner et al., "Deletion of Integrin alpha 1 by Homologous Recombination Permits Normal Murine Development but Gives Rise to a Specific Deficit in Cell Adhesion", Developmental Biology, 175, 301-313, 1996.
Gaspari et al., "Contact Hypersensitivity" Current Protocols in Immunology J.E. Coligan et al., Editors, John Wiley & Sons, New York, Section 4.2.1-4.2.5 (1991).
Go et al: "Antithrombotic Therapy for Stroke Prevention in Atrial Fibrillation", Progress in Cardiovascular Diseases, Saunders, Philadelphia, PA, US, vol. 48, No. 2, Sep. 1, 2005 (Sep. 1, 2005), pp. 108-124, XP005127137, ISSN: 0033-0620, DOI: DOI:10.1016/J. PCAD.2005.06.007.

FIG. 1A

```
atg gcc cct cgg ccc cgc gcc cgc cca ggg gtc gct gtc gcc tgc tgc tgg ctc ctc act  60
 M   A   P   R   P   R   A   R   P   G   V   A   V   A   C   C   W   L   L   T  20 gtt gtt cta cgc tgc tgc gta tca ttc aat gtt gat gtg aaa aat tca atg act ttc agc 120
 V   V   L   R   C   C   V   S   F   N   V   D   V   K   N   S   M   T   F   S  40 ggc ccg gtg gaa gac atg ttt gga tat act gtt caa caa tat gaa aat gaa gaa gga aaa 180
 G   P   V   E   D   M   F   G   Y   T   V   Q   Q   Y   E   N   E   E   G   K  60 tgg gtg ctt att ggt tct ccg tta gtt ggc caa ccc aaa aac aga act gga gat gtc tat 240
 W   V   L   I   G   S   P   L   V   G   Q   P   K   N   R   T   G   D   V   Y  80 aag tgt cca gtt ggg aga ggt gaa tca tta cct tgt gta aag ttg gat cta cca gtt aat 300
 K   C   P   V   G   R   G   E   S   L   P   C   V   K   L   D   L   P   V   N 100 aca tca att ccc aat gtc aca gaa gta aag gag aac atg aca ttt gga tca act tta gtc 360
 T   S   I   P   N   V   T   E   V   K   E   N   M   T   F   G   S   T   L   V 120 acc aac cca aat gga gga ttt ctg gct tgt ggg ccc tta tat gcc tat aga tgt gga cat 420
 T   N   P   N   G   G   F   L   A   C   G   P   L   Y   A   Y   R   C   G   H 140 ttg cat tac aca act gga atc tgt tct gac gtc agc ccc aca ttt caa gtc gtg aat tcc 480
 L   H   Y   T   T   G   I   C   S   D   V   S   P   T   F   Q   V   V   N   S 160
                  _____ att gcc cct gta caa gaa tgc agc act caa ctg gac ata gtc ata gtg ctg gat ggt tcc 540
 I   A   P   V   Q   E   C   S   T   Q   L   D   I   V   I   V   L   D   G   S 180
_____ aac agt att tac cca tgg gac agt gtt aca gct ttt tta aat gac ctt ctt gaa aga atg 600
 N   S   I   Y   P   W   D   S   V   T   A   F   L   N   D   L   L   E   R   M 200
_____ gat att ggt cct aaa cag aca cag gtt gga att gta cag tat gga gaa aac gtg acc cat 660
 D   I   G   P   K   Q   T   Q   V   G   I   V   Q   Y   G   E   N   V   T   H 220
_____ gag ttc aac ctc aat aag tat tct tcc acc gaa gag gta ctt gtt gca gca aag aaa ata 720
 E   F   N   L   N   K   Y   S   S   T   E   E   V   L   V   A   A   K   K   I 240
_____ gtc cag aga ggt ggc cgc cag act atg aca gct ctt gga ata gac aca gca aga aag gag 780
 V   Q   R   G   G   R   Q   T   M   T   A   L   G   I   D   T   A   R   K   E 260
_____ gca ttc acg gaa gcc cgg ggt gcc cga aga gga gtt aaa aaa gtc atg gtt att gtg aca 840
 A   F   T   E   A   R   G   A   R   R   G   V   K   K   V   M   V   I   V   T 280
_____ gat gga gag tct cat gac aat cat cga ctg aag aag gtc atc caa gac tgt gaa gat gaa 900
 D   G   E   S   H   D   N   H   R   L   K   K   V   I   Q   D   C   E   D   E 300
_____ aac att caa cgg ttt tcc ata gct att ctt ggc agc tat aac cga gga aat tta agc act 960
 N   I   Q   R   F   S   I   A   I   L   G   S   Y   N   R   G   N   L   S   T 320
_____
```

FIG. 1B

```
gaa aaa ttt gtg gag gaa ata aaa tca att gca agt gaa ccc act gaa aag cat ttc ttc 1020
 E   K   F   V   E   E   I   K   S   I   A   S   E   P   T   E   K   H   F   F  340 aat gtc tct gat gaa ttg gct cta gtc acc att gtt aaa act ctg gga gaa aga ata ttt 1080
 N   V   S   D   E   L   A   L   V   T   I   V   K   T   L   G   E   R   I   F  360 gcc ctg gaa gcc aca gct gac cag tca gca gct tca ttt gaa atg gaa atg tct cag act 1140
 A   L   E   A   T   A   D   Q   S   A   A   S   F   E   M   E   M   S   Q   T  380 ggc ttc agt gct cat tat tca cag gac tgg gtc atg ctt gga gca gta gga gcc tat gat 1200
 G   F   S   A   H   Y   S   Q   D   W   V   M   L   G   A   V   G   A   Y   D  400 tgg aat gga aca gtt gtc atg cag aag gct agt caa atc ata atc cct cga aac aca acc 1260
 W   N   G   T   V   V   M   Q   K   A   S   Q   I   I   I   P   R   N   T   T  420 ttt aat gtt gag tct acc aaa aag aat gaa ccg ctt gct tct tat tta ggt tac act gta 1320
 F   N   V   E   S   T   K   K   N   E   P   L   A   S   Y   L   G   Y   T   V  440 aac tct gct act gct tct tct gga gat gtg ctc tat att gct gga cag cct cgg tac aat 1380
 N   S   A   T   A   S   S   G   D   V   L   Y   I   A   G   Q   P   R   Y   N  460 cat aca ggc cag gtc att atc tac agg atg gaa gat gga aac atc aaa att ctc cag acg 1440
 H   T   G   Q   V   I   I   Y   R   M   E   D   G   N   I   K   I   L   Q   T  480 ctc agt gga gaa cag att ggt tcc tac ttt ggc agt att tta aca aca act gac att gac 1500
 L   S   G   E   Q   I   G   S   Y   F   G   S   I   L   T   T   T   D   I   D  500 aag gat tct aat act gac att ctt cta gtc gga gcc cct atg tac atg gga aca gag aag 1560
 K   D   S   N   T   D   I   L   L   V   G   A   P   M   Y   M   G   T   E   K  520 gag gag caa gga aaa gtg tat gtg tat gct ctc aat cag aca agg ttt gaa tat caa atg 1620
 E   E   Q   G   K   V   Y   V   Y   A   L   N   Q   T   R   F   E   Y   Q   M  540 agc ctg gaa cct att aag cag acg tgc tgt tca tct cgg cag cac aat tca tgc aca aca 1680
 S   L   E   P   I   K   Q   T   C   C   S   S   R   Q   H   N   S   C   T   T  560 gaa aac aaa aat gag cca tgc ggg gct cgt ttt gga act gca att gct gct gta aaa gac 1740
 E   N   K   N   E   P   C   G   A   R   F   G   T   A   I   A   A   V   K   D  580 ctc aat ctt gat gga ttt aat gac atc gtg ata gga gct ccg ctg gaa gat gat cac ggg 1800
 L   N   L   D   G   F   N   D   I   V   I   G   A   P   L   E   D   D   H   G  600 gga gct gtg tac att tat cat gga agt ggc aag act ata agg aaa gag tat gca caa cgt 1860
 G   A   V   Y   I   Y   H   G   S   G   K   T   I   R   K   E   Y   A   Q   R  620 att cca tca ggt ggg gat ggt aag aca ctg aaa ttt ttt ggc cag tct atc cac gga gaa 1920
 I   P   S   G   G   D   G   K   T   L   K   F   F   G   Q   S   I   H   G   E  640
```

FIG. 1C

```
atg gat tta aat ggt gac ggt ctg aca gat gtg act att ggg ggc ctt ggt ggt gct gcc   1980
 M   D   L   N   G   D   G   L   T   D   V   T   I   G   G   L   G   G   A   A    660 ctc ttc tgg tcc cga gat gtg gcc gta gtt aaa gtg acc atg aat ttt gag cca aat aaa   2040
 L   F   W   S   R   D   V   A   V   V   K   V   T   M   N   F   E   P   N   K    680 gtg aat att caa aag aaa aac tgc cat atg gag gga aag gaa aca gta tgc ata aat gct   2100
 V   N   I   Q   K   K   N   C   H   M   E   G   K   E   T   V   C   I   N   A    700 aca gtg tgt ttt gat gtg aaa tta aag tct aaa gaa gac acg att tat gaa gct gat ttg   2160
 T   V   C   F   D   V   K   L   K   S   K   E   D   T   I   Y   E   A   D   L    720 cag tac cgt gtc acc cta gat tca cta aga caa ata tca cga agt ttt ttc tct gga act   2220
 Q   Y   R   V   T   L   D   S   L   R   Q   I   S   R   S   F   F   S   G   T    740 caa gag aga aag gtt caa agg aac atc aca gtt cga aaa tca gaa tgc act aag cac tcc   2280
 Q   E   R   K   V   Q   R   N   I   T   V   R   K   S   E   C   T   K   H   S    760 ttc tac atg ttg gac aag cat gac ttt cag gac tct gtg aga ata acg ttg gac ttt aat   2340
 F   Y   M   L   D   K   H   D   F   Q   D   S   V   R   I   T   L   D   F   N    780 ctt acc gat cca gaa aat ggg cct gtt ctt gat gat tct cta cca aac tca gta cat gaa   2400
 L   T   D   P   E   N   G   P   V   L   D   D   S   L   P   N   S   V   H   E    800 tat att ccc ttt gcc aaa gat tgt gga aat aag gaa aaa tgt atc tca gac ctc agc ctg   2460
 Y   I   P   F   A   K   D   C   G   N   K   E   K   C   I   S   D   L   S   L    820 cat gtc gcc acc act gaa aag gac ctg ctg att gtc cga tcc cag aat gat aag ttc aac   2520
 H   V   A   T   T   E   K   D   L   L   I   V   R   S   Q   N   D   K   F   N    840 gtt agc ctc aca gtc aaa aat aca aag gac agt gcc tat aac acc agg aca ata gtg cat   2580
 V   S   L   T   V   K   N   T   K   D   S   A   Y   N   T   R   T   I   V   H    860 tat tct cca aat cta gtt ttt tca gga att gag gct atc caa aaa gac agt tgt gaa tct   2640
 Y   S   P   N   L   V   F   S   G   I   E   A   I   Q   K   D   S   C   E   S    880 aat cat aat atc aca tgt aaa gtt gga tat ccc ttc ctg aga aga gga gag atg gta act   2700
 N   H   N   I   T   C   K   V   G   Y   P   F   L   R   R   G   E   M   V   T    900 ttc aaa ata ttg ttt cag ttt aac aca tcc tat ctc atg gaa aat gtg acc att tat tta   2760
 F   K   I   L   F   Q   F   N   T   S   Y   L   M   E   N   V   T   I   Y   L    920 agt gca aca agt gac agc gaa gaa cct cct gaa acc ctt tct gat aat gta gta aac att   2820
 S   A   T   S   D   S   E   E   P   P   E   T   L   S   D   N   V   V   N   I    940 tct atc ccg gta aaa tat gaa gtt gga cta cag ttt tac agc tct gca agt gaa tac cac   2880
 S   I   P   V   K   Y   E   V   G   L   Q   F   Y   S   S   A   S   E   Y   H    960
```

FIG. 1D

```
att tca att gct gcc aat gag aca gtc cct gaa gtt att aat tct act gag gac att gga   2940
 I   S   I   A   A   N   E   T   V   P   E   V   I   N   S   T   E   D   I   G    980 aat gaa att aat atc ttc tac ttg att aga aaa agt gga tct ttt cca atg cca gag ctt   3000
 N   E   I   N   I   F   Y   L   I   R   K   S   G   S   F   P   M   P   E   L   1000 aag ctg tca att tca ttc ccc aat atg aca tca aat ggt tac cct gtg ctg tac cca act   3060
 K   L   S   I   S   F   P   N   M   T   S   N   G   Y   P   V   L   Y   P   T   1020 gga ttg tca tct tct gag aat gca aac tgc aga ccc cat atc ttt gag gat cct ttc agt   3120
 G   L   S   S   S   E   N   A   N   C   R   P   H   I   F   E   D   P   F   S   1040 atc aac tct gga aag aaa atg act aca tca act gac cat ctc aaa cga ggc aca att ctg   3180
 I   N   S   G   K   K   M   T   T   S   T   D   H   L   K   R   G   T   I   L   1060 gac tgc aat aca tgt aaa ttt gct acc atc aca tgt aat ctc act tct tct gac atc agc   3240
 D   C   N   T   C   K   F   A   T   I   T   C   N   L   T   S   S   D   I   S   1080 caa gtc aat gtt tcg ctt atc ttg tgg aaa cca act ttt ata aaa tca tat ttt tcc agc   3300
 Q   V   N   V   S   L   I   L   W   K   P   T   F   I   K   S   Y   F   S   S   1100 tta aat ctt act ata agg gga gaa ctt cgg agt gaa aat gca tct ctg gtt tta agt agc   3360
 L   N   L   T   I   R   G   E   L   R   S   E   N   A   S   L   V   L   S   S   1120 agc aat caa aaa aga gag ctt gct att caa ata tcc aaa gat ggg cta ccg ggc aga gtg   3420
 S   N   Q   K   R   E   L   A   I   Q   I   S   K   D   G   L   P   G   R   V   1140 cca tta tgg gtc atc ctg ctg agt gct ttt gcc gga ttg ttg ctg tta atg ctg ctc att   3480
 P   L   W   V   I   L   L   S   A   F   A   G   L   L   L   L   M   L   L   I   1160 tta gca ctg tgg aag att gga ttc ttc aaa aga cca ctg aaa aag aaa atg gag aaa tga   3540
 L   A   L   W   K   I   G   F   F   K   R   P   L   K   K   K   M   E   K   *   1180
```

```
Gln Ile Gln Leu Thr Gln Ser Pro Ser Ser Leu Ser Ala Ser Val Gly
Asp Arg Val Thr Ile Thr Cys Ser Ala Ser Ser Val Asn His Met
Phe Trp Tyr Gln Gln Lys Pro Gly Lys Ala Pro Lys Pro Trp Ile Tyr
Leu Thr Ser Asn Leu Ala Ser Gly Val Pro Ser Arg Phe Ser Gly Ser
Gly Ser Gly Thr Asp Tyr Thr Leu Thr Ile Ser Ser Leu Gln Pro Glu
Asp Phe Ala Thr Tyr Tyr Cys Gln Gln Trp Ser Gly Asn Pro Trp Thr
Phe Gly Gln Gly Thr Lys Val Glu Ile Lys
```

SEQ ID NO:4

FIG. 2A

```
Glu Val Gln Leu Val Glu Ser Gly Gly Gly Leu Val Gln Pro Gly Gly
Ser Leu Arg Leu Ser Cys Ala Ala Ser Gly Phe Thr Phe Ser Arg Tyr
Thr Met Ser Trp Val Arg Gln Ala Pro Gly Lys Gly Leu Glu Trp Val
Ala Thr Ile Ser Gly Gly Gly His Thr Tyr Tyr Leu Asp Ser Val Lys
Gly Arg Phe Thr Ile Ser Arg Asp Asn Ser Lys Asn Thr Leu Tyr Leu
Gln Met Asn Ser Leu Arg Ala Glu Asp Thr Ala Val Tyr Tyr Cys Thr
Arg Gly Phe Gly Asp Gly Gly Tyr Phe Asp Val Trp Gly Gln Gly Thr
Leu Val Thr Val Ser Ser
```

SEQ ID NO:5

FIG. 2B

```
Gln Ile Gln Leu Thr Gln Ser Pro Ser Ser Leu Ser Ala Ser Val Gly
Asp Arg Val Thr Ile Thr Cys Ser Ala Ser Ser Ser Val Asn His Met
Phe Trp Tyr Gln Gln Lys Pro Gly Lys Ala Pro Lys Pro Trp Ile Tyr
Leu Thr Ser Asn Leu Ala Ser Gly Val Pro Ser Arg Phe Ser Gly Ser
Gly Ser Gly Thr Asp Tyr Thr Leu Thr Ile Ser Ser Leu Gln Pro Glu
Asp Phe Ala Thr Tyr Tyr Cys Gln Gln Trp Ser Gly Asn Pro Trp Thr
Phe Gly Gln Gly Thr Lys Val Glu Ile Lys Arg Thr Val Ala Ala Pro
Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys
Val Gln Trp Lys Val Asp Asn Ala Leu Gln Ser Gly Asn Ser Gln Glu
Ser Val Thr Glu Gln Asp Ser Lys Asp Ser Thr Tyr Ser Leu Ser Ser
Thr Leu Thr Leu Ser Lys Ala Asp Tyr Glu Lys His Lys Val Tyr Ala
Cys Glu Val Thr His Gln Gly Leu Ser Ser Pro Val Thr Lys Ser Phe
Asn Arg Gly Glu Cys

SEQ ID NO:1
```

FIG. 3

```
Glu Val Gln Leu Val Glu Ser Gly Gly Gly Leu Val Gln Pro Gly Gly
Ser Leu Arg Leu Ser Cys Ala Ala Ser Gly Phe Thr Phe Ser Arg Tyr
Thr Met Ser Trp Val Arg Gln Ala Pro Gly Lys Gly Leu Glu Trp Val
Ala Thr Ile Ser Gly Gly Gly His Thr Tyr Tyr Leu Asp Ser Val Lys
Gly Arg Phe Thr Ile Ser Arg Asp Asn Ser Lys Asn Thr Leu Tyr Leu
Gln Met Asn Ser Leu Arg Ala Glu Asp Thr Ala Val Tyr Tyr Cys Thr
Arg Gly Phe Gly Asp Gly Gly Tyr Phe Asp Val Trp Gly Gln Gly Thr
Leu Val Thr Val Ser Ser Ala Ser Thr Lys Gly Pro Ser Val Phe Pro
Leu Ala Pro Ser Ser Lys Ser Thr Ser Gly Gly Thr Ala Ala Leu Gly
Cys Leu Val Lys Asp Tyr Phe Pro Glu Pro Val Thr Val Ser Trp Asn
Ser Gly Ala Leu Thr Ser Gly Val His Thr Phe Pro Ala Val Leu Gln
Ser Ser Gly Leu Tyr Ser Leu Ser Ser Val Val Thr Val Pro Ser Ser
Ser Leu Gly Thr Gln Thr Tyr Ile Cys Asn Val Asn His Lys Pro Ser
Asn Thr Lys Val Asp Lys Lys Val Glu Pro Lys Ser Cys Asp Lys Thr
His Thr Cys Pro Pro Cys Pro Ala Pro Glu Leu Leu Gly Gly Pro Ser
Val Phe Leu Phe Pro Pro Lys Pro Lys Asp Thr Leu Met Ile Ser Arg
Thr Pro Glu Val Thr Cys Val Val Val Asp Val Ser His Glu Asp Pro
Glu Val Lys Phe Asn Trp Tyr Val Asp Gly Val Glu Val His Asn Ala
Lys Thr Lys Pro Arg Glu Glu Gln Tyr Asn Ser Thr Tyr Arg Val Val
Ser Val Leu Thr Val Leu His Gln Asp Trp Leu Asn Gly Lys Glu Tyr
Lys Cys Lys Val Ser Asn Lys Ala Leu Pro Ala Pro Ile Glu Lys Thr
Ile Ser Lys Ala Lys Gly Gln Pro Arg Glu Pro Gln Val Tyr Thr Leu
Pro Pro Ser Arg Asp Glu Leu Thr Lys Asn Gln Val Ser Leu Thr Cys
Leu Val Lys Gly Phe Tyr Pro Ser Asp Ile Ala Val Glu Trp Glu Ser
Asn Gly Gln Pro Glu Asn Asn Tyr Lys Thr Thr Pro Pro Val Leu Asp
Ser Asp Gly Ser Phe Phe Leu Tyr Ser Lys Leu Thr Val Asp Lys Ser
Arg Trp Gln Gln Gly Asn Val Phe Ser Cys Ser Val Met His Glu Ala
Leu His Asn His Tyr Thr Gln Lys Ser Leu Ser Leu Ser Pro Gly

SEQ ID NO:2
```

FIG. 4

ANTI-VLA1 (CD49A) ANTIBODY PHARMACEUTICAL COMPOSITIONS

RELATED APPLICATIONS

This application is a national phase application under 35 U.S.C. § 371 of PCT International Application No. PCT/US2013/026034 filed on Feb. 14, 2013, which claims priority to U.S. Provisional Application No. 61/599,827, filed on Feb. 16, 2012. The entire content of each of the foregoing applications is hereby incorporated herein.

SEQUENCE LISTING

The instant application contains a Sequence Listing which has been submitted in ASCII format via EFS-Web and is hereby incorporated by reference in its entirety. Said ASCII copy, created on Feb. 13, 2013, is named C2095-7004WO_SL.txt and is 35,968 bytes in size.

BACKGROUND

Integrins are a superfamily of cell surface receptors that mediate cell-cell and cell-matrix adhesion. These heterodimeric proteins, composed of two noncovalently linked polypeptide chains, α and β, provide anchorage as well as signals for cellular growth, migration and differentiation during development and tissue repair. Integrins have also been implicated in immune and inflammatory processes, which require the extravasation of cells out of blood vessels, into tissues and towards the site of infection.

VLA-1 (also called α1β1) belongs to a class of integrins called VLA ("Very Late Antigen") integrins. VLA-1 binds collagen (both types I and IV) and laminin, and has been implicated in cell adhesion and migration on collagen; contraction and reorganization of collagen matrices; and regulation of expression of genes involved in extracellular matrix remodeling.

VLA-1 has been shown to be involved in the development of rheumatoid arthritis, a chronic inflammatory disease associated with bone resorption. Infiltrating T cells in the arthritic synovium of patients express high levels of VLA-1, and its blockade with antibodies significantly reduces the inflammatory response and the development of arthritis in animal models.

SUMMARY

The invention is based, at least in part, on the development of formulations containing high concentrations of anti-VLA-1 antibody. Some embodiments are particularly well suited for delivery to a subject, such as a human, for example, a human patient, by subcutaneous (SC) delivery. The anti-VLA-1 antibody can be SAN-300, for example, and the antibody is at a concentration of about ≥100 mg/mL to about 225 mg/mL. The formulations provide a therapeutic effect for an inflammatory, immune, or autoimmune disorder. For example, the formulation can provide a therapeutic effect for an inflammatory disorder, such as rheumatoid arthritis (RA).

In one aspect, the invention features an aqueous pharmaceutical composition, such as a stable aqueous pharmaceutical composition, containing an anti-VLA-1 antibody at a concentration of ≥100 mg/mL, for example, at least about 110 mg/mL, at least about 120 mg/mL, at least about 130 mg/mL, at least about 140 mg/mL, at least about 150 mg/mL, at least about 160 mg/mL, at least about 170 mg/mL, at least about 180 mg/mL, at least about 190 mg/mL, or at least about 200 mg/mL. In one embodiment, the composition comprises an anti-VLA-1 antibody at a concentration of less than about 200 mg/mL, less than about 205 mg/mL, less than about 210 mg/mL, less than about 215 mg/mL, less than about 220 mg/mL or less than about 225 mg/mL. In another embodiment, the composition comprises an anti-VLA-1 antibody at a concentration of about 155 mg/mL to about 165 mg/mL, about 165 mg/mL to about 175 mg/mL, about 175 mg/mL to about 185 mg/mL, about 180 mg/mL to about 190 mg/mL, about 185 mg/mL to about 195 mg/mL, about 195 mg/mL to about 205 mg/mL, about 205 mg/mL to about 215 mg/mL or about 215 mg/mL to about 225 mg/mL. In another embodiment, the composition comprises an anti-VLA-1 antibody at a concentration of greater than about 100 mg/mL to about 225 mg/mL, such as about 160 mg/mL to about 210 mg/mL, about 175 mg/mL to about 195 mg/mL, or about 180 mg/mL to about 190 mg/mL.

In one embodiment, the aqueous pharmaceutical composition comprising an anti-VLA-1 antibody further comprises a buffer, such as an acetate, histidine, succinate, or phosphate buffer. The buffer can be at a concentration of about 10 mM to about 50 mM, for example, about 20 mM to about 40 mM, such as about 30 mM. For example, the composition can contain a histidine buffer at a concentration of about 10 mM to about 50 mM, for example, about 20 mM to about 40 mM, such as about 30 mM. In one embodiment, the composition contains an acetate buffer at a concentration of about 10 mM to about 50 mM, for example, about 20 mM to about 40 mM, such as about 30 mM.

In another embodiment, the aqueous pharmaceutical composition further comprises an excipient, such as sorbitol, sodium chloride (NaCl), sucrose, trehelose, or mannitol. The composition can include an excipient at a concentration of about 100 mM to about 300 mM, for example, 110 mM to about 270 mM, about 120 mM to about 230 mM, or about 130 mM to about 210 mM, about 170 mM to about 200 mM, or about 180 mM to about 200 mM. For example, the composition can contain sorbitol at a concentration of about 180 mM to about 300 mM, for example, about 200 mM to about 300 mM, about 200 mM to about 240 mM, about 230 mM to about 270 mM, or about 240 mM to about 260 mM. In another example, the composition can contain NaCl at a concentration of about 100 mM to about 200 mM, for example, about 110 mM to about 190 mM, about 120 mM to about 180 mM, or about 130 mM to about 170 mM. In another example, the composition can contain sucrose at a concentration of about 200 mM to about 240 mM, about 230 mM to about 270 mM, or about 240 mM to about 260 mM. In another example, the composition can contain trehalose at a concentration of about 200 mM to about 240 mM, about 230 mM to about 270 mM, or about 240 mM to about 260 mM. In yet another example, the composition can contain mannitol at a concentration of about 200 mM to about 240 mM, about 230 mM to about 270 mM, or about 240 mM to about 260 mM.

In another embodiment, the aqueous pharmaceutical composition further comprises a surfactant, such as a polysorbate, for example, polysorbate 80 or polysorbate 20. In one embodiment, the concentration of surfactant is at a concentration of about 0.001% to about 0.5%, about 0.001% to about 0.1%, for example, about 0.005% to about 0.05%, such as about 0.01%.

As used herein, a "surfactant" is a substance that lowers surface tension of a liquid, and are used to prevent surface adsorption and act as stabilizers against protein aggregation. Exemplary surfactants suitable for use herein include, for example, polysorbate 80 (also called Tween 80), polysorbate 20 (also called Tween 20). Other surfactants of similar strength can also be used.

In yet another embodiment, the aqueous pharmaceutical composition has a pH of about 4.5 to about 7, for example, pH of about 5 to about 7, pH of about 5 to about 6, pH of about 5.5 to about 7, or pH of about 5.5 to about 6.5. In one embodiment composition has a pH of about 4.5, a pH of about 5, a pH of about 5.5, a pH of about 6, a pH of about 6.5, or a pH of about 7.

In one embodiment, the aqueous pharmaceutical composition comprises a buffer, an excipient, and a surfactant. For example, in one embodiment, the aqueous pharmaceutical composition comprises acetate, sorbitol, and polysorbate 80. In one embodiment, acetate is at concentration of about 20 mM to about 40 mM, sorbitol is at a concentration of about 180 mM to about 240 mM, polysorbate 80 is at a concentration of about 0.005% to about 0.05%, and the composition has pH of about 4.5 to about 6. In another embodiment, acetate is at concentration of about 20 mM to about 40 mM, sorbitol is at a concentration of about 200 mM to about 300 mM, polysorbate 80 is at a concentration of about 0.0055% to about 0.05%, and the composition has pH of about 4.5 to about 5.5. In one embodiment, acetate is at a concentration of about 30 mM, sorbitol is at a concentration of about 180 mM to about 250 mM, polysorbate 80 is at a concentration of about 0.01%, and the formulation has pH of about 5.5.

In another embodiment, the composition comprises histidine, sorbitol, and polysorbate 20. For example, histidine is at a concentration of about 20 mM to about 40 mM, sorbitol is at a concentration of about 180 mM to about 270 mM, polysorbate 20 is at a concentration of about 0.005% to 0.05%, and the composition has pH of about 6 to about 7. In one embodiment, histidine is at a concentration of about 30 mM, sorbitol is at a concentration of about 180 mM to about 250 mM, polysorbate 20 is at a concentration of about 0.01% and the composition has pH of about 6.0.

In another embodiment, the aqueous pharmaceutical composition comprises acetate, NaCl, and polysorbate 80. In one embodiment, acetate is at a concentration of about 20 mM to about 40 mM, NaCl is at a concentration of about 120 mM to about 180 mM, polysorbate 80 is at a concentration of about 0.005% to about 0.05%, and the composition has pH of about 4.5 to about 6. In one embodiment, acetate is at a concentration of about 30 mM, NaCl is at a concentration of about 150 mM, polysorbate 80 is at a concentration of about 0.01%, and the formulation has pH of about 5.5.

In another embodiment, the composition comprises histidine, NaCl, and polysorbate 20. For example, histidine is at a concentration of about 20 mM to about 40 mM, NaCl is at a concentration of about 120 mM to about 180 mM, polysorbate 20 is at a concentration of about 0.005% to about 0.05%, and the composition has pH of about 6 to about 7. In one embodiment, histidine is at a concentration of about 30 mM, NaCl is at a concentration of about 150 mM, polysorbate 20 is at a concentration of about 0.01% and the composition has pH of about 6.0.

In another embodiment, the anti-VLA-1 antibody in the aqueous pharmaceutical composition is a monoclonal antibody. In another embodiment, the anti-VLA-1 antibody is a CDR-grafted antibody. In yet another embodiment, the anti-VLA-1 antibody is a humanized antibody.

In another embodiment, the anti-VLA-1 antibody is a humanized monoclonal antibody, such as SAN-300. In another embodiment, the anti-VLA-1 antibody is a variant of SAN-300. For example, in some embodiments, the light chain variable region of the antibody has an amino acid sequence that differs by one or more amino acid residues, but not more than 2 amino acid residues, 3 amino acid residues, 4 amino acid residues, 5 amino acid residues, or 6 amino acid residues of the light chain variable region of SAN-300, and/or the heavy chain variable region has an amino acid sequence that differs by one or more amino acid residues, but not more than 2 amino acid residues, 3 amino acid residues, 4 amino acid residues, 5 amino acid residues, or 6 amino acid residues of the heavy chain variable region of SAN-300. In some embodiments, some or all differences are conservative changes.

In another embodiment, the anti-VLA-1 antibody has one or both of a light chain variable region having the amino acid sequence of SEQ ID NO:4 (FIG. 2A), and a heavy chain variable region having the amino acid sequence of SEQ ID NO:5 (FIG. 2B). In other embodiments, the anti-VLA-1 antibody is a variant of one of these antibodies. For example, in some embodiments, the light chain variable region has an amino acid sequence that differs by one or more amino acid residues, but not more than 2 amino acid residues, 3 amino acid residues, 4 amino acid residues, 5 amino acid residues, 6 amino acid residues, 7 amino acid residues, 8 amino acid residues, 9 amino acid residues or 10 amino acid residues from the sequence in SEQ ID NO:4, and/or the heavy chain variable region has an amino acid sequence that differs by one or more amino acid residues, but not more than 2 amino acid residues, 3 amino acid residues, 4 amino acid residues, 5 amino acid residues, 6 amino acid residues, 7 amino acid residues, 8 amino acid residues, 9 amino acid residues or 10 amino acid residues as defined by SEQ ID NO:5. In other embodiments, the light chain variable region has an amino acid sequence that is 80%, 85%, 90% or 95% identical with the sequence of SEQ ID NO:4, and/or the heavy chain variable region has an amino acid sequence that is 80%, 85%, 90% or 95% identical with the sequence of SEQ ID NO:5.

In yet another embodiment, the anti-VLA-1 antibody has one or both of a light chain amino acid sequence of SEQ ID NO:1 (FIG. 3), and a heavy chain amino acid sequence of SEQ ID NO:2 (FIG. 4). In other embodiments, the VLA-1 antibody is a variant of one of these antibodies. For example, in some embodiments, the light chain of the antibody has an amino acid sequence that differs by one or more amino acid residues, but not more than 2 amino acid residues, 3 amino acid residues, 4 amino acid residues, 5 amino acid residues, 6 amino acid residues, 7 amino acid residues, 8 amino acid residues, 9 amino acid residues or 10 amino acid residues from the sequence of SEQ ID NO:1, and/or the heavy chain of the antibody has an amino acid sequence that differs by one or more amino acid residues, but not more than 2 amino acid residues, 3 amino acid residues, 4 amino acid residues, 5 amino acid residues, 6 amino acid residues, 7 amino acid residues, 8 amino acid residues, 9 amino acid residues or 10 amino acid residues from the sequence of SEQ ID NO:2. In other embodiments, the light chain of the antibody has an amino acid sequence that is 80%, 85%, 90% or 95% identical with the sequence of SEQ ID NO:1, and/or the heavy chain of the antibody has an amino acid sequence that 80%, 85%, 90% or 95% identical with the sequence of SEQ ID NO:2.

A first amino acid sequence "differs" or is "different" or displays a "difference" as compared to a second amino acid sequence when there is a difference in the identity of an amino acid (for example, a substitution of a different amino acid for an amino acid in SEQ ID NO:4 or 5 referred to above), or a deletion or insertion. A difference can be, for example, in a framework region, a CDR, a hinge, or a constant region. A difference can be internal or at the end of a sequence of protein. In some embodiments, some or all differences are conservative changes as compared to the recited sequence.

In another embodiment, the composition comprises less than 20 mM citrate, and in another embodiment the composition is substantially free of citrate. For example, the level of citrate comprises less than 20 mM citrate, or the level of citrate is such that it has no effect on a property described herein, such as, injection site pain when embodiments are administered to a subject.

In another embodiment, the aqueous pharmaceutical composition comprising an anti-VLA-1 antibody is stable for at least 6 months, at least 12 months, at least 18 months, at least 24 months, at least 30 months, or at least 36 months or longer (for example, at least 1 year, at least 2 years, at least 3 years or longer). For example, the composition can be stable for at least 6 months, at least 12 months, at least 18 months, at least 24 months, at least 30 months, at least 36 months or longer (for example, at least 1 year, at least 2 years, at least 3 years, or longer), at a temperature of about 2° C. to about 8° C. (for example, about 4° C., about 5° C.). In one embodiment, the composition is stable for at least 24 months (at least 2 years) at a temperature of about 2° C. to about 8° C. In another embodiment, the composition is stable for at least 2 days, at least 3 days, at least 4 days, at least 5 days, at least 6 days, or at least 7 days or longer (for example, at least one week, or at least 12 days or at least 14 days or longer) at ambient temperature (about 20° C. to about 30° C., such as about 25° C.).

In one embodiment, less than about 1%, less than about 2%, less than about 5%, less than about 10%, or less than about 15% of the antibody in the anti-VLA-1 antibody composition has aggregated after a period of 6 months, 12 months, 18 months, 24 months, 30 months, or 36 months or longer, such as after a period of 1 year, 2 years or 3 years or longer. In another embodiment, less than about 1%, less than about 2%, less than about 5%, less than about 10%, or less than about 15% of the antibody in the anti-VLA-1 antibody composition has fragmented after a period of 6 months, 12 months, 18 months, 24 months, 30 months, or 36 months or longer, such as after a period of 1 year, 2 years, 3 years or longer.

In certain embodiments, aggregation or protein fragmentation is measured by dynamic light scattering (DLS), size exclusion chromatography (SEC), color/clarity, UV light scattering or size exclusion chromatography. In one embodiment, aggregation is measured by DLS. DLS can be performed by methods known those of ordinary skill in the art such as those described, for example, in Nobbmann et al., "Dynamic Light Scattering as a Relative Tool for Assessing the Molecular Integrity and Stability of Monoclonal Antibodies" Biotech. and Genetic Engineering Rev. 24:117-128, 2007. In another embodiment, aggregation is measured by SEC. SEC can be performed by methods known to those of ordinary skill in the art such as those described, for example, in Skoog, D. A.; Principles of Instrumental Analysis, 6th ed.; Thompson Brooks/Cole: Belmont, Calif., 2006, Chapter 28.

In one embodiment, less than about 1%, less than about 2%, less than about 5%, less than about 10%, less than about 15% or less than about 20% of the antibody in the aqueous pharmaceutical composition has undergone fragmentation after a period of 6 months, 12 months, 18 months, 24 months, 30 months, or 36 months or longer (for example, after a period of 1 year, 2 years, 3 years or longer).

In one embodiment, less than about 1%, less than about 2%, less than about 5%, less than about 10%, less than about 15% or less than about 20% of the antibody in the aqueous pharmaceutical composition has undergone deamidation after a period of 6 months, 12 months, 18 months, 24 months, 30 months, or 36 months or longer (for example, after a period of 1 year, 2 years, 3 years or longer). In another embodiment, deamidation is assayed by measuring protein loss, such as by spectroscopy, for example, UV-Vis ("Ultraviolet-visible") spectroscopy. Use of UV-Vis spectroscopy is reviewed in, for example, Schmid, "Biological Macromolecules: UV-visible spectrophotometry" Encyclopedia of Life Sciences, pp. 1-4, published online Apr. 19, 2001.

In one embodiment, anti-VLA-1 antibody in the aqueous pharmaceutical composition exhibits less than a preselected level of aggregation when the formulation is stored in a closed container at about 2° C. to about 8° C., such as at about 4° C., for a preselected period of time, such as after storage for at least 30 days, at least 60 days, at least 90 days, at least 180 days, at least 1 year, at least 1.5 years, at least 2 years, at least 2.5 years, at least 3 years or longer. In another embodiment, anti-VLA-1 antibody in the aqueous pharmaceutical composition exhibits less than a preselected level of protein loss due to aggregation when the formulation is stored in a closed container at about 2° C. to about 8° C., for example, at about 4° C., for a preselected period of time. In one embodiment, the preselected level of protein loss is less than about 40%, less than about 35%, less than about 30%, less than about 20%, less than about 15%, less than about 10%, less than about 8%, less than about 5%, less than about 3%, less than about 1%, or less than about 0.5%. In one embodiment, after 6 months, one year, two years or three years, less than about 1%, less than about 2%, less than about 5%, less than about 10%, less than about 15%, less than about 20%, less than about 30%, less than about 35%, or less than about 40% of the antibody in the formulation has undergone aggregation.

Protein loss can be measured, for example, by spectroscopy, such as by UV-Vis spectroscopy. In certain embodiments, aggregation is measured by dynamic light scattering (DLS), color/clarity, UV light scattering or size exclusion chromatography.

In another embodiment, anti-VLA-1 antibody in the aqueous pharmaceutical composition exhibits less than a preselected level of protein loss when the formulation is subjected to a preselected number of freeze/thaw cycles, for example, 2, 3, 4, 5, 6, 7, 8 or more freeze/thaw cycles. In one embodiment, the preselected number of freeze/thaw cycles is 5. A "freeze/thaw cycle" is a sequence comprising at least one period in which the sample is a frozen solid followed by a period in which the samples is a liquid, or a sequence comprising at least one period in which the sample is liquid followed by a period in which the samples is a frozen solid. The periods can be equal to, or longer than, for example, 5 minutes, 10 minutes, 15 minutes, 20 minutes, 30 minutes, 45 minutes, 60 minutes, or 120 minutes, 2 hours, 3 hours, 4 hours, 6 hours, 24 hours, 48 hours, or 3 days, 5 days, 10 days, or 20 days in length. The liquid and solid periods need not be of the same length. The solid periods can be held at 0° C. or less, for example, −10° C., −20° C., −30° C., −40° C., −60° C., or −80° C. The solid period can be at least, for example, 2 hours, 3 hours, 4 hours, or more. The solid period can be followed by thawing, for example, at 18° C., 20° C., 23° C., or higher, until melted. The sample can remain melted for 20 minutes, 30 minutes, one hour, or two hours or longer, prior to freezing the sample again, to begin another freeze/thaw cycle. The sample can be stored in the frozen state or in the melted state between freeze/thaw cycles. In one embodiment, the preselected level of protein loss following 2, 3, 4, 5, 6, 7, 8 or more freeze/thaw cycles is, for example, less than about 40%, less than about 35%, less than about 30%, less than about 20%, less than about 15%, less than about 10%, less than about 8%, less than about 5%, less than about 3%, less than about 1%, or less than about 0.5%. Protein loss can be measured, for example, by UV-Vis spectroscopy.

In yet another embodiment, anti-VLA-1 antibody in the aqueous pharmaceutical composition exhibits less than a preselected level of protein loss when the formulation is subjected to photo stress, such as when the composition is stored in a closed container at 2° C. to 8° C., for example, 4° C., and exposed to 1.2 lux hours white light and then 200 W/m² UV energy. In one embodiment, the preselected level of protein loss is less than about 40%, less than about 35%, less than about 30%, less than about 20%, less than about 15%, less than about 10%, less than about 8%, less than about 5%, less than about 3%, less than about 1%, or less than about 0.5%. Protein loss can be measured, for example, by UV-Vis spectroscopy.

In another embodiment, anti-VLA-1 antibody in the aqueous pharmaceutical composition exhibits less than a preselected level of protein loss when the formulation is subjected to agitation, for example, shaking at 550 rpm, 600 rpm, 650 rpm, 700 rpm, 750 rpm, or faster, for a preselected period of time, such as for 1 day, 2 days, 3 days, 4 days, 5 days or longer (for example, for 24 hours, 48 hours, 72 hours, 96 hours, 120 hours or longer at room temperature. In one embodiment, the preselected level of protein loss is less than about 40%, less than about 35%, less than about 30%, less than about 20%, less than about 15%, less than about 10%, less than about 8%, less than about 5%, less than about 3%, less than about 2%, less than about 1.5%, less than about 1%, less than about 0.5%, or less than about 0.25%. Protein loss can be measured, for example, by UV-Vis spectroscopy.

In one embodiment, anti-VLA-1 antibody in the aqueous pharmaceutical composition exhibits less than a preselected level of protein loss when the formulation is subjected to a preselected level of oxidation stress. The preselected level of oxidation stress can be provided by the presence of hydrogen peroxide at a final concentration of 0.04% (v/v) with incubation at 37° C. for a preselected period of time, such as for 2 hours, 3 hours, 4 hours, 5 hours, or 6 hours or longer. In one embodiment, the preselected level of protein loss is less than about 35%, less than about 30%, less than about 25%, less than about 20%, less than about 15%, or less than about 10%. Protein loss can be measured, for example, by UV-Vis spectroscopy.

In one embodiment, the anti-VLA-1 antibody in the aqueous pharmaceutical composition exhibits less than a preselected level of protein loss when the formulation is subjected to a preselected level of deamidation stress. The preselected level of deamidation can be provided by raising the pH of the composition, such as to a pH≥9, such as in the presence of Tris (tris(hydroxymethyl)aminomethane) buffer, and then incubating the composition at about 25° C. for a preselected period of time, such as for 2 days, 3 days, 4 days, 5 days, 6 days or longer. In one embodiment, the preselected level of protein loss is less than about 20%, less than about 15%, less than about 10%, less than about 5%, less than about 3%, or less than about 1%. Protein loss can be measured, for example, by UV-Vis spectroscopy.

In one embodiment, the aqueous pharmaceutical composition comprising an anti-VLA-1 antibody formulation is for subcutaneous (SC) administration.

In one embodiment, the aqueous pharmaceutical composition has a syringeability for patient self administration to a subcutaneous site. For example, the aqueous composition, when disposed in a syringe suitable for subcutaneous delivery can be expelled and thereby injected into a subcutaneous site of the patient, using pressure sufficient to depress the plunger for patient self administration. The pressure, or "plunger force" can be, for example, equal to or less than 4 lbs. In one embodiment, the plunger force will allow delivery of a unit dosage in 10 seconds or less. In another embodiment, about 1 mL of an aqueous pharmaceutical composition, disposed in a syringe having a needle of a preselected gauge, can be expelled at a preselected rate with a plunger force of no more than a preselected amount. In another embodiment, about 2 mL of aqueous pharmaceutical composition, disposed in a syringe having a needle of a preselected gauge, can be expelled at a preselected rate with a plunger force of no more than a preselected amount. For example, about 1 mL aqueous pharmaceutical composition, disposed in a syringe having a 25 gauge needle, a 27 gauge needle, or a 30 gauge needle can be expelled at 10 mL/minute with a plunger force of no more than 4 lbs.

As used herein, a "unit dosage" is an amount suitable for administration at one time. The unit dosage can provide a therapeutically effective amount of anti-VLA-1 antibody, for example an amount of anti-VLA-1 antibody to relieve one or more symptoms of an inflammatory disorder, such as one or more symptoms of arthritis or IBD.

In one embodiment, the aqueous pharmaceutical composition comprising an anti-VLA-1 antibody has a viscosity suitable for subcutaneous delivery with a syringe, such as a viscosity of less than 21 cP (centipoises), less than 18 cP, less than 15 cP, less than 14 cP, such as at 3 rpm, 5 rpm, 7 rpm, or 9 rpm. In one embodiment, the composition has a viscosity of about 10 cP to about 20 cP, about 10 cP to about 15 cP, about 10 cP to about 14 cP, or for example, 10 cP to 13 cP, at for example 3 rpm, 5 rpm, 7 rpm, or 9 rpm.

"Viscosity" is a measure of the resistance of a fluid that is being deformed by either shear or tensile stress. A thicker substance has higher resistance, and thus higher viscosity, than a thinner substance.

In one embodiment, the aqueous pharmaceutical composition is for administration by a healthcare professional.

In one aspect, the invention features an aqueous pharmaceutical composition comprising an anti-VLA-1 antibody comprising a light chain having the sequence of SEQ ID NO: 1 and a heavy chain having the sequence of SEQ ID NO:2; acetate at a concentration of about 10 mM to about 50 mM; sorbitol at a concentration of about 180 mM to about 275 mM; polysorbate 80 at 0.005% to 0.5%; and pH of about 4.5 to pH of about 6.0. In one embodiment, the antibody concentration is ≥100 mg/mL to about 225 mg/mL, for example, about 120 mg/mL to about 210 mg/mL, about 140 mg/mL to about 200 mg/mL. In another embodiment, the antibody is at a concentration of about 155 mg/mL to about 195 mg/mL, about 160 mg/mL to about 190 mg/mL, or about 170 mg/mL to about 180 mg/mL. In some embodiments, the antibody is at a concentration of about 160 mg/mL, about 165 mg/mL, about 175 mg/mL, about 180 mg/mL or about 190 mg/mL.

In one embodiment, the aqueous pharmaceutical composition comprises acetate at a concentration of about 20 mM to about 40 mM, for example about 30 mM. In another embodiment, the aqueous pharmaceutical composition contains sorbitol at a concentration of about 180 mM to about 275 mM, for example, about 200 mM to about 240 mM. In one embodiment, the aqueous pharmaceutical composition contains sorbitol at a concentration of about 250 mM. In one embodiment, the aqueous pharmaceutical composition contains polysorbate 80 at a concentration of about 0.005% to about 0.05%, such as at about 0.01%. In yet another embodiment, the aqueous pharmaceutical composition has a pH of about 5.5.

In one embodiment, the aqueous pharmaceutical composition comprising an anti-VLA-1 antibody has an osmolality of about 80 mOsm/kg to about 500 mOsm/kg, for example, about 100 mOsm/kg to about 450 mOsm/kg, about 150 mOsm/kg to about 400 mOsm/kg, about 200 mOsm/kg to about 350 mOsm/kg, for example, about 280 mOsm/kg to about 350 mOsm/kg, for example, about 300 mOsm/kg to about 325 mOsm/kg. In one example, the aqueous pharmaceutical composition comprising an anti-VLA-1 antibody has an osmolality of less than about 500 mOsm/kg, less than about 455 mOsm/kg, less than about 405 mOsm/kg, less than about 355 mOsm/kg, less than about 305 mOsm/kg, or less than about 255 mOsm/kg.

In another embodiment, the aqueous pharmaceutical composition contains an anti-VLA-1 antibody comprising a light chain having the sequence of SEQ ID NO:1 and a heavy chain having the sequence of SEQ ID NO:2 at a concentration of about 170 mg/mL to about 210 mg/mL. In one embodiment, the composition also includes acetate at a concentration of about 25 mM to about 35 mM, sorbitol at a concentration of about 180 mM to about 275 mM, polysorbate 80 at a concentration of about 0.005% to about 0.02%, and a pH of about 5.5.

In one embodiment, the aqueous pharmaceutical composition includes an anti-VLA-1 antibody comprising a light chain having the sequence of SEQ ID NO:1 and a heavy chain having the sequence of SEQ ID NO:2 at a concentration of about 185 mg/mL to about 195 mg/mL; acetate at a concentration of about 30 mM; sorbitol at a concentration of about 250 mM; polysorbate 80 at a concentration of about 0.01%; and a pH of about 5.5.

In one embodiment, the aqueous pharmaceutical composition comprises anti-VLA-1 antibody at a concentration of about 190 mg/mL.

In one aspect, the invention features an aqueous pharmaceutical composition comprising an anti-VLA-1 antibody comprising a light chain having the sequence of SEQ ID NO: 1 and a heavy chain having the sequence of SEQ ID NO:2; acetate at a concentration of about 10 mM to about 50 mM; NaCl at a concentration of about 120 mM to about 180 mM; polysorbate 80 at a concentration of about 0.005% to about 0.05%; and a pH of about 4.5 to about 6.0. In one embodiment, the antibody is at a concentration of ≥100 mg/mL to about 225 mg/mL, for example, about 120 mg/mL to about 210 mg/mL, about 140 mg/mL to about 200 mg/mL. In another embodiment, the antibody is at concentration of about 155 mg/mL to about 195 mg/mL, about 160 mg/mL to about 190 mg/mL, or about 170 mg/mL to about 180 mg/mL. In some embodiments, the antibody is at a concentration of about 160 mg/mL, about 165 mg/mL, about 175 mg/mL, about 180 mg/mL or about 190 mg/mL.

In one embodiment, the aqueous pharmaceutical composition comprises acetate at a concentration of about 20 mM to about 40 mM, for example about 30 mM. In another embodiment, the aqueous pharmaceutical composition contains NaCl at a concentration of about 130 mM to about 170 mM, for example, about 140 mM to about 160 mM. In one embodiment, the aqueous pharmaceutical composition contains NaCl at a concentration of about 150 mM. In one embodiment, the aqueous pharmaceutical composition contains polysorbate 80 at a concentration of about 0.005% to about 0.05%, such as at about 0.01%. In yet another embodiment, the aqueous pharmaceutical composition has a pH of about 5.5.

In one embodiment, the aqueous pharmaceutical composition comprising an anti-VLA-1 antibody has an osmolality is 80 mOsm/kg to 350 mOsm/kg.

In another embodiment, the aqueous pharmaceutical composition contains an anti-VLA-1 antibody comprising a light chain having the sequence of SEQ ID NO:1 and a heavy chain having the sequence of SEQ ID NO:2 at a concentration of about 170 mg/mL to about 210 mg/mL. In one embodiment, the composition also includes acetate at a concentration of about 25 mM to about 35 mM, NaCl at a concentration of about 120 mM to about 180 mM, polysorbate 80 at a concentration of about 0.005% to about 0.02%, and a pH of about 5.5.

In one embodiment, the aqueous pharmaceutical composition includes an anti-VLA-1 antibody comprising a light chain having the sequence of SEQ ID NO:1 and a heavy chain having the sequence of SEQ ID NO:2 at a concentration of about 185 mg/mL to about 195 mg/mL; acetate at a concentration of about 30 mM; NaCl at a concentration of about 150 mM; polysorbate 80 at about 0.01%; and a pH of about 5.5.

In one embodiment, the aqueous pharmaceutical composition comprises anti-VLA-1 antibody at a concentration of about 190 mg/mL.

In one aspect, the invention features an aqueous pharmaceutical composition comprising an anti-VLA-1 antibody comprising a light chain having the sequence of SEQ ID NO:1 and a heavy chain having the sequence of SEQ ID NO:2; histidine at a concentration of about 10 mM to about 50 mM; sorbitol at a concentration of about 180 mM to about 300 mM; polysorbate 20 at a concentration of about 0.005% to about 0.05%; and a pH of about 5.5 to about 7.0. In one embodiment, the antibody is at a concentration of ≥100 mg/mL to about 225 mg/mL, for example, about 120 mg/mL to about 210 mg/mL, about 140 mg/mL to about 200 mg/mL. In another embodiment, the antibody is at a concentration of about 155 mg/mL to about 195 mg/mL, about 160 mg/mL to about 190 mg/mL, or about 170 mg/mL to about 180 mg/mL. In some embodiments, the antibody is at a concentration of about 160 mg/mL, about 165 mg/mL, about 175 mg/mL, about 180 mg/mL or about 190 mg/mL.

In one embodiment, the composition includes histidine at a concentration of 20 mM to 40 mM, such as at a concentration of about 30 mM. In another embodiment, the composition comprises sorbitol at a concentration of 220 mM to 280 mM, for example, 240 mM to 260 mM, such as about 250 mM. In another embodiment, the composition comprises polysorbate 20 at a concentration of about 0.005% to 0.05%, such as about 0.01%. In another embodiment, the composition has a pH of about 6.0, and in yet another embodiment, the composition has an osmolality of about 280 mOsm/kg to about 350 mOsm/kg.

In one embodiment, the aqueous pharmaceutical composition includes an anti-VLA-1 antibody comprising a light chain having the sequence of SEQ ID NO:1 and a heavy chain having the sequence of SEQ ID NO:2 at a concentration of about 160 mg/mL to about 200 mg/mL; histidine at a concentration of about 25 mM to about 35 mM histidine; sorbitol at a concentration of about 240 mM to about 260 mM; polysorbate 20 at a concentration of about 0.005% to about 0.02%; and a pH of about 6.

In another embodiment, the composition includes an anti-VLA-1 antibody comprising a light chain having the sequence of SEQ ID NO:1 and a heavy chain having the sequence of SEQ ID NO:2 at a concentration of about 170 mg/mL to about 180 mg/mL; histidine at a concentration of about 30 mM; sorbitol at a concentration of about 250 mM; polysorbate 20 at a concentration of about 0.01%; and a pH of about 6.

In one embodiment, the composition includes antibody at a concentration of about 180 mg/mL.

In one aspect, the invention features an aqueous pharmaceutical composition comprising an anti-VLA-1 antibody comprising a light chain having the sequence of SEQ ID NO:1 and a heavy chain having the sequence of SEQ ID NO:2; histidine at a concentration of about 10 mM to about 50 mM; NaCl at a concentration of about 120 mM to about 180 mM; polysorbate 20 at a concentration of about 0.005% to about 0.05%; and a pH of about 5.5 to about 7.0. In one embodiment, the antibody concentration is at a concentration of ≥100 mg/mL to about 225 mg/mL, for example, about 120 mg/mL to about 210 mg/mL, or about 140 mg/mL to about 200 mg/mL. In another embodiment, the antibody concentration is about 155 mg/mL to about 195 mg/mL, about 160 mg/mL to about 190 mg/mL, or about 170 mg/mL to about 180 mg/mL. In some embodiments, the antibody concentration is about 160 mg/mL, about 165 mg/mL, about 175 mg/mL, about 180 mg/mL or 190 mg/mL.

In one embodiment, the composition includes histidine at a concentration of about 20 mM to about 40 mM, such as at a concentration of about 30 mM. In another embodiment, the composition comprises NaCl at a concentration of about 130 mM to about 170 mM, for example, about 140 mM to about 160 mM, such as about 150 mM. In another embodiment, the composition comprises polysorbate 20 at a concentration of about 0.005% to about 0.05%, such as about 0.01%. In another embodiment, the composition has a pH of about 6.0, and in yet another embodiment, the composition has an osmolality of about 280 mOsm/kg to about 350 mOsm/kg.

In one embodiment, the aqueous pharmaceutical composition includes an anti-VLA-1 antibody comprising a light chain having the sequence of SEQ ID NO:1 and a heavy chain having the sequence of SEQ ID NO:2 at a concentration of about 160 mg/mL to about 200 mg/mL; histidine at a concentration of about 25 mM to about 35 mM histidine; NaCl at a concentration of about 140 mM to about 160 mM; polysorbate 20 at a concentration of about 0.005% to about 0.02%; and a pH of about 6.

In another embodiment, the composition includes an anti-VLA-1 antibody comprising a light chain having the sequence of SEQ ID NO:1 and a heavy chain having the sequence of SEQ ID NO:2 at a concentration of about 170 mg/mL to about 180 mg/mL; histidine at a concentration of about 30 mM; NaCl at a concentration of about 150 mM; polysorbate 20 at about 0.01%; and a pH of about 6.

In one embodiment, the composition includes antibody at a concentration of about 180 mg/mL.

In one aspect, the invention features an aqueous pharmaceutical composition containing an anti-VLA-1 antibody in an amount effective for treatment of inflammatory disease; and means for delivering the effective amount of the antibody in a formulation suitable for subcutaneous delivery.

In one aspect, the invention features a unit dosage form of an aqueous pharmaceutical composition described herein. In one embodiment, the composition includes about 200 mg of anti-VLA-1 antibody. In another embodiment, the composition includes an anti-VLA-1 antibody at about 155 mg to about 165 mg, about 165 mg to about 175 mg, about 175 mg to about 185 mg, about 185 mg to about 195 mg, about 195 mg to about 205 mg, about 205 mg to about 215 mg, or about 215 mg to about 225 mg. In one embodiment, the composition includes anti-VLA-1 antibody at about 160 mg to about 210 mg of antibody, for example, about 180 mg or about 190 mg.

In one embodiment, the aqueous pharmaceutical composition containing an anti-VLA-1 antibody, when administered to a human will deliver about 2.0 mg antibody per kg of body weight to about 4.0 mg antibody per kg of body weight to the human.

In another embodiment, the aqueous pharmaceutical composition has a volume of about 0.25 mL to about 1.5 mL, such as about 0.5 mL, about 0.75 mL, or about 1.0 mL. In one embodiment, a unit dose delivers an anti-VLA-1 antibody at about 80 mg to about 315 mg, such as about 100 mg, about 160 mg, about 180 mg, about 190 mg, about 210 mg, about 250 mg, or about 300 mg.

In another aspect, the invention features a unit dose of an aqueous formulation of anti-VLA-1 antibody, where administration of the unit dose will deliver an anti-VLA-1 antibody at about 0.03 mg per kg body weight to about 10 mg per kg body weight, about 0.03 mg per kg body weight to about 6 mg per kg body weight, about 0.1 mg per kg body weight to about 6 mg per kg body weight, about 0.3 mg per kg body weight about 6 mg per kg body weight, about 0.3 mg per kg body weight to about 3 mg per kg body weight, about 1 mg per kg body weight about 3 mg per kg body weight, about 2.0 mg per kg body weight to about 4.0 mg per kg body weight. For example, administration of the unit dose to a human will deliver about 2.1 mg/kg, about 2.2 mg/kg, about 2.3 mg/kg, about 2.5 mg/kg, about 2.8 mg/kg, about 3.0 mg/kg, about 3.1 mg/kg, about 3.2 mg/kg, about 3.3 mg/kg, about 3.4 mg/kg, or about 3.6 mg/kg.

In one aspect, the invention features a plurality of unit dosage forms of an aqueous pharmaceutical composition described herein. In one embodiment, the plurality is two.

In one embodiment, the plurality of unit dosage forms, when taken together, comprise at least about 160 mg anti-VLA-1 antibody, at least about 170 mg anti-VLA-1 antibody, at least about 180 mg anti-VLA-1 antibody, at least about 190 mg anti-VLA-1 antibody, at least about 200 mg anti-VLA-1 antibody, at least about 300 mg anti-VLA-1 antibody, at least about 400 mg anti-VLA-1 antibody, at least about 500 mg anti-VLA-1 antibody, at least about 600 mg anti-VLA-1 antibody, at least about 700 mg anti-VLA-1 antibody, at least about 800 mg anti-VLA-1 antibody, at least about 900 mg anti-VLA-1 antibody, at least about 1000 mg anti-VLA-1 antibody. In another embodiment, the plurality of unit dosage forms, when taken together, comprise about 155 mg anti-VLA-1 antibody to about 165 mg anti-VLA-1 antibody, about 165 mg anti-VLA-1 antibody to about 175 mg anti-VLA-1 antibody, about 175 mg anti-VLA-1 antibody to about 185 mg anti-VLA-1 antibody, about 185 mg anti-VLA-1 antibody to about 195 mg anti-VLA-1 antibody, about 195 mg anti-VLA-1 antibody to about 205 mg anti-VLA-1 antibody, about 205 mg anti-VLA-1 antibody to about 215 mg anti-VLA-1 antibody, about 215 mg anti-VLA-1 antibody to about 225 mg anti-VLA-1 antibody. In yet another embodiment, the plurality of unit dosage forms, when taken together, include about 160 mg anti-VLA-1 antibody to about 210 mg anti-VLA-1 antibody, for example, about 180 mg anti-VLA-1 antibody, or about 190 mg anti-VLA-1 antibody.

In one embodiment, the plurality of unit dosage forms, when taken together, when administered to a human, will deliver about 0.03 mg anti-VLA-1 antibody per kg of body weight to about 10.0 mg anti-VLA-1 antibody per kg body weight.

In one embodiment, each of the plurality of unit dosage forms has a volume of about 0.25 mL to about 3 mL, for example, about 1 mL, about 1.5 mL, about 2 mL, or about 2.5 mL.

In one embodiment, each dosage form can contain an equal amount of antibody.

In one aspect, the invention features a kit comprising a unit dosage form as described herein.

In one aspect, the invention features a container, having disposed therein, an aqueous pharmaceutical composition described herein. In one embodiment, the container has disposed therein, a unit dosage formulation as described herein.

In one embodiment, the container is a delivery device, such as a syringe. In another embodiment, the container is suitable for subcutaneous administration.

In one aspect, the invention features a method of administering an aqueous pharmaceutical composition described herein by activating a delivery device, and then administering the anti-VLA-1 antibody disposed in the delivery device to the patient.

In one embodiment, activating the device comprises one of more of removing the device from a packaging, removing a cover from the needle or orifice of the device, or shaking the device. In another embodiment, activating the device further includes inspecting the device for the presence of precipitate, colored material, or turbidity, or opalescence.

In one embodiment, the patient, for example, a patient who has an inflammatory disorder, performs one or both steps of administering the composition.

In one embodiment the patient has arthritis, such as rheumatoid arthritis; inflammatory bowel disease; lupus; transplant rejection; or psoriasis.

The invention features methods that optimize provision of a liquid formulation of an anti-VLA-1 antibody, such as SAN-300, to a patient.

In one embodiment, the method allows for a gradual increase in the concentration of the antibody provided. This allows ramp-up of antibody concentration and can allow monitoring of the patient for tolerance, reactions and the like as the concentration is increased. For example, the method can start by providing SAN-300 to the patient at one or more initial or relatively low concentrations followed by providing SAN-300 to the patient at a final, higher concentration. Exemplary formulations for the initial concentration will typically have an antibody concentration of less than about 80%, less than about 70%, less than about 50%, less than about 30%, less than about 20% or less than about 10% of the final higher concentration. Typical initial concentrations can be, for example, about 20 mg/mL, about 30 mg/mL, or about 40 mg/mL. Typical final concentrations will be, for example, about 150 mg/mL to about 225 mg/mL, for example, about 160 mg/mL, about 170 mg/mL, about 175 mg/mL, about 180 mg/mL, about 190 mg/mL, or about 200 mg/mL. In some embodiments, the patient will receive one, or a plurality of administrations at one or a plurality of initial concentrations. For example, in one embodiment, the patient will receive increasing concentrations over a number of administrations. In some embodiments, the patient will receive 2, 3, 4, 5, 6, 7, or 8 administrations at one or more initial concentrations prior to reaching the final concentration. For example, the patient will receive one or more administrations at a first initial concentration, and one or more administrations at a second higher concentration. In some embodiments, the patient is assessed after one or more administrations for symptoms, including adverse symptoms. In some embodiments, the patient is administered a formulation having an increased concentration of SAN-300 only after determining that the patient does not have an unacceptable adverse reaction to the previous administration.

In one embodiment, the anti-VLA-1 antibody composition is provided prepackaged in a container, which can be, for example, a delivery device, such as a syringe.

In another aspect, the invention features a method of instructing a patient in need of an anti-VLA-1 antibody therapy how to administer a formulation described herein. The method includes (i) providing the patient with at least one unit dose of a formulation of an anti-VLA-1 antibody described herein; and (ii) instructing the patient to self-administer the at least one unit dose subcutaneously. Another method included in the invention is a method of treatment that includes (i) providing the patient with at least two unit doses of a formulation of anti-VLA-1 antibody; and (ii) instructing the patient to self-administer the unit doses subcutaneously, for example, subcutaneously, one dose at a time.

In one embodiment, the patient has an inflammatory, immune, or autoimmune disorder, such as an arthritic disorder, such as rheumatoid arthritis, juvenile arthritis, psoriatic arthritis, or ankylosing spondylitis; tissue or organ graft rejection or graft-versus-host disease; acute CNS injury, such as stroke or spinal cord injury; chronic renal disease; allergy, such as allergic asthma; type 1 diabetes; an inflammatory bowel disorder, such as Crohn's disease or ulcerative colitis; myasthenia gravis; fibromyalgia; an inflammatory/immune skin disorder, such as psoriasis, vitiligo, dermatitis, or lichen planus; systemic lupus erythematosus; Sjogren's Syndrome; a hematological cancer, such as multiple myeloma, leukemia, or lymphoma; a solid cancer, such as a sarcoma or carcinoma, such as of the lung, breast, prostate, or brain; or a fibrotic disorder, such as pulmonary fibrosis, myelofibrosis, liver cirrhosis, mesangial proliferative glomerulonephritis, crescentic glomerulonephritis, diabetic nephropathy, or renal interstitial fibrosis.

In another aspect, the invention features a method of treating a patient by administering to the patient a composition containing an anti-VLA-1 antibody in a formulation for subcutaneous administration, for example, a composition as described herein. In one embodiment, the patient has an inflammatory disorder, such as arthritis, for example, rheumatoid arthritis (RA); an inflammatory bowel disease; lupus; transplant rejection; psoriasis; fibrosis; or Crohn's disease. In another embodiment, the composition is administered as a regimen. In another embodiment, the method further includes selecting a patient suitable for treatment with the composition. A patient suitable for treatment, for example, has demonstrated a sign or symptom indicative of disease onset, such as a sign or symptom indicative of RA. In yet another embodiment, the method further includes administering to the patient a second therapeutic agent, such as an anti-inflammatory, an antihistamine, an analgesic or a corticosteroid.

In one embodiment, the patient has rheumatoid arthritis, and is selected on the basis that the patient has demonstrated an inadequate response to a prior alternate treatment for rheumatoid arthritis. A "prior alternate treatment" refers to any treatment other than a treatment comprising an anti-VLA-1 antibody as described herein. The prior alternate treatment for rheumatoid arthritis can be, for example, a DMARD (Disease Modifying Antirheumatic Drug) or a TNF-α (Tumor Necrosis Factor-α) inhibitor. The DMARD can be, for example, methotrexate, leflunomide, sulfasalazine, or hydroxychloroquine. In one embodiment, the TNF-α inhibitor is an antibody, such as infliximab, adalimumab, certolizumab pegol, or golimumab; or a fusion protein, such as etanercept. In another embodiment, the first therapeutic agent is an inhibitor of VLA-2, such as an anti-VLA-2 antibody, for example GBR 500.

In one embodiment, the method of treating a patient further comprises administering to the patient a second therapeutic agent, such as a corticosteroid, an anti-inflammatory, an antihistamine or an analgesic, such as acetaminophen.

In another embodiment, the second therapeutic agent is a B cell-depleting agent, such as an anti-CD20 antibody, for example rituximab (Rituxan, Genentech, Inc., South San Francisco, Calif.; and IDEC Pharmaceutical, San Diego, Calif.). In yet another embodiment, the second therapeutic agent is an inhibitor of a Janus kinase (JAK) family member or a Spleen tyrosine kinase (SYK) family member. JAK family members include JAK1, JAK2, JAK3 and TYK2, and SYK family members include SYK and ZAP-70. In one embodiment, the second therapeutic agent is an inhibitor of JAK3, such as the small molecule inhibitor CP-690,550 (tofacitinib). In another embodiment, the second therapeutic agent is a SYK inhibitor, such as the small molecule inhibitor R406, or its prodrug R788.

In one embodiment, the patient has an inflammatory bowel disease (IBD), and is selected on the basis that the patient has demonstrated an inadequate response to a prior alternate treatment for IBD. The prior alternate treatment for IBD can be, for example, an inhibitor of an integrin, such as MAdCAM-1 (Mucosal Vascular Addressin Cell Adhesion Molecule-1, α4β7 integrin). The MAdCAM-1 inhibitor can be an anti-MAdCAM-1 antibody, such as vedolizumab (MLN0002, Millennium Pharmaceuticals, Cambridge, Mass.).

In another embodiment, a subject is treated with one or more therapeutic agents prior to receiving an anti-VLA-1 antibody therapy, such as an infusion of an anti-VLA-1 therapy, such as to prevent or ameliorate adverse reactions to the anti-VLA-1 administration, for example, to prevent or ameliorate adverse events associated with infusion of an anti-VLA-1 antibody. For example, in one embodiment, pre-treatment includes administration of one or more of an analgesic, such as acetaminophen, an antihistamine, or a corticosteroid, such as methylprednisolone.

In one embodiment, the pretreatment is administered 15 minutes to one hour or more, for example, 15 minutes, 30 minutes, 45 minutes, or one hour or more, prior to administration of the anti-VLA-1 antibody, such as prior to infusion of the anti-VLA-1 antibody.

In one embodiment, a subject, such as an RA patient, is administered one or both of acetaminophen and an antihistamine prior to administration of an anti-VLA-1 antibody, such as prior to infusion with an anti-VLA-1 antibody. In one embodiment, an RA patient is administered a corticosteroid (also called a glucocorticoid), such as methylprednisolone, prior to treatment with an anti-VLA-1 antibody.

In one embodiment, the pretreatment is administered at a dose of from about 50 mg per 75 kg human to about 150 mg per 75 kg human. For example, the pretreatment, such as methylprenisolone administration, is delivered at a dose or from about 50 mg per 75 kg human, about 75 mg per 75 kg human, about 100 mg per 75 kg human, about 125 mg per 75 kg human, or about 150 mg per 75 kg human.

In another embodiment, the pretreatment is administered 15 minutes to one hour or more, for example, 15 minutes, 30 minutes, 45 minutes, or one hour or more prior to administration of the anti-VLA-1 antibody, such as prior to infusion of the anti-VLA-1 antibody.

The pretreatment can be administered, for example, by intravenous delivery, such as by infusion.

In another aspect, the invention features a method of evaluating a patient by determining if the patient meets a preselected criterion, and if the patient meets the preselected criterion approving, providing, prescribing, or administering an anti-VLA-1 antibody formulation described herein to the patient. In one embodiment, the preselected criterion is the failure of the patient to adequately respond to a prior alternate therapeutic treatment or regimen, such as for treatment of RA. In another embodiment, the criterion is as described in co-owned application Ser. No. 61/498,263, filed Jun. 17, 2011, which is hereby incorporated by reference in its entirety.

In another aspect, the invention features a method of instructing a recipient on the administration of a formulation of SAN-300. The method includes instructing the recipient, such as an end user, that the drug should be administered to a patient subcutaneously. In some embodiments, the end user is a patient, physician, retail or wholesale pharmacy, distributor, or pharmacy department at a hospital, nursing home clinic or HMO (Health Maintenance Organization).

In one aspect, the invention features a method of making an aqueous composition comprising about ≥100 mg/mL to about 225 mg/mL of an anti-VLA-1 antibody, for example, an aqueous composition described herein, by combining antibody, buffer, excipient, and a surfactant in proportion to obtain an aqueous composition comprising ≥100 mg/mL to about 225 mg/mL of the anti-VLA-1 antibody.

As used herein the term "excipient" is a pharmacologically inactive substance used as a carrier for the active ingredients of a medication.

In one embodiment, the buffer is histidine, and in another embodiment, the buffer is acetate. In another embodiment, the excipient is sorbitol, and in another embodiment, the excipient is sodium chloride. In yet another embodiment, the surfactant is polysorbate 80, and in another embodiment the surfactant is polysorbate 20. In one embodiment the surfactant is polysorbate 80, and in another embodiment the surfactant is polysorbate 20.

In another embodiment, the anti-VLA-1 antibody comprises a light chain having the sequence of SEQ ID NO:1 and a heavy chain having the sequence of SEQ ID NO:2.

In another aspect, a method of distributing a composition described herein is provided. The composition contains a formulation of SAN-300 and is suitable for subcutaneous administration. The method includes providing a recipient, such as an end user, with a package containing sufficient unit dosages of the drug to treat a patient for at least 6 months, at least 12 months, at least 24 months, or at least 36 months. In some embodiments, the end user is a patient, a physician, a retail or wholesale pharmacy, a distributor, a pharmacy department at a hospital, a nursing home clinic or an HMO.

In another aspect, the invention features a method of evaluating the quality of a package or lot of packages of a composition described herein containing an anti-VLA-1 antibody. The method includes, for example, evaluating whether the package has expired. The expiration date is at least 6 months, at least 12 months, at least 18 months, at least 24 months, at least 36 months, or at least 48 months, for example, greater than 24 months or greater than 36 months, from a preselected event, such as manufacturing, assaying, or packaging. In some embodiments, a decision or step is taken as a result of the analysis. For example, the antibody in the package is used or discarded, classified, selected, released or withheld, shipped, moved to a new location, released into commerce, sold, or offered for sale, withdrawn from commerce or no longer offered for sale, depending on whether the product has expired.

In another aspect, the invention features a package containing at least 2 unit doses of an aqueous composition containing an anti-VLA-1 antibody. In one embodiment, all of the unit doses contain the same amount of antibody, and in other embodiments, there are unit dosages of two or more strengths, or two or more different formulations. For example, different formulations can have different strengths or release properties. In one embodiment, at least one dosage contains anti-VLA-1 antibody at about 80 mg to about 315 mg, for example, about 100 mg, about 160 mg, about 180 mg, about 190 mg, about 210 mg, about 250 mg, about 300 mg, about 325 mg, about 350 mg, about 360 mg, about 400 mg, about 450 mg, or about 500 mg.

In another aspect, the invention includes a method of instructing a recipient on the administration of an aqueous formulation containing anti-VLA-1 antibody. The method includes instructing the recipient (for example, an end user, patient, physician, retail or wholesale pharmacy, distributor, or pharmacy department at a hospital, nursing home clinic or HMO) that the antibody should be administered to a patient prior to the expiration date. The expiration date is at least 6 months, at least 12 months, at least 18 months, at least 24 months, at least 36 months, or at least 48 months, for example, greater than 18 months, greater than 24 months or greater than 36 months, from a preselected event, such as a manufacturing, assaying, or packaging event. In one embodiment, the recipient also receives a supply of the antibody, such as a supply of unit dosages of the antibody.

In another aspect, the invention features the use of a method or system for distributing a formulation described herein, monitoring or tracking the provision of a formulation described herein to a pharmacy, infusion center, or patient, monitoring one or more patients, selecting patients, or compiling or reporting data on the use of a formulation described herein.

In another aspect, the invention features a method of analyzing a product or a process, such as a manufacturing process. The method includes providing an aqueous formulation of an anti-VLA-1 antibody composition, for example, one made by a process described herein, and providing an evaluation of the formulation by assessing a solution parameter, such as color (for example, colorless to slightly yellow, or colorless to yellow), clarity (for example, clear to slightly opalescent or clear to opalescent), or viscosity (for example, about 5 cP to about 30 cP (for example, about 10 cP or about 20 cP) when measured at ambient temperature, such as at about 20° C. to about 30° C., for example, about 25° C.). The evaluation can include an assessment of one or more solution parameters. Optionally, a determination of whether the solution parameter meets a preselected criteria is determined, for example, whether the preselected criteria is present, or is present in a preselected range, is determined, thereby analyzing the process.

In one embodiment, the invention includes a measure of the stability of the anti-VLA-1 antibody formulation. Stability of the antibody formulation can be measured, for example, by aggregate formation, which is assayed, for example, by size exclusion high pressure liquid chromatography (HPLC), by color, clarity, or viscosity as described herein. A formulation can be determined to be stable, and therefore acceptable for further processing or distribution, if the change in an assay parameter is less than about 10%, less than about 5%, less than about 3%, less than about 2%, less than about 1%, less than about 0.5%, less than about 0.05%, or less than about 0.005% or less, over a pre-set period of time, and optionally at a given temperature. In one embodiment, a liquid anti-VLA-1 antibody formulation is stable for 1 day, 2 days, 3 days, 4 days, or 5 days or more at room temperature, such as at about 18° C., about 19° C., about 20° C., about 21° C., about 22° C., about 23° C., about 24° C., or about 25° C.

In one embodiment, the method further includes comparing the value determined with a reference value, to thereby analyze the manufacturing process.

In one embodiment, the method further includes maintaining the manufacturing process based, at least in part, upon the analysis. In one embodiment, the method further includes altering the manufacturing process based upon the analysis.

In another embodiment the method includes evaluating a process, such as a manufacturing process, of an aqueous formulation of an anti-VLA-1 antibody made by a selected process, that includes making a determination about the process based upon a method or analysis described herein. In one embodiment, the method further includes maintaining or altering the manufacturing process based, at least in part, upon the method or analysis. Thus, in another embodiment the party making the evaluation does not practice the method or analysis described herein but merely relies on results which are obtained by a method or analysis described herein.

In another embodiment the method includes comparing two or more preparations in a method of monitoring or controlling batch-to-batch variation or to compare a preparation to a reference standard.

In yet another embodiment, the method can further include making a decision, such as a decision to classify, select, accept or discard, release or withhold, process into a drug product, ship, move to a different location, formulate, label, package, release into commerce, sell or offer for sale the preparation, based, at least in part, upon the determination.

In another aspect, the invention features a method of storing, distributing, or using an anti-VLA-1 antibody formulation, such as a SAN-300 formulation, described herein. The method includes:

storing the formulation at a suitable temperature, such as at 2° C. to 8° C.;

providing the formulation to a recipient, for example, an end-user, such as for example, a patient or healthcare provider;

instructing the recipient to store the formulation at a suitable temperature, such as at 2° C. to 8° C.; and after receipt by the recipient, storing the formulation for up to 24 months, 36 months, or 48 months at the suitable temperature, such as at 2° to 8° C.

In another aspect, the invention features a method of complying with a regulatory requirement, such as a post approval requirement of a regulatory agency, such as the FDA. The method includes providing an evaluation of an antibody formulation for a solution parameter, such as color (for example, colorless to slightly yellow, or colorless to yellow), clarity (for example, clear to slightly opalescent or clear to opalescent), or viscosity (for example, about 5 cP to about 30 cP when measured at ambient temperature, such as at 20° C. to 30° C.). The post approval requirement can include a measure of one more of the above parameters. The method also includes, optionally, determining whether the observed solution parameter meets a preselected criteria or if the parameter is in a preselected range; optionally, memorializing the value or result of the analysis, or communicating with the agency, such as by transmitting the value or result to the regulatory agency.

In another aspect, the invention features a method of making a batch of an aqueous formulation of anti-VLA-1 antibody having a preselected property, for example, meeting a release specification, label requirement, or compendial requirement, for example, a property described herein. The method includes providing a test antibody preparation; analyzing the test antibody preparation according to a method described herein; determining if the test antibody preparation satisfies a preselected criteria, such as by having a preselected relationship with a reference value, such as one or more reference values disclosed herein, and selecting the test antibody preparation to make a batch of product.

In another aspect, the invention features multiple batches of an aqueous formulation of anti-VLA-1 antibody, wherein one or more solution parameters (for example, a value or solution parameter determined by a method described herein), for each batch varies less than a preselected range from a pre-selected desired reference value or criteria, for example, a range or criteria described herein. In some embodiments, one or more parameters for one or more batches of an antibody formulation, is determined and a batch or batches selected as a result of the determination. Some embodiments include comparing the results of the determination to a preselected value or criteria, such as a reference standard. Other embodiments include adjusting the dose of the batch to be administered, such as based on the result of the determination of the value or parameter.

In another aspect, the invention features a method of one or more of: providing a report to a report-receiving entity, evaluating a sample of an aqueous formulation of anti-VLA-1 antibody for compliance with a reference standard, such as an FDA requirement, seeking indication from another party that a preparation of the anti-VLA-1 antibody meets some predefined requirement, or submitting information about a preparation of an anti-VLA-1 antibody to another party. Exemplary receiving entities or other parties include a government, such as the U.S. federal government, of a government agency, such as the FDA. The method includes one or more (or all) of the following steps for making and/or testing an aqueous formulation of anti-VLA-1 antibody in a first country, such as the US; sending at least an aliquot of the sample outside the first country, for example, sending it outside the United States, to a second country; preparing, or receiving, a report which includes data about the structure of the preparation of the anti-VLA-1 antibody, for example, data related to a structure and/or chain described herein, such as data generated by one or more of the methods described herein; and providing said report to a report recipient entity.

In one embodiment, the report-receiving entity can determine if a predetermined requirement or reference value is met by the data and, optionally, a response from the report-receiving entity is received, such as by a manufacturer, distributor or seller of an aqueous formulation of an anti-VLA-1 antibody. In one embodiment, upon receipt of approval from the report recipient entity, the preparation of anti-VLA-1 antibody is selected, packaged, or placed into commerce.

In one aspect, the invention features a method of evaluating the quality of a composition described herein, where the method includes evaluating the composition for a preselected parameter, and determining whether the value meets a preselected criteria. Responsive to the evaluation, the composition can be classified, selected, accepted or discarded, released or withheld, processed into a drug product, shipped, moved to a different location, formulated, labeled, packaged, released into commerce, or sold or offered for sale. In another embodiment, the composition evaluated is provided as a unit dosage form.

In one embodiment, the preselected parameter is selected from aggregation, stability, color, clarity, viscosity, or plunger force.

In one embodiment, the method includes providing a comparison of the value determined for a parameter with a reference value, or values, to thereby evaluate the sample. The comparison can include, for example, determining if the test value has a preselected relationship with the reference value, for example, determining if it meets the reference value. The value need not be a numerical value but can be merely an indication of whether the subject entity is present.

In one embodiment, the method includes determining if a test value is equal to or greater than a reference value, if it is less than or equal to a reference value, or if it falls within a range (either inclusive or exclusive of one or both endpoints).

In some embodiments, the test value, or an indication of whether the preselected relationship is met, can be memorialized, such as in a computer readable record.

In some embodiments, a decision or step is taken, for example, the sample is classified, selected, accepted or discarded, released or withheld, processed into a drug product, shipped, moved to a different location, formulated, labeled, packaged, released into commerce, or sold or offered for sale, depending on whether the preselected relationship is met. For example, based on the result of the determination, or upon comparison to a reference standard, the batch from which the sample is taken can be processed, such as just described.

In one aspect, the invention features a method of evaluating an aqueous formulation of anti-VLA-1 antibody. The method includes receiving data with regard to the presence or level of anti-VLA-1 antibody; providing a record which includes said data and optionally includes an identifier for a batch of anti-VLA-1 antibody; submitting said record to a decision-maker, for example, a government agency, such as the FDA; optionally, receiving a communication from the decision maker; optionally, deciding whether to release or market the batch of anti-VLA-1 antibody based on the communication from the decision maker. In one embodiment, the method further includes releasing the sample.

Exemplary formulations include the following:

1. SAN-300 at a concentration of ≥100 mg/mL to about 210 mg/mL, or about 180 mg/mL to about 200 mg/mL, for example, about 180 mg/mL;

histidine buffer at a concentration of about 1 mM to about 100 mM, about 5 mM to about 50 mM, or about 5 mM to about 40 mM, for example, about 30 mM;

sorbitol at a concentration of about 50 mM to about 300 mM, about 100 mM to about 290 mM, or about 200 mM to about 280 mM, for example, about 250 mM;

polysorbate 20 at a concentration of about 0.001% to about 0.1%, about 0.005% to about 0.08%, or about 0.008% to about 0.04%, for example, about 0.01%, and pH of about 6.0;

2. SAN-300 at a concentration of ≥100 mg/mL to about 210 mg/mL or about 180 mg/mL to about 200 mg/mL, for example, about 190 mg/mL;

acetate buffer at a concentration of about 1 mM to about 100 mM, about 5 mM to about 50 mM, or about 5 mM to about 40 mM, for example, about 30 mM;

sorbitol at a concentration of about 50 mM to about 300 mM, about 100 mM to about 280 mM, or about 200 mM to about 250 mM, for example, about 220 mM or about 250 mM;

polysorbate 80 at a concentration of about 0.001% to about 0.1%, about 0.005% to about 0.08%, or about 0.008% to about 0.04%, for example, about 0.01%, and
pH of about 5.5;
3. about 180 mg/mL SAN-300;
histidine buffer at a concentration of about 1 mM to about 100 mM, about 5 mM to about 50 mM, or about 5 mM to about 40 mM, for example, about 30 mM;
250 mM sorbitol;
0.01% polysorbate 20, and
pH 6.0;
4. 190 mg/mL SAN-300;
acetate buffer at 1 mM to 100 mM, 5 mM to 50 mM, or 5 mM to 40 mM, for example, 30 mM;
about 220 mM sorbitol;
about 0.01% polysorbate 80, and
pH 5.5;
5. about 180 mg/mL SAN-300;
about 30 mM histidine buffer;
sorbitol at a concentration of about 50 mM to about 300 mM, about 100 mM to about 290 mM, or about 200 mM to about 280 mM, for example, about 250 mM;
about 0.01% polysorbate 20; and
pH 6.0;
6. about 190 mg/mL SAN-300;
about 30 mM acetate buffer;
sorbitol at a concentration of about 50 mM to about 300 mM, about 100 mM to about 280 mM, or about 200 mM to about 250 mM, for example, about 220 mM;
about 0.01% polysorbate 80; and
pH 5.5;
7. about 180 mg/mL SAN-300;
about 30 mM histidine buffer;
about 250 mM sorbitol;
polysorbate 20 at a concentration of about 0.001% to about 0.1%, about 0.005% to about 0.08%, or about 0.008% to about 0.04%, for example, about 0.01%, and
pH 6.0;
8. about 190 mg/mL SAN-300;
about 30 mM acetate buffer;
about 220 mM sorbitol;
polysorbate 80 at about 0.001% to about 0.1%, about 0.005% to about 0.08%, or about 0.008% to about 0.04%, for example, about 0.01%, and
pH 5.5;
9. SAN-300 at a concentration of about 160 mg/mL to about 210 mg/mL, or about 180 mg/mL to about 200 mg/mL, for example, about 180 mg/mL;
about 30 mM histidine buffer;
about 250 mM sorbitol;
about 0.01% polysorbate 20;
pH 6.0;
10. SAN-300 at a concentration of about 160 mg/mL to about 210 mg/mL or about 180 mg/mL to about 200 mg/mL, for example, about 190 mg/mL;
about 30 mM acetate buffer;
about 220 mM sorbitol;
about 0.01% polysorbate 80; and
pH 5.5;
11. about 180 mg/mL SAN-300;
about 30 mM histidine buffer;
about 250 mM sorbitol;
about 0.01% polysorbate 20; and
pH 6.0;
12. about 190 mg/mL SAN-300;
about 30 mM acetate buffer;
about 220 mM sorbitol;
about 0.01% polysorbate 80 and
pH 5.5.
13. SAN-300 at a concentration of ≥100 mg/mL to about 210 mg/mL, or about 180 mg/mL to about 200 mg/mL, for example, about 180 mg/mL;
histidine buffer at about 1 mM to about 100 mM, about 5 mM to about 50 mM, or about 5 mM to about 40 mM, for example, about 30 mM;
NaCl at a concentration of about 50 mM to about 300 mM, about 100 mM to about 200 mM, or about 140 mM to about 160 mM, for example, about 150 mM;
polysorbate 20 at a concentration of about 0.001% to about 0.1%, about 0.005% to about 0.08%, or about 0.008% to about 0.04%, for example, about 0.01%, and
pH 6.0;
14. SAN-300 at a concentration of ≥100 mg/mL to about 210 mg/mL or about 180 mg/mL to about 200 mg/mL, for example, about 190 mg/mL;
acetate buffer at a concentration of about 1 mM to about 100 mM, about 5 mM to about 50 mM, or about 5 mM to about 40 mM, for example, about 30 mM;
NaCl at a concentration of about 50 mM to about 300 mM, about 100 mM to about 200 mM, or about 140 mM to about 160 mM, for example, about 150 mM;
polysorbate 80 at a concentration of about 0.001% to about 0.1%, about 0.005% to about 0.08%, or about 0.008% to about 0.04%, for example, about 0.01%, and
pH 5.5;
15. about 180 mg/mL SAN-300;
histidine buffer at a concentration of about 1 mM to about 100 mM, about 5 mM to about 50 mM, or about 5 mM to about 40 mM, for example, about 30 mM;
about 150 mM NaCl;
about 0.01% polysorbate 20, and
pH 6.0;
16. about 190 mg/mL SAN-300;
acetate buffer at a concentration of about 1 mM to about 100 mM, about 5 mM to about 50 mM, or about 5 mM to about 40 mM, for example, about 30 mM;
about 150 mM NaCl;
about 0.01% polysorbate 80, and
pH 5.5;
17. about 180 mg/mL SAN-300;
about 30 mM histidine buffer;
NaCl at a concentration of about 50 mM to about 300 mM, about 100 mM to about 200 mM, or about 140 mM to about 160 mM, for example, about 150 mM;
about 0.01% polysorbate 20; and
pH 6.0;
18. about 190 mg/mL SAN-300;
about 30 mM acetate buffer;
NaCl at a concentration of about 50 mM to about 300 mM, about 100 mM to about 200 mM, or about 140 mM to about 160 mM, for example, about 150 mM;
about 0.01% polysorbate 80; and
pH 5.5;
19. about 180 mg/mL SAN-300;
about 30 mM histidine buffer;
about 150 mM NaCl;
polysorbate 20 at a concentration of about 0.001% to about 0.1%, about 0.005% to about 0.08%, or about 0.008% to about 0.04%, for example, about 0.01%, and
pH 6.0;
20. about 190 mg/mL SAN-300;
about 30 mM acetate buffer;
about 150 mM NaCl;

polysorbate 80 at a concentration of about 0.001% to about 0.1%, about 0.005% to about 0.08%, or about 0.008% to about 0.04%, for example, about 0.01%, and pH 5.5;

21. SAN-300 at a concentration of about 160 mg/mL to about 210 mg/mL, or about 180 mg/mL to about 200 mg/mL, for example, about 180 mg/mL;

about 30 mM histidine buffer;
about 150 mM NaCl;
about 0.01% polysorbate 20;
pH 6.0;

22. SAN-300 at a concentration about 160 mg/mL to about 210 mg/mL or about 180 mg/mL to about 200 mg/mL, for example, about 190 mg/mL;

about 30 mM acetate buffer;
about 150 mM NaCl;
about 0.01% polysorbate 80; and
pH 5.5;

23. about 180 mg/mL SAN-300;
about 30 mM histidine buffer;
about 150 mM NaCl;
about 0.01% polysorbate 20; and
pH 6.0;

24. about 190 mg/mL SAN-300;
about 30 mM acetate buffer;
about 150 mM NaCl;
about 0.01% polysorbate 80 and
pH 5.5.

In some embodiments, any of the above formulations 1 to 24 can be essentially free of an amino acid, such as arginine.

Methods and compositions disclosed herein can be used where the presence, distribution, or amount, of one or more structures in the mixture may possess or impinge on the biological activity. The methods are also useful from a structure-activity prospective, to evaluate or ensure biological equivalence.

An "anti-VLA-1 antibody formulation" as used herein, refers to an aqueous formulation containing an anti-VLA-1 antibody, such as SAN-300, at a concentration of ≥100 mg/mL to about 225 mg/mL, for example, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 205 mg/mL, about 210 mg/mL, about 215 mg/mL, about 220 mg/mL.

"Suitable for subcutaneous administration" means that a composition, provided, e.g., as unit dosage, provides antibody at a concentration sufficient to allow a therapeutic effect from an amount, typically from about 0.5 mL to about 3 mL, that can be delivered by subcutaneous injection. It may be free of components, such as citrate, that cause unwanted injection site symptoms, such as burning or stinging.

The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject.

A "stable" formulation of anti-VLA-1 antibody exhibits little or no signs of any one or more of aggregation, precipitation, fragmentation, deamidation, oxidation, denaturation, size modification, chemical alteration, or change in biological activity, such as the ability to bind VLA-1, over a predetermined period of time. The predetermined period of time can be, for example, equal to or more than 4 days, 10 days, 14 days, 21 days, 30 days or longer, such as for 6 months, 12 months, 24 months, 36 months, 1 year, 2 years, 3 years, for example, when stored under suitable conditions. Exemplary suitable conditions include, for example, a temperature of about 2° C. to about 8° C., for example, at about 4° C., in darkness, in a closed container. In one embodiment, the container is the same type that the composition will be provided to the end user. In another embodiment, a stable formulation will meet manufacturer or regulatory (such as Food and Drug Administration (FDA), or a foreign counterpart to the FDA) release or package label or insert requirements, such as for the times and conditions mentioned above. For example, in one embodiment, less than about 1%, less than about 2%, less than about 5%, less than about 10%, or less than about 15% of the composition is aggregated, fragmented, or oxidized at the end of the predetermined period or otherwise at the time of evaluation for stability. Aggregation, precipitation, and/or denaturation can be assessed by known methods, such as visual examination of color and/or clarity, or by UV light scattering, size exclusion chromatography, dynamic light scattering (DLS), or differential scanning calorimetry (DSC). The ability of the protein to retain its biological activity can be assessed by detecting and quantifying chemically altered forms of the antibody. Size modification, such as clipping, can be evaluated using size exclusion chromatography, SDS-PAGE and/or matrix-assisted laser desorption ionization/time-of-flight mass spectrometry (MALDI/TOF MS), or peptide mapping of endoproteinase-treated antibody, for example. Other types of chemical alteration include charge alteration, such as that may occur as a result of deamidation, can be evaluated by ion-exchange chromatography, for example. An antibody "retains its biological activity" in a pharmaceutical formulation, if the biological activity of the antibody at a given time is within about 1%, about 2%, about 5%, about 10%, or about 15% of the biological activity exhibited at the time the pharmaceutical formulation was prepared as determined, for example, in an antigen binding assay.

"Aggregation" as used herein, refers to the formation of insoluble structures from completely or partially unfolded polypeptides, such as anti-VLA-1 antibodies. "Fragmentation" as used herein, refers to partially degraded proteins, such as anti-VLA-1 antibodies. "Deamidation" refers to the removal of an amide group from a polypeptide, such as an anti-VLA-1 antibody. Deamidation typically occurs at glutaminyl or asparaginyl amino acid residues, and can cause structural changes in the protein that affect protein function, such as binding affinity for a VLA-1 ligand.

As used herein, "syringeability" refers to the suitability of a composition for delivery with a syringe. One component of syringeability is the ability of a composition, such as an anti-VLA-1 antibody composition, to be expelled from a syringe, such as by a patient for self-administration, or by a health-care provider. Self-administration by the patient can be, for example, by subcutaneous administration. The pressure, or "plunger force" can be, for example, such that a patient, for example, an elderly or weak patient, can self administer the composition. In embodiments the plunger force is equal to or less than 4 lbs.

In one embodiment, the plunger force will allow delivery of a unit dosage in 10 seconds or less. In another embodiment, about 1 mL of an aqueous pharmaceutical composition, disposed in a syringe having a needle of a preselected gauge, can be expelled at a preselected rate with a plunger force of no more than a preselected amount. In another embodiment, about 2 mL of aqueous pharmaceutical composition, disposed in a syringe having a needle of a preselected gauge, can be expelled at a preselected rate with a plunger force of no more than a preselected amount. For example, about 1 mL aqueous pharmaceutical composition, disposed in a syringe having a 25 gauge needle, a 27 gauge needle, or a 30 gauge needle can be expelled at 10 mL/minute with a plunger force of no more than 4 lbs.

In one embodiment, a suitable plunger force, such as a force equal to or less than 4 lbs, will allow delivery of a unit dosage within a preselected time period, such as in 10 seconds or less.

Syringeability also refers to the ability of the protein to survive passage though a needle without fragmenting by more than about 1%, more than about 2%, more than about 5%, more than about 10% or more than about 15%.

An "anti-VLA-1 antibody" refers to an antibody that binds to a VLA-1 integrin, such as to the α1 subunit of the VLA-1 integrin, and at least partially inhibits an activity of VLA-1, particularly a binding activity of a VLA-1 integrin or a signaling activity, such as the ability to transduce a VLA-1 mediated signal. For example, an anti-VLA-1 antibody may inhibit binding of VLA-1 to a cognate ligand of VLA-1, for example, an extracellular matrix component, such as collagen, for example, collagen I or collagen IV, or laminin. An anti-VLA-1 antibody may bind to either the α1 subunit or the β1 subunit, or to both. In one embodiment, the antibody binds an epitope on the I domain of α1. An anti-VLA-1 antibody may bind to VLA-1 with a $K_d$ of less than about $10^{-6}$, less than about $10^{-7}$, less than about $10^{-8}$, less than about $10^{-9}$, less than about $10^{-10}$, or less than about $10^{-11}$M. VLA-1 is also known as α1/β1 and CD49a/CD29.

As used herein, the term "antibody" refers to a protein that includes at least one immunoglobulin variable region, such as an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (such as single chain antibodies, Fab fragments, F(ab')$_2$ fragments, Fd fragments, Fv fragments, and dAb fragments) as well as complete antibodies, for example, intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody dependent cytotoxicity and/or complement-mediated cytotoxicity, or may be non-functional for one or both of these activities.

An immunoglobulin variable domain sequence is an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), for example, a structure that interacts with VLA-1.

The VH and VL regions can be further subdivided into regions of hypervariability, termed "complementarity determining regions" ("CDR"), interspersed with regions that are more conserved, termed "framework regions" (FR). The extent of the FRs and CDRs has been precisely defined (see, Kabat, E. A., et al. (1991) *Sequences of Proteins of Immunological Interest, Fifth Edition*, U.S. Department of Health and Human Services, NIH Publication No. 91-3242; and Chothia, C. et al. (1987) *J. Mol. Biol.* 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (such as effector cells) and the first component (Clq) of the classical complement system.

One or more regions of an antibody can be human, effectively human, or humanized. For example, one or more of the variable regions can be human or effectively human. For example, one or more of the CDRs, such as HC CDR1, HC CDR2, HC CDR3, LC CDR1, LC CDR2, and LC CDR3, can be human (HC, heavy chain; LC, light chain). In one embodiment, each of the light chain CDRs can be human. In one embodiment, HC CDR3 is human. One or more of the framework regions can be human, such as FR1, FR2, FR3, and/or FR4 of the HC or LC. In one embodiment, all the framework regions are human, for example, derived from a human somatic cell, such as a hematopoietic cell that produces immunoglobulins or a non-hematopoietic cell. In one embodiment, the human sequences are germline sequences, for example, encoded by a germline nucleic acid. One or more of the constant regions can be human, effectively human, or humanized. In another embodiment, at least about 70%, at least about 75%, at least about 80%, at least about 85%, at least about 90%, at least about 92%, at least about 95%, or at least about 98% of the framework regions, such as FR1, FR2, and FR3, collectively, or FR1, FR2, FR3, and FR4, collectively, or the entire antibody can be human, effectively human, or humanized. For example, FR1, FR2, and FR3 collectively can be at least about 70%, at least about 75%, at least about 80%, at least about 85%, at least about 90%, at least about 92%, at least about 95%, at least about 98%, or at least about 99% identical to a human sequence encoded by a human germline segment.

An effectively human immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A humanized immunoglobulin variable region is an immunoglobulin variable region that is modified such that the modified form elicits less of an immune response in a human than does the non-modified form. For example, a humanized immunoglobulin variable region can be modified to include a sufficient number of human framework amino acid positions such that the immunoglobulin variable region does not elicit an immunogenic response in a normal human. Descriptions of humanized immunoglobulins include, for example, U.S. Pat. No. 6,407,213 and U.S. Pat. No. 5,693,762. In some embodiments, a humanized immunoglobulin includes a non-human amino acid at one or more framework amino acid positions.

All or part of an antibody can be encoded by an immunoglobulin gene or a segment thereof. Exemplary human immunoglobulin genes include the kappa, lambda, a (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids) are similarly encoded by a variable region gene (about 116 amino acids) and one of the other aforementioned constant region genes, such as gamma (encoding about 330 amino acids).

The term "antigen-binding fragment" of a full length antibody refers to one or more fragments of a full-length antibody that retain the ability to specifically bind to a target of interest, such as VLA-1. Examples of binding fragments encompassed within the term antigen-binding fragment of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See for example, Bird et al. (1988) *Science* 242:423-426; and Huston et al. (1988) *Proc. Natl. Acad. Sci. USA* 85:5879-5883.

Calculations of homology or sequence identity between two sequences (the terms are used interchangeably herein) are performed as follows. The sequences are aligned for optimal comparison purposes (for example, gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Certain advantages are provided by embodiments of the invention. In some cases, it is difficult to make high concentration formulations of proteins, such as antibodies, for use in pharmaceutical compositions. Methods of preparing such formulations are presented herein. Pharmaceutical compositions containing high concentrations of protein, such as anti-VLA-1 antibody, can be useful for administration over a shorter time frame. A formulation of, for example, anti-VLA-1 antibody, can also be administered by simplified methods (for example, subcutaneously).

In one aspect, the disclosure provides an aqueous pharmaceutical composition comprising
(a) 150 to 210 mg/mL, 155 to 205 mg/mL, 160 to 200 mg/mL, or 165 to 190 mg/mL of an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 25 to 35 mM acetate or 25 to 35 mM histidine;
(c) 170 to 288 mM sorbitol; and
(d) 0.008 to 0.012% polysorbate, e.g., polysorbate 20 or polysorbate 80;
wherein the aqueous pharmaceutical composition has a pH of 5 to 7.

In one embodiment, the aqueous pharmaceutical composition comprises
(a) 150 to 210 mg/mL of an anti-VLA-1 antibody having a light chain sequence of SEQ ID NO:1 and a heavy chain sequence of SEQ ID NO:2;
(b) 25 to 35 mM acetate or 25 to 35 mM histidine;
(c) 170 to 288 mM sorbitol; and
(d) 0.008 to 0.012% polysorbate, wherein the polysorbate is polysorbate 20 or polysorbate 80;
wherein the aqueous pharmaceutical composition has a pH of 5 to 7. In embodiments, the composition comprises histidine and the polysorbate is polysorbate 20. In embodiments, the composition comprises acetate and the polysorbate is polysorbate 80.

In some embodiments, the aqueous pharmaceutical composition has an osmolality of 270 mOsm/kg to 380 mOsm/kg.

In embodiments, the aqueous pharmaceutical composition has a viscosity of less than 15 cP or less than 14 cP. In embodiments, the aqueous pharmaceutical composition described herein has a viscosity of 10 to 14 cP, 11 to 14 cP, 13 to 14 cP, or 11 to 12 cP.

In one embodiment, the aqueous pharmaceutical composition comprises
(a) 165 to 190 mg/mL of an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 25 to 35 mM histidine;
(c) 170 to 288 mM sorbitol; and
(d) 0.008 to 0.012% polysorbate, e.g., polysorbate 20;

wherein the aqueous pharmaceutical composition has a pH of 5 to 7.

In a certain embodiment, the aqueous pharmaceutical composition comprises
(a) 180 mg/mL of an anti-VLA-1 antibody having
  a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
  a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 30 mM histidine;
(c) 250 mM sorbitol; and
(d) 0.01% polysorbate, e.g., polysorbate 20;

wherein the aqueous pharmaceutical composition has a pH of 5 to 7.

In embodiments, variability, e.g., a variability of 1 to 5%, 5 to 10%, 10 to 15%, or 15 to 20%, is permitted in the amounts of one or more components of the above embodiment. In some such embodiments, the aqueous pharmaceutical composition comprises
(a) 180 mg/mL±1%, 2%, 3%, 4%, 5%, 6%, 7%, 8%, 9%, 10%, 11%, 12%, 13%, 14%, 15%, 16%, 17%, 18%, 19%, or 20% of the antibody;
(b) 30 mM±1%, 2%, 3%, 4%, 5%, 6%, 7%, 8%, 9%, 10%, 11%, 12%, 13%, 14%, 15%, 16%, 17%, 18%, 19%, or 20% histidine;
(c) 250 mM±1%, 2%, 3%, 4%, 5%, 6%, 7%, 8%, 9%, 10%, 11%, 12%, 13%, 14%, 15%, 16%, 17%, 18%, 19%, or 20% sorbitol; and
(d) 0.01%±1%, 2%, 3%, 4%, 5%, 6%, 7%, 8%, 9%, 10%, 11%, 12%, 13%, 14%, 15%, 16%, 17%, 18%, 19%, or 20% polysorbate, e.g., polysorbate 20;

wherein the aqueous pharmaceutical composition has a pH of 5 to 7. The variability permitted in the individual components is independently selected (e.g., the antibody can be present at a concentration of 180 mg/mL±10%, the histidine at a concentration of 30 mM±5%, the sorbitol at a concentration of 250 mM±7%, and the polysorbate 20 at 0.01%±2%). In some embodiments, the aqueous pharmaceutical composition has a pH of 5.5 to 6.5. In some embodiments, the aqueous pharmaceutical composition has a pH of 5.6 to 6.4, 5.7 to 6.3, 5.8 to 6.2, or 5.9 to 6.1. In some embodiments, the aqueous pharmaceutical composition has a pH of 6.0.

In another embodiment, the aqueous pharmaceutical composition comprises
(a) 165 to 200 mg/mL of an anti-VLA-1 antibody having
  a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
  a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 25 to 35 mM acetate;
(c) 170 to 253 mM sorbitol; and
(d) 0.008 to 0.012% polysorbate, e.g., polysorbate 80;

wherein the aqueous pharmaceutical composition has a pH of 4.5 to 6.5.

In a certain embodiment, the aqueous pharmaceutical composition comprises
190 mg/mL of an anti-VLA-1 antibody having
  a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
  a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 30 mM acetate;
(c) 220 mM sorbitol; and
(d) 0.01% polysorbate, e.g., polysorbate 80;

wherein the aqueous pharmaceutical composition has a pH of 4.5 to 6.5.

In embodiments, variability, e.g., a variability of 1 to 5%, 5 to 10%, 10 to 15%, or 15 to 20%, is permitted in the amounts of one or more components of the above embodiment. In some such embodiments, the aqueous pharmaceutical composition comprises
(a) 190 mg/mL±1%, 2%, 3%, 4%, 5%, 6%, 7%, 8%, 9%, 10%, 11%, 12%, 13%, 14%, 15%, 16%, 17%, 18%, 19%, or 20% of the antibody;
(b) 30 mM±1%, 2%, 3%, 4%, 5%, 6%, 7%, 8%, 9%, 10%, 11%, 12%, 13%, 14%, 15%, 16%, 17%, 18%, 19%, or 20% acetate;
(c) 220 mM±1%, 2%, 3%, 4%, 5%, 6%, 7%, 8%, 9%, 10%, 11%, 12%, 13%, 14%, 15%, 16%, 17%, 18%, 19%, or 20% sorbitol; and
(d) 0.01%±1%, 2%, 3%, 4%, 5%, 6%, 7%, 8%, 9%, 10%, 11%, 12%, 13%, 14%, 15%, 16%, 17%, 18%, 19%, or 20% polysorbate, e.g., polysorbate 80;

wherein the aqueous pharmaceutical composition has a pH of 4.5 to 6.5. The variability permitted in the individual components is independently selected (e.g., the antibody can be present at a concentration of 180 mg/mL±10%, the acetate at a concentration of 30 mM±5%, the sorbitol at a concentration of 220 mM±7%, and the polysorbate 80 at 0.01%±2%). In some embodiments, the aqueous pharmaceutical composition has a pH of 5.0 to 6.0. In some embodiments, the aqueous pharmaceutical composition has a pH of 5.1 to 5.9, 5.2 to 5.8, 5.3 to 5.7, or 5.4 to 5.6. In some embodiments, the aqueous pharmaceutical composition has a pH of 5.5.

In embodiments, an aqueous pharmaceutical composition described herein has a viscosity of less than 15 cP or less than 14 cP. In embodiments, a aqueous pharmaceutical composition described herein has a viscosity of 10 to 14 cP.

In embodiments, an aqueous pharmaceutical composition described herein (e.g., a aqueous pharmaceutical composition described herein that comprises histidine, sorbitol, and polysorbate, e.g., polysorbate 20) has a viscosity of 13 to 14 cP. In embodiments, such an aqueous pharmaceutical composition has a viscosity of less than 12 cP. In embodiments, such an aqueous pharmaceutical composition has a viscosity of 11 to 12 cP.

In embodiments, 1 mL of an aqueous pharmaceutical composition described herein has ≤6000 particles that are ≥10 μM and/or has ≤600 particles that are ≥25 μM.

In embodiments, the antibody that is included in an aqueous pharmaceutical composition described herein demonstrates binding to the integrin α1 I domain as assessed using ELISA. In embodiments, the antibody that is included in an aqueous pharmaceutical composition described herein demonstrates a potency of 80%-125% of a reference standard (e.g., an antibody that is from the same lot (e.g., production batch) but that is not formulated in the aqueous pharmaceutical composition).

In embodiments, an aqueous pharmaceutical composition described herein shows <15% impurities by reducing CE-SDS.

In embodiments, an aqueous pharmaceutical composition described herein shows ≤10% total aggregation as assessed by size exclusion chromatography.

In embodiments, an aqueous pharmaceutical composition described herein has ≤90.0 EU/mL endotoxin.

In embodiments, 1 mL of an aqueous pharmaceutical composition described herein has ≤6000 particles that are ≥10 μM. In embodiments, 1 mL an aqueous pharmaceutical composition described herein has ≤600 particles that are ≥25 μM. In embodiments, 1 mL of an aqueous pharmaceutical composition described herein has ≤6000 particles that are ≥10 μM and ≤600 particles that are ≥25 μM. In embodiments, an aqueous pharmaceutical composition described herein complies with USP<71>.

In some embodiments, an aqueous pharmaceutical composition described herein (e.g., a histidine formulation) meets one or more of the criteria described in Table 32.

In one embodiment, the aqueous pharmaceutical composition comprises
(a) 165 to 190 mg/mL an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 25 to 35 mM histidine;
(c) 170 to 288 mM sorbitol; and
(d) 0.008 to 0.012% polysorbate, e.g., polysorbate 20;
wherein the aqueous pharmaceutical composition has pH 5 to 7.

In a certain embodiment, the aqueous pharmaceutical composition comprises
(a) 180 mg/mL an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 30 mM histidine;
(c) 250 mM sorbitol; and
(d) 0.01% polysorbate, e.g., polysorbate 20;
wherein the aqueous pharmaceutical composition has pH 5 to 7.

In some embodiments, the aqueous pharmaceutical composition is disposed in a container with a final fill volume of 1 mL. In embodiments, the container is a 2 mL USP Type 1 borosilicate glass vial with a 13 mm chlorobutyl based stopper with flourotech coating on plug and B2 coating on the top and an aluminum over seal with flip top cap.

In some embodiments, the aqueous pharmaceutical composition meets the criterion (see Table 32) for 1, 2, 3, 4, 5, 6, 7, 8, 9, 10, 11, 12, 13, or 14 of attributes A to M, either immediately after production or after storage under conditions described herein (e.g., as described herein in the Examples, e.g., after storage for up to 12 months (e.g., after storage for 1 month, 3 months, 6 months, 9 months, or 12 months), e.g., storage at −75° C., at 2 to 8° C., at 30° C. and 65% RH, or at 40° C. and 75% RH). In some embodiments, the aqueous pharmaceutical composition meets the criterion for all attributes A to M. In some embodiments, the aqueous pharmaceutical composition meets the criterion for at least one attribute in each of Groups 1 to 4. In some embodiments, the aqueous pharmaceutical composition meets the criterion for at least two attributes in each of Groups 1 to 4.

In some embodiments, the aqueous pharmaceutical composition meets the criterion for attributes G and/or H, K, and I and/or J. In embodiments, the aqueous pharmaceutical composition meets the criterion for attributes G, K, and I; for attributes H, K, and I; for attributes G, K, and J; or for attributes H, K, and J. In embodiments, the aqueous pharmaceutical composition meets the criterion for attributes G, H, K, and I; for attributes G, H, K, and J; for attributes G, K, I, and J; or for attributes H, K, I, and J. In embodiments, the aqueous pharmaceutical composition meets the criterion for attributes G, H, K, I and J.

TABLE 32

Criteria for Liquid Formulations, e.g., Histidine Formulations

| | Attribute | | Criterion |
|---|---|---|---|
| General (Group 1) | A | Appearance | Clear to opalescent Slightly yellow to yellow Essentially free from visible particulate matter |
| | B | pH | 5-7 |
| | C | Particulates | ≥10 μm particles: ≤6000 particles per container ≥25 μm particles: ≤600 particles per container |
| | D | Osmolality[1] | 270-380 mOsm/Kg |
| | E | Protein Concentration (A280) | 165-190 mg/mL |
| Identity (Group 2) | F | Charge Profile by Imaging Capillary Isoelectric Focusing (icIEF) | pI of the main peak is ±0.1 from that of the reference standard |
| | G | Potency (ELISA) | Demonstrates Binding to Integrin α1 I domain |
| Biological Potency (Group 3) | H | Potency (ELISA) | 80%-125% of Reference Standard |
| Purity and impurities (Group 4) | I | Impurities by Reducing CE-SDS | Total Impurities <15.0% |
| | J | Impurities by Non-Reducing CE-SDS | Total impurities <15.0% |
| | K | Aggregation by Size Exclusion Chromatography (SEC) | ≤10.0% Total Aggregation |
| Safety (Group 5) | L | Endotoxin | ≤90.0 EU/mL |
| | M | Sterility | Complies with USP requirements |

In some embodiments, an aqueous pharmaceutical composition described herein (e.g., an acetate formulation) meets one or more of the criteria described in Table 33.

In one embodiment, the aqueous pharmaceutical composition comprises
(a) 165 to 200 mg/mL of an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 25 to 35 mM acetate;
(c) 170 to 253 mM sorbitol; and
(d) 0.008 to 0.012% polysorbate, e.g., polysorbate 80;
wherein the aqueous pharmaceutical composition has pH 4.5 to 6.5.

In a certain embodiment, the aqueous pharmaceutical composition comprises
(a) 190 mg/mL of an anti-VLA-1 antibody having
a light chain sequence described herein, e.g., a sequence of SEQ ID NO:1 or a sequence that differs from SEQ ID NO:1 by at least one but not more than 2, 3, 4, 5, 6, 7, 9, or 10 amino acid residues; and
a heavy chain sequence described herein, e.g., a sequence of SEQ ID NO:2 or a sequence that differs from SEQ ID NO:2 by at least one but not more than 2, 3, 4, 5, 6, 7, 9, or 10 amino acid residues;
(b) 30 mM acetate;
(c) 220 mM sorbitol; and
(d) 0.01% polysorbate, e.g., polysorbate 80;
wherein the aqueous pharmaceutical composition has a pH of 4.5 to 6.5.

In some embodiments, the aqueous pharmaceutical composition is disposed in a container with a final fill volume of 1 mL. In embodiments, the container is a 2 mL USP Type 1 borosilicate glass vial with a 13 mm chlorobutyl based stopper with flourotech coating on plug and B2 coating on the top and an aluminum over seal with flip top cap.

In some embodiments, the aqueous pharmaceutical composition meets the criterion (see Table 33) for 1, 2, 3, 4, 5, 6, 7, 8, 9, 10, 11, 12, 13, or 14 of attributes A to M. In some embodiments, the aqueous pharmaceutical composition meets the criterion for all attributes A to M. In some embodiments, the aqueous pharmaceutical composition meets the criterion for at least one attribute in each of Groups 1 to 4. In some embodiments, the aqueous pharmaceutical composition meets the criterion for at least two attributes in each of Groups 1 to 4.

In some embodiments, the aqueous pharmaceutical composition meets the criterion for attributes G and/or H, K, and I and/or J. In embodiments, the aqueous pharmaceutical composition meets the criterion for attributes G, K, and I; for attributes H, K, and I; for attributes G, K, and J; or for attributes H, K, and J. In embodiments, the aqueous pharmaceutical composition meets the criterion for attributes G, H, K, and I; for attributes G, H, K, and J; for attributes G, K, I, and J; or for attributes H, K, I, and J. In embodiments, the aqueous pharmaceutical composition meets the criterion for attributes G, H, K, I and J.

TABLE 33

Criteria for Liquid Formulations. e.g., Acetate Formulations

| | | Attribute | Criterion |
|---|---|---|---|
| General (Group 1) | A | Appearance | Clear to opalescent Slightly yellow to yellow Essentially free from visible particulate matter |
| | B | pH | 4.5-6.5 |
| | C | Particulates | ≥10 μm particles: ≤6000 particles per container ≥25 μm particles: ≤600 particles per container |

TABLE 33-continued

Criteria for Liquid Formulations. e.g., Acetate Formulations

| | | Attribute | Criterion |
|---|---|---|---|
| | D | Osmolality[1] | 270-380 mOsm/Kg |
| | E | Protein Concentration (A280) | 165-200 mg/mL |
| Identity (Group 2) | F | Charge Profile by Imaging Capillary Isoelectric Focusing (icIEF) | pI of the main peak is ±0.1 from that of the reference standard |
| | G | Potency (ELISA) | Demonstrates Binding to Integrin α1 I domain |
| Biological Potency (Group 3) | H | Potency (ELISA) | 80%-125% of Reference Standard |
| Purity and impurities (Group 4) | I | Impurities by Reducing CE-SDS | Total Impurities <15.0% |
| | J | Impurities by Non-Reducing CE-SDS | Total impurities <15.0% |
| | K | Aggregation by Size Exclusion Chromatography (SEC) | ≤10.0% Total Aggregation |
| Safety (Group 5) | L | Endotoxin | ≤90.0 EU/mL |
| | M | Sterility | Complies with USP requirements |

In some embodiments, the aqueous pharmaceutical composition is stable. In some embodiments, stability is established based on testing the aqueous pharmaceutical composition after storage under controlled conditions for a preselected period of time, e.g., 1 month, 3 months, 6, months, 9 months or 12 months. Controlled conditions are described herein in the Examples. For example, controlled conditions can include storage at a fixed temperature or fixed temperature range, controlled humidity conditions, controlled light levels (e.g., storage in darkness), and/or storage in sterile sealed vials, e.g., sterile, depyrogenated type I borosilicate glass vials (e.g., at a volume of 1 mL), that are sealed with FluroTec® stoppers, e.g. 13 mm FluroTec® stoppers. In embodiments, the aqueous pharmaceutical composition is stored at −75° C., 2 to 8° C., 30° C. and 65% RH, or 40° C. and 75% RH, e.g., as described herein in the Examples.

In some embodiments, stability is established based on testing of parameters such as, e.g., appearance, protein content, pH, particle counts, % heavy chain, % light chain, % IgG, % intact IgG loss, In some embodiments, stability is established based on appearance. In some embodiments, the aqueous pharmaceutical composition is clear to opalescent. In some embodiments, the aqueous pharmaceutical composition is slightly yellow to yellow. In some embodiments, the aqueous pharmaceutical composition is essentially free from visible particulate matter.

In some embodiments, stability is established based on particle counts, e.g., counts of particles ≥10 μM and/or particles ≥25 μM, as determined using a liquid particle counter, e.g., a particle counter as described herein in the Examples.

In some embodiments, stability is established based on protein content. In some embodiments, there is no detectable loss in protein content after storage for a preselected period of time, e.g., 1 month, 3 months, 6, months, 9 months or 12 months. In some embodiments, stability is assessed based on purity. In some embodiments, purity is determined based on the % heavy chain, % light chain, % IgG, and/or % intact IgG loss, as assessed using reduced SDS-PAGE, e.g., as described herein in the examples. In some embodiments, purity is determined based on the the monomer average % area, the % fragmentation (this is 100-monomer average % area), the aggregate 3 average % area, the aggregate 2 average % area, the aggregate 1 average % area, the LMWI 1 average % area, and/or the LMWI 2 average % area, as assessed using SEC, e.g., as described herein in the examples.

In some embodiments, stability is assessed based on charge heterogeneity as assessed using CEX, e.g., as described herein in the examples. In embodiments, an aqueous pharmaceutical composition described herein is stable if the particle counts meet particle limits for injection set by USP<788>. In embodiments, an aqueous pharmaceutical composition described herein is stable if the particle counts for particles for ≥10 µM particles are less than 6000 or the particle counts for ≥25 µM particles are less than 600. In embodiments, an aqueous pharmaceutical composition described herein is stable if the particle counts for particles for ≥10 µM particles are less than 6000 and the particle counts for ≥25 µM particles are less than 600.

In embodiments, an aqueous pharmaceutical composition described herein is stable after storage at −75° C. for up to 12 months (e.g., for up to 12 months (e.g., for 1 month, 3 months, 6 months, 9 months or 12 months)), as indicated by the presence of less than 1600, 1700, 1800, 1900, 2000, 2100, 2200, 2300, 2400, 2500, 2600, 2700, 2800, 2900, or 3000 particles/mL as assessed by the cumulative counts/mL for ≥10 µM particles using a liquid particle counter. In an embodiment, the aqueous pharmaceutical composition is stable after storage at −75° C. for 12 months, as indicated by the presence of less than 1600 particles/mL as assessed by the cumulative counts/mL for ≥10 µM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at −75° C. for up to 12 months (e.g., for up to 12 months (e.g., for 1 month, 3 months, 6 months, 9 months or 12 months)), as indicated by the presence of less than 600, 700, 800, 900, 1000, 1100, 1200, 1300, 1400, or 1500 particles/mL as assessed by the cumulative counts/mL for ≥10 µM particles using a liquid particle counterIn an embodiment, the aqueous pharmaceutical composition is stable after storage at −75° C. for 12 months, as indicated by the presence of less than 600 particles/mL as assessed by the cumulative counts/mL for ≥10 µM particles using a liquid particle counter.

In embodiments, an aqueous pharmaceutical composition described herein is stable after storage at −75° C. for up to 12 months (e.g., for up to 12 months (e.g., for 1 month, 3 months, 6 months, 9 months or 12 months)), as indicated by the presence of less than 210, 220, 230, 240, 250, 300, 350, 400, 500, or 600, particles/mL as assessed by the cumulative counts/mL for ≥25 µM particles using a liquid particle counter. In an embodiment, the the aqueous pharmaceutical composition is stable after storage at −75° C. for 12 months, as indicated by the presence of less than 250 particles/mL as assessed by the cumulative counts/mL for ≥25 µM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at −75° C. for up to 12 months (e.g., for up to 12 months (e.g., for 1 month, 3 months, 6 months, 9 months or 12 months)), as indicated by the presence of less than 100, 90, 80, 70, 50, 40, or 30 particles/mL as assessed by the cumulative counts/mL for ≥25 µM particles using a liquid particle counter. In an embodiment, the aqueous pharmaceutical composition is stable after storage at −75° C. for 12 months, as indicated by the presence of less than 100 particles/mL as assessed by the cumulative counts/mL for ≥25 µM particles using a liquid particle counter.

In embodiments, an aqueous pharmaceutical composition described herein is stable after storage at 2 to 8° C. for up to 12 months (e.g., for up to 12 months (e.g., for 1 month, 3 months, 6 months, 9 months or 12 months)), as indicated by the presence of less than 2600, 2700, 2800, 2900, 3000, 3500, 4000, 4500, 5000, 5500, or 6000 particles/mL as assessed by the cumulative counts/mL for ≥10 µM particles using a liquid particle counter. In an embodiment, the aqueous pharmaceutical composition is stable after storage at 2- to 8° C. for 12 months, as indicated by the presence of less than 2600 particles/mL as assessed by the cumulative counts/mL for ≥10 µM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at 2 to 8° C. for up to 12 months (e.g., for up to 12 months (e.g., for 1 month, 3 months, 6 months, 9 months or 12 months)), as indicated by the presence of less than 1500, 1600, 1700, 1800, 1900, 2000, 2100, 2200, 2300, 2400, or 2500 particles/mL as assessed by the cumulative counts/mL for ≥10 µM particles using a liquid particle counter. In an embodiment, the aqueous pharmaceutical composition is stable after storage at 2 to 8° C. for 12 months, as indicated by the presence of less than 1500 particles/mL as assessed by the cumulative counts/mL for ≥10 µM particles using a liquid particle counter.

In embodiments, an aqueous pharmaceutical composition described herein is stable after storage at 2 to 8° C. for up to 12 months (e.g., for up to 12 months (e.g., for 1 month, 3 months, 6 months, 9 months or 12 months)), as indicated by the presence of less than 210, 220, 230, 240, 250, 300, 350, 400, 500, or 600 particles/mL as assessed by the cumulative counts/mL for ≥25 µM particles using a liquid particle counter. In an embodiment, the aqueous pharmaceutical composition is stable after storage at 2- to 8° C. for 12 months, as indicated by the presence of less than 250 particles/mL as assessed by the cumulative counts/mL for ≥25 µM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at 2 to 8° C. for up to 12 months (e.g., for up to 12 months (e.g., for 1 month, 3 months, 6 months, 9 months or 12 months)), as indicated by the presence of less than 50, 60, 70, 80, 90, 100, 110, 120, 130, 140, 150, 160, 170, or 180 particles/mL as assessed by the cumulative counts/mL for ≥25 µM particles using a liquid particle counter. In an embodiment, the aqueous pharmaceutical composition is stable after storage at 2 to 8° C. for 12 months, as indicated by the presence of less than 50 particles/mL as assessed by the cumulative counts/mL for ≥25 µM particles using a liquid particle counter.

In embodiments, an aqueous pharmaceutical composition described herein is stable after storage at 30° C. for up to 12 months (e.g., for 1 month, 3 months, 6 months, 9 months or 12 months), as indicated by the presence of less than 2600, 2700, 2800, 2900, 3000, 3500, 4000, 4500, 5000, 5500, or 6000 particles/mL as assessed by the cumulative counts/mL for ≥10 μM particles using a liquid particle counter. In an embodiment, the aqueous pharmaceutical composition is stable after storage at 30° C. for 12 months, as indicated by the presence of less than 2600 particles/mL as assessed by the cumulative counts/mL for ≥10 μM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at 30° C. for up to 12 months (e.g., for 1 month, 3 months, 6 months, 9 months or 12 months), as indicated by the presence of less than 2500, 2400, or 2300 particles/mL as assessed by the cumulative counts/mL for ≥10 μM particles using a liquid particle counter. In an embodiment, the aqueous pharmaceutical composition is stable after storage at 30° C. for 12 months, as indicated by the presence of less than 2300 particles/mL as assessed by the cumulative counts/mL for ≥10 μM particles using a liquid particle counter.

In embodiments, an aqueous pharmaceutical composition described herein is stable after storage at 30° C. for up to 12 months (e.g., for 1 month, 3 months, 6 months, 9 months or 12 months), as indicated by the presence of less than 210, 220, 230, 240, 250, 300, 350, 400, 500, or 600 particles/mL as assessed by the cumulative counts/mL for ≥25 μM particles using a liquid particle counter. In an embodiment, the aqueous pharmaceutical composition is stable after storage at 30° C. for 12 months, as indicated by the presence of less than 250 particles/mL as assessed by the cumulative counts/mL for ≥25 μM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at 30° C. for up to 12 months (e.g., for 1 month, 3 months, 6 months, 9 months or 12 months), as indicated by the presence of less than 120, 130, 140, 150, 160, 170, 180, or 190 particles/mL as assessed by the cumulative counts/mL for ≥25 μM particles using a liquid particle counter. In an embodiment, the aqueous pharmaceutical composition is stable after storage at 30° C. for 12 months, as indicated by the presence of less than 120 particles/mL as assessed by the cumulative counts/mL for ≥25 μM particles using a liquid particle counter.

In embodiments, an aqueous pharmaceutical composition described herein is stable after storage at 40° C. for up to 6 months (e.g., 1 month, 3 months, or 6 months), as indicated by the presence of less than 2600, 2700, 2800, 2900, 3000, 3500, 4000, 4500, 5000, 5500, or 6000 particles/mL as assessed by the cumulative counts/mL for ≥10 μM particles using a liquid particle counter. In an embodiment, the aqueous pharmaceutical composition is stable after storage at 40° C. for 6 months, as indicated by the presence of less than 2600 particles/mL as assessed by the cumulative counts/mL for ≥10 μM particles using a liquid particle counter.

In embodiments, an aqueous pharmaceutical composition described herein (e.g., an aqueous pharmaceutical composition described herein that comprises histidine, sorbitol, and polysorbate, e.g., polysorbate 20) is stable after storage at 40° C. for up to 6 months (e.g., for 1 month, 3 months, or 6 months), as indicated by the presence of less than 120, 130, 140, 150, 160, 170, 180, or 190 particles/mL as assessed by the cumulative counts/mL for ≥10 μM particles using a liquid particle counter. In an embodiment, the aqueous pharmaceutical composition is stable after storage at 40° C. for 6 months, as indicated by the presence of less than 120 particles/mL as assessed by the cumulative counts/mL for ≥10 μM particles using a liquid particle counter.

In embodiments, an aqueous pharmaceutical composition described herein is stable after storage at −75° C. for up to 12 months (e.g., for 1 month, 3 months, 6 months, 9 months or 12 months), as indicated by less than 1%, 2%, or 3% relative loss of intact IgG as assessed using reduced SDS-PAGE. As used in this context, "relative loss" refers to loss compared with a reference standard, e.g., an antibody that is from the same lot (e.g., production batch) but that is not formulated in the aqueous pharmaceutical composition. In an embodiment, the aqueous pharmaceutical composition is stable after storage at −75° C. for 12 months, as indicated by less than 1% relative loss of intact IgG as assessed using reduced SDS-PAGE.

In embodiments, an aqueous pharmaceutical composition described herein (e.g., an aqueous pharmaceutical composition described herein that comprises histidine, sorbitol, and polysorbate, e.g., polysorbate 20) is stable after storage at −75° C. for up to 12 months (e.g., for 1 month, 3 months, 6 months, 9 months or 12 months), as indicated by less than 0.5%, 0.6%, 0.7%, or 0.8% relative loss of intact IgG as assessed using reduced SDS-PAGE. In an embodiment, the aqueous pharmaceutical composition is stable after storage at −75° C. for 12 months, as indicated by less than 0.5% relative loss of intact IgG as assessed using reduced SDS-PAGE.

In embodiments, an aqueous pharmaceutical composition described herein is stable after storage at 2 to 8° C. for up to 12 months (e.g., for 1 month, 3 months, 6 months, 9 months or 12 months), as indicated by less than 7%, 8%, 9%, 10%, 11%, 12%, 13%, 14%, or 15% relative loss of intact IgG as assessed using reduced SDS-PAGE. In an embodiment, aqueous pharmaceutical composition is stable after storage at 2- to 8° C. for 12 months, as indicated by less than 10% relative loss of intact IgG as assessed using reduced SDS-PAGE.

In embodiments, an aqueous pharmaceutical composition described herein (e.g., an aqueous pharmaceutical composition described herein that comprises histidine, sorbitol, and polysorbate, e.g., polysorbate 20) is stable after storage at 2 to 8° C. for up to 12 months (e.g., for 1 month, 3 months, 6 months, 9 months, or 12 months), as indicated by less than 3%, 4%, 5%, or 6% relative loss of intact IgG as assessed using reduced SDS-PAGE. In an embodiment, the aqueous pharmaceutical composition is stable after storage at 2- to 8° C. for 12 months, as indicated by less than 3% relative loss of intact IgG as assessed using reduced SDS-PAGE.

In embodiments, an aqueous pharmaceutical composition described herein is stable after storage at 30° C. for up to 12 months (e.g., for 1 month, 3 months, 6 months, 9 months or 12 months), as indicated by less than 23%, 24%, 25%, 26%, 27%, 28%, 29%, or 30% relative loss of intact IgG as assessed using reduced SDS-PAGE. In an embodiment, the aqueous pharmaceutical composition is stable after storage at 30° C. for 12 months, as indicated by less than 25% relative loss of intact IgG as assessed using reduced SDS-PAGE.

In embodiments, an aqueous pharmaceutical composition described herein is stable after storage at 40° C. for up to 6 months (e.g., for 1 month, 3 months, or 6 months), as indicated by less than 30% relative loss of intact IgG as assessed using reduced SDS-PAGE. In an embodiment, the aqueous pharmaceutical composition is stable after storage at 40° C. for 6 months, as indicated by less than 30% relative loss of intact IgG as assessed using reduced SDS-PAGE.

In embodiments, an aqueous pharmaceutical composition described herein is stable after storage at 40° C. for up to 6 months (e.g., for 1 month, 3 months, or 6 months), as indicated by less than 25% relative loss of intact IgG as assessed using reduced SDS-PAGE. In an embodiment, the aqueous pharmaceutical composition is stable after storage at 40° C. for 6 months, as indicated by less than 25% relative loss of intact IgG as assessed using reduced SDS-PAGE.

In embodiments, an aqueous pharmaceutical composition described herein is stable after storage at −75° C. for up to 12 months (e.g., for 1 month, 3 months, 6 months, 9 months or 12 months), as indicated by less than 4%, 5%, 6%, 7%, 8%, 9%, or 10% fragmentation as assessed using size exlusion chromatography. In an embodiment, the aqueous pharmaceutical composition is stable after storage at −75° C. 12 months, as indicated by less than 4% fragmentation as assessed using size exlusion chromatography.

In embodiments, an aqueous pharmaceutical composition described herein is stable after storage at 2 to 8° C. for up to 12 months (e.g., for 1 month, 3 months, 6 months, 9 months or 12 months), as indicated by less than 5%, 6%, 7%, 8%, 9%, or 10% fragmentation as assessed using size exlusion chromatography. In an embodiment, the aqueous pharmaceutical composition is stable after storage at 2- to 8° C. for 12 months, as indicated by less than 5% fragmentation as assessed using size exlusion chromatography.

In embodiments, an aqueous pharmaceutical composition described herein is stable after storage at 30° C. for up to 12 months (e.g., for 1 month, 3 months, 6 months, 9 months or 12 months), as indicated by less than 13%, 14%, 15%, 16%, 17%, 18%, 19%, or 20% fragmentation as assessed using size exlusion chromatography.

In embodiments, an aqueous pharmaceutical composition described herein (e.g., an aqueous pharmaceutical composition described herein that comprises histidine, sorbitol, and polysorbate, e.g., polysorbate 20) is stable after storage at 30° C. for up to 12 months (e.g., for 1 month, 3 months, 6 months, 9 months or 12 months), as indicated by less than 12% fragmentation as assessed using size exlusion chromatography.

In embodiments, an aqueous pharmaceutical composition described herein is stable after storage at 40° C. for up to 6 months (e.g., for 1 month, 3 months, or 6 months), as indicated by less than 16, 17, 18, 19, 20, 21, 22, 23, 24, or 25% fragmentation as assessed using size exlusion chromatography.

In embodiments, an aqueous pharmaceutical composition described herein is stable after storage at 40° C. for up to 6 months (e.g., for 1 month, 3 months, or 6 months), as indicated by less than 20, 21, 22, 23, 24, 25, 26, 27, 28, 29, or 30% fragmentation as assessed using size exlusion chromatography In embodiments, an aqueous pharmaceutical composition described herein (e.g., an aqueous pharmaceutical composition described herein that comprises histidine, sorbitol, and polysorbate, e.g., polysorbate 20) is stable after storage at 40° C. for up to 6 months (e.g., for 1 month, 3 months, or 6 months), as indicated by less than 17, 18, 19, or 20% fragmentation as assessed using size exlusion chromatography.

In embodiments, an aqueous pharmaceutical composition described herein is stable after storage at 30° C. for up to 12 months (e.g., for 1 month, 3 months, 6 months, 9 months or 12 months), as indicated by less than 5, 6, 7, 8, 9 or 10 LMWI 1 average % area as assessed using size exlusion chromatography.

In embodiments, an aqueous pharmaceutical composition described herein (e.g., an aqueous pharmaceutical composition described herein that comprises histidine, sorbitol, and polysorbate, e.g., polysorbate 20) is stable after storage at 30° C. for up to 12 months (e.g., for 1 month, 3 months, 6 months, 9 months or 12 months), as indicated by less than 3, 4, or 5 LMWI 1 average % area as assessed using size exlusion chromatography.

In embodiments, an aqueous pharmaceutical composition described herein is suitable for subcutaneous administration.

Also provided herein is a unit dosage form of an aqueous pharmaceutical composition, e.g., an aqueous pharmaceutical composition described herein. In embodiments, the unit dosage form will, when administered to a human, deliver antibody at about 2.0 mg per kg of body weight to about 4.0 mg per kg of body weight to the human.

In embodiments, a plurality of unit dosage forms of an aqueous pharmaceutical composition (e.g., an aqueous pharmaceutical composition described herein) is provided.

In embodiments, a kit comprising the unit dosage form, or the plurality of unit dosage forms, is provided.

In embodiments, an aqueous pharmaceutical composition described herein is disposed in a container. In embodiments, the container has disposed therein a unit dosage form of the pharmaceutical composition. In embodiments, the container is a delivery device. In embodiments, the container is suitable for administering the pharmaceutical composition subcutaneously. In embodiments, the container is a syringe, e.g., a prefilled syringe. In embodiments, the container is a sealed vial.

In one aspect, the disclosure provides a method of treating a patient in need of anti-VLA-1 therapy, comprising administering to the patient an effective amount of an aqueous pharmaceutical composition described herein. In some embodiments, the patient has an inflammatory disorder. In some embodiments, the patient has a disorder selected from the group consisting of arthritis, inflammatory bowel disease, lupus, transplant rejection, psoriasis, and sarcoidosis. In some embodiments, the patient has sarcoidosis. In some embodiments, the patient has arthritis. In some embodiments, the patient has rheumatoid arthritis. In some embodiments, the patient has moderately to severely active rheumatoid arthritis. In some embodiments, the patient has an inflammatory bowel disease. In some embodiments, the patient has Crohn's disease. In some embodiments, the patient has ulcerative colitis. In some embodiments, the patient has lupus nephritis. In some embodiments, the method is effective to treat the disorder from which the patient in need of anti-VLA-1 therapy is suffering (e.g., the inflammatory disorder or the disorder selected from the group consisting of arthritis, inflammatory bowel disease, lupus, transplant rejection, psoriasis, and sarcoidosis).

In some embodiments, the patient has moderately to severely active rheumatoid arthritis.

In some embodiments, the patient is an adult. In some embodiments, the patient is an adult with moderately to severely active rheumatoid arthritis.

In some embodiments, the aqueous pharmaceutical composition is administered subcutaneously. In some embodiments, the composition is administered weekly. In some embodiments, the composition is administered every 4, 5, 6, 7, 8, 9, or 10 days. In some embodiments, the composition is administered every two weeks. In some embodiments, the composition is administered every three weeks or every four weeks.

In some embodiments, the composition is administered for at least 2, 3, 4, 5, 6, 7, 8, 9, 10, 11, or 12 weeks. In some embodiments, the composition is administered weekly for at least 6 weeks.

In some embodiments, the composition is administered at a dose of 0.5 mg/kg to 6 mg/kg. In some embodiments, the composition is administered at a dose of 0.5 mg/kg, 1.0 mg/kg, 2.0 mg/kg, 4.0 mg/kg, or 6.0 mg/kg. In some embodiments, the composition is administered at a dose of 2.0 mg/kg to 6.0 mg/kg. In some embodiments, the composition is administered at a dose of 2.0 mg/kg, 4.0 mg/kg, or 6.0 mg/kg.

In some embodiments, the method reduces a sign or symptom (e.g., a sign or symptom of the disorder from which the patient is suffering, e.g., a sign or symptom of rheumatoid arthritis), slows progression of structural damage (e.g., structural damage associated with the disorder from which the patient is suffering, e.g., structural damage associated with rheumatoid arthritis), or improves physical function. In some embodiments, treating the patient according to the method for at least 2 weeks, 3 weeks, 4 weeks, 5 weeks, 6 weeks, 7 weeks, or 8 weeks reduces a sign or symptom, slows progression of structural damage, or improves physical function.

The efficacy of the method (e.g., efficacy in reducing a sign or symptom, slowing progression of structural damage, or improving physical function) can be assessed using measures known in the art. In embodiments, efficacy is assessed using ACR20, ACR50, ACR70, DAS28 CRP, HAQ-DI, and/or MRI results.

In some embodiments, the method is not associated with any adverse events in the patient or in a clinical study of patients who have the same disease as the patient to be treated. In some events, the method is not associated with any severe or moderate adverse events in the patient or in a clinical study of patients who have the same disease as the patient to be treated.

In some embodiments, the subject has rheumatoid arthritis. In some embodiments, the patient is an adult. In some embodiments, the patient has undergone a prior alternate treatment (e.g., a prior alternate treatment for the disorder from which the patient is suffering). A "prior alternate treatment," as used herein, refers to any treatment other than a treatment comprising an anti-VLA-1 antibody as described herein. In some embodiments, the patient has had an inadequate response to the prior alternate treatment.

In some embodiments, the patient has rheumatoid arthritis and has undergone a prior alternate treatment for rheumatoid arthritis. In some embodiments, the patient has had an inadequate response to the prior alternate treatment.

In an aspect, the disclosure provides a method of treating a patient (e.g., an adult patient) with rheumatoid arthritis (e.g., moderately to severely active rhematoid arthritis) who has had a prior alternate treatment (e.g., a prior alternate treatment for rhematoid arthritis), said method comprising subcutaneously administering to said patient a liquid formulation (e.g., an aqueous pharmaceutical composition) comprising
 (a) 150 to 210 mg/mL of an anti-VLA-1 antibody having a light chain sequence of SEQ ID NO:1 and a heavy chain sequence of SEQ ID NO:2;
 (b) 25 to 35 mM acetate or 25 to 35 mM histidine;
 (c) 170 to 288 mM sorbitol; and
 (d) 0.008 to 0.012% polysorbate, wherein the polysorbate is polysorbate 20 or polysorbate 80;
wherein the composition has a pH of 5 to 7.

In embodiments, the method reduces a sign or symptom of rheumatoid arthritis, slows progression of structural damage associated with rheumatoid arthritis, or improves physical function.

In embodiments, the liquid formulation (e.g., the aqueous pharmaceutical composition) comprises
 (a) 180 mg/mL an anti-VLA-1 antibody having a light chain sequence of SEQ ID NO:1 and a heavy chain sequence of SEQ ID NO:2;
 (b) 30 mM histidine;
 (c) 250 mM sorbitol; and
 (d) 0.01% polysorbate 20; and
wherein the composition has a pH of 6.0.

In embodiments, the liquid formulation is administered to the patient at a dose of 0.5 to 6.0 mg/kg. In embodiments, the liquid formulation is administered to the patient at a dose of 2 to 6 mg/kg. In embodiments, the liquid formulation is administered to the patient at a dose of 2 mg/kg, 4 mg/kg, or 6 mg/kg.

In embodiments, the liquid formulation or aqueous pharmaceutical composition is administered repeatedly, e.g., weekly. In embodiments, the liquid formulation or aqueous pharmaceutical composition is administered every 4, 5, 6, 7, 8, 9, or 10 days. In embodiments, the composition is administered every two weeks. In embodiments, the composition is administered every three weeks or every four weeks.

In embodiments, the liquid formulation or aqueous pharmaceutical composition is administered repeatedly (e.g., weekly) for at least 2, 4, 6, 8, 10, 12, 14, 16 or more weeks. In embodiments, the liquid formulation or aqueous pharmaceutical composition is administered for 2, 3, 4, 5, 6, 7, 8, 9, 10, 11, 12 or more weeks.

In embodiments, the liquid formulation is administered weekly. In embodiments, the liquid formulation is administered for at least 6 weeks. In embodiments, the liquid formulation is administered weekly for at least 6 weeks.

In embodiments, the prior alternate treatment comprises a DMARD (Disease Modifying Antirheumatic Drug) or a TNF-α (Tumor Necrosis Factor-α) inhibitor.

In embodiments, the DMARD is methotrexate, leflunomide, sulfasalazine, or hydroxychloroquine.

In embodiments, the prior alternate treatment comprises a biologic agent, e.g., a TNF-α inhibitor. In embodiments, the TNF-α inhibitor is infliximab, adalimumab, certolizumab pegol, golimumab or etanercept.

In embodiments, the prior alternate treatment comprises an agent selected from infliximab, adalimumab, certolizumab pegol, golimumab, etanercept abatacept, rituximab, tocilizumab, tofacitinib, methotrexate, leflunomide, sulfasalazine, and hydroxychloroquine In embodiments, the prior alternate treatment comprises an agent selected from abatacept, rituximab, tocilizumab, golimumab, and tofacitinib.

In some embodiments, the subject has had an inadequate response to the prior alternate treatment. In embodiments, the response is inadequate if assessed based on ACR criteria. In embodiments, the patient does not achieve ACR20 after the prior alternate treatment. In embodiments, the patient does not achieve ACR50 after the prior alternate treatment. In embodiments, the patient does not achieve ACR70 after the prior alternate treatment. In embodiments, the prior alternate treatment is determined to be inadequate after 6 months of treatment, or after 6 or more months of treatment.

In embodiments, the prior alternate treatment is determined to be inadequate after 1 or more, 2 or more, 3 or more, 4 or more, 5 or more, 6 or more, 7 or more, 8 or more, 9 or more, 10 or more, 11 or more, or 12 or more months of treatment.

In embodiments, the method further comprises administering to the patient a second therapeutic agent, e.g., a corticosteroid or an anti-inflammatory.

In embodiments, the method is associated with ≤10% infection risk.

In embodiments, the method is associated with greater than mild injection site reactions in ≤10% of patients, e.g., ≤10% of patients in a clinical study.

In one embodiment, the method comprises treating an adult patient with moderately to severely active rheumatoid arthritis who has had an inadequate response to a prior alternate treatment, e.g., a prior alternate treatment comprising a biologic agent, said method comprising subcutaneously administering once weekly to said patient a liquid formulation (e.g., an aqueous pharmaceutical composition) comprising
  (a) 165 to 190 mg/mL of an anti-VLA-1 antibody having a light chain sequence of SEQ ID NO:1 and a heavy chain sequence of SEQ ID NO:2;
  (b) 25 to 35 mM histidine;
  (c) 170 to 288 mM sorbitol; and
  (d) 0.008 to 0.012% polysorbate 20; and
wherein the liquid formulation (e.g., the aqueous pharmaceutical composition) has a pH of 5 to 7. In embodiments, the method reduces a sign or symptom of rheumatoid arthritis, slows progression of structural damage associated with rheumatoid arthritis, or improves physical function. In embodiments, the liquid formulation is administered at a dose of 2 to 6 mg/kg.

In an aspect provided herein is a method of making an aqueous pharmaceutical composition comprising 150 to 210 mg/mL of an anti-VLA-1 antibody having a light chain sequence of SEQ ID NO:1 and a heavy chain sequence of SEQ ID NO:2; the method comprising combining said antibody with a buffer selected from histidine and acetate, a surfactant selected from polysorbate 20 and polysorbate 80, and sorbitol to obtain an aqueous pharmaceutical composition comprising
  (a) 150 to 210 mg/mL of an anti-VLA-1 antibody having a light chain sequence of SEQ ID NO:1 and a heavy chain sequence of SEQ ID NO:2;
  (b) 25 to 35 mM acetate or 25 to 35 mM histidine;
  (c) 170 to 288 mM sorbitol; and
  (d) 0.008 to 0.012% polysorbate, wherein the polysorbate is polysorbate 20 or polysorbate 80;
wherein the aqueous pharmaceutical composition has a pH of 4.5 to 7.

In some embodiments, the buffer is histidine. In some embodiments, the polysorbate is polysorbate 20. In some embodiments, the buffer is histidine and the polysorbate is polysorbate 20.

In some embodiments, the buffer is acetate. In some embodiments, the polysorbate is polysorbate 80. In some embodiments, the buffer is acetate and the polysorbate is polysorbate 80.

In embodiments, the aqueous pharmaceutical composition comprises
  (a) 165 to 190 mg/mL of an anti-VLA-1 antibody having a light chain sequence of SEQ ID NO:1 and a heavy chain sequence of SEQ ID NO:2;
  (b) 25 to 35 mM histidine;
  (c) 170 to 288 mM sorbitol; and
  (d) 0.008 to 0.012% polysorbate 20; and
the aqueous pharmaceutical composition has a pH of 5 to 7.

In an embodiment, the aqueous pharmaceutical composition comprises
  (a) 180 mg/mL of an anti-VLA-1 antibody having a light chain sequence of SEQ ID NO:1 and a heavy chain sequence of SEQ ID NO:2;
  (b) 30 mM histidine;
  (c) 250 mM sorbitol; and
  (d) 0.01% polysorbate 20; and
the aqueous pharmaceutical composition has a pH of 6.0.

In embodiments, the aqueous pharmaceutical composition comprises
  (a) 165 to 200 mg/mL of an anti-VLA-1 antibody having a light chain sequence of SEQ ID NO:1 and a heavy chain sequence of SEQ ID NO:2;
  (b) 25 to 35 mM acetate;
  (c) 170 to 253 mM sorbitol; and
  (d) 0.008 to 0.012% polysorbate 80; and
the aqueous pharmaceutical composition has a pH of 4.5 to 6.5.

In an embodiment, the aqueous pharmaceutical composition comprises
  (a) 190 mg/mL of an anti-VLA-1 antibody having a light chain sequence of SEQ ID NO:1 and a heavy chain sequence of SEQ ID NO:2;
  (b) 30 mM acetate;
  (c) 220 mM sorbitol; and
  (d) 0.01% polysorbate 80; and
wherein the aqueous pharmaceutical composition has a pH of 5.5.

Further specific aspects of the invention are disclosed below.

Aspect 1: An aqueous pharmaceutical composition comprising an anti-VLA-1 (Very Late Antigen-1) antibody at a concentration of greater than about 100 mg/mL.

Aspect 2: The aqueous pharmaceutical composition of Aspect 1, wherein said anti-VLA-1 antibody is a monoclonal antibody.

Aspect 3: The aqueous pharmaceutical composition of Aspect 1, wherein said anti-VLA-1 antibody is a CDR-grafted antibody.

Aspect 4: The aqueous pharmaceutical composition of Aspect 1, wherein said anti-VLA-1 antibody is a humanized antibody.

Aspect 5: The aqueous pharmaceutical composition of Aspect 1, wherein said anti-VLA-1 antibody comprises a light chain that is at least 80% identical with the light chain of SEQ ID NO:1 and a heavy chain that is at least 80% identical with the heavy chain of SEQ ID NO:2.

Aspect 6: The aqueous pharmaceutical composition of Aspect 1, wherein said anti-VLA-1 antibody comprises a light chain having no more than 5 amino acid differences from the light chain of SEQ ID NO:1 and a heavy chain having no more than 5 amino acid differences from the heavy chain of SEQ ID NO:2.

Aspect 7: The aqueous pharmaceutical composition of Aspect 1, wherein said anti-VLA-1 antibody comprises a light chain having the sequence of SEQ ID NO:1 and a heavy chain having the sequence of SEQ ID NO:2.

Aspect 8: The aqueous pharmaceutical composition of Aspect 1, wherein, said antibody concentration is at least about 160 mg/mL, at least about 170 mg/mL, at least about 180 mg/mL, at least about 190 mg/mL, or at least about 200 mg/mL.

Aspect 9: The aqueous pharmaceutical composition of Aspect 1, wherein, said antibody concentration is less than about 200 mg/mL, less than about 205 mg/mL, less than about 210 mg/mL, less than about 215 mg/mL, less than about 220 mg/mL, or less than about 225 mg/mL.

Aspect 10: The aqueous pharmaceutical composition of Aspect 1, wherein, said antibody is at a concentration of about 155 mg/mL to about 165 mg/mL, about 165 mg/mL to about 175 mg/mL, about 175 mg/mL to about 185 mg/mL, about 185 mg/mL to about 195 mg/mL, about 195 mg/mL to about 205 mg/mL, about 205 mg/mL to about 215 mg/mL, or about 215 mg/mL to about 225 mg/mL.

Aspect 11: The aqueous pharmaceutical composition of Aspect 1, wherein, said antibody is at a concentration of about 160 mg/mL to about 210 mg/mL.

Aspect 12: The aqueous pharmaceutical composition of Aspect 1, wherein the formulation is stable for at least 6 months, at least one year, at least two years, or at least three years.

Aspect 13: The aqueous pharmaceutical composition of Aspect 1, wherein after 6 months, one year, two years, or three years, less than about 1%, less than about 2%, less than about 5%, less than about 10%, or less than about 15% of the antibody in the formulation has undergone aggregation.

Aspect 14: The aqueous pharmaceutical composition of Aspect 13, wherein aggregation is determined by dynamic light scattering.

Aspect 15: The aqueous pharmaceutical composition of Aspect 1, wherein after 6 months, one year, two years, or three years, less than about 1%, less than about 2%, less than about 5%, less than about 10%, or less than about 15% of the antibody in the formulation has undergone fragmentation.

Aspect 16: The aqueous pharmaceutical composition of Aspect 15, wherein fragmentation is determined by dynamic light scattering.

Aspect 17: The aqueous pharmaceutical composition of Aspect 1, wherein after 6 months, one year, two years, or three years, less than about 1%, less than about 2%, less than about 5%, less than about 10%, or less than about 15% of the antibody in the formulation has undergone deamidation.

Aspect 18: The aqueous pharmaceutical composition of Aspect 17, wherein deamidation is determined by protein loss as measured by spectroscopy.

Aspect 19: The aqueous pharmaceutical composition of Aspect 1, wherein, when stored in a closed container, at 4° C., for a preselected period of time, said anti-VLA-1 antibody exhibits less than a preselected level of aggregation.

Aspect 20: The aqueous pharmaceutical composition of Aspect 19, wherein, said preselected level is less than a preselected reference value for level of aggregation.

Aspect 21: The aqueous pharmaceutical composition of Aspect 19, wherein, said preselected level is less than 35%.

Aspect 22: The aqueous pharmaceutical composition of Aspect 19, wherein said preselected period is 30 days, 60 days, 90 days, 180 days, 1 year, 1.5 years, 2 years, 2.5 years, or 3 years.

Aspect 23: The aqueous pharmaceutical composition of Aspect 19, wherein aggregation is determined by DLS.

Aspect 24: The aqueous pharmaceutical composition of Aspect 1, wherein, when subjected to a preselected number of freeze/thaw cycles, said anti-VLA-1 antibody exhibits less than a preselected level of protein loss.

Aspect 25: The aqueous pharmaceutical composition of Aspect 24, wherein, said preselected level is less than a preselected reference value of 35%.

Aspect 26: The aqueous pharmaceutical composition of Aspect 25, wherein, said preselected level is less than 10% protein loss.

Aspect 27: The aqueous pharmaceutical composition of Aspect 24, wherein said preselected number of freeze/thaw cycles is 3, 4, 5, 6, 7, or 8.

Aspect 28: The aqueous pharmaceutical composition of Aspect 24, wherein said preselected number of freeze/thaw cycles is 5.

Aspect 29: The aqueous pharmaceutical composition of Aspect 24, wherein a freeze/thaw cycle comprises incubation at −80° C. for 2 hours followed by thawing at 20° C. until melted.

Aspect 30: The aqueous pharmaceutical composition of Aspect 24, wherein protein loss is determined by spectroscopy.

Aspect 31: The aqueous pharmaceutical composition of Aspect 1, wherein, when stored in a closed container at 4° C., and exposed to 1.2 lux hours white light and 200 W/m$^2$ UV energy, said anti-VLA-1 antibody exhibits less than a preselected level of protein loss.

Aspect 32: The aqueous pharmaceutical composition of Aspect 1, wherein, when subjected to shaking at 650 rpm, for a preselected period of time, at room temperature said composition exhibits less than a preselected level of protein loss.

Aspect 33: The aqueous pharmaceutical composition of Aspect 32, wherein, said preselected level is less than 5%.

Aspect 34: The aqueous pharmaceutical composition of Aspect 32, wherein said preselected period of time is 24 hours, 48 hours, 72 hours or 96 hours.

Aspect 35: The aqueous pharmaceutical composition of Aspect 32, wherein said preselected period of time is 72 hours.

Aspect 36: The aqueous pharmaceutical composition of Aspect 32, wherein protein loss is determined by spectroscopy.

Aspect 37: The aqueous pharmaceutical composition of Aspect 1, wherein, when subjected to a preselected level of oxidation stress, said composition exhibits a preselected level of protein loss.

Aspect 38: The aqueous pharmaceutical composition of Aspect 37, wherein, said preselected level is less than 35%.

Aspect 39: The aqueous pharmaceutical composition of Aspect 37, wherein said preselected level of oxidation stress is provided by the presence of hydrogen peroxide at a final concentration of 0.04% (V/V) with incubation at 37° C., for a preselected period of time.

Aspect 40: The aqueous pharmaceutical composition of Aspect 39, wherein said preselected period of time is 2 hours, 3 hours, 4 hours, 5 hours or 6 hours.

Aspect 41: The aqueous pharmaceutical composition of Aspect 39, wherein said preselected period of time is 4 hours.

Aspect 42: The aqueous pharmaceutical composition of Aspect 39, wherein protein loss is determined by spectroscopy.

Aspect 43: The aqueous pharmaceutical composition of Aspect 1, having a syringeability suitable for patient self administration to a subcutaneous site.

Aspect 44: The aqueous pharmaceutical composition of Aspect 1, when disposed in a syringe suitable for subcutaneous delivery to a patient, can be expelled and thereby injected into a subcutaneous site of the patient, with a plunger force equal to or less than 4 lbs.

Aspect 45: The aqueous pharmaceutical composition of Aspect 1, in a form suitable for patient self-administration.

Aspect 46: The aqueous pharmaceutical composition of Aspect 44, wherein said pressure will allow delivery of a unit dosage in 10 seconds or less.

Aspect 47: The aqueous pharmaceutical composition of Aspect 1, wherein, when disposed in a 1 mL syringe having a needle of preselected gauge, can be expelled at a preselected rate with a plunger force of no more than a preselected amount.

Aspect 48: The aqueous pharmaceutical composition of Aspect 1, further comprising a Aspect 49: The aqueous pharmaceutical composition of Aspect 1, further comprising one or more of histidine, acetate, succinate or phosphate.

Aspect 50: The aqueous pharmaceutical composition of Aspect 1, further comprising one or more of histidine or acetate.

Aspect 51: The aqueous pharmaceutical composition of Aspect 1, further comprising histidine.

Aspect 52: The aqueous pharmaceutical composition of Aspect 51, wherein said histidine is at a concentration of about 10 mM to about 50 mM.

Aspect 53: The aqueous pharmaceutical composition of Aspect 51, wherein said histidine is at a concentration of about 20 mM to about 40 mM.

Aspect 54: The aqueous pharmaceutical composition of Aspect 51, wherein said histidine is at a concentration of about 30 mM.

Aspect 55: The aqueous pharmaceutical composition of Aspect 1, further comprising acetate.

Aspect 56: The aqueous pharmaceutical composition of Aspect 55, wherein said acetate is at a concentration of about 10 mM to about 50 mM.

Aspect 57: The aqueous pharmaceutical composition of Aspect 55, wherein said acetate is at a concentration of about 20 mM to about 40 mM.

Aspect 58: The aqueous pharmaceutical composition of Aspect 55, wherein said acetate is at a concentration of about 30 mM.

Aspect 59: The aqueous pharmaceutical composition of Aspect 1, further comprising an excipient.

Aspect 60: The aqueous pharmaceutical composition of Aspect 59, wherein said excipient is selected from sorbitol, sodium chloride, sucrose, trehelose, and mannitol.

Aspect 61: The aqueous pharmaceutical composition of Aspect 60, wherein said sorbitol is at a concentration of about 180 mM to about 300 mM.

Aspect 62: The aqueous pharmaceutical composition of Aspect 60, herein said sorbitol is at a concentration of about 200 mM to about 270 mM.

Aspect 63: The aqueous pharmaceutical composition of Aspect 60, wherein said sorbitol is at a concentration of about 200 mM to about 240 mM.

Aspect 64: The aqueous pharmaceutical composition of Aspect 60, wherein said sorbitol is at a concentration of about 230 mM to about 270 mM.

Aspect 65: The aqueous pharmaceutical composition of Aspect 60, wherein said sorbitol is at a concentration of about 230 mM to about 270 mM.

Aspect 66: The aqueous pharmaceutical composition of Aspect 60, wherein said sorbitol is at a concentration of about 240 mM to about 260 mM.

Aspect 67: The aqueous pharmaceutical composition of Aspect 60, wherein said sodium chloride is at a concentration of about 100 mM to about 200 mM.

Aspect 68: The aqueous pharmaceutical composition of Aspect 60, wherein said sucrose is at a concentration of about 230 mM to about 270 mM.

Aspect 69: The aqueous pharmaceutical composition of Aspect 60, wherein said trehalose is at a concentration of about 230 mM to about 270 mM.

Aspect 70: The aqueous pharmaceutical composition of Aspect 60, wherein said mannitol is at a concentration of about 230 mM to about 270 mM.

Aspect 71: The aqueous pharmaceutical composition of Aspect 1, wherein the osmolality is about 280 mOsm/kg to about 350 mOsm/kg.

Aspect 72: The aqueous pharmaceutical composition of Aspect 1, wherein the osmolality is less than about 455 mOsm/kg.

Aspect 73: The aqueous pharmaceutical composition of any of Aspects 1 to 72, further comprising a surfactant.

Aspect 74: The aqueous pharmaceutical composition of Aspect 1, further comprising a buffer and a surfactant.

Aspect 75: The aqueous pharmaceutical composition of Aspect 74, wherein the surfactant is polysorbate 20 or polysorbate 80.

Aspect 76: The aqueous pharmaceutical composition of Aspect 1, further comprising polysorbate 80.

Aspect 77: The aqueous pharmaceutical composition of Aspect 1, further comprising polysorbate 20.

Aspect 78: The aqueous pharmaceutical composition of Aspect 74, 75, 76, or 77, wherein the concentration of surfactant is about 0.001% to about 0.1%.

Aspect 79: The aqueous pharmaceutical composition of Aspect 74, 75, 76, or 77, wherein the concentration of surfactant is about 0.005% to about 0.05%.

Aspect 80: The aqueous pharmaceutical composition of Aspect 74, 75, 76, or 77, wherein the concentration of surfactant is about 0.01%.

Aspect 81: The aqueous pharmaceutical composition of Aspect 1, wherein the composition has a pH of 5 to 7.

Aspect 82: The aqueous pharmaceutical composition of Aspect 1, wherein the composition has a pH of 5 to 6.

Aspect 83: The aqueous pharmaceutical composition of Aspect 1, wherein the composition has a pH of 5.5 to 6.5

Aspect 84: The aqueous pharmaceutical composition of Aspect 1, wherein the composition has a pH of 5.5.

Aspect 85: The aqueous pharmaceutical composition of Aspect 1, wherein the composition has a pH of 6.

Aspect 86: The aqueous pharmaceutical composition of Aspect 1, wherein the composition has a pH of 6.5.

Aspect 87: The aqueous pharmaceutical composition of Aspect 1, wherein the composition has a pH of 7.0.

Aspect 88: The aqueous pharmaceutical composition of Aspect 1, having a viscosity suitable for subcutaneous delivery with a syringe.

Aspect 89: The aqueous pharmaceutical composition of Aspect 1, wherein the composition has a viscosity of less than 21 cP.

Aspect 90: The aqueous pharmaceutical composition of Aspect 1, wherein the composition has a viscosity of less than 18 cP.

Aspect 91: The aqueous pharmaceutical composition of Aspect 1, wherein the composition has a viscosity of less than 15 cP.

Aspect 92: The aqueous pharmaceutical composition of Aspect 1, wherein the composition has a viscosity of less than 14 cP.

Aspect 93: The aqueous pharmaceutical composition of Aspect 1, wherein the composition has a viscosity of 10 cP to 14 cP.

Aspect 94: The aqueous pharmaceutical composition of Aspect 1, wherein the composition has a viscosity of 10 cP to 13 cP.

Aspect 95: The aqueous pharmaceutical composition of Aspect 1, comprising a buffer, an excipient and a surfactant.

Aspect 96: The aqueous pharmaceutical composition of Aspect 1, further comprising a buffer, wherein the buffer is histidine, acetate, succinate or phosphate.

Aspect 97: The aqueous pharmaceutical composition of Aspect 1, further comprising an excipient, wherein the excipient is sorbitol, sodium chloride, sucrose, trehalose or mannitol.

Aspect 98: The aqueous pharmaceutical composition of Aspect 1, further comprising a surfactant, wherein the surfactant is polysorbate 20 or polysorbate 80.

Aspect 99: The aqueous pharmaceutical composition of Aspect 1, comprising acetate, sorbitol, and polysorbate 80.

Aspect 100: The aqueous pharmaceutical composition of Aspect 1, wherein said acetate is a concentration of about 20 mM to about 40 mM, said sorbitol is at a concentration of about 200 mM to about 300 mM, said polysorbate 80 is at a concentration of about 0.0055% to about 0.05%, and has pH 4.5 to 5.5.

Aspect 101: The aqueous pharmaceutical composition of Aspect 100, wherein the pH is 4.5.

Aspect 102: The aqueous pharmaceutical composition of Aspect 100, wherein the pH is 5.

Aspect 103: The aqueous pharmaceutical composition of Aspect 100, wherein the pH is 5.5

Aspect 104: The aqueous pharmaceutical composition of Aspect 1, wherein said acetate is at a concentration of about 30 mM, said sorbitol is at a concentration of about 250 mM, and said polysorbate 80 is at a concentration of about 0.01% and having pH 5.5.

Aspect 105: The aqueous pharmaceutical composition of Aspect 1, comprising histidine, sorbitol, and polysorbate 80 or polysorbate 20.

Aspect 106: The aqueous pharmaceutical composition of Aspect 1, comprising acetate, sodium chloride, and polysorbate 80 or polysorbate 20.

Aspect 107: The aqueous pharmaceutical composition of Aspect 1, comprising histidine, sodium chloride, and polysorbate 80 or polysorbate 20.

Aspect 108: The aqueous pharmaceutical composition of Aspect 1, wherein said histidine is at a concentration of about 20 mM to about 40 mM, said sorbitol is at a concentration of about 230 mM to about 270 mM, and said polysorbate 20 is at a concentration of about 0.005% to about 0.05% and having pH 6 to pH 7.

Aspect 109: The aqueous pharmaceutical composition of Aspect 108, wherein the pH is 6.

Aspect 110: The aqueous pharmaceutical composition of Aspect 108, wherein the pH is 6.5.

Aspect 111: The aqueous pharmaceutical composition of Aspect 108, wherein the pH is 7.

Aspect 112: The aqueous pharmaceutical composition of Aspect 1, wherein said histidine is at a concentration of about 30 mM, said sorbitol is at a concentration of about 250 mM, said polysorbate 20 is at a concentration of about 0.01% and having pH 6.0.

Aspect 113: The aqueous pharmaceutical composition of Aspect 1, wherein the composition is suitable for subcutaneous administration.

Aspect 114: The aqueous pharmaceutical composition of Aspect 1, wherein the composition is suitable for treatment of arthritis, inflammatory bowel disease, lupus, transplant rejection or psoriasis.

Aspect 115: The aqueous pharmaceutical composition of Aspect 1, wherein the composition is suitable for treatment of arthritis.

Aspect 116: The aqueous pharmaceutical composition of Aspect 1, wherein the composition is suitable for treatment of rheumatoid arthritis.

Aspect 117: The aqueous pharmaceutical composition of Aspect 1, wherein the composition is suitable for an inflammatory bowel disease.

Aspect 118: The aqueous pharmaceutical composition of Aspect 1, wherein the composition is disposed in a syringe.

Aspect 119: The aqueous pharmaceutical composition of Aspect 1, wherein the composition is suitable for administration by a healthcare professional.

Aspect 120: The aqueous pharmaceutical composition of Aspect 1, wherein the composition is suitable for self-administered by the patient.

Aspect 121: The aqueous pharmaceutical composition of Aspect 1, wherein the composition does not comprise arginine, or citrate.

Aspect 122: The aqueous pharmaceutical composition of Aspect 1, wherein the composition is substantially free of arginine.

Aspect 123: The aqueous pharmaceutical composition of Aspect 1, wherein the composition does not comprise arginine.

Aspect 124: The aqueous pharmaceutical composition of Aspect 1, wherein the composition comprises less than 20 mM citrate.

Aspect 125: The aqueous pharmaceutical composition of Aspect 1, wherein the composition is substantially free of citrate.

Aspect 126: The aqueous pharmaceutical composition of Aspect 1, wherein the composition does not comprise citrate.

Aspect 127: An aqueous pharmaceutical composition comprising:
an anti-VLA-1 antibody comprising a light chain having the sequence of SEQ ID NO:1 and a heavy chain having the sequence of SEQ ID NO:2;
acetate at a concentration of 10 mM to 50 mM;
sorbitol at a concentration of 180 mM to 300 mM;
polysorbate 80 at 0.005% to 0.05%; and
having a pH of 4.5 to 6.0.

Aspect 128: The aqueous pharmaceutical composition of Aspect 127, wherein, said antibody concentration is at least about 160 mg/mL, at least about 165 mg/mL, at least about 175 mg/mL, at least about 180 mg/mL, at least about 190 mg/mL, or at least about 200 mg/mL.

Aspect 129: The aqueous pharmaceutical composition of Aspect 127, wherein, said antibody at a concentration of about 155 mg/mL to about 200 mg/mL, about 160 mg/mL to about 200 mg/mL, or about 170 mg/mL to about 200 mg/mL.

Aspect 130: The aqueous pharmaceutical composition of Aspect 127, wherein, said antibody concentration is about 180 mg/mL.

Aspect 131: The aqueous pharmaceutical composition of Aspect 127, wherein said acetate is at a concentration of 20 mM to 40 mM.

Aspect 132: The aqueous pharmaceutical composition of Aspect 127, wherein said acetate is at a concentration of about 30 mM.

Aspect 133: The aqueous pharmaceutical composition of Aspect 127, wherein said sorbitol is at a concentration of 200 mM to 300 mM.

Aspect 134: The aqueous pharmaceutical composition of Aspect 127, wherein said sorbitol is at a concentration of 200 mM to 275 mM.

Aspect 135: The aqueous pharmaceutical composition of Aspect 127, wherein said sorbitol is at a concentration of 225 mM to 275 mM.

Aspect 136: The aqueous pharmaceutical composition of Aspect 127, wherein said sorbitol is at a concentration of about 250 mM.

Aspect 137: The aqueous pharmaceutical composition of Aspect 127, wherein said polysorbate 80 is at a concentration of about 0.005% to about 0.05%.

Aspect 138: The aqueous pharmaceutical composition of Aspect 127, wherein said polysorbate 80 is at a concentration of about 0.001% to about 0.05%.

Aspect 139: The aqueous pharmaceutical composition of Aspect 127, wherein said polysorbate 80 is at a concentration of about 0.01%.

Aspect 140: The aqueous pharmaceutical composition of Aspect 127, having pH 5.5.

Aspect 141: The aqueous pharmaceutical composition of Aspect 127, wherein the osmolality is about 280 mOsm/kg to about 350 mOsm/kg.

Aspect 142: The aqueous pharmaceutical composition of Aspect 127, comprising
an anti-VLA-1 antibody comprising a light chain having the sequence of SEQ ID NO:1 and a heavy chain having the sequence of SEQ ID NO:2 at a concentration of about 170 mg/mL to about 210 mg/mL,
acetate at a concentration of about 25 mM to about 35 mM,
sorbitol at a concentration of about 210 mM to 250 mM, and
polysorbate 80 at about 0.005% to about 0.02%, at pH 5.5.

Aspect 143: The aqueous pharmaceutical composition of Aspect 127, comprising:
an anti-VLA-1 antibody comprising a light chain having the sequence of SEQ ID NO:1 and a heavy chain having the sequence of SEQ ID NO:2 at 185 to 195 mg/mL;
acetate at a concentration of about 30 mM;
sorbitol at a concentration of about 250 mM;
polysorbate 80 at about 0.01%; and having a pH of about 5.5.

Aspect 144: The aqueous pharmaceutical composition of Aspect 127, wherein said antibody is at about 190 mg/mL.

Aspect 145: An aqueous pharmaceutical composition comprising:
an anti-VLA-1 antibody comprising a light chain having the sequence of SEQ ID NO:1 and a heavy chain having the sequence of SEQ ID NO:2;
histidine at a concentration of 10 mM to 50 mM;
sorbitol at a concentration of 180 mM to 300 mM;
polysorbate 20 or polysorbate 80 at from about 0.005% to 0.05%; and having a pH from 5.5 to 7.0.

Aspect 146: The aqueous pharmaceutical composition of Aspect 145, comprising:
an anti-VLA-1 antibody comprising a light chain having the sequence of SEQ ID NO:1 and a heavy chain having the sequence of SEQ ID NO:2 at 185 to 195 mg/mL;
histidine at a concentration of about 30 mM;
sorbitol at a concentration of about 250 mM;
polysorbate 80 or polysorbate 20 at about 0.01%; and having a pH of about 5.5.

Aspect 147: The aqueous pharmaceutical composition of Aspect 145, comprising polysorbate 20 from about 0.005% to about 0.05%.

Aspect 148: The aqueous pharmaceutical composition of Aspect 145, comprising polysorbate 80 from about 0.005% to about 0.05%.

Aspect 149: The aqueous pharmaceutical composition of Aspect 145, wherein, said antibody concentration is at least about 160 mg/mL, at least about 165 mg/mL, at least about 175 mg/mL, at least about 180 mg/mL, at least about 190 mg/mL or at least about 200 mg/mL.

Aspect 150: The aqueous pharmaceutical composition of Aspect 145, wherein, said antibody at a concentration of about 155 mg/mL to about 200 mg/mL, about 160 mg/mL to about 200 mg/mL, or about 170 mg/mL to about 200 mg/mL.

Aspect 151: The aqueous pharmaceutical composition of Aspect 145, wherein, said antibody concentration is about 180 mg/mL.

Aspect 152: The aqueous pharmaceutical composition of Aspect 127, comprising:
an anti-VLA-1 antibody comprising a light chain having the sequence of SEQ ID NO:1 and a heavy chain having the sequence of SEQ ID NO:2 at 185 to 195 mg/mL;
acetate at a concentration of about 30 mM;
sodium chloride at a concentration of about 150 mM;
polysorbate 80 or polysorbate 20 at about 0.01%; and having a pH of about 5 to 7.

Aspect 153: The aqueous pharmaceutical composition of Aspect 127, wherein, said antibody concentration is at least about 160 mg/mL, at least about 165 mg/mL, at least about 175 mg/mL, at least about 180 mg/mL, at least about 190 mg/mL or at least about 200 mg/mL.

Aspect 154: An aqueous pharmaceutical composition comprising:
an anti-VLA-1 antibody comprising a light chain having the sequence of SEQ ID NO:1 and a heavy chain having the sequence of SEQ ID NO:2;
histidine at a concentration of about 30 mM;
sodium chloride at a concentration of about 150 mM;
polysorbate 20 or polysorbate 80 at from about 0.01%; and
having a pH about 5 to 7.

Aspect 155: The aqueous pharmaceutical composition of Aspect 154, wherein, said antibody concentration is at least about 160 mg/mL, at least about 165 mg/mL, at least about 175 mg/mL, at least about 180 mg/mL, at least about 190 mg/mL or at least about 200 mg/mL.

Aspect 156: The aqueous pharmaceutical composition of Aspect 145, wherein said histidine is at a concentration of about 20 mM to about 40 mM.

Aspect 157: The aqueous pharmaceutical composition of Aspect 145, wherein said histidine is at a concentration of about 30 mM.

Aspect 158: The aqueous pharmaceutical composition of Aspect 145, wherein said sorbitol is at a concentration of about 220 mM to about 280 mM.

Aspect 159: The aqueous pharmaceutical composition of Aspect 145, wherein said sorbitol is at a concentration of about 240 mM to about 260 mM.

Aspect 160: The aqueous pharmaceutical composition of Aspect 145, wherein said sorbitol is at a concentration of about 250 mM.

Aspect 161: The aqueous pharmaceutical composition of Aspect 145, wherein said polysorbate 20 is at a concentration of about 0.005% to about 0.05%.

Aspect 162: The aqueous pharmaceutical composition of Aspect 145, wherein said polysorbate 20 is at a concentration of about 0.01%.

Aspect 163: The aqueous pharmaceutical composition of Aspect 145, having pH 6.0.

Aspect 164: The aqueous pharmaceutical composition of Aspect 145, wherein the osmolality is about 280 mOsm/kg to about 350 mOsm/kg.

Aspect 165: The aqueous pharmaceutical composition of Aspect 145, comprising anti-VLA-1 antibody comprising a light chain having the sequence of SEQ ID NO:1 and a heavy chain having the sequence of SEQ ID NO:2 at a concentration of about 160 mg/mL to about 200 mg/mL, histidine at a concentration of about 25 mM to about 35 mM, sorbitol at a concentration of about 240 mM to about 260 mM, and polysorbate 20 at a concentration of about 0.005% to about 0.02%, at pH 6.

Aspect 166: The aqueous pharmaceutical composition of Aspect 145, comprising:

an anti-VLA-1 antibody comprising a light chain having the sequence of SEQ ID NO:1 and a heavy chain having the sequence of SEQ ID NO:2 at 170 to 180 mg/mL;

histidine at a concentration of about 30 mM;

sorbitol at a concentration of about 250 mM;

polysorbate 20 at a concentration of about 0.01%; and having a pH of about 6.

Aspect 167: The aqueous pharmaceutical composition of Aspect 145, wherein said antibody is at a concentration of about 180 mg/mL.

Aspect 168: A unit dosage form of an aqueous pharmaceutical composition of any of Aspects 1, 127, 142, 143, 145, 166 or 167.

Aspect 169: The unit dosage form of Aspect 168, comprising at least about 160 mg of said antibody, at least about 170 mg of said antibody, at least about 180 mg of said antibody, at least about 190 mg of said antibody, or at least about 200 mg of said antibody.

Aspect 170: The unit dosage form of Aspect 168, comprising said antibody at about 155 mg to about 165 mg, about 165 mg to about 175 mg, about 175 mg to about 185 mg, about 185 mg to about 195 mg, about 195 mg to about 205 mg, about 205 mg to about 215 mg, about 215 mg to about 225 mg.

Aspect 171: The unit dosage form of Aspect 168, comprising said antibody at about 160 mg to about 210 mg.

Aspect 172: The unit dosage form of Aspect 168, comprising about 180 mg of said antibody.

Aspect 173: The unit dosage form of Aspect 168, comprising about 190 mg of said antibody.

Aspect 174: The unit dosage form of Aspect 168, which, when administered to a human will deliver antibody at about 2.0 mg per kg of body weight to about 4.0 mg per kg of body weight to the human.

Aspect 175: The unit dosage form of Aspect 168, having a volume of about 0.25 mL to about 1.5 mL.

Aspect 176: The unit dosage form of Aspect 168, having a volume of about 1 mL.

Aspect 177: A kit comprising the unit dosage form of Aspect 168.

Aspect 178: A plurality of unit dosage forms of an aqueous pharmaceutical composition of any of Aspects 1, 127, 142, 143, 145, 166 or 167.

Aspect 179: The plurality of unit dosage forms of Aspect 178, wherein said plurality is two.

Aspect 180: The plurality of unit dosage forms of Aspect 179, wherein said dosage forms, taken together, comprise at least about 160 mg of said antibody, at least about 170 mg of said antibody, at least about 180 mg of said antibody, at least about 190 mg of said antibody, or at least about 200 mg of said antibody.

Aspect 181: The plurality of unit dosage forms of Aspect 178, wherein each dosage form contains an equal amount of antibody.

Aspect 182: The plurality of unit dosage forms of Aspect 179, wherein said dosage forms, taken together, comprise said antibody at about 155 mg to about 165 mg, about 165 mg to about 175 mg, about 175 mg to about 185 mg, about 185 mg to about 195 mg, about 195 mg to about 205 mg, about 205 mg to about 215 mg, or about 215 mg to about 225 mg.

Aspect 183: The plurality of unit dosage forms of Aspect 182, wherein each dosage form contains an equal amount of antibody.

Aspect 184: The plurality of unit dosage forms of Aspect 179, wherein said dosage forms, taken together, comprise said antibody at about 160 mg to about 210 mg.

Aspect 185: The plurality of unit dosage forms of Aspect 184, wherein each dosage form contains an equal amount of antibody.

Aspect 186: The plurality of unit dosage forms of Aspect 179, wherein said dosage forms, taken together, comprise about 180 mg of said antibody.

Aspect 187: The plurality of unit dosage forms of Aspect 186, wherein each dosage form contains an equal amount of antibody.

Aspect 188: The plurality of unit dosage forms of Aspect 179, wherein said dosage forms, taken together, comprise about 190 mg of said antibody.

Aspect 189: The plurality of unit dosage forms of Aspect 188, wherein each dosage form contains an equal amount of antibody.

Aspect 190: The plurality of unit dosage forms of Aspect 179, wherein said dosage forms, taken together, when administered to a human will deliver about 2 mg and about 4 mg antibody per kg of body weight to the human.

Aspect 191: The plurality of unit dosage forms of Aspect 190, wherein each dosage form contains an equal amount of antibody.

Aspect 192: The plurality of unit dosage forms of Aspect 179, wherein said dosage forms each have a volume of about 0.25 mL to about 1.5 mL.

Aspect 193: The plurality of unit dosage forms of Aspect 178, wherein said dosage forms each have a volume of about 1 mL.

Aspect 194: A kit comprising the plurality of unit dosage forms of Aspect 178.

Aspect 195: A container, having disposed therein, an aqueous pharmaceutical composition of any of Aspects 1, 127, 142, 143, 145, 166 or 167.

Aspect 196: The container of Aspect 195, having disposed therein, a unit dosage formulation of any of Aspects 127 or 145.

Aspect 197: The container of Aspect 195, wherein said container is a delivery device.

Aspect 198: The container of Aspect 195, wherein said container is suitable for subcutaneous administration.

Aspect 199: The container of Aspect 195, wherein said container is a syringe.

Aspect 200: A method of administering an aqueous pharmaceutical composition of Aspects 1, 127, or 145 to a patient, comprising one or both of:

i) activating a delivery device; and ii) administering said antibody disposed in said delivery device to said patient, to thereby administer said composition.

Aspect 201: The method of Aspect 200, wherein activating comprises one of more of removing said device from packaging, removing a cover from the needle or orifice of said device, or shaking said device.

Aspect 202: The method of Aspect 200, further comprising inspecting said device for the presence of precipitate, colored material, or turbidity, or opalescence.

Aspect 203: The method of Aspect 200, wherein said patient performs one or both of steps i and ii.

Aspect 204: The method of Aspects 200, wherein the patient has an inflammatory disorder.

Aspect 205: The method of Aspect 200, wherein the patient has a disorder selected from the group consisting of arthritis, inflammatory bowel disease, lupus, transplant rejection, and psoriasis.

Aspect 206: A method of treating a patient in need of anti-VLA-1 therapy, comprising administering to said patient an effective amount of the composition of Aspect 1.

Aspect 207: The method of Aspect 206, wherein the patient has an inflammatory disorder.

Aspect 208: The method of Aspect 206, wherein the patient has a disorder selected from the group consisting of arthritis, inflammatory bowel disease, lupus, transplant rejection, and psoriasis.

Aspect 209: The method of Aspect 206, wherein the composition is administered as a regimen.

Aspect 210: The method of Aspect 206, further comprising selecting said patient for said treatment.

Aspect 211: The method of Aspect 210, wherein the patient has rheumatoid arthritis, and has demonstrated an inadequate response to a prior alternate treatment for rheumatoid arthritis.

Aspect 212: The method of Aspect 210, wherein the patient has rheumatoid arthritis, and is selected on the basis of having demonstrated an inadequate response to a prior alternate treatment for rheumatoid arthritis.

Aspect 213: The method of Aspect 211, wherein the prior alternate treatment for rheumatoid arthritis is a DMARD (Disease Modifying Antirheumatic Drug) or a TNF-α (Tumor Necrosis Factor-α) inhibitor.

Aspect 214: The method of Aspect 213, wherein the DMARD is methotrexate, leflunomide, sulfasalazine, or hydroxychloroquine.

Aspect 215: The method of Aspect 213, wherein the TNF-α inhibitor is infliximab, adalimumab, certolizumab pegol, golimumab or etanercept.

Aspect 216: The method of Aspect 206, further comprising administering to the patient a second therapeutic agent, wherein the second therapeutic agent is a corticosteroid or an anti-inflammatory.

Aspect 217: A method of treating a patient in need of anti-VLA-1 therapy, comprising administering to said patient an effective amount of a composition comprising
  180 mg/mL anti-VLA-1 antibody,
  30 mM histidine,
  250 mM sorbitol,
  0.1% polysorbate 20, and
  having pH 6.

Aspect 218: A method of treating a patient in need of anti-VLA-1 therapy, comprising administering to said patient an effective amount of a composition comprising
  180 mg/mL anti-VLA-1 antibody,
  30 mM histidine,
  150 mM sodium chloride,
  0.1% polysorbate 20, and
  having pH 6.

Aspect 219: A method of treating a patient in need of anti-VLA-1 therapy, comprising administering to said patient an effective amount of a composition comprising
  190 mg/mL anti-VLA-1 antibody,
  30 mM acetate,
  250 mM sorbitol,
  0.1% polysorbate 80, and
  having pH 5.5.

Aspect 220: A method of treating a patient in need of anti-VLA-1 therapy, comprising administering to said patient an effective amount of a composition comprising
  190 mg/mL anti-VLA-1 antibody,
  30 mM acetate,
  250 mM sodium chloride,
  0.1% polysorbate 80, and
  having pH 5.5.

Aspect 221: A method of evaluating a patient comprising (i) determining if the patient meets a preselected criterion, and (ii) if the patient meets said preselected criterion approving, providing, prescribing, or administering a composition of Aspect 1.

Aspect 222: The method of Aspect 221, wherein the patient has rheumatoid arthritis, and the patient has had an inadequate response to a prior alternate treatment for rheumatoid arthritis.

Aspect 223: A method of evaluating a patient comprising (i) determining if the patient meets a preselected criterion, and (ii) if the patient meets said preselected criterion approving, providing, prescribing, or administering a composition comprising
  180 mg/mL anti-VLA-1 antibody,
  30 mM histidine,
  250 mM sorbitol,
  0.1% polysorbate 20, and
  having pH 6.

Aspect 224: A method of evaluating a patient comprising (i) determining if the patient meets a preselected criterion, and (ii) if the patient meets said preselected criterion approving, providing, prescribing, or administering a composition comprising
  180 mg/mL anti-VLA-1 antibody,
  30 mM histidine,
  150 mM sodium chloride,
  0.1% polysorbate 20, and
  having pH 6.

Aspect 225: A method of evaluating a patient comprising (i) determining if the patient meets a preselected criterion, and (ii) if the patient meets said preselected criterion approving, providing, prescribing, or administering a composition comprising
  190 mg/mL anti-VLA-1 antibody,
  30 mM acetate,
  250 mM sorbitol,
  0.1% polysorbate 80, and
  having pH 5.5.

Aspect 226: A method of evaluating a patient comprising (i) determining if the patient meets a preselected criterion, and (ii) if the patient meets said preselected criterion approving, providing, prescribing, or administering a composition comprising
  190 mg/mL anti-VLA-1 antibody,
  30 mM acetate,
  250 mM sodium chloride,
  0.1% polysorbate 80, and
  having pH 5.5.

Aspect 227: A method of making an aqueous composition comprising 160 mg/mL to 210 mg/mL of an anti-VLA-1 antibody comprising, combining said antibody, a buffer, an excipient, and a surfactant in proportion to obtain a stable aqueous composition comprising 160 mg/mL to 210 mg/mL of said anti-VLA-1 antibody.

Aspect 228: The method of Aspect 227, wherein said buffer is histidine.

Aspect 229: The method of Aspect 227, wherein said buffer is acetate.

Aspect 230: The method of Aspect 227, wherein said surfactant is polysorbate 80.

Aspect 231: The method of Aspect 227, wherein said surfactant is polysorbate 20.

Aspect 232: The method of Aspect 227, wherein said anti-VLA-1 antibody comprises a light chain having the sequence of SEQ ID NO:1 and a heavy chain having the sequence of SEQ ID NO:2.

Aspect 233: The method of Aspect 227, wherein the composition comprises a viscosity of about 10 cP to about 20 cP.

Aspect 234: The method of Aspect 227, wherein the composition comprises a viscosity of about 10 cP to about 15 cP.

Aspect 235: The method of Aspect 227, wherein the composition comprises a viscosity of about 10 cP to about 14 cP.

Aspect 236: The method of Aspect 227, wherein said composition is the composition of Aspect 1.

Aspect 237: The method of Aspect 227, wherein said composition comprises
180 mg/mL anti-VLA-1 antibody,
30 mM histidine,
250 mM sorbitol,
0.1% polysorbate 20, and
having pH 6.

Aspect 238: The method of Aspect 227, wherein said composition comprises
180 mg/mL anti-VLA-1 antibody,
30 mM histidine,
150 mM sodium chloride,
0.1% polysorbate 20, and
having pH 6.

Aspect 239: The method of Aspect 227, wherein said composition comprises
190 mg/mL anti-VLA-1 antibody,
30 mM acetate,
250 mM sorbitol,
0.1% polysorbate 80, and
having pH 5.5.

Aspect 240: The method of Aspect 227, wherein said composition comprises
190 mg/mL anti-VLA-1 antibody,
30 mM acetate,
250 mM sodium chloride,
0.1% polysorbate 80, and
having pH 5.5.

Aspect 241: A method of evaluating the quality of a composition of Aspect 1, comprising:
evaluating the composition for a preselected parameter, and
determining whether said value meets a preselected criteria, thereby evaluating the quality of a composition.

Aspect 242: The method of Aspect 241, further comprising, responsive to said evaluation, said composition is: is classified, selected, accepted or discarded, released or withheld, processed into a drug product, shipped, moved to a different location, formulated, labeled, packaged, released into commerce, or sold or offered for sale.

Aspect 243: The method of Aspect 241, wherein said preselected parameter is selected from aggregation, stability, color, clarity, viscosity, or plunger force.

Aspect 244: The method of Aspect 241, wherein the composition evaluated is provided as a unit dosage form.

Aspect 245: An aqueous pharmaceutical composition comprising:
(i) an anti-VLA-1 antibody in an amount effective for treatment of inflammatory disease; and
(ii) means for delivering said effective amount of said anti-VLA-1 antibody in a subcutaneous formulation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1D is the cDNA (SEQ ID NO: 6) and amino acid sequence of human VLA-1 (Ref Seq No. NP_852478; SEQ ID NO:3). The I domain is underlined (see FIGS. 1A and 1B).

FIGS. 2A and 2B are sequence fragments of a light chain polypeptide (SEQ ID NO:4) and a heavy chain polypeptide (SEQ ID NO:5), respectively, for an anti-VLA-1 antibody. These sequence fragments include the light chain and heavy chain CDRs, respectively.

FIG. 3 is the sequence of the light chain polypeptide (SEQ ID NO:1) of SAN-300.

FIG. 4 is the sequence of the heavy chain polypeptide (SEQ ID NO:2) of SAN-300.

DETAILED DESCRIPTION

Figure 5:
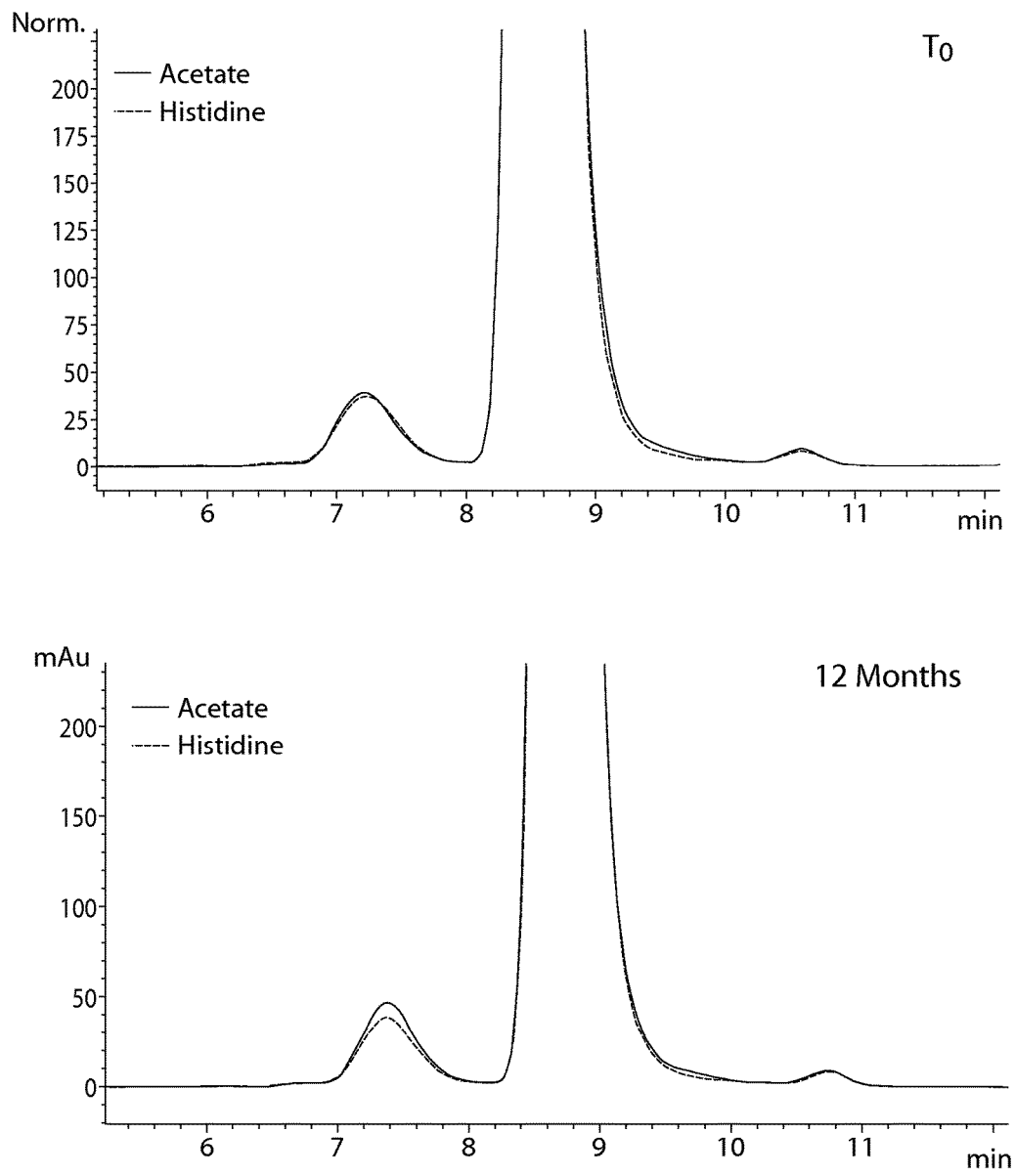
FIG. 5 shows representative chromatogram overlays for high-concentration SAN-300 formulations. The top panel shows NB1206p86A (solid line) and NB1206p86B (dashed line) at the initial time point. The bottom panel shows NB1206p86A (solid line) and NB1206p86B (dashed line) after 12 months at 2-8° C.

Provided herein are stable formulations of an anti-VLA-1 antibody particularly well suited for subcutaneous (SC) administration. The formulations featured in the invention contain from about ≥100 to about 225 mg/mL humanized anti-VLA-1 antibody, such as SAN-300.

Pharmaceutical Compositions

The compositions described herein are formulated as pharmaceutical compositions. An anti-VLA-1 antibody, such as SAN-300, can be provided, for example, in a buffered solution at a concentration of about 160 mg/mL to about 210 mg/mL, for example, about 160 mg/mL to about 200 mg/mL, about 170 mg/mL to about 190 mg/mL; for example, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL. In one embodiment, the anti-VLA-1 antibody, such as SAN-300, is provided in a buffered solution at a concentration greater than about 100 mg/mL and less than about 225 mg/mL. In another embodiment, the formulation is prepared at a higher concentration, for example, about 200 mg/mL to about 210 mg/mL, and then diluted back to the desired concentration, such as to about 180 mg/mL to about 190 mg/mL. In one embodiment, the formulation is administered at the stock concentration (for example, at about 110 mg/mL, about 120 mg/mL, about 130 mg/mL, about 140 mg/mL, about 150 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL).

The composition can be stored at a suitable temperature, such as at about 2° C. to about 8° C., for example, at about 4° C., about 5° C., about 6° C., or about 7° C.

In one embodiment, the anti-VLA-1 antibody can be formulated with an excipient, such as sorbitol or NaCl, a histidine buffer, and a surfactant, such as polysorbate 20 or polysorbate 80.

Acetate buffers are known in the art and include, for example, aqueous solutions of sodium acetate, triethylammonium acetate buffer, and Tris-acetate-EDTA buffer, brought to the proper pH.

Histidine buffers are also known in the art and include, for example, aqueous solutions of D-histidine, D-histidine monochloride monohydrate, DL-histidine, DL-histidine monochloride monohydrate, L-histidine, or L-histidine monochloride monohydrate, brought to the proper pH with either hydrochloric acid or sodium hydroxide, or other acid or base known in the art.

In one embodiment, the anti-VLA-1 antibody formulation can be substantially free of citrate. In another embodiment, the anti-VLA antibody formulation is substantially free of arginine.

A pharmaceutical composition may also include solvents, dispersion media, coatings, antibacterial and antifungal agents, isotonic and absorption delaying agents, and the like that are physiologically compatible. An "isotonic" formulation has equal osmotic pressure, such as caused by equal solute concentration inside and outside a cell.

A "pharmaceutically acceptable salt" refers to a salt that retains the desired biological activity of the antibody and does not impart any undesired toxicological effects (see, for example, Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, free amino acids, and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The formulations featured herein can include a pharmaceutically acceptable excipient, such as a surfactant, such as polysorbate 80, or polysorbate 20. In one embodiment, the formulations featured herein include a surfactant at a concentration of about 0.001% to about 0.8%, for example, about 0.005% to about 0.05%; for example, about 0.01% to about 0.01%. As used herein, the concentration of surfactant is provided as a percentage of weight to volume (w/v)

The pharmaceutical compositions containing anti-VLA-1 antibodies are in the form of a liquid solution, such as an injectable and infusible solution. Such compositions can be administered by a parenteral mode, such as by subcutaneous administration. The formulations are also suitable for intravenous (IV) administration, for example, when diluted into an acceptable infusion matrix, such as normal saline. The phrases "parenteral administration" and "administered parenterally" as used herein mean modes of administration other than enteral and topical administration, usually by injection, and include subcutaneous administration, as well as intramuscular, intravenous, intracapsular, intraorbital, intracardiac, intradermal, intraperitoneal, transtracheal, subcuticular, subcapsular, subarachnoid, intraspinal, epidural and intrasternal injection and infusion. In one embodiment, the formulations described herein are administered subcutaneously.

Pharmaceutical compositions are sterile and stable under the conditions of manufacture and storage. A pharmaceutical composition can also be tested to insure it meets regulatory and industry standards for administration.

Sterile injectable solutions can be prepared by incorporating an anti-VLA-1 antibody described herein in the required amount in an appropriate formulation as described above, followed by filtered sterilization.

In one embodiment, the final anti-VLA-1 antibody formulation is packaged as a liquid in a 3.0 mL fill vial with an extractable minimum volume of 1 mL. For example, the fill vial can include about 1.1 mL to about 1.5 mL (for example, about 1.1 mL, about 1.2 mL, about 1.3 mL, about 1.4 mL) of antibody formulation. In another embodiment, that antibody formulation is packaged in a pre-filled syringe, in an amount such that 1 mL of solution is injected into a patient upon use, and the 1 mL solution delivers the desired amount of antibody, for example, ≥100 mg SAN-300 to 225 mg SAN-300, for example, 180 mg SAN-300 or 190 mg SAN-300.

In some embodiments, parameters that describe the formulations, for example, parameters that may appear on the product label, are characterized. Such parameters include, for example, color (typically colorless to slightly yellow, or colorless to yellow), clarity (typically clear to slightly opalescent, or clear to opalescent), and viscosity (typically about 5 cP to about 30 cP when measured at ambient temperature, such as at about 20° C. to about 30° C.). Such parameters can be measured by methods known in the art. For example, clarity can be measured using commercially available opalescence standards (available from, for example, HunterLab Associates, Inc., Reston, Va.).

In some embodiments, the stability of the antibody formulations is assayed. Exemplary methods include, for example, aggregation studies, oxidation studies, fragmentation studies, sialylation studies, isoelectric point studies, half-antibody studies, heavy and light chain parity studies, and analysis of secondary structure, such as by circular dichroism; thermal denaturation, such as by circular dichroism of differential scanning calorimetry; tryptophan environment, such as by fluorescence; IgG fold, such as by far UV circular dichroism; and aromatic residue environment, such as by UV-Visible ("UV-Vis") spectroscopy.

SAN-300 and Other Anti-VIA-1 Antibodies

Antibodies suitable for an anti-VLA-1 antibody formulation described herein include SAN-300, a humanized α1 integrin binding antibody. The amino acid sequence of the light chain and heavy chain of SAN-300 prior to any in vivo modifications (such as clipping of amino acids) is shown in FIG. 3 and FIG. 4, respectively. The amino acid sequence of the light chain and heavy chain variable domains is shown in FIGS. 2A and 2B, respectively.

VLA-1 is a major collagen I, collagen IV and laminin receptor. It is expressed in many different cell types including those of hematopoietic, neuronal and mesenchymal origin. The VLA-1 integrin plays an important role in chronic inflammation and fibrosis processes. The α chain of VLA-1 contains an inserted I domain (also known as an A domain) that plays a central role in ligand binding. The I-domain of human VLA-1 is located at about from amino acids Thr145-Glu336 of VLA-1 (Ref Seq No. NP_852478; FIGS. 1A-1D). The I-domain has a dinucleotide-binding fold characterized by a β-sheet surrounded by α-helices. The I domain contains a conserved metal ion-dependent-adhesion site (MIDAS) that has been identified to constitute part of the ligand binding site. The acidic residue side-chains of a bound integrin ligand, such as a collagen, coordinates the metal ion of the I domain MIDAS site. Crystal structure studies have indicated that SAN-300 uses an aspartic acid to coordinate the VLA-1 I domain metal ion. SAN-300 inhibits VLA-1 at least by sterically preventing binding of the I-domain to collagen (Karpuses et al., *J. Mol. Biol.* 327: 1031-1041, 2003).

Anti-VLA-1 antibodies can block the interaction of pro-inflammatory leukocytes with components of the extracellular matrix including, but not limited to collagens, e.g., collagen I and IV, laminin and fibronectin. The VLA-1 is expressed, for example, on lymphocytes, and the I-domain of VLA-1 is important for binding of lymphocytes to extracellular matrix proteins, such as fibronectin (Fabbri et al., *Tissue Antigens* 48:47-51, 1996).

SAN-300 binds the α1 I domain of VLA-1 (see, e.g., U.S. Pat. No. 7,358,054). Further SAN-300 binds human but not rat α1-I domain (Id.).

SAN-300 and related anti-VLA-1 antibodies are described, for example, in U.S. Pat. No. 6,955,810, U.S. Pat. No. 7,462,353, U.S. Pat. No. 7,358,054, U.S. Pat. No. 7,723,073, and U.S. Pat. No. 7,910,099. The contents of these patents are incorporated herein by reference in their entirety. SAN-300 is a humanized version of murine monoclonal AQC2 antibody (see, for example, U.S. Pat. No. 6,955,810, and U.S. Pat. No. 7,358,054). Several additional anti-VLA-1 monoclonal antibodies include 1B3.1 (Chess et al. U.S. Pat. No. 5,788,966), TS2/7 and FB12 (Fabbri et al., *Tissue Antigens* 48:47-51, 1996), 5E8D9 (Luque et al., *FEBS Letters* 346:278-284, 1994), and SR-84 (Rikkonen et al., *Biochem. Biophys. Res. Commun.* 209:205-212, 1995).

Some anti-VLA-1 antibodies recognize epitopes of the α1 subunit that are involved in binding to a cognate ligand, such as collagen and laminin. Many such antibodies inhibit binding of VLA-1 to the cognate ligands.

An exemplary anti-VLA-1 antibody has one or more CDRs, for example, all three HC CDRs and/or all three LC CDRs of a particular antibody disclosed herein, or CDRs that are, in sum, at least 80%, at least 85%, at least 90%, at least 92%, at least 94%, at least 95%, at least 96%, at least 97%, at least 98%, or at least 99% identical to such an antibody, for example a SAN-300 antibody. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70%, at least 80%, at least 85%, at least 90%, at least 92%, at least 95%, at least 97%, at least 98%, at least 99%, or at least 100% identical to the amino acid sequence of the HC and/or LC variable domain of an antibody described herein, such as a SAN-300 antibody. The amino acid sequence of the HC and/or LC variable domain sequence can differ by at least one amino acid, but no more than ten, eight, six, five, four, three, or two amino acids from the corresponding sequence of an antibody described herein, such as a SAN-300 antibody. For example, the differences may be primarily or entirely in the framework regions.

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (for example, FR1, FR2, FR3, and/or FR4) of the HC and/or LC variable domain are at least 70%, at least 80%, at least 85%, at least 90%, at least 92%, at least 95%, at least 97%, at least 98%, at least 99%, or at least 100% identical to corresponding framework regions of the HC and LC variable domains of an antibody described herein. In one embodiment, one or more heavy or light chain framework regions (for example, HC FR1, FR2, and FR3) are at least 70%, at least 80%, at least 85%, at least 90%, at least 95%, at least 96%, at least 97%, at least 98%, or at least 100% identical to the sequence of corresponding framework regions from a human germline antibody.

Suitable antibodies for use in the methods described herein include: antibodies having one, two, or three light chain (LC) CDRs and one, two or three heavy chain (HC) CDRs, and in an embodiment all six CDRs, having the sequence of an antibody disclosed in U.S. Pat. No. 7,358,054; antibodies wherein each of the CDRs differs by no more than 1 or 2 amino acids from the CDRs of an antibody disclosed in U.S. Pat. No. 7,358,054 (variant amino acids, when used in this context, can be independently, or as a group, conservative on non-conservative changes).

In one embodiment, an anti-VLA-1 antibody useful for the methods described herein includes a LC variable region, a HC variable region, or both, from an antibody disclosed in U.S. Pat. No. 7,358,054; an antibody that binds an overlapping epitope with, or competes for binding with an antibody disclosed in U.S. Pat. No. 7,358,054; an antibody having a LC variable region, a HC variable region, or both, having at least 90%, at least 95%, or at least 99% amino acid homology with the corresponding portions of an antibody disclosed in U.S. Pat. No. 7,358,054; an antibody having a LC variable region which differs by no more than 10 amino acid residues, 5 amino acid residues, or 1 amino acid residue, a HC variable region which differs by no more than 10 amino acid residues, 5 amino acid residues, or 1 amino acid residue, or both, from the corresponding portions of an antibody disclosed in U.S. Pat. No. 7,358,054.

In one embodiment, an anti-VLA-1 antibody useful for the methods described herein includes a light chain variable region that is the same as or differs by no more than 10 amino acids, 5 amino acids, 3 amino acids, or 1 amino acid from the sequence of SEQ ID NO:4 (FIG. 2A), and a heavy chain variable region that is the same as or differs by no more than 10 amino acids, 5 amino acids, 3 amino acids, or 1 amino acid from the sequence of SEQ ID NO:5 (FIG. 2B).

In one embodiment, an anti-VLA-1 antibody has a light chain sequence that is the same as or differs by no more than 10 amino acids, 5 amino acids, 3 amino acids, or 1 amino acid from the sequence of SEQ ID NO:1 (FIG. 3) and a heavy chain sequence that is the same as or differs by no more than 10 amino acids, 5 amino acids, 3 amino acids, or 1 amino acid from the sequence of SEQ ID NO:2 (FIG. 4).

As discussed herein, exemplary anti-VLA-1 antibodies useful in the methods described herein include the antibodies described in U.S. Pat. No. 7,358,054, which is incorporated herein by reference in its entirety. Antibodies described in U.S. Pat. No. 7,358,054, include, for example, monoclonal antibody AJH10 (ATCC PTA-3580; deposited on Aug. 2, 2001, with the American Type Culture Collection, 10801 University Boulevard, Manassas, Va. 20110-2209), hAQC2 (ATCC PTA-3275; deposited on Apr. 18, 2001), haAQC2 (ATCC PTA-3274; deposited on Apr. 18, 2001), hsAQC2 (ATCC PTA-3356; deposited on May 4, 2001) and mAQC2 (ATCC PTA-3273). All of these antibodies were deposited under the Budapest Treaty.

In one embodiment, an anti-VLA-1 antibody useful for the methods described herein includes a light chain polypeptide comprising the sequence of SEQ ID NO:4 (FIG. 2A), and a heavy chain polypeptide comprising the sequence of SEQ ID NO:5 (FIG. 2B).

In one embodiment, an anti-VLA-1 antibody has a light chain sequence comprising the sequence of SEQ ID NO:1 (FIG. 3) and a heavy chain sequence comprising the sequence of SEQ ID NO:2 (FIG. 4). Other anti-VLA-1 antibodies include, e.g., monoclonal antibody 1B3 (ATCC HB-10536) described in U.S. Pat. Nos. 5,391,481 and 5,788,966, and Ha31/8.

In one embodiment, an anti-VLA-1 antibody inhibits the interaction between VLA-1 and a VLA-1 ligand (e.g., collagen), such as by physically blocking the interaction, decreasing the affinity of VLA-1 for its counterpart, disrupting or destabilizing VLA-1 complexes, sequestering VLA-1, or targeting VLA-1 for degradation. In one embodiment, the antibody can bind to VLA-1 at one or more amino acid residues that participate in the VLA-1/ligand binding interface. Such amino acid residues can be identified, e.g., by alanine scanning. In another embodiment, the antibody can bind to residues that do not participate in the VLA-1/ligand binding. For example, the antibody can alter a conformation of VLA-1 and thereby reduce binding affinity, or the antibody may sterically hinder VLA-1/ligand binding. In one embodiment, the antibody can reduce activation of a VLA-1-mediated event or activity.

Administration

The anti-VLA-1 antibody formulations described herein can be administered to a subject, such as a human subject, by a variety of methods. Typically, administration is by subcutaneous injection.

The formulation can be administered as a fixed dose, or in a mg/kg dose. Typically the administration is in a fixed dose. For example, the formulation is administered at a fixed unit dose of anti-VLA-1 antibody of about 80 mg to about 315 mg (for example, about 100 mg, about 110 mg, about 120 mg, about 130 mg, about 140 mg, about 150 mg, about 160 mg, about 180 mg, about 190 mg, about 210 mg, about 250 mg, or about 300 mg) of anti-VLA-1 antibody daily, twice per week, weekly, every two weeks, every 4 weeks (for example, monthly).

The formulation can also be administered to a subject, such as a human, in a bolus at a dose of anti-VLA-1 antibody of about 2.0 mg per kg of body weight to about 4.0 mg per kg of body weight (for example, about 2.1 mg per kg of body weight, about 2.2 mg per kg of body weight, about 2.3 mg per kg of body weight, about 2.5 mg per kg of body weight, about 2.8 mg per kg of body weight, about 3.0 mg per kg of body weight, about 3.1 mg per kg of body weight, about 3.2 mg per kg of body weight, about 3.3 mg per kg of body weight, about 3.4 mg per kg of body weight, or about 3.6 mg per kg of body weight).

Modified dose ranges include a dose of anti-VLA-1 antibody that is less than about 400 mg/subject, less than about 300 mg/subject, less than about 250 mg/subject, less than about 200 mg/subject, less than about 150 mg/subject or less than about 100 mg/subject, typically for administration every fourth week or once a month. The anti VLA-1 antibody can be administered, for example, every three to five weeks, for example, every fourth week, or monthly.

Dosage regimens can be adjusted to provide the desired response, such as a therapeutic response. As used herein, a "regimen" is a course of therapy regulated by a set course of drug administration. For example, the course of therapy can include administration of a specific amount of drug on specific days at defined intervals. The dosages can be consistent or varied, and the period of administration can be at regular intervals (such as daily or every two or three days), or the period of administration can vary (for example, every day for one week, then no drug for a week, then drug every other day as needed for pain).

A "therapeutic response" is an improvement in a condition, symptom, or parameter associated with a disorder, to either a statistically significant degree or to a degree detectable to one skilled in the art.

The dose of anti-VLA-1 antibody can be chosen to reduce or avoid production of antibodies against the anti-VLA-1 antibody, to achieve greater than 40%, greater than 50%, greater than 70%, greater than 75%, or greater than 80% saturation of the α1 subunit, to achieve to less than 80%, less than 70%, less than 60%, less than 50%, or less than 40% saturation of the α1 subunit, or to prevent an increase the level of circulating white blood cells.

Dosage unit form or "fixed dose" as used herein refers to physically discrete units suited as unitary dosages for the subjects to be treated; each unit contains a predetermined quantity of active antibody calculated to produce the desired therapeutic effect in association with the required pharmaceutical carrier and optionally in association with the other agent.

A pharmaceutical composition may include a "therapeutically effective amount" of an anti-VLA-1 antibody described herein, such as SAN-300. Such effective amounts can be determined based on the effect of the administered agent, or the combinatorial effect of an agent and secondary agent if more than one agent is used. A therapeutically effective amount of an agent may also vary according to factors such as the disease state, age, sex, and weight of the individual, and the ability of the antibody to elicit a desired response in the individual, such as amelioration of at least one disorder parameter, for example, a parameter of rheumatoid arthritis, or amelioration of at least one symptom of the disorder, for example, rheumatoid arthritis. A therapeutically effective amount is also one in which any toxic or detrimental effects of the composition are outweighed by the therapeutically beneficial effects.

Devices and Kits

Formulations having a high concentration of an anti-VLA-1 antibody (for example, SAN-300) can be administered with a medical device. The device can be designed with or have features such as portability, room temperature storage, and ease of use so that it can be used in emergency situations, such as by an untrained subject or by emergency personnel in the field, removed to medical facilities and other medical equipment. The device can be a container that includes, for example, one or more housings for storing pharmaceutical preparations that include an anti-VLA-1 antibody (e.g., SAN-300), and can be configured to deliver one or more unit doses of the agent.

A container, such as a delivery device, can contain a unit dosage formulation of anti-VLA-1 antibody. The container can be suitable for subcutaneous administration. For example, the container can be a syringe.

A pharmaceutical composition comprising an anti-VLA-1 antibody can be administered with a delivery device, such as a syringe, for example, a hypodermic or multichamber syringe. In one embodiment, the device is a prefilled syringe with an attached or integral needle. In other embodiments, the device is a prefilled syringe not having a needle attached. The needle can be packaged with the prefilled syringe. In one embodiment, the device is an auto-injection device, such as an auto-injector syringe. In another embodiment the injection device is a pen-injector. In yet another embodiment, the syringe is a staked needle syringe, luer lock syringe, or luer slip syringe. Other suitable delivery devices include stents, catheters, microneedles, and implantable controlled release devices. The composition can be administered intravenously with standard IV equipment, including, for example, IV tubings, with or without in-line filters. In certain embodiments, the device will be a syringe for use in SC or IM administration.

An anti-VLA-1 antibody, such as SAN-300, can be provided in a kit. In one embodiment, the kit includes one or more of: a container, such as in an injection device, such as a syringe that contains an antibody composition described herein; packaging material that encloses the container, and optionally, other elements of the kit; a container that contains a composition including a second agent; and informational material. The informational material can be descriptive, instructional, marketing or other material that relates to the methods described herein and/or the use of the agents for therapeutic benefit. In one embodiment, the kit also includes a second agent. For example, the kit includes a first container that contains a composition that includes the anti-VLA-1 antibody, and a second container that includes the second agent. In one embodiment, the kit includes one or more single-use syringes pre-filled with a high concentration liquid antibody formulation described herein.

The informational material of the kits is not limited in its form. In one embodiment, the informational material can include information about production of the antibody, concentration, date of expiration, batch or production site information, and so forth. In one embodiment, the informational material relates to methods of administering the anti-VLA-1 antibody, such as SAN-300, such as in a suitable dose, dosage form, or mode of administration, for example, a dose, dosage form, or mode of administration described herein, to treat a subject who has an inflammatory disease such as RA, or who is at risk for experiencing an episode associated with an inflammatory disease. The information can be provided in a variety of formats, including printed text, computer readable material, video recording, or audio recording, or information that provides a link or address to substantive material.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality, for example, a pack, of individual containers, each containing one or more unit dosage forms, such as a unit dosage form described herein, of the agents. The containers can include a combination unit dosage, for example, a unit that includes both the anti-VLA-1 antibody, such as SAN-300, and the second agent, such as in a desired ratio. For example, the kit includes a plurality of syringes, ampoules, foil packets, blister packs, or medical devices, for example, each containing a single combination unit dose. The containers of the kits can be air tight, waterproof, for example, impermeable to changes in moisture or evaporation, and/or light-tight.

The kit optionally includes a device suitable for administration of the composition, for example, a syringe or other suitable delivery device. The device can be provided preloaded with one or both of the agents or can be empty, but suitable for loading.

Rheumatoid Arthritis

Formulations having anti-VLA-1 antibody suitable for subcutaneous administration are useful for the treatment of inflammatory diseases, such as autoimmune arthritis, for example, rheumatoid arthritis or psoriatic arthritis; or other forms of inflammatory arthritis, such as arthritis associated with inflammatory bowel disease. Autoimmune arthritis is caused by abnormalities in the immune system that cause the body to start attacking its own joints and connective tissue. Examples of autoimmune arthritis include rheumatoid arthritis, juvenile arthritis, psoriatic arthritis, and ankylosing spondylitis. Rheumatoid arthritis is a chronic syndrome characterized by non-specific, usually symmetric inflammation of the peripheral joints, potentially resulting in progressive destruction of articular and periarticular structures, with or without generalized manifestations. Juvenile arthritis (arthritis beginning at or before age 16) is similar to adult rheumatoid arthritis, and tends to affect large and small joints, and may affect growth and development. Psoriatic arthritis, which occurs in about 7% of psoriasis patients, is an inflammatory arthritis associated with psoriasis of the skin or nails; and a negative test for RF (Rheumatoid factor). Ankylosing spondylitis is a systemic rheumatic disorder characterized by inflammation of the axial skeleton and large peripheral joints.

Other types of arthritis, particularly inflammatory arthritis, are suited for treatment by the methods featured in the invention. For example, arthritis associated with inflammatory bowel disease can be treated with an anti-VLA-1 antibody, such as when a first-line therapy fails or ceases to relieve arthritic symptoms.

Efficacy of an agent for treatment of arthritis may be measured by a number of available diagnostic tools, including but not limited to, for example, physical examination, including assaying the number of tender joint counts or swollen joint counts, joint X-rays, blood tests, or examination of fluid collected from affected joints. X-rays can reveal erosions, cysts and joint space narrowing that can occur in chronic rheumatoid arthritis. Blood tests that indicate elevated ESR (Erythrocyte Sedimentation Rate) levels or the presence of antibodies to altered γ-globulin (i.e., rheumatic factors, "RFs") are indicative of rheumatoid arthritis. Synovial fluid from joints of patients with rheumatoid arthritis is typically cloudy but sterile with reduced viscosity and usually 3,000 to 50,000 white blood cells (WBCs)/μL.

Symptoms of arthritis, including rheumatoid arthritis, include joint pain, joint swelling, joint deformities, reduced ability to move a joint, redness of the skin around a joint, stiffness, warmth around a joint, morning stiffness, and effusion (collection of liquid in the joints). Criteria for the diagnosis of rheumatoid arthritis is set forth in, for example, Aletaha et al., "2010 Rheumatoid Arthritis Classification Criteria," *Arthritis and Rheumatism* 62:2569-2581, 2010, and involves the assessment of the number of large and small joints affected in a subject, the levels of RF (rheumatoid factor) and ACPA (anti-citrullinated protein antibody) in serum, CRP (C-reactive protein) and ESR (erythrocyte sedimentation rate) levels, and whether the subject's symptoms have persisted for at least six weeks, or for less than six weeks. The duration of symptoms is determined by the patient's self-report of the duration of signs and symptoms of synovitis (pain, swelling, and tenderness) of any joint that is clinically involved at the time of assessment. Each of these factors provides a score, and a total score ≥6 (on a scale of 0-10), is indicative of rheumatoid arthritis.

"Large joints" include shoulders, elbows, hips, knees and ankles, and "small joints" include metacarpophalangeal, proximal interphalangeal (PIP), second through fifth metatarsophalangeal (MTP), and thumb interphalangeal (IP) joints, and the wrists.

RF and ACPA levels are usually reported in IU (International Units). Based on the upper limit of normal (ULN) for the respective laboratory test and assay the following definitions can be made: negative=less than or equal to the ULN for the laboratory test and assay; low-level positive=higher than the ULN but ≤3 times the ULN for the laboratory test and assay; high-level positive=>3 times the ULN for the laboratory test and assay.

CRP and ESR levels are scored as normal or abnormal based on the local laboratory standards. If results of at least one of these two tests are abnormal, the patient is scored as having an abnormal acute response.

Patients having arthritis, such as rheumatoid arthritis, also often have an increased level of VLA-1$^+$ cells, such as VLA-1$^+$ T cells or monocytes.

An "effective amount" of a therapy, such as a first line or second therapy, is an amount sufficient to cause beneficial or desired clinical results. An effective amount can be delivered in one or more administrations. An "effective amount" of a first line therapeutic will produce an "adequate response." An "adequate response" is manifested as an improvement in symptoms, such as a decrease in swollen joint count and/or tender joint count, or a decrease in joint pain. An "effective amount" of an anti-VLA-1 antibody is an amount sufficient to palliate, ameliorate, stabilize, reverse, slow or delay progression of arthritis, or a symptom of arthritis, in accordance with clinically acceptable standards.

A subject can be monitored for improvements in arthritic symptoms following treatment with an anti-VLA-1 antibody as a first line therapy or as a second line therapy. In one embodiment, a patient is administered a high concentration anti-VLA-1 antibody formulation, after failing to respond, or after having an inadequate response to a first line therapy. An "inadequate response" is manifested as failure to achieve an improvement in symptoms, such as failure to experience a decrease in swollen joint count and/or tender joint count, or a decrease in joint pain.

A subject can be monitored for improvements in arthritic symptoms upon treatment with a first or second-line therapy. For example, a subject can be monitored by assaying an ACR (American College of Rheumatology) score. For example, a score of ACR20 indicates that there is at least a 20% reduction in the total number of tender and swollen joints and a reduction of 20% in three of the following five parameters: physician global assessment of disease, patient global assessment of disease, patient assessment of pain, C-reactive protein or erythrocyte sedimentation rate, and degree of disability in Health Assessment Questionnaire (HAQ) score. Typically, a score of ACR20 indicates that a patient has significant improvement of arthritic symptoms following administration of a therapeutic agent, such as an anti-VLA-1 antibody or a first line therapy that is a drug other than an anti-VLA-1 antibody. A patient can exhibit more significant improvements with scores of ACR50 or ACR70, for example.

If a patient does not demonstrate a score of at least ACR20, for example, ACR20, ACR50 or ACR70, following administration of a therapy, then the patient can receive a negative assessment, or be determined to have an inadequate response to the therapy. In some embodiments, the patient's ACR score is monitored over the course of one or two weeks, or one or two months, or longer. In some embodiments, a patient will not meet a predetermined criterion that requires an ACR score of ACR20, ARC50, or ACR70 after treatment with a first line therapy, and the patient will be selected for treatment with an anti-VLA-1 antibody.

The HAQ is a validated questionnaire, self-administered by the patient, that includes twenty items relating to function and four items relating to aids and devices. The questions include eight subscales: dressing and grooming, arising, hygiene, reach, eating, walking, grip, and activities. Items are scored from 0 (able to function without difficulty) to 3 (unable to function). The HAQ disease index is a weighted sum of the scale scores, with a higher score indicating poorer function. Decreases in the HAQ disease index exceeding −0.19 to −0.22 (e.g., −0.2 or −0.21) are considered to be clinically important.

If a patient does not exhibit an improvement (an increase) in HAQ score by at least 0.19, for example, by at least 0.22 or more, following administration of a therapy, then the patient can receive a negative assessment, or be determined to have an inadequate response to the therapy. In some embodiments, the patient is monitored for an improvement in HAQ over the course of one or two weeks, or one or two months, or longer. In some embodiments, a patient will not meet a predetermined criterion that requires an improvement in HAQ score of at least 0.19 or at least 0.22 or more, and the patient will be selected for treatment with an anti-VLA-1 antibody.

A patient can also be monitored for improvements in arthritic symptoms upon treatment with a first or second-line therapy by assaying for an improvement in DAS (Disease Activity Score). DAS is a measure of the activity of rheumatoid arthritis that incorporates the following parameters: the total number of tender and swollen joints, ESR, and patient assessment of disease activity (Van der Heijde et al., "Development of disease activity score based on judgment in clinical practice by rheumatologists" *J. Rheumatol.* 20:579-81, 1993). If a patient does not exhibit an improvement in DAS, for example, a decrease in DAS by at least 1.6, at least 1.8, at least 2.0, at least 2.5, at least 3.0, at least 3.2, at least 3.6, or more, following administration of a therapy, then the patient can receive a negative assessment, or be determined to have an inadequate response to the therapy. In some embodiments, the patient is monitored for an improvement in DAS over the course of one or two weeks, or one or two months, or longer. In some embodiments, a patient will not meet a predetermined criterion that requires an improvement in DAS (a decrease in DAS) by at least 1.6, at least 2.0, at least 2.2, at least 2.8, at least 3.2, at least 3.6, or more, and the patient will be selected for treatment with an anti-VLA-1 antibody. Typically, a DAS score of 2.6 or less indicates remission of RA, and a DAS score of 3.2 or less indicates low disease activity. In one embodiment, patient will not meet a predetermined criterion that is a DAS of 2.6 or less, or a patient will not meet a predetermined criterion that is a DAS of 3.2 or less.

The DAS for 28-joint counts (DAS28-CRP measure) includes a composite of 4 variables: number of tender joints out of 28 joints, number of swollen joints out of 28 joints, CRP (in mg/L), and subject assessment of disease activity measure on a Visual Analogue Scale (VAS) of 100 millimeters (mm). DAS28-CRP values range from 0 to 9.31, with higher scores indicating more disease activity. Typically, a DAS28-CRP score of 2.6 or less indicates remission of RA, and a DAS28-CRP score or 3.2 or less indicates low disease activity. In one embodiment, patient will not meet a predetermined criterion that is a DAS of 2.6 or less, or a patient will not meet a predetermined criterion that is a DAS28 of 3.2 or less.

A patient can also be monitored for improvements in arthritic symptoms by a count of the total number of tender and swollen joints. If the total number of tender and swollen joints does not decrease by, for example, more than 1, 2, 3 or more following administration of a therapy, then the patient can receive a negative assessment, or be determined to have an inadequate response to the therapy. In some embodiments, the patient is monitored for a decrease in swollen or tender joint counts over the course of one or two weeks, or one or two months, or longer. In some embodiments, a patient will not meet a predetermined criterion that requires a decrease in swollen or tender joint count of 1, 2, 3 or more, and the patient will be selected for treatment with an anti-VLA-1 antibody. In some embodiments, a patient will not meet a predetermined criterion that requires a decrease in swollen or tender joint count of 15%, 20%, or 30% or more, and the patient will be selected for treatment with an anti-VLA-1 antibody.

A patient can also be monitored for improvements in arthritic symptoms by radiographic methods, such as MRI, ultrasound or X-ray. These methods provide images that can reveal the extent of synovitis, erosive changes, and edema. Failure to see a decrease in the extent of synovitis, a decrease in the rate of erosion in the joint, or a decrease in edema, such as over the course of one or two weeks or one or two months, or longer, for example, can indicate that the patient has an inadequate response to a therapy. In some embodiments, a patient will not meet a predetermined criterion that requires a decrease in the extent of synovitis, a decrease in the rate of erosion in the joint, or a decrease in "bone edema" or "osteitis" by 15%, 20%, 30% or more, and the patient will be selected for treatment with an anti-VLA-1 antibody.

A patient can also be monitored for improvements in arthritic symptoms upon treatment with a first or second-line therapy by assaying for the number of VLA-1$^+$ cells, for example, VLA-1$^+$ T cells or monocytes, in blood or synovial fluid. If the number of VLA-1$^+$ cells does not decrease by, for example, more than 15%, more than 20% or more than 30% or more following administration of a therapy, then the patient can receive a negative assessment, or be determined to have an inadequate response to the therapy. In some embodiments, the patient is monitored for a decrease in VLA-1$^+$ cells over the course of one or two weeks, or one or two months, or longer. In some embodiments, a patient will not meet a predetermined criterion that requires a decrease in VLA-1$^+$ cells of 15%, 20%, 30% or more, and the patient will be selected for treatment with an anti-VLA-1 antibody.

In some embodiments, a patient will not meet a predetermined criterion that requires an improvement in both tender and swollen joint counts of at least 15%, at least 20%, at least 30% or more, and an improvement of at least 15%, at least 20%, or at least 30% or more in three of the remaining five core measures: patient's assessment of pain (on the basis of a visual-analogue scale ranging from 1 to 100, with higher scores indicating more pain); levels of acute-phase reactants, such as CRP level; HAQ score; and patient and physician global assessment (each assessed on a scale of 0 to 100, with higher numbers indicating more severe disease).

Information regarding a patient's response to a first-line therapy can be acquired directly or indirectly. For example, information regarding the patient's response can be assessed by a clinician or caregiver who directly examines the patient for symptom improvements following administration of a first-line therapy. Alternatively, the information can be acquired indirectly, such as from patient records obtained from the records of a hospital or clinic, or clinician or caregiver, or from a database, such as an on-line database.

"Acquire" or "acquiring" as the terms are used herein, refer to obtaining possession of a physical entity, or a value, such as a numerical value, by "directly acquiring" or "indirectly acquiring" the physical entity or value. "Directly acquiring" means performing a process (for example, examining the patient or a patient sample) to obtain the physical entity or value. "Indirectly acquiring" refers to receiving the physical entity or value from another party or source (for example, a third party laboratory that directly acquired the physical entity or value).

Directly acquiring a physical entity includes performing a process that includes a physical change in a physical substance, such as a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond.

Directly acquiring a value includes performing a process that includes a physical change in a sample or another substance, for example, performing an analytical process which includes a physical change in a substance, such as a sample, an analyte, or a reagent (sometimes referred to herein as "physical analysis"), performing an analytical method, such as a method that includes one or more of the following: separating or purifying a substance, such as an analyte, or a fragment or other derivative thereof, from another substance; combining an analyte, or fragment or other derivative thereof, with another substance, such as a buffer, a solvent, or a reactant; or changing the structure of an analyte, or a fragment or other derivative thereof, such as by breaking or forming a covalent or non-covalent bond, between a first and a second atom of the analyte; or by changing the structure of a reagent, or a fragment or other derivative thereof, such as by breaking or forming a covalent or non-covalent bond, between a first and a second atom of the reagent.

"Analyzing" a sample includes performing a process that involves a physical change in a sample or another substance, such as a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Analyzing a sample can include performing an analytical process which includes a physical change in a substance, such as a sample, an analyte, or a reagent (sometimes referred to herein as "physical analysis"), performing an analytical method, such as a method which includes one or more of the following: separating or purifying a substance, such as an analyte, or a fragment or other derivative thereof, from another substance; combining an analyte, or fragment or other derivative thereof, with another substance, such as a buffer, a solvent, or a reactant; or changing the structure of an analyte, or a fragment or other derivative thereof, such as by breaking or forming a covalent or non-covalent bond, between a first and a second atom of the analyte; or by changing the structure of a reagent, or a fragment or other derivative thereof, such as by breaking or forming a covalent or non-covalent bond, between a first and a second atom of the reagent.

In one embodiment, determining whether a patient has improvements in arthritic symptoms, includes one or more of evaluating the patient, or analyzing a sample from the patient, requesting evaluation of the patient or analysis of the sample, requesting results from evaluation of the patient or analysis of the sample, or receiving the results from evaluation of the patient or analysis of the sample. Generally, analysis can include one or both of performing the underlying method, for example, assaying for the number of VLA-1$^+$ cells or monocytes in a patient sample, or receiving data from another who has performed the underlying method.

In addition to or prior to human studies, an animal model can be used to evaluate the efficacy of using the two agents. An exemplary animal model for RA is described in U.S. Pat. No. 7,358,054. For example, in an arthritis model in mice, anti-collagen type II antibodies are administered by i.p. injection, followed by i.p. injection of LPS (lipopolysaccharide). Mice develop symptoms such as swollen wrists, ankles and digits.

Other Disorders

The formulations and methods described herein can also be used to treat other inflammatory, immune, or autoimmune disorders, such as tissue or organ graft rejection or graft-versus-host disease; acute CNS injury, such as stroke or spinal cord injury; chronic renal disease; an allergy, such as allergic asthma; type 1 diabetes; inflammatory bowel disorders, such as Crohn's disease and ulcerative colitis; myasthenia gravis; fibromyalgia; an arthritic disorder, such as psoriatic arthritis; an inflammatory/immune skin disorders, such as psoriasis, vitiligo, dermatitis, and lichen planus; systemic lupus erythematosus; Sjogren's Syndrome; a hematological cancer, such as multiple myeloma, leukemia, and lymphoma; a solid cancer, such as a sarcoma or carcinoma, such as of the lung, breast, prostate, or brain; and a fibrotic disorder, such as pulmonary fibrosis, myelofibrosis, liver cirrhosis, mesangial proliferative glomerulonephritis, crescentic glomerulonephritis, diabetic nephropathy, and renal interstitial fibrosis.

For example, a formulation containing a high concentration of anti-VLA-1 antibody, such as SAN-300, can be administered subcutaneously to treat these and other inflammatory, immune, or autoimmune disorders.

Exemplary Second Agents

In some cases, the formulations described herein, for example, formulations containing an anti-VLA-1 antibody suitable for SC administration, are administered in combination with a formulation containing a second agent. Typically, the anti-VLA-1 antibody formulation, and the formulation containing the second agent are separate formulations.

In one implementation, the antibody and the second agent are provided as separate formulations, and the step of administering includes sequentially administering the antibody and the second agent. The sequential administrations can be provided on the same day, for example, within one hour of one another or at least 3 hours, at least 6 hours, or at least 12 hours apart, or on different days. The second agent can be administered before administration of an anti-VLA-1 antibody or antigen-binding fragment thereof, after administration of an anti-VLA-1 antibody or antigen-binding fragment thereof, or at the same time as administration of an anti-VLA-1 antibody or antigen-binding fragment thereof.

Generally, the antibody and the second agent are each administered as a plurality of doses separated in time. The antibody and the second agent are generally each administered according to a regimen. The regimen for one or both may have a regular periodicity. The regimen for the antibody can have a different periodicity from the regimen for the second agent, for example, one can be administered more frequently than the other. In one implementation, one of the antibody and the second agent is administered once weekly and the other is administered once monthly. The antibody and the second agent can be administered by any appropriate method, for example, subcutaneously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

The second agent can be, for example, an anti-inflammatory, an antihistamine, an analgesic, such as acetaminophen, or a corticosteroid.

Non-limiting examples of second agents for treating rheumatoid arthritis in combination with an anti-VLA-1 antibody include a DMARD, such as gold salts; hydroxychloroquine; an antifolate, such as methotrexate; a pyrimidine synthesis inhibitor, such as leflunomide; or a sulfa drug, such as sulfasalazine. In another embodiment, the second agent for treating rheumatoid arthritis is a TNF-α inhibitor, such as an anti-TNF-α antibody, for example, infliximab, adalimumab, certolizumab pegol, or golimumab; or etanercept.

Other exemplary second agents include a JAK (Janus Kinase) inhibitor (e.g., a JAK1, JAK2, JAK3 or TYK2 inhibitor), a SYK (Spleen Tyrosine Kinase) inhibitor (for example, an inhibitor of SYK or ZAP-70), a VLA-2 inhibitor, an IL-6 inhibitor, an IL-17 inhibitor, an IL-12/IL-23 inhibitor, a MAdCAM-1 inhibitor, a CD20 inhibitor or another biologic agent. For example, the second therapeutic agent can be methotrexate, leflunomide, sulfasalazine, or hydroxychloroquine, infliximab, adalimumab, certolizumab pegol, golimumab, etanercept, rituximab, tocilizumab or abatacept.

The second agent can be, for example, an inhibitor of JAK3, such as the small molecule inhibitor CP-690,550 (tofacitinib), or the second agent can be the SYK inhibitor R406, or its prodrug R788.

The second agent can alternatively be a B cell-depleting agent, such as an anti-CD20 antibody, for example rituximab (Rituxan, Genentech, Inc., South San Francisco, Calif.; and IDEC Pharmaceutical, San Diego, Calif.), an anti-VLA-2 antibody, such as GBR 500; or an anti-MAdCAM-1 antibody, such as vedolizumab.

Non-limiting examples of second agents for treating IBD in combination with an anti-VLA-1 antibody include, for example, an anti-MAdCAM-1 antibody, such as vedolizumab.

In one embodiment, the second therapeutic agent is methotrexate, administered at a dose of about 35 mg/week, about 30 mg/week, about 25 mg/week, about 20 mg/week, or about 15 mg/week, or less. In another embodiment, the second therapeutic agent is leflunomide, administered at a dose of about 30 mg/day, about 25 mg/day, about 20 mg/day, about 15 mg/day, about 10 mg/day or less. In another embodiment the second therapeutic agent is sulfasalazine, administered at a dose of about 4000 mg/day, about 3500 mg/day, about 3000 mg/day, about 2500 mg/day, about 2000 mg/day, or less. In another embodiment, the second therapeuctic agent is hydroxychloroquine, administered at a dose of about 500 mg/day, about 450 mg/day, about 400 mg/day, about 350 mg/day, about 300 mg/day or less.

In one embodiment, the patient is administered a third therapeutic agent, which can be, for example, methotrexate, leflunomide, sulfasalazine, hydroxychloroquine, infliximab, adalimumab, certolizumab pegol, golimumab, etanercept, rituximab, tocilizumab or abatacept.

In one embodiment, administration of the first and second, and optionally the third, therapeutic agents results in a greater improvement of symptoms than is observed following administration of either the first or the second (or third) therapeutic agents alone.

In some embodiments, a subject is treated with one or more therapeutic agents prior to receiving an anti-VLA-1 antibody therapy, such as an infusion of an anti-VLA-1 therapy, such as to prevent or ameliorate adverse reactions to the anti-VLA-1 administration, for example, to prevent or ameliorate adverse events associated with infusion of an anti-VLA-1 antibody. Exemplary pre-treatment regimens include, for example treatment with one or more of an analgesic, such as acetaminophen, an antihistamine, or a steroid, such as a corticosteroid, such as methylprednisolone. In one embodiment, a subject, such as an RA patient is administered acetaminophen and an antihistamine prior to administration of an anti-VLA-1 antibody, such as prior to infusion with an anti-VLA-1 antibody. In one embodiment, an RA patient is administered a corticosteroid (also called a glucocorticoid), such as methylprednisolone, prior to treatment with an anti-VLA-1 antibody.

In one embodiment, the pretreatment, such as the corticosteroid, such as methylprednisolone, is administered at a dose of about 50 mg/75 kg human, about 75 mg/75 mg human, about 100 mg/75 kg human, about 125 mg/75 kg human, or about 150 mg/75 kg human.

In another embodiment, the pretreatment is administered for about 15 minutes to about one hour or more, for example, about 15 minutes, about 30 minutes, about 45 minutes, or about one hour or more prior to administration of the anti-VLA-1 antibody, such as prior to infusion of the anti-VLA-1 antibody.

The pretreatment can be administered, for example, by intravenous delivery, such as by infusion.

In some embodiments, a second agent may be used to treat one or more symptoms or side effects of RA.

In addition to a second agent, it is also possible to deliver still other agents to the subject. However, in some embodiments, no protein or biologic agent, other than the anti-VLA-1 antibody and second agent, are administered to the subject as a pharmaceutical composition. The anti-VLA-1 antibody and the second agent may be the only agents that are delivered by injection. In embodiments in which the anti-VLA-1 antibody and the second agent are recombinant proteins, the anti-VLA-1 antibody and second agent may be the only recombinant agents administered to the subject, or at least the only recombinant agents that modulate immune or inflammatory responses. In still other embodiments, the anti-VLA-1 antibody alone is the only recombinant agent or the only biologic administered to the subject.

All references and publications included herein are incorporated by reference. The following examples are not intended to be limiting.

EXAMPLES

Example 1. Biophysical Characteristics of the Anti-VLA-1 Antibody were Evaluated in Various Antibody Formulations Biophysical characteristics of the anti-VLA-1 antibody were examined to, inter alia, determine the thermal and conformational stability of the antibody in the presence of various buffers and excipients.

The buffers listed in Table 1 were evaluated to assess the conformational stability of SAN-300.

TABLE 1

| Buffers | |
| --- | --- |
| Buffer | pH |
| 30 mM Glutamate | 4.5 |
|  | 5.0 |
| 30 mM Acetate | 4.5 |
|  | 5.5 |
| 30 mM Citrate | 5.0 |
|  | 6.0 |
| 30 mM Succinate | 5.5 |
|  | 6.5 |
| 30 mM Histidine | 6.0 |
|  | 7.0 |
| 30 mM Phosphate | 6.5 |
|  | 7.5 |

The target protein concentration for the biophysical studies was 2 mg/mL. The protein samples were buffer exchanged using Amicon Ultra-4 (30 k MWCO, RC Membrane) concentrators into the buffers listed in Table 1. The protein concentration in the samples was measured by UV-Vis spectroscopy using an extinction coefficient of 1.53 mL/mg*cm. For the initial biophysical screening, thermal and conformational stability of the protein in various buffers was determined using differential scanning calorimetry (DSC) and dynamic light scattering (DLS). DSC measures denaturation, melting temperature and enthalpy. DLS provides a measure of aggregation. The samples were analyzed at 2 mg/mL in the various formulation buffers. The final volume for each formulation was ~1.0 mL (~24 mg of protein for the entire study).

The DSC data is summarized in Table 2. The formulations A-L in Table 2 are provided in order of increasing pH. Glutamate did not provide clear peaks, see Formulation A, indicating that it is less desirable.

TABLE 2

| DSC Results | | | | | |
| --- | --- | --- | --- | --- | --- |
| Formulation | Buffer | Temperature of Onset (° C.) | Tm1 (° C.) | Tm2 (° C.) | Tm3 (° C.) |
| A | 30 mM Glutamate, pH 4.5 | NAa | 76.99 | NA | NA |

TABLE 2-continued

DSC Results

| Formulation | Buffer | Temperature of Onset (° C.) | Tm1 (° C.) | Tm2 (° C.) | Tm3 (° C.) |
|---|---|---|---|---|---|
| B | 30 mM Glutamate, pH 5.0 | 58 | 66.96 | 78.63 | 81.13[b] |
| C | 30 mM Acetate, pH 4.5 | 53 | 62.28 | 76.11 | 80.90[b] |
| D | 30 mM Acetate, pH 5.5 | 60 | 70.01 | 79.01 | 83.38[b] |
| E | 30 mM Citrate, pH 5.0 | 54 | 64.20 | 76.02 | 81.26[b] |
| F | 30 mM Citrate, pH 6.0 | 60 | 69.78 | 77.62 | 83.29 |
| G | 30 mM Succinate, pH 5.5 | 58 | 68.71 | 78.05 | 83.22 |
| H | 30 mM Succinate, pH 6.5 | 61 | 71.43[b] | 77.81 | 83.65 |
| I | 30 mM Histidine, pH 6.0 | 58 | 68.82 | 78.49 | 83.16 |
| J | 30 mM Histidine, pH 7.0 | 60 | 71.80[b] | 77.89 | 84.06 |
| K | 30 mM Phosphate, pH 6.5 | 61 | 71.45[b] | 77.56 | 83.73 |
| L | 30 mM Phosphate, pH 7.5 | 58 | 71.29[b] | 76.94 | 82.94 |

$T_m 1$ means the temperature for onset of melting.
[a] Data was insufficient for Temperature of Onset determination.
[b] Peak presented as a shoulder on the DSC curve, and was unable to be identified by peak picking software. The value shown was picked manually.

The DLS data is summarized in the Table 3. Z-avg is the average diameter of all species. Pdi, the polydispersity index, is a measure of polydispersability and is correlated positively with aggregation. A value of less than 0.2 for Pdi is desired. Values approaching 0.2 are less desirable, for example, the 0.185 value for Formulation B is less desirable. See Table 3.

Generally, stability of the formulations increased with increased pH. A pH of 4.5 or less was determined not to be optimal. No aggregation was observed in any of the buffer conditions, and the melting temperature was found to be >50° C. ($T_{M1}$>50° C.). Glutamate was determined to be the least favorable buffer, and citrate did not have clearly preferred properties.

TABLE 3

DLS results

| Buffer | pH | Z-Avg | Pdi | Pk1 Mean Int (d · nm) | Pk2 Mean Int (d · nm) | Pk3 Mean Int (d · nm) | Pk1 Width (d · nm) | Pk2 Width Int (d · nm) | Pk3 Width Int (d · nm) |
|---|---|---|---|---|---|---|---|---|---|
| 30 mM Glutamate | 4.5 | 11.28 | 0.106 | 11.48 | N/A | N/A | 1.438 | N/A | N/A |
| 30 mM Glutamate | 5.0 | 12.45 | 0.185 | 12.05 | 1608 | 5017 | 1.77 | 856.6 | 524.2 |
| 30 mM Acetate | 4.5 | 11.15 | 0.065 | 11.53 | N/A | N/A | 1.398 | N/A | N/A |
| 30 mM Acetate | 5.5 | 10.96 | 0.026 | 11.21 | N/A | N/A | 1.078 | N/A | N/A |
| 30 mM Citrate | 5.0 | 11.41 | 0.075 | 11.84 | N/A | N/A | 1.61 | N/A | N/A |
| 30 mM Citrate | 6.0 | 11.23 | 0.019 | 11.44 | N/A | N/A | 1.109 | N/A | N/A |
| 30 mM Succinate | 5.5 | 11.82 | 0.12 | 11.95 | N/A | N/A | 1.55 | N/A | N/A |
| 30 mM Succinate | 6.5 | 11.24 | 0.079 | 11.69 | N/A | N/A | 2.589 | N/A | N/A |
| 30 mM Histidine | 6.0 | 10.84 | 0.067 | 11.22 | N/A | N/A | 2.025 | N/A | N/A |
| 30 mM Histidine | 7.0 | 10.32 | 0.077 | 10.62 | N/A | N/A | 1.88 | N/A | N/A |
| 30 mM Phosphate | 6.5 | 10.89 | 0.032 | 11.18 | N/A | N/A | 1.674 | N/A | N/A |
| 30 mM Phosphate | 7.5 | 11.93 | 0.016 | 11.11 | N/A | N/A | 1.229 | N/A | N/A |

Excipients Screening.

The conformational and thermal stability of formulations comprising SAN-300 and various excipients were assessed after exchange into the formulations listed below. For the excipient screening, buffer effects on the protein (~2 mg/mL) were characterized using DSC and DLS.

Temperature of onset and Tm as determined by DSC is shown in Table 4. DLS data are shown in Table 5.

DSC data indicated that none of the excipients tested had a dramatic effect on melting temperature (Tm1). For all excipients, the melting temperature was >50° C. The freezing temperature in NaCl was lower, as expected, and the

TABLE 4

Results of excipient screening by DSC

| Formulation | Buffer | Excipient | Temperature of Onset (° C.) | Tm1 (° C.) | Tm2 (° C.) | Tm3 (° C.) |
|---|---|---|---|---|---|---|
| A | 30 mM | 150 mM NaCl | 57 | 65.06 | 76.25 | 82.26 |
| B | Acetate, | 250 mM Sorbitol | 59 | 67.82 | 78.49 | 83.66 |
| C | pH 5.0 | 250 mM Sucrose | 59 | 68.12 | 78.65 | 83.84 |
| D | | 250 mM Trehalose | 58 | 67.06 | 77.76 | 83.45a |
| E | | 250 mM Mannitol | 59 | 67.82 | 78.48 | 83.68a |
| F | 30 mM | 150 mM NaCl | 60 | 70.31 | 77.50 | 83.68 |
| G | Succinate, | 250 mM Sorbitol | 60 | 71.35[a] | 77.98 | 84.32 |
| H | pH 6.0 | 250 mM Sucrose | 62 | 71.60[a] | 78.19 | 84.71 |
| I | | 250 mM Trehalose | 62 | 71.89[a] | 78.43 | 84.77 |
| J | | 250 mM Mannitol | 60 | 71.45[a] | 77.90 | 84.39 |
| K | 30 mM | 150 mM NaCl | 62 | 69.30 | 77.32 | 83.34 |
| L | Histidine, | 250 mM Sorbitol | 63 | 72.04[a] | 78.44 | 84.77 |
| M | pH 6.5 | 250 mM Sucrose | 62 | 72.27[a] | 78.58 | 84.93 |
| N | | 250 mM Trehalose | 63 | 72.33[a] | 78.83 | 85.01 |
| O | | 250 mM Mannitol | 62 | 71.84[a] | 78.29 | 84.62 |
| P | 30 mM | 150 mM NaCl | 60 | 71.28[a] | 77.06 | 83.41 |
| Q | Phosphate, | 250 mM Sorbitol | 61 | 72.27[a] | 76.14 | 83.48 |
| R | pH 7.0 | 250 mM Sucrose | 61 | 72.11[a] | 76.48 | 83.51 |
| S | | 250 mM Trehalose | 61 | 73.15[a] | 76.79 | 83.81 |
| T | | 250 mM Mannitol | 60 | 71.94[a] | 75.92 | 83.26 |

[a]Peak presented as a shoulder on the DSC curve, and was unable to be identified by peak picking software. The value shown was picked manually.

TABLE 5

Results of excipient screening by DLS

| Formulation[a] | Z-Avg (d · nm) | PdI | Pk1 Mean Int (d · nm) | Pk2 Mean Int (d · nm) | Pk3 Mean Int (d · nm) | Pk1 Width (d · nm) | Pk2 Width (d · nm) | Pk3 Width (d · nm) |
|---|---|---|---|---|---|---|---|---|
| A | 11.71 | 0.095 | 12 | 0 | 0 | 1.754 | 0 | 0 |
| B | 11.74 | 0.052 | 12.46 | 0 | 0 | 2.521 | 0 | 0 |
| C | 17.72 | 0.387 | 14.26 | 183.1 | 0 | 2.478 | 49.72 | 0 |
| D | 14.43 | 0.276 | 15.82 | 1380 | 1.591 | 3.475 | 640 | 0.111 |
| E | 12.52 | 0.159 | 13.25 | 1688 | 0 | 3.529 | 863.6 | 0 |
| F | 11.22 | 0.016 | 11.41 | 0 | 0 | 1.097 | 0 | 0 |
| G | 11.98 | 0.048 | 12.64 | 0 | 0 | 2.187 | 0 | 0 |
| H | 18.01 | 0.435 | 14.99 | 245.6 | 0 | 2.725 | 77.19 | 0 |
| I | 14.51 | 0.287 | 15.95 | 2038 | 1.631 | 3.347 | 1025 | 0.1261 |
| J | 12.47 | 0.113 | 13.71 | 0 | 0 | 3.79 | 0 | 0 |
| K | 11.56 | 0.122 | 12.71 | 0 | 0 | 4.188 | 0 | 0 |
| L | 11.43 | 0.093 | 12.43 | 0 | 0 | 2.162 | 0 | 0 |
| M | 21.57 | 0.582 | 13.93 | 128.8 | 767.1 | 2.303 | 38.08 | 317.6 |
| N | 12.06 | 0.226 | 14.53 | 1.417 | 0 | 3.035 | 0.1048 | 0 |
| O | 12.07 | 0.167 | 12.81 | 0 | 0 | 2.415 | 0 | 0 |
| P | 11.46 | 0.09 | 11.93 | 0 | 0 | 2.74 | 0 | 0 |
| Q | 13.19 | 0.171 | 14.29 | 101.7 | 338.7 | 4.074 | 42.57 | 112.8 |
| R | 17.23 | 0.383 | 14.79 | 150.7 | 0 | 2.88 | 40.26 | 0 |
| S | 13.37 | 0.226 | 15.74 | 1.473 | 4842 | 3.386 | 0.1095 | 686.7 |
| T | 12.27 | 0.116 | 13.7 | 0 | 0 | 3.284 | 0 | 0 |

Pk1 = peak corresponding to anti-VLA-1 antibody
PK2 and Pk3 = peaks corresponding to aggregates
[a]Formulations are as described in Table 4.

melting temperature in sugar and in the polyols was similar. Trehalose, mannitol and sucrose were less preferred. The polyol sorbitol and NaCl were more preferred.

Example 2. Solubility Characteristics of the Anti-VLA-1 Antibody

Solubility studies were conducted to, inter alia, maximize the concentration of the SAN-300 antibody. The solubility of SAN-300 was evaluated using various formulations. The formulations and results are provided in Table 6.

Approximately 1900 mg of protein were used for the entire study.

Example 3. Surfactant Studies

The role of surfactant in reducing protein loss and minimizing aggregation was evaluated. Samples were analyzed by appearance, UV-Vis, DLS and SEC-HPLC to assess stability/aggregation in the stressed samples. The formulations used in the surfactant studies are summarized in Table 7.

TABLE 6

Solubility Data

| Buffer | Excipient | Arginine | Approx. Total Protein after First Concentration (mg) | Approx. Content Accounting for Sample Withdrawn (mg) | Spin Time for Final Concentration (min) | Approx. Volume after Final Concentration (mL) | Protein Content after Final Concentration (mg/mL) |
|---|---|---|---|---|---|---|---|
| 30 mM Acetate, pH 5.0 | 150 mM NaCl | 0 mM | 76.2 | 72.4 | 15.0 | 0.300 | 223.3 |
|  |  | 20 mM | 88.9 | 84.5 | 15.0 | 0.325 | 215.8 |
|  | 250 mM Sorbitol | 0 mM | 80.3 | 76.6 | 15.0 | 0.275 | 225.1 |
|  |  | 20 mM | 77.4 | 73.5 | 15.0 | 0.250 | 220.6 |
| 30 mM Succinate, pH 6.0 | 150 mM NaCl | 0 mM | 91.2 | 86.7 | 15.0 | 0.350 | 218.7 |
|  |  | 20 mM | 88.2 | 83.5 | 15.0 | 0.325 | 219.0 |
|  | 250 mM Sorbitol | 0 mM | 90.1 | 85.6 | 15.0 | 0.300 | 212.8 |
|  |  | 20 mM | 83.0 | 78.5 | 15.0 | 0.300 | 212.9 |
| 30 mM Histidine, pH 6.5 | 150 mM NaCl | 0 mM | 81.1 | 76.7 | 15.0 | 0.325 | 209.1 |
|  |  | 20 mM | 87.5 | 82.8 | 15.0 | 0.325 | 215.5 |
|  | 250 mM Sorbitol | 0 mM | 81.4 | 77.3 | 15.0 | 0.325 | 196.5 |
|  |  | 20 mM | 77.6 | 73.7 | 15.0 | 0.350 | 219.4 |
| 30 mM Phosphate, pH 7.0 | 150 mM NaCl | 0 mM | 92.8 | 88.2 | 25.0 | 0.300 | 255.7 |
|  |  | 20 mM | 86.0 | 81.7 | 25.0 | 0.275 | 259.7 |
|  | 250 mM Sorbitol | 0 mM | 92.4 | 88.0 | 25.0 | 0.300 | 256.6 |
|  |  | 20 mM | 99.7 | 95.1 | 25.0 | 0.300 | 219.1 |

Sample Preparation.

The protein samples were exchanged into the indicated buffers using Amicon Ultra-4 (30K MWCO) concentrators. The concentrators were pre-rinsed with 3 mL of buffer followed by centrifugation at ~3000×g for 5 minutes. For each formulation, 1.7 mL SAN-300 (69 mg/m L) were diluted with 2.3 mL of the appropriate buffer in a rinsed concentrator, and the volume reduced to ~2 mL by centrifugation at ~3000×g, resulting in a protein concentration of ~60 mg/mL. This process was repeated for a total of four rounds of buffer exchange. Protein concentration was then measured in duplicate by UV-Vis spectroscopy using disposable Eppendorf UVettes (1.0 cm pathlength) and an extinction coefficient of 1.53 mL/mg*cm. A 10 μL volume of the concentrated samples was diluted in 990 μL of the appropriate buffer to a concentration ~0.5 mg/mL.

Samples were next concentrated at 3000×g (or lower) until precipitation was observed or the sample volume was reduced by half, at which point the protein concentration was measured as described above with an appropriate increase in the dilution volume. Each sample was further concentrated and measured according to the table, or until precipitation was observed. Protein concentrations and percent recoveries were reported for each formulation.

TABLE 7

Formulations for surfactant studies

| Buffer | Excipient | Tween-80 Concentration (%) |
|---|---|---|
| 30 mM Acetate, pH 5.0 | 150 mM NaCl | 0 |
|  |  | 0.005 |
|  |  | 0.020 |
|  | 250 mM Sorbitol | 0 |
|  |  | 0.005 |
|  |  | 0.020 |
| 30 mM Succinate, pH 6.0 | 150 mM NaCl | 0 |
|  |  | 0.005 |
|  |  | 0.020 |
|  | 250 mM Sorbitol | 0 |
|  |  | 0.005 |
|  |  | 0.020 |
| 30 mM Histidine, pH 6.5 | 150 mM NaCl | 0 |
|  |  | 0.005 |
|  |  | 0.020 |
|  | 250 mM Sorbitol | 0 |
|  |  | 0.005 |
|  |  | 0.020 |
| 30 mM Phosphate, pH 7.0 | 150 mM NaCl | 0 |
|  |  | 0.005 |
|  |  | 0.020 |
|  | 250 mM Sorbitol | 0 |
|  |  | 0.005 |
|  |  | 0.020 |

Results. Surfactant was analysed for its effect on protein loss and aggregation. Polysorbate 80 (Tween 80) was assessed at two concentration levels for each of agitation and freeze/thaw.

Agitation stress samples showed significant opalescence without Tween 80. Tween 80 was found to have an impact on agitation stress. The effect was not concentration dependent at the concentrations evaluated.

Tween 80 had no impact on aggregation, at either concentration, in freeze/thaw.

In SEC (size exclusion chromatography) studies, Tween 80 had no impact at either concentration. Acetate and histidine had preferred buffering properties. Less aggregation was observed in acetate and histidine, and thus these were preferred buffers.

In DLS studies, Tween 80 protected against the effects of agitation although the effect was independent of concentration at the concentrations studied. No effect of Tween was observed in freeze/thaw experiments, and sorbitol appeared to perform better.

Sample Preparation for Example 3. SAN-300 was formulated with and without Tween 80 (i.e., polysorbate 80) at a SAN-300 target concentration of ~200 mg/mL. The protein samples were buffer exchanged using Amicon Ultra concentrators (30K MWCO, Ultracel Membrane, Cat #UFC 903008) into the buffer/excipient combinations (excluding surfactant) listed in table 7.

A total of ~1600 mg (23 mL) of SAN-300 was used for each buffer/excipient combination and the volume was split into two concentrators which were diluted with the appropriate buffer to a volume of 15 mL. The samples were concentrated to ~7.5 mL and diluted in the appropriate buffer to a total volume of 15 mL. This process was repeated for a total of 4 cycles. The sample volumes were then reduced until the target concentration (~2 mL per tube) was reached. The duplicate concentrates were pooled, and the protein content determined in duplicate by UV-Vis spectroscopy by diluting 50 µL into 49.95 mL of 0.9% SFI volumetrically and using an extinction coefficient of 1.53 mL/mg*cm.

The pooled samples were then split into three aliquots of 1.2 mL and Tween 80 was spiked into the aliquoted samples at the specified concentration. The formulated samples were subjected to stress via freeze-thaw cycling and mechanical stress by agitation, in addition to a small aliquot reserved as a no-stress control (stored at 2-8° C.) for SEC-HPLC analysis. For both forms of stress, 0.5 mL of sample were transferred to type 1 borosilicate glass vials (2 mL size). For freeze-thaw cycling, the sample was frozen at −80° C. for ≥90 minutes and then allowed to thaw to room temperature. This was repeated for a total of 5 cycles. The sample was then stored at 2° C. to 8° C. until analysis. For agitation stress, the samples were placed on a microplate shaker for 24 to 48 hours at room temperature. Samples were then stored at 2° C. to 8° C. until analysis.

Example 4. Pre-Formulation Design of Experiments (DOE)

The buffers in Table 8 were evaluated at 200 mg/mL SAN-300 for the preformulation DOE (Design of Experiments). Samples 1 to 28 were for evaluation of Tween 80. Samples 29 to 36 were generated to test the suitability of Tween-20 as an excipient. For the DOE, each axial pH sample was prepared in duplicate, with center point pH samples prepared in triplicate. For Tween-20 investigations, duplicate samples were prepared at center point pHs.

TABLE 8

Buffers for preformulation DOE (Design of Experiments)

| Sample No. | Buffer | pH | Excipient | Surfactant |
|---|---|---|---|---|
| 1 | 30 mM Acetate | 4.5 | 150 mM NaCl | 0.01% Tween 80 |
| 2 | 30 mM Acetate | 4.5 | 150 mM NaCl | 0.01% Tween 80 |
| 3 | 30 mM Acetate | 5.0 | 150 mM NaCl | 0.01% Tween 80 |
| 4 | 30 mM Acetate | 5.0 | 150 mM NaCl | 0.01% Tween 80 |
| 5 | 30 mM Acetate | 5.0 | 150 mM NaCl | 0.01% Tween 80 |
| 6 | 30 mM Acetate | 5.5 | 150 mM NaCl | 0.01% Tween 80 |
| 7 | 30 mM Acetate | 5.5 | 150 mM NaCl | 0.01% Tween 80 |
| 8 | 30 mM Acetate | 4.5 | 250 mM Sorbitol | 0.01% Tween 80 |
| 9 | 30 mM Acetate | 4.5 | 250 mM Sorbitol | 0.01% Tween 80 |
| 10 | 30 mM Acetate | 5.0 | 250 mM Sorbitol | 0.01% Tween 80 |
| 11 | 30 mM Acetate | 5.0 | 250 mM Sorbitol | 0.01% Tween 80 |
| 12 | 30 mM Acetate | 5.0 | 250 mM Sorbitol | 0.01% Tween 80 |
| 13 | 30 mM Acetate | 5.5 | 250 mM Sorbitol | 0.01% Tween 80 |
| 14 | 30 mM Acetate | 5.5 | 250 mM Sorbitol | 0.01% Tween 80 |
| 15 | 30 mM Histidine | 6.0 | 150 mM NaCl | 0.01% Tween 80 |
| 16 | 30 mM Histidine | 6.0 | 150 mM NaCl | 0.01% Tween 80 |
| 17 | 30 mM Histidine | 6.5 | 150 mM NaCl | 0.01% Tween 80 |
| 18 | 30 mM Histidine | 6.5 | 150 mM NaCl | 0.01% Tween 80 |
| 19 | 30 mM Histidine | 6.5 | 150 mM NaCl | 0.01% Tween 80 |
| 20 | 30 mM Histidine | 7.0 | 150 mM NaCl | 0.01% Tween 80 |
| 21 | 30 mM Histidine | 7.0 | 150 mM NaCl | 0.01% Tween 80 |
| 22 | 30 mM Histidine | 6.0 | 250 mM Sorbitol | 0.01% Tween 80 |
| 23 | 30 mM Histidine | 6.0 | 250 mM Sorbitol | 0.01% Tween 80 |
| 24 | 30 mM Histidine | 6.5 | 250 mM Sorbitol | 0.01% Tween 80 |
| 25 | 30 mM Histidine | 6.5 | 250 mM Sorbitol | 0.01% Tween 80 |
| 26 | 30 mM Histidine | 6.5 | 250 mM Sorbitol | 0.01% Tween 80 |
| 27 | 30 mM Histidine | 7.0 | 250 mM Sorbitol | 0.01% Tween 80 |
| 28 | 30 mM Histidine | 7.0 | 250 mM Sorbitol | 0.01% Tween 80 |
| 29 | 30 mM Acetate | 5.0 | 150 mM NaCl | 0.01% Tween 20 |
| 30 | 30 mM Acetate | 5.0 | 150 mM NaCl | 0.01% Tween 20 |
| 31 | 30 mM Acetate | 5.0 | 250 mM Sorbitol | 0.01% Tween 20 |
| 32 | 30 mM Acetate | 5.0 | 250 mM Sorbitol | 0.01% Tween 20 |
| 33 | 30 mM Histidine | 6.5 | 150 mM NaCl | 0.01% Tween 20 |
| 34 | 30 mM Histidine | 6.5 | 150 mM NaCl | 0.01% Tween 20 |
| 35 | 30 mM Histidine | 6.5 | 250 mM Sorbitol | 0.01% Tween 20 |
| 36 | 30 mM Histidine | 6.5 | 250 mM Sorbitol | 0.01% Tween 20 |

Results. One vial of each formulation was placed at 5° C. and one at 50° C. (stress condition) for the 28 day incubation. Data collected after 28 days storage were analyzed for statistical significance.

Acetate data sets indicated that a preferred formulation contains sorbitol and has a pH~5.50.

Histidine data sets indicated that pH~6.00 is preferred. With the exception of HPLC data, all other indicators supported sorbitol as a preferred excipient. The effects of sorbitol and NaCl in histidine samples were more similar than was observed for the acetate formulations.

Size Exclusion data was essentially identical for NaCl and sorbitol, while the highly qualitative 50° C. CEX response data indicated that NaCl is a preferred excipient for histidine formulations. CEX chromatograms also indicated a higher level of degradation in the presence of acetate as compared to histidine.

These conclusions were from formulations that contained the surfactant PS-80 at a concentration of about 0.01%. To evaluate the effect of an alternative surfactant, off-DOE samples were prepared at center point pHs that contained about 0.01% PS-20. Evaluation of the data revealed no clear difference between the two surfactant types, as indicated by SEC (size-exclusion chromatography), CEX (cation exchange chromatography), DSC, and UV-Vis methods. However, DLS and appearance testing results were less optimal with PS-20. Light scattering measurements of 30 mM acetate, 150 mM NaCl, PS-20, pH 5.0, samples showed excessive polydispersity, which was not observed in comparable PS-80-containing samples. Polydispersity, however, was evident in respective PS-80, acetate/NaCl samples at pH 4.5. Furthermore, during appearance testing at 4 weeks, it was observed that a total of 9 samples (out of 72) contained apparent particulate matter. Of these, six were PS-20 formulations (~38% of 16 samples). Given no clear advantage of PS-20 over PS-80, the latter surfactant was preferred for carrying on to further studies.

The sorbitol-containing acetate formulation was slightly preferred over the histidine formulation under all conditions tested except HPLC. This favorability for acetate was primarily supported by DLS data. This data, however, also indicated that the preferred acetate formulation was predicted to have a higher percentage of aggregate species (by ~1%) relative to the preferred histidine formulation. The increased propensity for aggregate formation in acetate could alone be enough to support the histidine/sorbitol formulation in further studies. However, one advantage of the acetate/sorbitol formulation was its reduced viscosity. In further evaluation of SAN-300, this reduced viscosity could allow for higher concentration formulations in addition to easing the burden on tangential flow filtration systems.

Thus, the following candidate formulations were selected for forced degradation and formulation development studies:

1. 30 mM acetate, 250 mM sorbitol, 0.01% PS-80, pH 5.5 and
2. 30 mM histidine, 250 mM sorbitol, 0.01% PS-80, pH 6.0.

Since for histidine formulations, polysorbate 20 results were similar to polysorbate 80, a histidine formulation was designed wherein polysorbate 20 was substituted for the polysorbate 80 to avoid any yellowing effect that sometimes occurs with polysorbate 80/Histidine formulations.

Sample Preparation for Example 4. Samples were buffer exchanged and concentrated using Amicon-15 concentrators (Cat. #UFC903024). The concentrators were pre-rinsed with the appropriate buffer by adding 5 mL of buffer to the filter, followed by spinning at ~3200×g for 5 minutes. For each formulation, a total of 13 mL of SAN-300 (69 mg/mL) were split between duplicate Amicon-15 concentrators and diluted to 15 mL with the appropriate formulation buffer. In the case of a single center point sample for each formulation, a total of 19.5 mL of SAN-300 were split between triplicate concentrators to account for the volume of sample necessary for osmolality and viscosity testing. Tween-20 formulations were prepared using 13 mL of SAN-300. For buffer exchange, the concentrators were centrifuged until the volume reached ~7.5 mL, and the samples were diluted with formulation buffer to 15 mL for a total of 4 rounds. A total of ~33 g of protein was used for the study Following buffer exchange of SAN-300 into the various buffers, the samples were concentrated to <1.5 mL, and the contents of duplicate (or triplicate) concentrators were pooled into a single fraction. A prior surfactant screening study showed a protein loss of 20-32% during an identical buffer exchange and concentration process. Assuming a worst-case 35% loss, the starting 13 mL of SAN-300 would produce ~2.9 mL of 200 mg/mL concentrate. Material was mixed by pipetting up and down prior to transferring to 15 mL conical tubes. The protein concentration in the samples was measured by UV-Vis spectroscopy using an extinction coefficient of 1.53 mL/mg*cm and a pathlength of 1 cm. To dilute the samples to the target of ~0.5 mg/mL, 50 µL of the concentrate was diluted into 25 mL of 0.9% NaCl volumetrically and in duplicate. Duplicate $A_{280}$ readings must be within 5% of each other. A third dilution was prepared and measured where the $A_{280}$ readings were not within 5% of each other. The samples were diluted or further concentrated as necessary to achieve the target concentration of 200 mg/mL+/−10 mg/mL.

Following achievement of 200 mg/mL concentrations for each formulation, the appropriate volume of 10% PS-80 (Surfact-Amps, Thermo-Fisher, C/N 28328) or 10% PS-20 (C/N 28320) was added to achieve a final concentration of about 0.01%. The formulations were sterile filtered using Millipore Ultrafree-CL GV 0.22 µM sterile concentrators (Cat. #UFC40GV0S). To sterile filter, the entire volume of each formulation was transferred to a separate sterile filter, only opening the top part of the filter. The Ultrafree-CL units were spun at ~3200×g for 5 minutes or until the entire solution had passed through the 0.22 µM membrane. Following centrifugation, the filtering units were not reopened until the time of vialing, which was performed inside a biosafety cabinet (BSC).

Prior to vialing, ~75 2.0 mL Vials (West Cat #68000314) and a similar number of FluroTec stoppers (West Cat #19500040) were triple rinsed in WFI (water for injection). Stoppers were double-bagged in autoclave bags and autoclaved to sterilize. Vials were dried in an oven at 80° C. After drying, the basket of vials was double wrapped in tin foil then depyrogenated by heating at ~200° C.

For vialing, a biosafety cabinet was used. Prior to use, the BSC was turned on for at least 15 minutes then sprayed down with 70% IPA. Sterile gloves and arm covers were also used. All items entering the hood were sprayed with 70% IPA prior to entering. Filter units containing sterile formulations were brought into the biosafety cabinet. A minimum of 1.0 mL filling volume was used. There were 2 vials per formulation with the remainder to stay in the sterile filter to use as the Time Zero sample. Appearance at Time Zero was performed using one of the vials for each formulation prior to staging.

Example 5A. Formulation Development Studies

For formulation development, SAN-300 samples were evaluated for the following properties: syringeability, viscosity, osmolality, and filter compatibility.

Syringeability Study.

The syringeability of high-concentration SAN-300 was evaluated at the target concentration. For this study, a total of 10 mL was used for each candidate formulation. The force (pounds-force (lbf) required to expel each solution was determined via use of Instron instrument using a 1 mL syringe and 25 G, 27 G, and 30 G needles. Each data point was performed in triplicate, with fresh sample used for each measurement. Samples were expelled at a rate of 20 inches/minute (approximately 10 mL/min) and collected in a glass vial. The post-expulsion samples were analyzed by DLS (undiluted), SEC, and appearance. A sample of pre-expulsion formulated material was analyzed as a control.

Results of the syringeability study are shown in Table 13.

TABLE 13

Formulation development for Syringability

| Formulation | Needle | Sample | Average Load (lbf) | Maximum Load (lbf) | Mean Average Load (lbf) | Mean Maximum Load (lbf) |
|---|---|---|---|---|---|---|
| 30 mM Acetate 220 mM Sorbitol 0.01% PS-80 pH 5.5 | 25 Guage | 1 | 1.57 | 1.59 | 1.45 ± 0.11 | 1.49 ± 0.09 |
| | | 2 | 1.44 | 1.48 | | |
| | | 3 | 1.35 | 1.41 | | |
| | 27 Guage | 1 | 3.49 | 3.58 | 3.47 ± 0.08 | 3.54 ± 0.12 |
| | | 2 | 3.38 | 3.42 | | |
| | | 3 | 3.54 | 3.64 | | |
| | 30 Guage | 1 | 11.64 | 11.97 | 10.72 ± 0.79 | 11.09 ± 0.77 |
| | | 2 | 10.26 | 10.60 | | |
| | | 3 | 10.26 | 10.70 | | |
| 30 mM Histidine 220 mM Sorbitol 0.01% PS-20 pH 6.0 | 25 Guage | 1 | 1.26 | 1.28 | 1.28 ± 0.04 | 1.32 ± 0.04 |
| | | 2 | 1.25 | 1.30 | | |
| | | 3 | 1.33 | 1.36 | | |
| | 27 Guage | 1 | 2.92 | 3.04 | 2.88 ± 0.04 | 2.94 ± 0.08 |
| | | 2 | 2.86 | 2.89 | | |
| | | 3 | 2.86 | 2.90 | | |
| | 30 Guage | 1 | 13.12 | 13.28 | 11.01 ± 1.89 | 11.21 ± 1.89 |
| | | 2 | 9.45 | 9.59 | | |
| | | 3 | 10.47 | 10.74 | | |

Viscosity Measurements.

Acetate/Sorbitol/PS-80 and Histidine/Sorbitol/PS-80 samples (5° C.) from the DOE were pooled together, regardless of pH. The samples were next diluted to 190 mg/mL and 180 mg/mL in the appropriate buffer, and the viscosities and protein content measured (Table 14).

Viscosity for SAN-300 was measured using a Brookfield DV-III Ultra Programmable Rheometer. Prior to sample measurement, viscometer performance was calibrated using a certified viscosity standard. Following the standard measurement, 0.5 mL of neat sample was loaded into the viscometer. The viscosity measurements were performed at multiple percentage torque values.

Undiluted samples displayed non-Newtonian behavior, as evidenced by the small drop in viscosity at higher shear speeds. The behavior of both buffers becomes more Newtonian as SAN-300 is diluted.

TABLE 14

Results of Viscosity Studies

| Buffer | Excipient | pH | Target Conc. (mg/mL) | Viscosity 3 rpm (cP) | Viscosity 6 rpm (cP) | Viscosity 9 rpm (cP) |
|---|---|---|---|---|---|---|
| 30 mM Acetate | 250 mM Sorbitol | ~5.0 | Neat | 17.8 | 17.3 | 17.2 |
| 30 mM Histidine | | ~6.5 | Neat | 24.7 | 24.2 | 23.8 |
| 30 mM Acetate | | ~5.0 | 190 | 14.0 | 13.7 | 13.6 |
| 30 mM Histidine | | ~6.5 | 190 | 18.0 | 17.6 | 17.5 |
| 30 mM Acetate | | ~5.0 | 180 | 11.1 | 11.0 | 11.0 |
| 30 mM Histidine | | ~6.5 | 180 | 14.1 | 13.7 | 13.7 |

Filter Compatibility Studies.

To assess membrane compatibility, 1 mL of SAN-300 solution was filled into a 1 mL syringe (BD Cat. #. 309586) and ejected through the following filter types:

i) 0.22 µM pore size PES membrane (Millipore Cat. #SLGPM33RS)

ii) 0.22 µM pore size PVDF membrane (Millipore Cat. # SLGVM33RS)

iii) 0.22 µM pore size Cellulose Acetate membrane (Whatman, Cat. #10462200)

The appearance was recorded prior to and following filtration. Samples were analyzed by UV-Vis, DLS (undiluted), and SEC. Data were compared to an unprocessed control sample.

Table 15 shows protein loss following ejection through different filter types.

TABLE 15

Results of Filter Compatibility Studies

| Buffer | Excipient | pH | Condition | Starting Conc. (mg/mL) | Final Conc. (mg/mL) | Protein Loss (%) |
|---|---|---|---|---|---|---|
| 30 mM Acetate | 220 mM Sorbitol, 0.01% PS-80 | 5.5 | 5° C. Control | 189.1 | 186.4 | 1.4 |

TABLE 15-continued

Results of Filter Compatibility Studies

| Buffer | Excipient | pH | Condition | Starting Conc. (mg/mL) | Final Conc. (mg/mL) | Protein Loss (%) |
|---|---|---|---|---|---|---|
| 30 mM Histidine | 250 mM Sorbitol, 0.01% PS-20 | 6.0 | 5° C. Control | 174.4 | 173.3 | 0.6 |

TABLE 15-continued

Results of Filter Compatibility Studies

| Buffer | Excipient | pH | Condition | Starting Conc. (mg/mL) | Final Conc. (mg/mL) | Protein Loss (%) |
|---|---|---|---|---|---|---|
| 30 mM Acetate | 220 mM Sorbitol, 0.01% PS-80 | 5.5 | Cellulose Acetate | 189.1 | 186.0 | 1.6 |
| 30 mM Histidine | 250 mM Sorbitol, 0.01% PS-20 | 6.0 | Cellulose Acetate | 174.4 | 176.1 | −1.0 |
| 30 mM Acetate | 220 mM Sorbitol, 0.01% PS-80 | 5.5 | PES | 189.1 | 186.4 | 1.4 |
| 30 mM Histidine | 250 mM Sorbitol, 0.01% PS-20 | 6.0 | PES | 174.4 | 175.4 | −0.6 |
| 30 mM Acetate | 220 mM Sorbitol, 0.01% PS-80 | 5.5 | PVDF | 189.1 | 185.3 | 2.0 |
| 30 mM Histidine | 250 mM Sorbitol, 0.01% PS-20 | 6.0 | PVDF | 174.4 | 174.8 | −0.2 |

Example 5B. Forced Degradation Studies

Forced degradation studies of SAN-300 were performed to ensure the ability of analytical methods to detect and resolve potential degradation products in two different formulations. A total of 4.5 mL (9×0.5 mL vials) of concentrated SAN-300 was used per formulation.

Formulation Controls.

For formulation controls, 1 vial of each SAN-300 formulation was stored at 5° C. for the duration of the photo stress study (see below), followed by storage at 2° C. to 8° C. until analysis.

Freeze/Thaw Stress.

For freeze/thaw studies, freezing was performed by placing 1 vial of each SAN-300 formulation at −80° C. for ≥2 hours. The samples were thawed at room temperature and then returned to −80° C. for at least 90 minutes. Samples were exposed to 5 freeze/thaw cycles and then stored at 2° C. to 8° C. until analysis.

Heat Stress.

For heat-stress studies, 1 vial of each SAN-300 formulation was stored at 50° C. After 1 week, the samples were pulled for testing. Pulled samples were stored at 2° C. to 8° C. until analysis.

Photo Stress.

Photostability studies were performed following ICH Q1B guidelines for exposure of the product to cool white light and near UV light. One vial of each SAN-300 formulation was exposed to 1.2 million lux hours of white light and 200 W/m² of UV energy. First, the samples were exposed to 8.00 k lux of cool white light for 150 hours. Following this exposure, the samples were exposed to 10.00 W/m² UV light for 20 hours. The chamber temperature was maintained at 5° C. for the duration of the study. A negative control for each formulation that is double wrapped with aluminum foil was subjected to identical conditions (i.e., the formulation controls). Following stress, the samples were removed from the stability chamber and stored at 2° C. to 8° C. until analysis.

Controls for Hydrolysis and Agitation Studies.

To account for the effects of temperature in the hydrolysis and agitation stress studies, 1 vial of each SAN-300 formulation was stored at 25° C. for the duration of the hydrolysis/agitation studies, and then stored at 2° C. to 8° C. until analysis.

Deamidation/Base Hydrolysis.

For base-catalyzed deamidation studies, 1 vial of each SAN-300 formulation was titrated to pH≥9.0 with 1 M Tris. The sample was then placed at 25° C. for three days. At the end of the incubation period, the sample was buffer exchanged back into the appropriate formulation buffer using a 10 kDa MWCO concentrator (Millipore, Cat. No UFC801024) and stored at 2° C. to 8° C. until analysis.

Deamidation/Acid Hydrolysis.

For acid-catalyzed deamidation studies, 1 vial of each SAN-300 formulation was titrated to pH 3.5 to pH 4.0 with 1 N HCl. The sample was then placed at 25° C. for three days. At the end of the incubation period, the sample was buffer exchanged back into the appropriate formulation buffer using a 10 kDa MWCO concentrator and stored at 2° C. to 8° C. until analysis.

Agitation/Shear Stress.

For agitation studies, 1 vial of each SAN-300 formulation was placed vertically on a microplate shaker at ~650 rpm for three days at room temperature. Samples were then stored at 2° C. to 8° C. until analysis.

Forced Oxidation Stress.

For forced oxidation studies, 1 vial of each SAN-300 formulation was spiked with hydrogen peroxide to a final concentration of 0.04% (V/V) and then incubated at 37° C. for 4 hours. At the end of the incubation period, the sample was buffer exchanged back into the appropriate formulation buffer using a 10 kDa MWCO concentrator and stored at 2° C. to 8° C. until analysis.

TABLE 16

Results of Forced Degradation Studies

| Buffer | Excipient | pH | Condition | Starting Conc. (mg/mL) | Final Conc. (mg/mL) | Protein Loss (%) |
|---|---|---|---|---|---|---|
| 30 mM Acetate | 220 mM Sorbitol, 0.01% PS-80 | 5.5 | 5° C. Control | 189.1 | 186.4 | 1.4 |
| 30 mM Histidine | 250 mM Sorbitol, 0.01% PS-20 | 6.0 | 5° C. Control | 174.4 | 173.3 | 0.6 |
| 30 mM Acetate | 220 mM Sorbitol, 0.01% PS-80 | 5.5 | Form. Control | 189.1 | 184.7 | 2.3 |
| 30 mM Histidine | 250 mM Sorbitol, 0.01% PS-20 | 6.0 | Form. Control | 174.4 | 175.1 | −0.4 |

TABLE 16-continued

Results of Forced Degradation Studies

| Buffer | Excipient | pH | Condition | Starting Conc. (mg/mL) | Final Conc. (mg/mL) | Protein Loss (%) |
|---|---|---|---|---|---|---|
| 30 mM Acetate | 220 mM Sorbitol, 0.01% PS-80 | 5.5 | Photo Stress | 189.1 | 181.3 | 4.1 |
| 30 mM Histidine | 250 mM Sorbitol, 0.01% PS-20 | 6.0 | Photo Stress | 174.4 | 171.6 | 1.6 |
| 30 mM Acetate | 220 mM Sorbitol, 0.01% PS-80 | 5.5 | Hydr. Control | 189.1 | 186.2 | 1.5 |
| 30 mM Histidine | 250 mM Sorbitol, 0.01% PS-20 | 6.0 | Hydr. Control | 174.4 | 175.7 | −0.8 |
| 30 mM Acetate | 220 mM Sorbitol, 0.01% PS-80 | 5.5 | Acid Hydrolysis | 189.1 | 130.4$^a$ | 31.0 |
| 30 mM Histidine | 250 mM Sorbitol, 0.01% PS-20 | 6.0 | Acid Hydrolysis | 174.4 | 121.7$^a$ | 30.2 |
| 30 mM Acetate | 220 mM Sorbitol, 0.01% PS-80 | 5.5 | Base Hydrolysis | 189.1 | 175.3$^a$ | 7.3 |
| 30 mM Histidine | 250 mM Sorbitol, 0.01% PS-20 | 6.0 | Base Hydrolysis | 174.4 | 141.6$^a$ | 18.8 |
| 30 mM Acetate | 220 mM Sorbitol, 0.01% PS-80 | 5.5 | Oxidation | 189.1 | 163.9$^a$ | 13.3 |
| 30 mM Histidine | 250 mM Sorbitol, 0.01% PS-20 | 6.0 | Oxidation | 174.4 | 158.6$^a$ | 9.1 |
| 30 mM Acetate | 220 mM Sorbitol, 0.01% PS-80 | 5.5 | Agitation | 189.1 | 188.0 | 0.6 |
| 30 mM Histidine | 250 mM Sorbitol, 0.01% PS-20 | 6.0 | Agitation | 174.4 | 176.2 | −1.0 |
| 30 mM Acetate | 220 mM Sorbitol, 0.01% PS-80 | 5.5 | Freeze-Thaw | 189.1 | 185.4 | 2.0 |
| 30 mM Histidine | 250 mM Sorbitol, 0.01% PS-20 | 6.0 | Freeze-Thaw | 174.4 | 165.5 | 5.1 |
| 30 mM Acetate | 220 mM Sorbitol, 0.01% PS-80 | 5.5 | Heat Stress | 189.1 | 184.6 | 2.4 |
| 30 mM Histidine | 250 mM Sorbitol, 0.01% PS-20 | 6.0 | Heat Stress | 174.4 | 170.7 | 2.1 |

$^a$Values represent protein concentration measured at ~400 μl post-buffer exchange.

Useful formulations were as follows:
Formulation 1:
189.1 mg/mL SAN-300
30 mM Acetate
220 mM Sorbitol
0.01% polysorbate 80 (PS-80)
pH 5.5
Viscosity 3 rpm: 13.2 cP
Viscosity 5 rpm: 12.8 cP
Viscosity 7 rpm: 12.6 cP
Viscosity 9 rpm: 12.6 cP
Formulation 2:
174.4 mg/mL SAN-300
30 mM Histidine
250 mM Sorbitol
0.01% polysorbate 20 (PS-20)
pH 6.0
Viscosity 3 rpm: 10.4 cP
Viscosity 5 rpm: 10.2 cP
Viscosity 7 rpm: 10.1 cP
Viscosity 9 rpm: 10.0 cP

Example 5C. Sample Preparation for Formulation Development and Forced Degradation Studies Samples for use in formulation development and forced degradation studies were prepared as follows:
1. 30 mM Acetate, 250 mM Sorbitol, 0.01% PS-80, pH 5.5
2. 30 mM Histidine, 250 mM Sorbitol, 0.01% PS-20, pH 6.0

DoE samples had concentrations of ~215 mg/mL and viscosity of 18 (acetate) and 21 (histidine). For subcutaneous formulations, a theoretical viscosity target <15 cps is desired, and thus the concentrations were adjusted to bring viscosity into an acceptable range:
Acetate ~190 mg/mL, 13.7 cps
Histidine ~180 mg/mL, 13.8 cps Thus, the final SAN-300 concentration of the acetate solution was 190 mg/mL, while the final SAN-300 concentration in histidine was 180 mg/mL.

Sample Preparation.

Buffer-exchange of SAN-300 into the candidate formulations was performed using Amicon Ultra-15 concentrators (30 k MWCO, Ultracel Membrane, Cat #UFC 903096). Assuming a target concentration of 180 mg/mL to 190 mg/mL and a worst-case protein loss of 40%, a total of ~90 mL of SAN-300 was buffer-exchanged into each candidate formulation (i.e., ~12.4 g of starting material to be consumed in total), where a total of 12 Amicon concentrators was used in parallel for each formulation to process the required amount of SAN-300. The concentrators were rinsed with the appropriate buffer prior to the addition of protein. To each concentrator, 7.5 mL of SAN-300 (69 mg/mL) was added, and then diluted to 15 mL with the appropriate buffer. The volume was reduced to ~7.5 mL by centrifugation, followed by dilution with the appropriate buffer to 15 mL.

This process was repeated for a total of 4 cycles. Following buffer exchange, the samples were concentrated to the target concentration and pooled. Final SAN-300 concentration of the samples was determined by UV-Vis spectroscopy using an extinction coefficient of 1.53 mL/mg*cm.

Prior to final sample preparation, the osmolality measurements were performed using a freezing point depression osmometer. The Osmette XL 5007 osmometer was calibrated using deionized water (zero mOsm/kg), 100 mOsm/kg, and 500 mOsm/kg standard solutions before sample measurements. Following osmometer calibration, 0.25 mL of sample was used for measurement. If needed, additional excipients may be evaluated to target isotonic formulation composition (i.e., 280 to 350 mOsm/kg).

Samples were syringe filtered using 0.22 μm PVDF membranes (Millipore, Cat. #SLGVM33RS). Following filtration, samples were pooled and the concentration of SAN-300 again determined by UV-Vis spectroscopy. Samples allocated for Forced Degradation were filled (0.5 mL) into 2 mL Type 1 borosilicate glass vials (West Pharmaceuticals Cat #68000314) and stoppered with 13 mm Fluorotec stoppers (West Pharmaceuticals, Cat #19500040). A total of 9 vials was sealed for each formulation. Sample allocated for Formulation Development studies were placed in a 40 mL conical tube.

Samples were exchanged into the appropriate buffers and slightly over-concentrated, relative to the target SAN-300 concentration ((i) Acetate/Sorbitol/PS-80/pH 5.5: target 190 mg/mL Ab; (ii) Histidine/Sorbitol/PS-20/pH 6.0: target 180 mg/mL Ab)

The proper surfactants were added, protein content was determined, and the viscosity measured (Table 9 and Table 10).

TABLE 9

Sample formulations.

| Buffer | Excipient | pH | Sample | Diluted Conc. (mg/mL) | Final Conc. (mg/mL) | Avg. Final Conc. (mg/mL) |
|---|---|---|---|---|---|---|
| 30 mM Acetate | 250 mM Sorbitol | 5.5 | 1 | 0.44 | 218.9 | 217.4 |
|  |  |  | 2 | 0.43 | 215.9 |  |
| 30 mM Histidine |  | 6.0 | 1 | 0.42 | 210.5 | 214.5 |
|  |  |  | 2 | 0.44 | 218.5 |  |

TABLE 10

Starting concentrations and osmolality of sample formulations

| Buffer | Conc. (mg/mL) | Osmolality (mOsm/kg) |
|---|---|---|
| 30 mM Acetate, 250 mM Sorbitol, 0.01% PS-80, pH 5.5 | 217.4 | 384 |
| 30 mM Histidine, 250 mM Sorbitol, 0.01% PS-20, pH 6.0 | 214.5 | 354 |

Samples were then diluted to obtain the target concentrations listed above. For example, in order to obtain a suitable osmolality for the acetate formulation (280-350 mOsm/kg), this sample was diluted to the target concentration using 30 mM acetate, 0.01% PS-80, pH 5.5. After dilution, the final sorbitol concentration of this sample was 220 mM, Osmolality was again measured for the final samples (Table 11).

TABLE 11

Target Concentration and osmolality of sample formulations

| Buffer | Conc. (mg/mL) | Osmolality (mOsm/kg) |
|---|---|---|
| 30 mM Acetate, 250 mM Sorbitol, 0.01% PS-80, pH 5.5 | 196.5 | 318 |
| 30 mM Histidine, 250 mM Sorbitol, 0.01% PS-20, pH 6.0 | 174.8 | 341 |

Before vialing for the Forced Degradation study, samples were syringe-filtered through a 0.22 μm PVDF membrane (Millipore, C/N SLGVM33RS), and the protein content was again determined (Table 12).

TABLE 12

Concentration and viscosity following syringe-filtering.

| Buffer | Conc. (mg/mL) | Viscosity 3 rpm (cP) | Viscosity 5 rpm (cP) | Viscosity 7 rpm (cP) | Viscosity 9 rpm (cP) |
|---|---|---|---|---|---|
| 30 mM Acetate, 250 mM Sorbitol, 0.01% PS-80, pH 5.5 | 189.1 | 13.2 | 12.8 | 12.6 | 12.6 |
| 30 mM Histidine, 250 mM Sorbitol, 0.01% PS-20, pH 6.0 | 174.4 | 10.4 | 10.2 | 10.1 | 10.0 |

Example 6: Production and Stability Testing of SAN-300 Formulations: Materials, Methods and Experimental Design Overview Long-term stability studies were undertaken for SAN-300, an anti-VLA1 IgG1 monoclonal antibody, to evaluate several formulations. The protein was formulated in 30 mM histidine, 250 mM sorbitol, 0.01% PS-20, pH 6.0 and 30 mM acetate, 220 mM sorbitol, 0.01% PS-80, pH 5.5 at both high (180-190 mg/mL) and low (120 mg/mL) concentrations for a total of four formulations. These samples were prepared by tangential flow filtration, sealed in type 1 borosilicate vials, and staged at prospective storage conditions (−75° C. and 2-8° C.), an accelerated condition (30° C./65% RH), and a stressed condition (40° C./75% RH). Samples were maintained under these conditions to assess the chemical, physical, and structural stability of the protein. Lower concentration formulations were tested for a period of 6 months under all conditions. Both higher concentration formulations were evaluated through 12 months under all conditions, with the exception of samples stored at 40° C./75% RH, which were tested through 6 months. The results of the long term stability studies described in Examples 6-12 established that histidine was a superior buffering system to acetate, and that SAN-300 remained stable at −75° C. and 2-8° C. for up to 12 months at high concentration.

LIST OF ABBREVIATIONS

A280, A320 Absorbance at 280, 320 nm
AU Absorbance Units
CE Capillary Electrophoresis
CEX Cation Exchange Chromatography
C/N Catalog Number
DI Deionized Water
dP Pressure Differential (P Feed−P Ret)
HC Heavy Chain
HMW High Molecular Weight
HPLC High Performance Liquid Chromatography
LC Light Chain
LMWI Low Molecular Weight Impurity
P Feed Feed Pressure
P Ret Retentate Pressure
PS-20, PS-80 Polysorbate-20, Polysorbate 80
RH Relative Humidity
RSD Relative Standard Deviation
SDS Sodium Dodecyl Sulfate
SEC Size Exclusion Chromatography
TFF Tangential Flow Filtration
TMP Transmembrane Pressure ((P Feed+P Ret)/2)
UV Ultraviolet
Vis Visible
WFI Water For Injection
Materials
The following materials were used in Examples 6-12.
SAN-300, Lot #CP4-04-109 (69 mg/mL)
SAN-300, Lot #CP4-04-106 (60 mg/mL)
Pellicon XL 30 kDa cassettes, Millipore, C/N PXB030A50
10% Tween-20 Surfact-Amp, Thermo, C/N 28320
10% Tween-80 Surfact-Amp, Thermo, C/N 28328
Colloidal Blue Staining Kit Stainer A&B, Invitrogen, C/N 46-7015
D-Sorbitol, Sigma, C/N 85529
DryEase® Mini-gel Drying System, Invitrogen, C/N N12387
Gel Drying Solution, Invitrogen, C/N LC1001
Hydrochloric Acid (6 N), J. T. Baker, C/N H31513 or equivalent
L-Histidine, J. T. Baker, C/N 2080-05
Mark 12 Molecular Marker, Invitrogen, C/N LC5677
NuPAGE® Sample Reducing Agent, Invitrogen, C/N NP0004
Sodium Acetate, Sigma, C/N S1429
Sodium Chloride, Sigma, C/N S1679 or equivalent
Sodium Hydroxide (6 N), J. T. Baker, C/N H41521 or equivalent
Sodium Phosphate Dibasic Anhydrous, Sigma, C/N S9763 or equivalent
Sodium Phosphate Monobasic Monohydrate, Sigma, C/N S9638 or equivalent
Tris-Glycine Gels (4-20% Gradient), 15 well, Invitrogen, C/N EC60255BOX
Tris-Glycine SDS Sample Buffer, Invitrogen, C/N LC2676
UVettes, Eppendorf, C/N 952010051
HyClone WFI water, Thermo, C/N SH30221.10
CEX Column: ProPac WCX-10 CEX Column, 4×250 mm, Dionex, C/N 054993
CEX Guard Column: Propac WCX-10G Guard Column, 4×50 mm, Dionex, C/N 054994
SEC Column: G3000SWx1 7.8×300 mm, 5 μm, Tosoh, C/N 08541
SEC Guard Column: SWx1 6×40 mm, 7 μm, Tosoh, C/N 08543
Viscosity Standard, Brookfield, C/N 10 cps
Vials (13 mm, 2 mL), West, C/N 68000314
Stoppers (13 mm), West, C/N 19500040
Lids (13 mm), West, C/N 54130240
Equipment
1100 HPLC System, Agilent
Sevenmulti pH/Conductivity Meter, Mettler Toledo
BioRad Power Supply, Power Pac Basic
DV-III Ultra Programmable Rheometer, Brookfield
GeneGenius Bioimaging System
HIAC Liquid Particle Counter, HACH, model 9703
Labscale TFF System, Millipore,
Observation Lamp, Eisai Machinery, model MIH-DX
Osmette™ XL Automatic Osmometer model 5007
S40 pH Meter, Mettler Toledo
Stability Chamber, Environmental Specialties, model ES2000
UV/Vis Spectrophotometer, Agilent, model 8453
Xcell Surelock Mini-Cell, Invitrogen, C/N EI00001
Methods
Protein Content.

50 μL of concentrated protein solution was diluted volumetrically into 25.0 mL of 0.9% NaCl. Diluted samples were measured using UVette disposable cuvettes in an Agilent UV/Vis spectrophotometer, model 8453. Protein concentration was determined according to the following equations:

$$\text{Correction Factor} = A320 + (A320 - A360)$$

$$\text{Corrected } A280 = A280 - \text{Correction Factor}$$

$$\text{Protein Concentration (mg/mL)} = (\text{Corrected } A280 * \text{Dilution Factor})/1.53 \text{ mL/mg*cm}$$

If duplicate samples displayed >5% relative standard deviation (RSD), a third dilution was evaluated, and the outlying data point discarded.

pH.

pH measurements of all sample solutions were performed according to GTM-0015 "Determination of pH" using a calibrated SV40 pH Meter (Mettler Toledo) with an automatic temperature compensation electrode.

Conductivity.

Conductivity measurements were performed using a calibrated Sevenmulti pH and Conductivity Meter.

Sample Preparation and Study Design

The indicated lot of SAN-300 drug substance was formulated into the following buffers by tangential flow filtration (TFF) using a Millipore Labscale TFF System fitted with three Millipore Pellicon XL 30 kDa cassettes operating in series (150 cm2 total area). Transmembrane pressure (TMP) was maintained at ≤20 psi for all TFF processes.

i) Lot #CP4-04-106 (60 mg/mL): 30 mM Acetate, 220 mM Sorbitol, pH 5.5 ii) Lot #CP4-104-109 (69 mg/mL): 30 mM Histidine, 250 mM Sorbitol, pH 6.0

To monitor the progress during TFF processing, aliquots were removed at different stages for in-process pH, conductivity, and protein content testing (Table 17 and Table 18).

TABLE 17

Aliquot Withdrawal Schedule and In-Process Testing Results for TFF Processing of SAN-300 Drug Substance

| Formulation | Sample # | Sample Point | Aliquot Removed | Protein Content (mg/m L) | pH | Conductivity (mS/cm) |
|---|---|---|---|---|---|---|
| 30 mM Acetate 220 mM Sorbitol pH 5.5 | — | Diafiltration Buffer | — | — | 5.56 | 2.26 |
| | IP-1 | Drug Substance | 3 × 1 mL | 60.0 | 6.09 | 1.73 |
| | IP-2 | Post-Concentration Retentate | 1 mL | 111.1 | — | — |
| | IP-3 | Post-Concentration Filtrate | 3 × 1 mL | 2.1 | — | — |
| | IP-4 | After 5 Diafiltrations (Retentate) | 3 × 1 mL | — | — | — |
| | IP-5 | After 5 Diafiltrations (Filtrate) | 10 × 1 mL | 2.8 | 5.50 | 2.38 |
| | IP-6 | After 7 Diafiltrations (Retentate) | 3 × 1 mL | 113.2 | — | — |
| | IP-7 | After 7 Diafiltrations (Filtrate) | 10 × 1 mL | 2.1 | 5.44 | 2.42 |
| | IP-8 | After Overconcentration | 1 mL | 231.2 | — | — |
| | IP-9 | System Rinse | — | 56.6 | — | — |
| | IP-10 | Post-Rinse Addition | — | 193.4 | — | — |
| 30 mM Histidine 250 mM Sorbitol pH 6.0 | — | Diafiltration Buffer | — | — | 6.08 | 1.32 |
| | IP-1 | Drug Substance | 3 × 1 mL | 69.0 | NA[a] | NA[a] |
| | IP-2 | Post-Concentration Retentate | 1 mL | 123.0 | — | — |
| | IP-3 | Post-Concentration Filtrate | 3 × 1 mL | 0.7 | — | — |
| | IP-4 | After 5 Diafiltrations (Retentate) | 3 × 1mL | — | — | — |
| | IP-5 | After 5 Diafiltrations (Filtrate) | 10 × 1 mL | −0.1 | 6.06 | 1.38 |
| | IP-6 | After 7 Diafiltrations (Retentate) | 3 × 1 mL | 141.2 | — | — |
| | IP-7 | After 7 Diafiltrations (Filtrate) | 10 × 1 mL | 1.3 | 5.97 | 1.32 |
| | IP-8 | After Overconcentration | 1 mL | 219.1 | — | — |
| | IP-9 | System Rinse | — | 37.1 | — | — |
| | IP-10 | Post-Rinse Addition | — | 182.2 | — | — |

[a]Measurement was not taken for sample

TABLE 18

Protein Content Determinations of Aliquots Withdrawn for In-Process Testing

| Formulation | Condition | Sample | A280 (AU) | A320 (AU) | A360 (AU) | Correction (AU) | A280 Corrected (AU) | Diluted Conc. (mg/mL) | Final Conc. (mg/mL) | Average Final Conc. (mg/mL) | % RSD |
|---|---|---|---|---|---|---|---|---|---|---|---|
| 30 mM Acetate 220 mM Sorbitol pH 5.5 | IP-1 | 1 | 0.21840 | 0.02684 | 0.01608 | 0.03761 | 0.18079 | 0.12 | 59.1 | 60.0 | 2.3 |
| | | 2 | 0.18525 | −0.00708 | −0.01272 | −0.00145 | 0.18670 | 0.12 | 61.0 | | |
| | IP-2 | 1 | 0.35282 | 0.00780 | 0.00070 | 0.01490 | 0.33792 | 0.22 | 110.4 | 111.1 | 0.8 |
| | | 2 | 0.34576 | −0.00018 | −0.00419 | 0.00383 | 0.34193 | 0.22 | 111.7 | | |
| | IP-3 | 1 | −0.00494 | −0.00623 | 0.00004 | −0.01250 | 0.00756 | 0.00 | 2.5 | 2.1 | 25.4 |
| | | 2 | −0.01202 | −0.01333 | 0.00938 | −0.01728 | 0.00526 | 0.00 | 1.7 | | |
| | IP-5 | 1 | −0.01665 | −0.01893 | −0.01271 | −0.02515 | 0.00850 | 0.01 | 2.8 | 2.8 | 1.9 |
| | | 2 | −0.01081 | −0.01559 | −0.01162 | −0.01955 | 0.00874 | 0.01 | 2.9 | | |

TABLE 18-continued

Protein Content Determinations of Aliquots Withdrawn for In-Process Testing

| Formulation | Condition | Sample | A280 (AU) | A320 (AU) | A360 (AU) | Correction (AU) | A280 Corrected (AU) | Diluted Conc. (mg/mL) | Final Conc. (mg/mL) | Average Final Conc. (mg/mL) | % RSD |
|---|---|---|---|---|---|---|---|---|---|---|---|
| | IP-6 | 1 | 0.34230 | −0.00146 | −0.00159 | −0.00132 | 0.34362 | 0.22 | 112.3 | 113.2 | 1.1 |
| | | 2 | 0.34244 | −0.00710 | −0.00771 | −0.00650 | 0.34894 | 0.23 | 114.0 | | |
| | IP-7 | 1 | −0.01433 | −0.01487 | −0.01200 | −0.01774 | 0.00341 | 0.00 | 1.1 | 2.1 | 64.7 |
| | | 2 | −0.01927 | −0.02167 | −0.01493 | −0.02842 | 0.00914 | 0.01 | 3.0 | | |
| | IP-8 | 1 | 0.68642 | −0.02048 | −0.01783 | −0.02313 | 0.70955 | 0.46 | 231.9 | 231.2 | 0.4 |
| | | 2 | 0.68393 | −0.01673 | −0.01182 | −0.02164 | 0.70557 | 0.46 | 230.6 | | |
| | IP-9 (Rinse) | 1 | 0.19040 | 0.00407 | −0.00859 | 0.01673 | 0.17367 | 0.11 | 56.8 | 56.6 | 0.4 |
| | | 2 | 0.18056 | −0.00083 | −0.00956 | 0.00790 | 0.17266 | 0.11 | 56.4 | | |
| | IP-10 | 1 | 0.58275 | −1.2217E−02 | −2.1278E−02 | −0.00316 | 0.58591 | 0.38 | 191.5 | 193.4 | 1.4 |
| | | 2 | 0.61120 | 7.4577E−04 | −1.2146E−02 | 0.01364 | 0.59756 | 0.39 | 195.3 | | |
| 30 mM Histidine 250 mM Sorbitol pH 6.0 | IP-2 | 1 | 0.37486 | −0.00234 | −0.00556 | 0.00089 | 0.37397 | 0.24 | 122.2 | 123.0 | 0.9 |
| | | 2 | 0.38775 | 0.00684 | 0.00443 | 0.00924 | 0.37851 | 0.25 | 123.7 | | |
| | IP-3 | 1 | 0.00531 | 0.00209 | −0.00454 | 0.00872 | −0.00340 | 0.00 | −1.1 | 0.7 | 351.2 |
| | | 2 | −0.01455 | −0.01648 | −0.01043 | −0.02254 | 0.00799 | 0.01 | 2.6 | | |
| | After 4th Diafiltration | 1 | 0.37145 | −0.00682 | −0.00769 | −0.00596 | 0.37741 | 0.25 | 123.3 | 120.7 | 3.0 |
| | | 2 | 0.37566 | 0.00874 | 0.00340 | 0.01409 | 0.36157 | 0.24 | 118.2 | | |
| | IP-5 | 1 | −0.00936 | −0.00685 | −0.00431 | −0.00939 | 0.00004 | 0.00 | 0.0 | −0.1 | −157.9 |
| | | 2 | −0.01815 | −0.01492 | −0.01237 | −0.01748 | −0.00068 | 0.00 | −0.2 | | |
| | IP-6 | 1 | 0.40677 | −0.01602 | −0.00584 | −0.02621 | 0.43298 | 0.28 | 141.5 | 141.2 | 0.3 |
| | | 2 | 0.41610 | −0.01461 | −0.01419 | −0.01503 | 0.43113 | 0.28 | 140.9 | | |
| | IP-7 | 1 | −0.01297 | −0.01053 | −0.00233 | −0.01873 | 0.00577 | 0.00 | 1.9 | 1.3 | 60.3 |
| | | 2 | −0.00631 | −0.00604 | −0.00346 | −0.00863 | 0.00232 | 0.00 | 0.8 | | |
| | Conc. to 115 mL | 1 | 0.59934 | 0.00308 | 0.00170 | 0.00445 | 0.59489 | 0.39 | 194.4 | 194.4 | 0.0 |
| | | 2 | 0.58662 | −0.00413 | −0.00013 | −0.00813 | 0.59475 | 0.39 | 194.4 | | |
| | IP-8 | 1 | 0.66784 | 0.00237 | 0.00483 | −0.00008 | 0.66792 | 0.44 | 218.3 | 219.1 | 0.5 |
| | | 2 | 0.64941 | −0.01297 | −0.00253 | −0.02340 | 0.67281 | 0.44 | 219.9 | | |
| | IP-9 (Rinse) | 1 | 0.11225 | −0.00660 | −0.00911 | −0.00409 | 0.11634 | 0.08 | 38.0 | 37.1 | 3.5 |
| | | 2 | 0.11000 | −0.00567 | −0.01068 | −0.00067 | 0.11067 | 0.07 | 36.2 | | |
| | IP-10 | 1 | 0.54739 | −0.01053 | −0.00573 | −0.01532 | 0.56271 | 0.37 | 183.9 | 182.2 | 1.3 |
| | | 2 | 0.54346 | −0.00355 | 0.00168 | −0.00878 | 0.55224 | 0.36 | 180.5 | | |

To begin, ~450 mL of CP4-04-106 or ~430 mL of CP4-04-109 were concentrated to roughly half the starting volume (Table 19). Feed and retentate pressure (P Feed and P Ret) were monitored during initial concentration at several time points.

TABLE 19

Summary of Initial Concentration Data for TFF Processing of SAN-300 Drug Substance

| Formulation | Time | P Feed (psi) | P Ret (psi) | dP (psi) | TMP (psi) | Flux (mL/min) | Flux (LMH) | Permeate Volume (mL) |
|---|---|---|---|---|---|---|---|---|
| 30 mM Acetate 220 mM Sorbitol pH 5.5 | 5 | 25.0 | 5.0 | 20.0 | 15.0 | 4.0 | 16.0 | 20 |
| | 20 | 26.0 | 5.0 | 21.0 | 15.5 | 3.7 | 14.8 | 75 |
| | 35 | 27.0 | 5.0 | 22.0 | 16.0 | 3.5 | 14.1 | 128 |
| | 45 | 29.0 | 5.0 | 24.0 | 17.0 | 3.1 | 12.4 | 159 |
| | 65 | 33.0 | 5.0 | 28.0 | 19.0 | 2.9 | 11.4 | 216 |
| 30 mM Histidine 250 mM Sorbitol pH 6.0 | 1 | 22.5 | 7.5 | 15.0 | 15.0 | — | — | — |
| | 8 | 22.5 | 7.5 | 15.0 | 15.0 | — | — | 26 |
| | 34 | 30.0 | 5.0 | 25.0 | 17.5 | — | — | 96 |
| | 62 | 30.0 | 3.0 | 20.0 | 18.0 | — | — | 173 |

The mass of permeate was recorded at each of these time points and permeate volume determined. The pressure drop (dP; P Feed−P Ret) and transmembrane pressure (TMP; (P Feed+P Ret)/2) were also calculated. For the acetate formulation, filtrate flow rate was recorded at each time point (Flux, mL/min), and this measurement was normalized for membrane area ((L*h−1)/m2).

The concentrated drug substance was next exchanged into the appropriate formulation buffer by seven rounds of continuous diafiltration (Table 20). For each diavolume, feed pressure, retentate pressure and filtration rate were measured, and the associated parameters calculated as described above. Flux was observed to increase by ~50% for the acetate formulation, and ~30% for the histidine formulation by the fifth diavolume.

TABLE 20

Summary of Diafiltration Data for TFF Processing of SAN-300 Drug Substance

| Formulation | Diavolume | P Feed (psi) | P Ret (psi) | dP (psi) | TMP (psi) | Flux (mL/min) | Flux (LMH) | Total Time (hr:min) |
|---|---|---|---|---|---|---|---|---|
| 30 mM Acetate 220 mM Sorbitol pH 5.5 | 1 | 33.0 | 3.0 | 30.0 | 18.0 | 2.8 | 11.0 | 01:24 |
| | 2 | 34.0 | 5.0 | 29.0 | 19.5 | 3.0 | 12.0 | 02:37 |
| | 3 | 33.0 | 5.0 | 28.0 | 19.0 | 3.0 | 12.0 | 03:40 |
| | 4 | 33.0 | 5.0 | 28.0 | 19.0 | 3.8 | 15.2 | 04:37 |
| | 5 | 34.0 | 5.0 | 29.0 | 19.5 | 4.2 | 16.9 | 05:32 |
| | 6 | 34.0 | 5.0 | 29.0 | 19.5 | 4.3 | 17.0 | 06:22 |
| | 7 | 34.0 | 5.0 | 29.0 | 19.5 | 4.7 | 18.8 | 07:12 |
| 30 mM Histidine 250 mM Sorbitol pH 6.0 | 1 | 37.0 | 2.0 | 35.0 | 19.5 | 2.5 | 10.0 | 01:34 |
| | 2 | 36.0 | 3.0 | 33.0 | 19.5 | 2.6 | 10.4 | 02:53 |
| | 3 | 36.0 | 3.0 | 33.0 | 19.5 | 3.5 | 14.0 | 04:06 |
| | 4 | 37.0 | 3.0 | 34.0 | 20.0 | 3.2 | 12.9 | 05:14 |
| | 5 | 36.0 | 3.0 | 33.0 | 19.5 | 3.3 | 13.2 | 06:16 |
| | 6 | 37.0 | 0.0 | 37.0 | 18.5 | 3.3 | 13.2 | 07:29 |
| | 7 | 39.0 | 1.0 | 38.0 | 20.0 | 3.3 | 13.2 | 08:38 |

Following the completion of diafiltration, formulated drug substance was overconcentrated relative to the final SAN- 300 target concentration (Table 17). The final pH and conductivity of the over-concentrated solutions were nearly identical to the associated diafiltration buffer (Table 17). After removing the sample, the TFF system was flushed with diafiltration buffer and the protein content of the flush determined. This flush was used to dilute the over-concentrated SAN-300 to a level only slightly above the final target (Table 17). The volume of this solution was determined by weight using a density of 1.089 g/mL. Finally, the percent yield was estimated using protein content determinations made throughout TFF processing (Table 21). While no apparent SAN-300 loss was observed for the acetate formulation, exchange into histidine buffer resulted in a yield of 89%.

TABLE 21

Estimated Percent Yield for SAN-300 TFF Processing

| Formulation | Sample | Volume (mL) | Conc. (mg/mL) | Total Protein (mg) |
|---|---|---|---|---|
| 30 mM Acetate 220 mM Sorbitol 0.01% PS-80 pH 5.5 | Post-Concentration Aliquot[a] | 1.3 | 111.1 | 138.9 |
| | Post-5 Diafiltrations Aliquot | 3.0 | 111.1[b] | 333.3 |
| | Post-7 Diafiltrations Aliquot[c] | 3.5 | 113.2 | 396.2 |
| | Over-Concentration Aliquot[c] | 1.5 | 231.2 | 346.8 |
| | Final Over-Concentrated Sample | 109.7 | 231.2 | 25362.6 |
| | Rinse[b] | 22.0 | 56.6 | 1245.2 |
| | Total (mg): | | | 27823.0 |
| | Starting Drug Substance | 450.0 | 60.0 | 27000.0 |
| | Percent Yield: | | | 103.0 |
| 30 mM Histidine 250 mM Sorbitol 0.01% PS-20 pH 6.0 | Post-Concentration Aliquot[a] | 2.0 | 123.0 | 246.0 |
| | 4th Diafiltration Aliquot | 1.0 | 120.7 | 120.7 |
| | Post-5 Diafiltrations Aliquot | 3.0 | 120.7[b] | 362.1 |
| | Post-7 Diafiltrations Aliquot[c] | 3.5 | 141.2 | 494.2 |

TABLE 21-continued

Estimated Percent Yield for SAN-300 TFF Processing

| Formulation | Sample | Volume (mL) | Conc. (mg/mL) | Total Protein (mg) |
|---|---|---|---|---|
| | Conc. To 115 mL Aliquot | 0.5 | 194.4 | 97.2 |
| | Over-Concentration Aliquot[c] | 1.5 | 219.1 | 328.7 |
| | Final Over-Concentrated Sample | 108.7 | 219.1 | 23816.2 |
| | Rinse[b] | 25.5 | 37.1 | 946.1 |
| | Total (mg): | | | 26411.1 |
| | Starting Drug Substance | 430.0 | 69.0 | 29670.0 |
| | Percent Yield: | | | 89.0 |

[a]Includes 1.0 mL sample withdrawn for A280 testing
[b]Concentration not determined, the value shown is an estimate used to approximate the amount of material withdrawn for this aliquot
[c]Includes 0.5 mL sample withdrawn for A280 testing To reach the final target concentration, a small volume of formulation buffer including the sample-appropriate polysorbate (acetate, PS-80; histidine, PS-20) was added to achieve a surfactant concentration of 0.01%. A 40 mL aliquot of formulated SAN-300 at the target concentration was removed and diluted to 120 mg/mL using formulation buffer including 0.01% polysorbate. A total of four SAN-300 formulations were generated at the indicated target concentrations:

High Concentration:
NB1206p86A: 190 mg/mL, 30 mM Acetate, 220 mM Sorbitol, 0.01% PS-80, pH 5.5
NB1206p86B: 180 mg/mL, 30 mM Histidine, 250 mM Sorbitol, 0.01% PS-20 pH 6.0

Low Concentration:
NB1206p86C: 120 mg/mL 30 mM Acetate, 220 mM Sorbitol, 0.01% PS-80, pH 5.5
NB1206p86D: 120 mg/mL 30 mM Histidine, 250 mM Sorbitol, 0.01% PS-20 pH 6.0

Prior to vialing, the final protein content for all formulations was measured before and after filtration through a 0.22 μm PES membrane. The results are shown in Table 22.

TABLE 22

Final Protein Content Determination for SAN-300 Formulations used in Stability Study

| Formulation | Target Conc. (mg/mL) | Filtered | Sample | A280 (AU) | A320 (AU) | A360 (AU) | Correction (AU) | A280 Corrected (AU) | Diluted Conc. (mg/mL) | Final Conc. (mg/mL) | Average Final Conc. (mg/mL) | % RSD |
|---|---|---|---|---|---|---|---|---|---|---|---|---|
| 30 mM Acetate 220 mM Sorbitol 0.01% PS-80 pH 5.5 | 190 | Pre- | 1 | 0.56786 | −0.01349 | −0.01702 | −0.00995 | 0.57781 | 0.38 | 188.8 | 189.4 | 0.4 |
| | | | 2 | 0.55664 | −0.02798 | −0.03137 | −0.02459 | 0.58123 | 0.38 | 189.9 | | |
| | | Post- | 1 | 0.56776 | −0.01310 | −0.01250 | −0.01369 | 0.58145 | 0.38 | 190.0 | 187.6 | 1.8 |
| | | | 2 | 0.57070 | −0.00423 | −0.01231 | 0.00385 | 0.56685 | 0.37 | 185.2 | | |
| | 120 | Pre- | 1 | 0.34587 | −0.02212 | −0.01862 | −0.02563 | 0.37150 | 0.24 | 121.4 | 119.8 | 1.8 |
| | | | 2 | 0.33867 | −0.02524 | −0.02718 | −0.02330 | 0.36197 | 0.24 | 118.3 | | |
| | | Post- | 1 | 0.34845 | −0.02428 | −0.02173 | −0.02684 | 0.37529 | 0.25 | 122.6 | 121.7 | 1.1 |
| | | | 2 | 0.34747 | −0.02325 | −0.02449 | −0.02200 | 0.36947 | 0.24 | 120.7 | | |
| 30 mM Histidine 250 mM Sorbitol 0.01% PS-20 pH 6.0 | 180 | Pre- | 1 | 0.52190 | −0.01683 | −0.01887 | −0.01480 | 0.53670 | 0.35 | 175.4 | 174.1 | 1.0 |
| | | | 2 | 0.49998 | −0.02657 | −0.02423 | −0.02890 | 0.52888 | 0.35 | 172.8 | | |
| | | Post- | 1 | 0.54108 | −0.00328 | −0.00087 | −0.00569 | 0.54677 | .036 | 178.7 | 177.4 | 1.0 |
| | | | 2 | 0.52670 | −0.01604 | −0.01957 | −0.01250 | 0.53920 | 0.35 | 176.2 | | |
| | 120 | Pre- | 1 | 0.34107 | −0.01813 | −0.01766 | −0.01860 | 0.35967 | 0.24 | 117.5 | 116.9 | 0.8 |
| | | | 2 | 0.35011 | −0.00864 | −0.01161 | −0.00567 | 0.35578 | 0.23 | 116.3 | | |
| | | Post- | 1 | 0.34101 | −0.01342 | −0.01537 | −0.01146 | 0.35247 | 0.23 | 115.2 | 115.5 | 0.3 |
| | | | 2 | 0.33710 | −0.01865 | −0.02027 | −0.01702 | 0.35412 | 0.23 | 115.7 | | |

The four formulations were vialed into sterile, depyrogenated type I borosilicate glass vials at a volume of 1 mL, sealed using 13 mm FluroTec® stoppers, and stored at 2-8° C. until staging. For stability testing, samples were maintained at prospective storage conditions (−75° C. and 2-8° C.), an accelerated condition (30° C./65% RH), and a stressed condition (40° C./75% RH). In addition, some vials were stored in an inverted position at 2-8° C. to determine if container closure impacts SAN-300 stability. The analytical testing schedule is shown in Table 23.

TABLE 23

Analytical Testing Schedule for SAN-300 Stability Study

| Formulation | Condition | $T_0$ | 1 Month | 3 Months | 6 Months | 9 Months | 12 Months |
|---|---|---|---|---|---|---|---|
| NB1206p86A | −75° C. | $X^a$ | — | — | X | — | X |
| NB1206p86B | 2-8° C. |  | $X^b$ | $X^b$ | X | X | X |
| (High Conc.) | 2-8° C. (Inverted) | — | — | X | — | X |  |
|  | 30° C./65% RH |  | X | X | X | X | X |
|  | 40° C./75% RH |  | X | X | X | — | — |

TABLE 23-continued

Analytical Testing Schedule for SAN-300 Stability Study

| Formulation | Condition | $T_0$ | 1 Month | 3 Months | 6 Months | 9 Months | 12 Months |
|---|---|---|---|---|---|---|---|
| NB1206p86C | −75° C. | $X^a$ | — | — | X | — | — |
| NB1206p86D | 2-8° C. |  | — | $X^b$ | X | — | — |
| (Low Conc.) | 2-8° C. (Inverted) | — | — | X | — | — |  |
|  | 30° C./65% RH |  | — | X | X | — | — |
|  | 40° C./75% RH |  | — | X | X | — | — |

X: Testing included appearance, protein content, pH, HIAC, reduced SDS-PAGE, SEC, and CEX
[a] Additional osmolality and viscosity testing
[b] Additional osmolality testing Example 7. Viscosity and Osmolality of SAN-300 Formulations The viscosity of SAN-300 formulations (as described in Example 6) was assessed at at the initial time point. Osmolality of the formulations was assessed at the initial time point and after 1 and 3 months of storage at 2-8° C.

Methods

Methods for Assessing Viscosity.

A shear rheometer was calibrated with Brookfield viscosity standard fluid #10, and 0.5 mL of sample was measured at various spindle speeds (shear rates). Samples displaying constant viscosity (cP) readings over all shear rates were considered Newtonian over this range, while samples with shear rate-dependent viscosity values would be considered non-Newtonian.

Methods for Assessing_Osmolality.

Osmolality measurements were performed using a freezing point depression osmometer, which measures the decrease in a solution's freezing point as solute concentration increases. The Osmette XL 5007 osmometer was calibrated using deionized water (zero mOsm/kg), 100 mOsm/kg, and 500 mOsm/kg standard solutions.

Following the osmometer calibration, 250 μL of sample was measured.

Results

The viscosity and osmolality results are shown in Table 24.

TABLE 24

Summary of Viscosity and Osmolality Results for SAN-300 Stability Study

| Sample Lot | Formulation | Conc. (mg/mL) | Condition | Time Point | Viscosity (cP) | Osmolality (mOsm/kg) |
|---|---|---|---|---|---|---|
| NB1206p86A | 30 mM Acetate 220 mM Sorbitol 0.01% PS-80 pH 5.5 | 190 | Initial |  | 13.7 | 295 |
|  |  |  | 2-8° C. | 1M | — | 318 |
|  |  |  |  | 3M | — | 310 |
| NB1206p86C |  | 120 | Initial |  | 4.4 | 299 |
|  |  |  | 2-8° C. | 3M | — | 321 |
| NB1206p86B | 30 mM Histidine 250 mM Sorbitol 0.01% PS-20 pH 6.0 | 180 | Initial |  | 11.9 | 289 |
|  |  |  | 2-8° C. | 1M | — | 331 |
|  |  |  |  | 3M | — | 319 |
| NB1206p86D |  | 120 | Initial |  | 4.3 | 287 |
|  |  |  | 2-8° C. | 3M | — | 316 |

Viscosity Results.

Formulation viscosity was evaluated for all formulations at the initial time point. The results are shown in Table 24. Newtonian behavior was observed for all samples, where both high concentration histidine and acetate formulations displayed viscosities <15 cP (11.9 and 13.7 cP, respectively). Low concentration histidine and acetate formulation viscosities were 4.3 and 4.4 cP, respectively. All viscosities measured were consistent with historical values.

Osmolality Results.

Osmolality measurements were performed at the initial time point (Table 24). Readings for both high-concentration acetate (295 mOsm/kg) and histidine (289 mOsm/kg) formulations were somewhat lower than historical values and, thus, re-evaluation of sample osmolality was performed at 1 and 3 months using samples stored at 2-8° C. The resulting values for the acetate formulation were 318 and 310 mOsm/kg for samples at 1 month and 3 months, respectively, while histidine-containing samples showed osmolality of 331 and 319 mOsm/kg. These data were fully consistent with historical readings, and show that sample osmolality remained constant within this time-frame. The osmolality of low concentration acetate and histidine formulations at the 3 month time point was 321 and 316 mOsm/kg, respectively.

Example 9. Long Term Stability of SAN-300 Formulations: Appearance, Protein Content, and pH The appearance, protein content, and pH of SAN-300 Formulations was assessed to determine their long term stability using the experimental design described in Example 7.

Methods

Appearance.

Prior to unsealing vials for analytical testing, sample appearance was evaluated against a white and dark background. Each sample was tested against an identical vial filled with DI water for color, clarity (opalescence), and the presence of visible particulate matter.

Protein Content and pH.

Protein content and pH were assessed as described in Example 7.

Results

The results are shown in Table 25 below. All formulations maintained consistent appearance, protein content, and pH over the course of the study

TABLE 25

| Sample Lot | Formulation | Condition | Time Point | Protein Content (mg/mL) | pH | Osmolality (mOsm/kg) | Appearance[a] |
|---|---|---|---|---|---|---|---|
| Table 25A. Acetate Formulation: Summary of Protein Content, pH, and Appearance Results for SAN-300 Stability Samples | | | | | | | |
| NB1206p86A | 190 mg/mL SAN-300 30 mM Acetate 220 mM Sorbitol 0.01% PS-80, pH 5.5 | Initial | | 185.9 | 5.6 | 295 | slightly yellow (•), slightly opalescent, no visible particles |
| | | −75° C. | 6M | 194.2 | 5.7 | — | slightly yellow (•), slightly opalescent, no visible particles |
| | | | 12M | 181.6 | 5.7 | | slightly yellow (•), slightly opalescent, no visible particles |
| | | 2-8° C. | 1M | 186.7 | 5.6 | 318 | slightly yellow (•), slightly opalescent, no visible particles |
| | | | 3M | 184.9 | 5.7 | 310 | slightly yellow (•), slightly opalescent, no visible particles |
| | | | 6M | 192.0 | 5.6 | — | slightly yellow (•), slightly opalescent, no visible particles |
| | | | 9M | 187.1 | 5.6 | — | slightly yellow (•), slightly opalescent, no visible particles |
| | | | 12M | 181.5 | 5.7 | — | slightly yellow (•), slightly opalescent, no visible particles |
| | | 2-8° C. (Inverted) | 6M | 194.1 | 5.6 | — | slightly yellow (•), slightly opalescent, no visible particles |
| | | | 12M | 186.6 | 5.7 | — | slightly yellow (•), slightly opalescent, no visible particles |
| | | 30° C./65% RH | 1M | 187.7 | 5.7 | — | slightly yellow (•), slightly opalescent, no visible particles |
| | | | 3M | 189.3 | 5.7 | — | slightly yellow (•), slightly opalescent, no visible particles |
| | | | 6M | 189.5 | 5.7 | — | slightly yellow (•), slightly opalescent, no visible particles |
| | | | 9M | 192.9 | 5.7 | — | slightly yellow (•), slightly opalescent, no visible particles |
| | | | 12M | 188.3 | 5.7 | — | slightly yellow (•), slightly opalescent, no visible particles |
| | | 40° C./75% RH | 1M | 189.5 | 5.7 | — | slightly yellow (•), slightly opalescent, no visible particles |
| | | | 3M | 188.3 | 5.7 | — | slightly yellow (•), slightly opalescent, no visible particles |
| | | | 6M | 193.8 | 5.7 | — | slightly yellow (•), slightly opalescent, no visible particles |
| NB1206p86C | 120 mg/mL SAN-300 30 mM Acetate 220 mM Sorbitol 0.01% PS-80, pH 5.5 | Initial | | 120.9 | 5.6 | 299 | slightly yellow (-), slightly opalescent, no visible particles |
| | | −75° C. | 6M | 122.3 | 5.6 | — | slightly yellow (-), slightly opalescent, no visible particles |
| | | 2-8° C. | 3M | 121.0 | 5.6 | 321 | slightly yellow (-), slightly opalescent, no visible particles |
| | | | 6M | 124.6 | 5.6 | — | slightly yellow (-), slightly opalescent, no visible particles |
| | | 2-8° C. (Inverted) | 6M | 122.9 | 5.6 | — | slightly yellow (-), slightly opalescent, no visible particles |
| | | 30° C./65% RH | 3M | 122.7 | 5.6 | — | slightly yellow (-), slightly opalescent, no visible particles |
| | | | 6M | 124.4 | 5.6 | — | slightly yellow (-), slightly opalescent, no visible particles |
| | | 40° C./75% RH | 3M | 124.4 | 5.6 | — | slightly yellow (-), slightly opalescent, no visible particles |
| | | | 6M | 125.6 | 5.7 | — | slightly yellow (-), slightly opalescent, no visible particles |

TABLE 25-continued

Table 25B: Histidine Formulation: Summary of Protein Content, pH, and Appearance Results for SAN-300 Stability Samples (Continued)

| Sample Lot | Formulation | Condition | Time Point | Protein Content (mg/mL) | pH | Osmolality (mOsm/kg) | Appearance[a] |
|---|---|---|---|---|---|---|---|
| NB1206p86B | 180 mg/mL SAN-300 30 mM Histidine 250 mM Sorbitol 0.01% PS-20, pH 6.0 | Initial | | 174.1 | 6.2 | 289 | slightly yellow (•), slightly opalescent, no visible particles |
| | | −75° C. | 6M | 179.4 | 6.2 | — | slightly yellow (•), slightly opalescent, no visible particles |
| | | | 12M | 173.8 | 6.3 | — | slightly yellow (•), slightly opalescent, few visible particles |
| | | 2-8° C. | 1M | 176.5 | 6.2 | 331 | slightly yellow (•), slightly opalescent, no visible particles |
| | | | 3M | 175.8 | 6.2 | 319 | slightly yellow (•), slightly opalescent, no visible particles |
| | | | 6M | 180.1 | 6.2 | — | slightly yellow (•), slightly opalescent, no visible particles |
| | | | 9M | 178.9 | 6.2 | — | slightly yellow (•), slightly opalescent, no visible particles |
| | | | 12M | 170.9 | 6.3 | — | slightly yellow (•), slightly opalescent, no visible particles |
| | | 2-8° C. (Inverted) | 6M | 184.5 | 6.2 | — | slightly yellow (•), slightly opalescent, no visible particles |
| | | | 12M | 170.1 | 6.3 | — | slightly yellow (•), slightly opalescent, no visible particles |
| | | 30° C./65% RH | 1M | 179.9 | 6.2 | — | slightly yellow (•), slightly opalescent, no visible particles |
| | | | 3M | 179.5 | 6.2 | — | slightly yellow (•), slightly opalescent, no visible particles |
| | | | 6M | 180.2 | 6.2 | — | slightly yellow (•), slightly opalescent, no visible particles |
| | | | 9M | 177.7 | 6.2 | — | slightly yellow (•), slightly opalescent, no visible particles |
| | | | 12M | 172.2 | 6.2 | — | slightly yellow (+), slightly opalescent, no visible particles |
| | | 40° C./75% RH | 1M | 176.5 | 6.2 | — | slightly yellow (•), slightly opalescent, no visible particles |
| | | | 3M | 184.3 | 6.2 | — | slightly yellow (•), slightly opalescent, no visible particles |
| | | | 6M | 180.6 | 6.2 | — | slightly yellow (+), slightly opalescent, no visible particles |
| NB1206p86D | 120 mg/mL SAN-300 30 mM Histidine 250 mM Sorbitol 0.01% PS-20, pH 6.0 | Initial | | 117.8 | 6.1 | 287 | slightly yellow (−), slightly opalescent, no visible particles |
| | | −75° C. | 6M | 120.9 | 6.2 | — | slightly yellow (-), slightly opalescent, no visible particles |
| | | 2-8° C. | 3M | 119.4 | 6.1 | 316 | slightly yellow (−), slightly opalescent, no visible particles |
| | | | 6M | 120.7 | 6.2 | — | slightly yellow (−), slightly opalescent, no visible particles |
| | | 2-8° C. (Inverted) | 6M | 122.5 | 6.2 | — | slightly yellow (−), slightly opalescent, no visible particles |
| | | 30° C./65% RH | 3M | 118.4 | 6.1 | — | slightly yellow (−), slightly opalescent, no visible particles |
| | | | 6M | 119.9 | 6.1 | — | slightly yellow (−), slightly opalescent, no visible particles |
| | | 40° C./75% RH | 3M | 121.0 | 6.1 | — | slightly yellow (−), slightly opalescent, no visible particles |
| | | | 6M | 118.8 | 6.1 | — | slightly yellow (−), slightly opalescent, no visible particles |

[a]The degree of sample coloration increases from (−) to (•) to (+). Low concentration (120 mg/mL) samples were retroactively graded as slightly yellow (−) for time points earlier than 6 months.

Appearance.

Visual inspection of unopened sample vials was used to evaluate sample color, clarity, and the presence of particulate matter. As shown in Table 25, all samples were slightly opalescent and essentially free of visible particles, where high concentration formulations were noticeably more yellow than those at low concentration. While somewhat increased yellow color was observed in histidine formulations maintained at higher temperatures (after 6 months at 40° C., 12 months at 30° C.), formulations generally displayed consistent appearance by visual evaluation over the course of the study.

Protein Content.

Protein content was assessed for all samples over the course of the stability study (Table 25). No detectable loss of SAN-300 was observed for any of the formulations, regardless of storage conditions.

pH.

Formulation pH was measured for all study samples. The initial pH readings for high concentration histidine and acetate formulations were 6.2 and 5.6, respectively. As shown in Table 25, pH remained constant throughout the duration of the study, not varying more than 0.1 units from the initial reading in any formulation.

Example 10. Long Term Stability of SAN-300 Formulations: Particulate Matter

The particulate matter in SAN-300 Formulations was assessed to determine their long term stability using the experimental design described in Example 7.

Methods for Assessing Particulate Matter

A Liquid Particle Counting System (Hach Model 9703, Sensor Model: HRLD-150 (HIAC)) was used for determining particle size and abundance in SAN-300 samples. The data was obtained using a single 500 µL draw of sample. Due to the small sample volumes used in this study, the results generated do not fulfill USP <788> "Particulate Matter in Injections" requirements.

Briefly, the HIAC system was allowed to warm up for approximately 30 minutes, and both the syringe (1 mL) and system were flushed with deionized water for at least 10 cycles before use. Environment suitability was tested by showing that 25 mL of deionized water contained no more than 25 particles ≥10 µm in size. If environment suitability failed, the system was flushed with deionized water until a passing measurement was obtained. System suitability was confirmed by analyzing a single 500 µL draw of 15 µm standard using 10 µm and 25 µm channel sizes. If cumulative counts/mL for the 10 m channel fell within the specification given for the standard, then the system was deemed suitable for sample testing. Before each sample, the system was again flushed with deionized water, until a single 500 µL draw of deionized water showed no particles greater than 10 µm in size. Sample was analyzed using a single 500 µL draw, and cumulative counts/mL for 10 µm and 25 µm channels were determined and reported to the nearest whole number.

Results

Particle counting by HIAC was performed for all samples over the course of the stability study. The results are shown in Table 26.

TABLE 26

Summary of HIAC Results for SAN-300 Stability Samples (time points are measured in months)

| Sample Lot | Formulation | Condition | Time Point | Cumulative Counts/mL[a] 10 µm | 25 µm |
|---|---|---|---|---|---|
| NB1206p86A | 190 mg/mL SAN-300 30 mM Acetate 220 mM Sorbitol 0.01% PS-80, pH 5.5 | | Initial | 1492 | 22 |
| | | −75° C. | 6 M | 1446 | 200 |
| | | | 12 M | 1550 | 142 |
| | | 2-8° C. | 1 M | 2540 | 154 |
| | | | 3 M | 36 | 4 |
| | | | 6 M | 1200 | 186 |
| | | | 9 M | 150 | 64 |
| | | | 12 M | 966 | 68 |
| | | 2-8° C. (Inverted) | 6 M | 22 | 2 |
| | | | 12 M | 1126 | 104 |
| | | 30° C./65% RH | 1 M | 1682 | 140 |
| | | | 3 M | 8 | 6 |
| | | | 6 M | 44 | 0 |
| | | | 9 M | 414 | 4 |
| | | | 12 M | 940 | 28 |
| | | 40° C./75% RH | 1 M | 2310 | 104 |
| | | | 3 M | 42 | 6 |
| | | | 6 M | 212 | 16 |
| NB1206p86C | 120 mg/mL SAN-300 30 mM Acetate 220 mM Sorbitol 0.01% PS-80, pH 5.5 | | Initial | 154 | 0 |
| | | −75° C. | 6 M | 48 | 2 |
| | | 2-8° C. | 3 M | 24 | 4 |
| | | | 6 M | 142 | 44 |
| | | 2-8° C. (Inverted) | 6 M | 20 | 0 |
| | | 30° C./65% RH | 3 M | 10 | 0 |
| | | | 6 M | 58 | 8 |
| | | 40° C./75% RH | 3 M | 4 | 0 |
| | | | 6 M | 46 | 0 |
| NB1206p86B | 180 mg/mL SAN-300 30 mM Histidine 250 mM Sorbitol 0.01% PS-20, pH 6.0 | | Initial | 802 | 10 |
| | | −75° C. | 6 M | 356 | 20 |
| | | | 12 M | 582 | 12 |
| | | 2-8° C. | 1 M | 1464 | 46 |
| | | | 3 M | 38 | 10 |
| | | | 6 M | 426 | 46 |
| | | | 9 M | 34 | 8 |
| | | | 12 M | 478 | 8 |
| | | 2-8° C. (Inverted) | 6 M | 432 | 28 |
| | | | 12 M | 930 | 0 |
| | | 30° C./65% RH | 1 M | 2280 | 110 |
| | | | 3 M | 118 | 42 |
| | | | 6 M | 48 | 2 |
| | | | 9 M | 2 | 0 |
| | | | 12 M | 2 | 0 |
| | | 40° C./75% RH | 1 M | 1818 | 48 |
| | | | 3 M | 88 | 28 |
| | | | 6 M | 198 | 10 |

TABLE 26-continued

Summary of HIAC Results for SAN-300 Stability Samples (time points are measured in months)

| Sample Lot | Formulation | Condition | Time Point | Cumulative Counts/mL[a] 10 μm | 25 μm |
|---|---|---|---|---|---|
| NB1206p86D | 120 mg/mL SAN-300 30 mM Histidine 250 mM Sorbitol 0.01% PS-20, pH 6.0 | Initial | | 80 | 0 |
| | | −75° C. | 6 M | 104 | 34 |
| | | 2-8° C. | 3 M | 52 | 12 |
| | | | 6 M | 80 | 12 |
| | | 2-8° C. (Inverted) | 6 M | 146 | 40 |
| | | 30° C./65% RH | 3 M | 46 | 6 |
| | | | 6 M | 22 | 0 |
| | | 40° C./75% RH | 3 M | 22 | 0 |
| | | | 6 M | 82 | 4 |

[a]Determined by a single sample draw of 500 μL

For all formulations and conditions, particle counts were well below the particle limits for injection set by USP <788> (6000 for 10 μm, and 600 for 25 μm particles). All formulations adequately suppressed particle formation during long-term SAN-300 storage under both intended storage conditions (−75° C. and 2-8° C.) and accelerated or stressed conditions (30° C. or 40° C.).

Example 11. Long Term Stability of SAN-300 Formulations: Purity

The purity of SAN-300 Formulations was assessed with reduced SDS-PAGE and size exclusion chromatography using the experimental design described in Example 7.

Methods

Reduced Polyacrylamide Gel Electrophoresis.

Denaturing polyacrylamide gel electrophoresis (SDS-PAGE) was used to assess SAN-300 sample purity by size separation of sample proteins/peptides. Samples, controls and reference standard were prepared to 2.0 mg/mL in 1× Tris-Glycine SDS sample buffer (containing NuPAGE® sample reducing agent), centrifuged, and heat denatured for 1 minute at 95° C. followed by an additional centrifugation step. Gels were loaded at 20 μg per lane, and electrophoresis was performed for 60 minutes at maximum voltage, 250 watts, and 30 mAmp/gel. Following electrophoresis, gels were stained for a minimum of 3 hours with Colloidal Blue and destained overnight. Gels were dried with a DryEase® mini-gel drying system, imaged, and analyzed by densitometry using the GeneGenius Bioimaging system.

The percent heavy chain (HC), light chain (LC), and IgG were determined from densitometry data for each SDS-PAGE sample, in addition to total lane density (raw volume). To better account for variability between gels, the abundances of HC, LC, and IgG were reported relative to the internal reference standard run on each gel. For visualization purposes, percent IgG loss was also reported. Material from both Lots of SAN-300 (CP4-04-109 and CP4-04-106) used to generate stability samples were run at $T_0$ and deemed equivalent. CP4-04-109 was used as reference for the remainder of the study.

Size Exclusion Chromatography.

Size exclusion chromatography (SEC) was used to evaluate the quantity of aggregates and degradation products present in SAN-300 samples. An Agilent 1100 HPLC system was fitted with a TSKgel G3000SWx1 SEC column (Tosoh, 7.8 mm×30 cm, 5 μm particle size) and SWx1 guard column (Tosoh, 6 mm×4 cm, 7 μm particle size). Samples were diluted to 1 mg/mL in SEC mobile phase (100 mM sodium phosphate, 200 mM sodium chloride, pH 7.2) and 40 μL of sample was injected in duplicate. The system was run using a flow rate of 1.0 mL/min, and eluted protein was detected by absorbance measured at 215 nm. The percent total chromatogram area was reported for the monomer peak, in addition to each individual high molecular weight (HMW) species and low molecular weight impurity (LMWI). Material from both Lots of SAN-300 (CP4-04-109 and CP4-04-106) used to generate stability samples were run at T0 and deemed equivalent. CP4-04-109 was used as reference for the remainder of the study. Samples were run in the following sequence order: blank (1×), reference (1×), samples (2×), reference (1×), blank (1×), where a bracketing reference injection was performed after every 15 samples (30 injections).

Results

Reduced Polyacrylamide Gel Electrophoresis.

The purity of all stability samples was evaluated by reduced SDS-PAGE. The results are shown in Table 27.

TABLE 27

Summary of Reduced SDS-PAGE Results for SAN-300 Stability Samples (time points are measured in months)

| Sample Lot | Formulation | Condition | Time Point | Heavy Chain (%)[a] | Light Chain (%)[a] | IgG (%)[a] | Intact IgG Loss (%) |
|---|---|---|---|---|---|---|---|
| NB1206p86A | 190 mg/mL SAN-300 30 mM Acetate 220 mM Sorbitol | Initial | | 98.1 | 101.4 | 99.2 | 0.8 |
| | | −75° C. | 6M | 101.8 | 102.1 | 101.9 | −1.9 |
| | | | 12M | 99.2 | 99.0 | 99.2 | 0.8 |

TABLE 27-continued

Summary of Reduced SDS-PAGE Results for SAN-300 Stability Samples (time points are measured in months)

| Sample Lot | Formulation | Condition | Time Point | Heavy Chain (%)[a] | Light Chain (%)[a] | IgG (%)[a] | Intact IgG Loss (%) |
|---|---|---|---|---|---|---|---|
| | 0.01% PS-80, pH 5.5 | 2-8° C. | 1M | 94.3 | 99.7 | 96.0 | 4.0 |
| | | | 3M | 94.1 | 92.7 | 93.6 | 6.4 |
| | | | 6M | 97.6 | 102.4 | 99.1 | 0.9 |
| | | | 9M | 97.6 | 95.9 | 97.1 | 2.9 |
| | | | 12M | 93.5 | 95.0 | 93.9 | 6.1 |
| | | 2-8° C. (Inverted) | 6M | 101.0 | 102.7 | 101.5 | −1.5 |
| | | | 12M | 94.4 | 94.3 | 94.4 | 5.6 |
| | | 30° C./65% RH | 1M | 95.8 | 99.9 | 97.1 | 2.9 |
| | | | 3M | 88.9 | 82.3 | 86.6 | 13.4 |
| | | | 6M | 89.6 | 82.8 | 87.5 | 12.5 |
| | | | 9M | 80.8 | 77.3 | 79.6 | 20.4 |
| | | | 12M | 79.3 | 73.9 | 77.7 | 22.3 |
| | | 40° C./75% RH | 1M | 86.9 | 94.0 | 89.0 | 11.0 |
| | | | 3M | 77.2 | 75.8 | 76.7 | 23.3 |
| | | | 6M | 78.0 | 78.4 | 78.1 | 21.9 |
| NB1206p86C | 120 mg/mL SAN-300 30 mM Acetate 220 mM Sorbitol 0.01% PS-80, pH 5.5 | Initial | | 103.4 | 97.2 | 101.4 | −1.4 |
| | | −75° C. | 6M | 98.2 | 105.8 | 100.7 | −0.7 |
| | | 2-8° C. | 3M | 98.2 | 96.7 | 97.7 | 2.3 |
| | | | 6M | 100.7 | 96.8 | 99.4 | 0.6 |
| | | 2-8° C. (Inverted) | 6M | 100.7 | 98.9 | 97.8 | 2.2 |
| | | 30° C./65% RH | 3M | 95.7 | 92.2 | 94.6 | 5.4 |
| | | | 6M | 88.2 | 88.7 | 88.4 | 11.6 |
| | | 40° C./75% RH | 3M | 83.3 | 77.5 | 81.5 | 18.5 |
| | | | 6M | 85.3 | 79.3 | 83.3 | 16.7 |
| NB1206p86B | 180 mg/mL SAN-300 30 mM Histidine, 250 mM Sorbitol, 0.01% PS-20, pH 6.0 | Initial | | 101.5 | 103.9 | 102.3 | −2.3 |
| | | −75° C. | 6M | 97.5 | 105.3 | 100.1 | −0.1 |
| | | | 12M | 98.8 | 101.6 | 99.6 | 0.4 |
| | | 2-8° C. | 1M | 99.9 | 97.3 | 99.1 | 0.9 |
| | | | 3M | 98.3 | 100.5 | 99.0 | 1.0 |
| | | | 6M | 97.8 | 101.6 | 99.1 | 0.9 |
| | | | 9M | 101.4 | 98.5 | 100.5 | −0.5 |
| | | | 12M | 96.7 | 99.3 | 97.4 | 2.6 |
| | | 2-8° C. (Inverted) | 6M | 100.7 | 99.0 | 100.1 | −0.1 |
| | | | 12M | 93.5 | 94.6 | 93.8 | 6.2 |
| | | 30° C./65% RH | 1M | 95.8 | 92.0 | 94.5 | 5.5 |
| | | | 3M | 92.2 | 94.6 | 93.0 | 7.0 |
| | | | 6M | 88.3 | 93.2 | 89.9 | 10.1 |
| | | | 9M | 80.5 | 81.0 | 80.6 | 19.4 |
| | | | 12M | 80.9 | 76.3 | 79.5 | 20.5 |
| | | 40° C./75% RH | 1M | 87.9 | 84.7 | 86.8 | 13.2 |
| | | | 3M | 81.2 | 83.7 | 82.0 | 18.0 |
| | | | 6M | 71.3 | 76.2 | 72.9 | 27.1 |
| NB1206p86D | 120 mg/mL SAN-300 30 mM Histidine, 250 mM Sorbitol, 0.01% PS-20, pH 6.0 | Initial | | 102.3 | 98.7 | 101.1 | −1.1 |
| | | −75° C. | 6M | 97.2 | 99.1 | 97.8 | 2.2 |
| | | 2-8° C. | 3M | 100.0 | 94.8 | 98.3 | 1.7 |
| | | | 6M | 97.4 | 98.3 | 97.7 | 2.3 |
| | | 2-8° C. (Inverted) | 6M | 99.6 | 102.6 | 100.5 | −0.5 |
| | | 30° C./65% RH | 3M | 93.1 | 91.4 | 92.6 | 7.4 |
| | | | 6M | 90.7 | 88.5 | 90.0 | 10.0 |
| | | 40° C./75% RH | 3M | 83.5 | 88.1 | 85.0 | 15.0 |
| | | | 6M | 78.2 | 82.8 | 79.6 | 20.4 |

[a]Data are reported relative to the internal reference run on the same gel.

Given the variability inherent to this method, the abundances of heavy chain, light chain, and IgG in stability samples were reported relative to values obtained for the internal reference run on each gel. In addition, the percent IgG loss was also reported.

Both high-concentration formulations trended comparably under all storage conditions and remained stable after 12 months at 2-8° C. Histidine slightly outperformed acetate at a majority of time points for 2-8° C. and 30° C. samples. Small reductions in IgG content (~5%) were observed for upright 2-8° C. samples for both formulations after 12 months, with comparable results for inverted samples held at this temperature. Twelve month samples maintained at −75° C. for both formulations were comparable to measurements at the initial time point. Lower SAN-300 concentration samples showed a small apparent increase in stability, relative to associated high-concentration solutions. While this concentration-dependent effect on intact IgG was nearly undetectable at 2-8° C. at the six month time point, it was more pronounced at elevated temperatures (>5% at 40° C.).

Size Exclusion Chromatography (SEC).

The purity of SAN-300 stability study samples was evaluated by SEC (Table 28), where the percent abundances of all HMW and LMWI species observed were reported.

TABLE 28

Summary of SEC Results for SAN-300 Stability Samples (time points are measured in months)

| Sample Lot | Formulation | Condition | Time Point | Aggregate 3 Average % Area | Aggregate 2 Average % Area | Aggregate 1 Average % Area | Monomer Average % Area | LMWI 1 Average % Area | LMWI 2 Average % Area |
|---|---|---|---|---|---|---|---|---|---|
| NB1206p86A | 190 mg/mL SAN-300 30 mM Acetate 220 mM Sorbitol 0.01% PS-80, pH 5.5 | Initial | | — | 0.1 | 2.6 | 96.9 | — | 0.5 |
| | | 75° C. | 6M | — | 0.1 | 2.6 | 96.9 | — | 0.5 |
| | | | 12M | — | <0.1 | 2.3 | 97.3 | — | 0.5 |
| | | 2-8° C. | 1M | — | 0.1 | 2.7 | 96.8 | — | 0.5 |
| | | | 3M | — | 0.1 | 3.0 | 96.4 | — | 0.5 |
| | | | 6M | — | 0.1 | 3.2 | 96.2 | — | 0.5 |
| | | | 9M | — | 0.1 | 3.1 | 96.3 | — | 0.5 |
| | | | 12M | — | 0.1 | 3.3 | 96.1 | — | 0.5 |
| | | 2-8° C. (Inverted) | 6M | — | 0.1 | 3.4 | 96.0 | — | 0.5 |
| | | | 12M | — | 0.1 | 3.3 | 96.1 | — | 0.5 |
| | | 30° C./65% RH | 1M | — | 0.1 | 3.5 | 95.8 | — | 0.6 |
| | | | 3M | — | 0.2 | 4.4 | 94.5 | — | 0.9 |
| | | | 6M | — | 0.3 | 5.2 | 93.3 | — | 1.3 |
| | | | 9M | — | 0.2 | 5.2 | 92.9 | — | 1.6 |
| | | | 12M | — | 0.4 | 5.7 | 88.0 | 4.1 | 1.9 |
| | | 40° C./75% RH | 1M | — | 0.2 | 4.4 | 94.6 | — | 0.9 |
| | | | 3M | — | 0.6 | 6.2 | 91.2 | — | 2.0 |
| | | | 6M | 0.3 | 1.0 | 8.8 | 80.1 | 3.3 | 6.6 |
| NB1206p86C | 120 mg/mL SAN-300 30 mM Acetate 220 mM Sorbitol 0.01% PS-80, pH 5.5 | Initial | | — | 0.1 | 2.0 | 97.4 | — | 0.5 |
| | | −75° C. | 6M | — | <0.1 | 2.1 | 97.4 | — | 0.5 |
| | | 2-8° C. | 3M | — | <0.1 | 2.4 | 97.1 | — | 0.5 |
| | | | 6M | — | 0.1 | 2.7 | 96.8 | — | 0.5 |
| | | 2-8° C. (Inverted) | 6M | — | 0.1 | 2.6 | 96.8 | — | 0.5 |
| | | 30° C./65% RH | 3M | — | 0.1 | 3.3 | 95.8 | — | 0.9 |
| | | | 6M | — | 0.1 | 3.7 | 94.9 | — | 1.2 |
| | | 40° C./75% RH | 3M | — | 0.2 | 4.6 | 93.3 | — | 1.9 |
| | | | 6M | 0.1 | 0.5 | 6.0 | 83.4 | 3.0 | 7.0 |
| NB1206p86B | 180 mg/mL SAN-300 30 mM Histidine, 250 mM Sorbitol, 0.01% PS-20, pH 6.0 | Initial | | — | 0.1 | 2.6 | 96.9 | — | 0.4 |
| | | −75° C. | 6M | <0.1 | 0.1 | 2.8 | 96.6 | — | 0.5 |
| | | | 12M | <0.1 | 0.1 | 2.5 | 97.0 | — | 0.4 |
| | | 2-8° C. | 1M | — | 0.1 | 2.5 | 97.0 | — | 0.4 |
| | | | 3M | — | 0.1 | 2.8 | 96.7 | — | 0.5 |
| | | | 6M | <0.1 | 0.1 | 3.1 | 96.3 | — | 0.5 |
| | | | 9M | <0.1 | 0.1 | 2.7 | 96.6 | — | 0.5 |
| | | | 12M | <0.1 | 0.1 | 2.8 | 96.6 | — | 0.5 |
| | | 2-8° C. (Inverted) | 6M | <0.1 | 0.1 | 2.9 | 96.5 | — | 0.5 |
| | | | 12M | <0.1 | 0.1 | 2.8 | 96.6 | — | 0.5 |
| | | 30° C./65% RH | 1M | — | 0.1 | 2.9 | 96.5 | — | 0.5 |
| | | | 3M | — | 0.2 | 3.6 | 95.4 | — | 0.8 |
| | | | 6M | <0.1 | 0.2 | 4.2 | 94.4 | — | 1.2 |
| | | | 9M | <0.1 | 0.2 | 4.5 | 93.7 | — | 1.6 |
| | | | 12M | <0.1 | 0.3 | 5.0 | 88.9 | 4.0 | 1.9 |
| | | 40° C./7% RH | 1M | — | 0.1 | 3.4 | 95.7 | — | 0.8 |
| | | | 3M | — | 0.4 | 5.0 | 92.9 | — | 1.7 |
| | | | 6M | 0.2 | 0.6 | 6.6 | 83.9 | 2.8 | 5.9 |
| NB1206p86D | 120 mg/mL SAN-300 30 mM Histidine, 250 mM Sorbitol, 0.01% PS-20, pH 6.0 | Initial | | — | 0.1 | 2.3 | 97.2 | — | 0.4 |
| | | −75° C. | 6M | <0.1 | 0.1 | 2.5 | 97.0 | — | 0.5 |
| | | 2-8° C. | 3M | — | 0.1 | 2.3 | 97.2 | — | 0.5 |
| | | | 6M | <0.1 | 0.1 | 2.5 | 96.9 | — | 0.5 |
| | | 2-8° C. (Inverted) | 6M | <0.1 | 0.1 | 2.4 | 97.0 | — | 0.5 |
| | | 30° C./65% RH | 3M | — | 0.1 | 2.7 | 96.3 | — | 0.8 |
| | | | 6M | <0.1 | 0.1 | 3.2 | 95.4 | — | 1.2 |
| | | 40° C./75% RH | 3M | — | 0.2 | 3.7 | 94.4 | — | 1.8 |
| | | | 6M | 0.1 | 0.3 | 4.8 | 85.6 | 2.9 | 6.3 |

Figure 6:
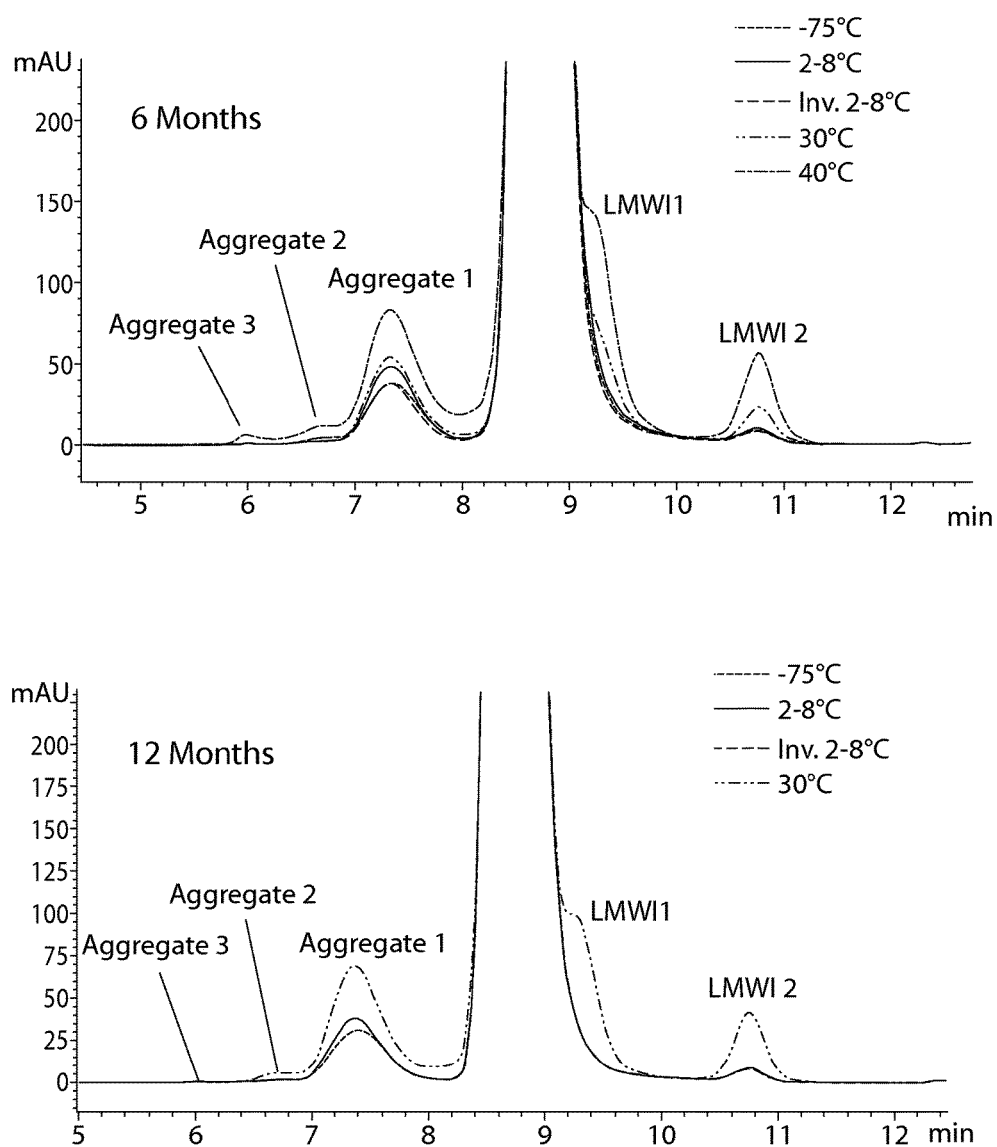
FIG. 6 shows representative SEC chromatogram overlays for high concentration NB1206p86B samples. The top panel shows NB1206p86B samples at the 6 month time point. Samples were held at −75° C., 2-8° C., inverted at 2-8° C., 30° C., and 40° C. The bottom panel shows NB1206p86B samples at the 12 month time point. Samples were held at −75° C., 2-8° C., inverted at 2-8° C., and 30° C.

Similar to SDS-PAGE data, SEC results showed that high-concentration SAN-300 formulated in histidine results in reduced degradation of monomer relative to acetate. At the 12 month time point, histidine samples at 2-8° C. (96.6% monomer) were nearly indistinguishable from material at the initial time point (96.9% monomer), while the acetate formulation displayed somewhat elevated levels of HMW material (FIG. 5). Data for inverted and frozen samples for both formulations were comparable to results for the upright 2-8° C. samples. Samples under accelerated and stressed conditions revealed more dramatic differences between the performances of the two high-concentration formulations. At the 6 month time point for example, 40° C. histidine samples showed monomer content of ~84%, while counterpart acetate samples showed only ~80%. These differences in monomer content were associated almost entirely with aggregate content, as LMWI formation did not appear to be buffer-dependent. As shown in the representative overlays presented in FIG. 6, a total of three HMW species were observed over the course of the study, where Aggregate 1 (dimer) represented the majority of HMW content. Formation of the higher-order Aggregates 2 and 3 was both temperature- and buffer-dependent, where histidine was again superior to acetate buffer. In addition to the SAN-300 fragment LMWI 2, observed in all samples to varying degrees, accelerated and stressed conditions led to the for mation of LMWI 1, which presented as a trailing shoulder off the monomer peak.

Results for low-concentration formulations mirrored those described above, where acetate-buffered samples displayed reduced monomer content compared with corresponding histidine samples (Table 28). As would be expected, both low concentration formulations had reduced propensity for aggregate formation relative to their high-concentration counterparts. This effect was strongly temperature dependent, where differences in total aggregate between low and high-concentration samples were ~0.5% for 2-8° C. samples and up to 3.5% for those at 40° C. Fragmentation into LMWI was not SAN-300 concentration-dependent.

Example 12. Long Term Stability of SAN-300 Formulations: Charge Heterogeneity

The charge heterogeneity of SAN-300 formulations was assessed with cation exchange chromatography using the experimental design described in Example 7.

Method

An Agilent 1100 HPLC system was fitted with a ProPac WCX-10 CEX column (Dionex, 4×250 mm) and a Propac WCX-10G Guard Column, (Dionex, 4×50 mm). SAN-300 samples were diluted to 1.0 mg/mL in mobile phase A (10 mM sodium phosphate, pH 7.5) and 75 µL was injected in duplicate. A gradient was run using buffer B (10 mM sodium phosphate, 100 mM sodium chloride, pH 7.5) and buffer C (10 mM sodium phosphate, 2 M sodium chloride, pH 7.5), where protein was detected by absorbance measured at 280 nm.

The abundances of main peak, acidic variants, and basic variants were reported for each sample as percent total chromatogram peak area. The two Lots of SAN-300 (CP4-04-109 and CP4-04-106) used to generate formulations for the present study displayed slightly different charge profiles as determined by CEX. To account for this variability, percent main, acidic, and basic species were also reported relative to the Lot-appropriate reference standard run within a given HPLC sequence. Samples were run in the following sequence order: blank (1×), CP4-04-109 reference (1×), CP4-04-106 reference (1×), samples (2×), CP4-04-109 reference (1×), CP4-04-106 reference, blank (1×), where bracketing reference injections were performed after every 15 samples (30 injections).

Results

Charge heterogeneity was determined by CEX for all stability samples. The results are shown in Table 29 and Table 30. The percent abundances of main peak, and total acidic and basic charge variants were reported.

TABLE 29

Summary of CEX Results for SAN-300 Stability Samples
(time points are measured in months)

| Sample Lot | Formulation | Condition | Time Point | Acidic Peaks Average % Area | Main Peak Average % Area | Basic Peaks Average % Area |
|---|---|---|---|---|---|---|
| NB1206p86A | 190 mg/mL SAN-300 | Initial | | 34.7 | 56.4 | 9.0 |
| | 30 mM Acetate | −75° C. | 6M | 34.8 | 56.2 | 9.0 |
| | 220 mM Sorbitol | | 12M | 34.8 | 55.8 | 9.4 |
| | 0.01% PS-80, | 2-8° C. | 1M | 34.4 | 53.5 | 12.1 |
| | pH 5.5 | | 3M | 33.6 | 54.5 | 11.9 |
| | | | 6M | 34.9 | 56.5 | 8.6 |
| | | | 9M | 33.5 | 57.4 | 9.0 |
| | | | 12M | 33.7 | 58.3 | 8.0 |
| | | 2-8° C. (Inverted) | 6M | 34.9 | 56.7 | 8.4 |
| | | | 12M | 34.2 | 57.9 | 8.0 |
| | | 30° C./65% RH | 1M | 37.7 | 53.2 | 9.1 |
| | | | 3M | 46.8 | 46.6 | 6.7 |
| | | | 6M | 69.2 | 27.6 | 3.1 |
| | | | 9M | 78.4 | 17.4 | 4.2 |
| | | | 12M | 85.8 | 12.5 | 1.7 |
| | | 40° C./75% RH | 1M | 50.3 | 42.6 | 7.1 |
| | | | 3M | 76.8 | 19.6 | 3.7 |
| | | | 6M | NA[a] | NA[a] | NA[a] |
| NB1206p86C | 120 mg/mL SAN-300 | Initial | | 34.6 | 56.9 | 8.6 |
| | 30 mM Acetate | −75° C. | 6M | 35.4 | 56.1 | 8.5 |
| | 220 mM Sorbitol | 2-8° C. | 3M | 34.9 | 55.0 | 10.1 |
| | 0.01% PS-80, | | 6M | 34.9 | 57.2 | 7.9 |
| | pH 5.5 | 2-8° C. (Inverted) | 6M | 35.1 | 57.1 | 7.8 |
| | | 30° C./65% RH | 3M | 47.4 | 47.0 | 5.6 |
| | | | 6M | 70.1 | 27.5 | 2.4 |
| | | 40° C./75% RH | 3M | 76.6 | 19.8 | 3.6 |
| | | | 6M | NA[a] | NA[a] | NA[a] |
| NB1206p86B | 180 mg/mL SAN-300 | Initial | | 32.4 | 59.5 | 8.1 |
| | 30 mM Histidine | −75° C. | 6M | 33.3 | 58.3 | 8.4 |
| | 250 mM Sorbitol | | 12M | 32.8 | 58.6 | 8.6 |
| | 0.01% PS-20, | 2-8° C. | 1M | 32.6 | 55.8 | 11.6 |
| | pH 6.0 | | 3M | 33.2 | 57.3 | 9.5 |
| | | | 6M | 34.4 | 58.7 | 6.9 |
| | | | 9M | 32.5 | 60.7 | 6.8 |
| | | | 12M | 34.0 | 59.7 | 6.4 |
| | | 2-8° C. (Inverted) | 6M | 34.1 | 59.0 | 6.9 |
| | | | 12M | 34.3 | 59.0 | 6.7 |

TABLE 29-continued

Summary of CEX Results for SAN-300 Stability Samples
(time points are measured in months)

| Sample Lot | Formulation | Condition | Time Point | Acidic Peaks Average % Area | Main Peak Average % Area | Basic Peaks Average % Area |
|---|---|---|---|---|---|---|
| | | 30° C./65% RH | 1M | 36.4 | 56.3 | 7.3 |
| | | | 3M | 46.1 | 49.4 | 4.5 |
| | | | 6M | 65.9 | 32.3 | 1.8 |
| | | | 9M | 75.2 | 22.8 | 2.0 |
| | | | 12M | 81.3 | 17.0 | 1.7 |
| | | 40° C./75% RH | 1M | 46.9 | 46.6 | 6.5 |
| | | | 3M | 72.0 | 23.8 | 4.2 |
| | | | 6M | NA[a] | NA[a] | NA[a] |
| NB1206p86D | 120 mg/mL SAN-300 30 mM Histidine 250 mM Sorbitol 0.01% PS-20, pH 6.0 | Initial | | 32.3 | 59.3 | 8.5 |
| | | −75° C. | 6M | 31.9 | 60.5 | 7.6 |
| | | 2-8° C. | 3M | 31.3 | 58.7 | 10.0 |
| | | | 6M | 32.8 | 61.4 | 5.8 |
| | | 2-8° C. (Inverted) | 6M | 32.3 | 61.9 | 5.8 |
| | | 30° C./65% RH | 3M | 45.1 | 49.7 | 5.2 |
| | | | 6M | 65.9 | 33.0 | 1.1 |
| | | 40° C./75% RH | 3M | 72.4 | 24.5 | 3.1 |
| | | | 6M | NA[a] | NA[a] | NA[a] |

[a]Due to excessive degradation, samples were not integrated.

Unlike other analytical methods used in the present study, a small variation in charge heterogeneity was observed between the two SAN-300 Lots used in preparation of the study samples. For this reason, CEX results were also reported as the percent change, relative to the lot specific reference standard run in a given HPLC sequence (see Table 30).

TABLE 30

Summary of CEX Results for SAN-300 Stability Samples: Relative to Internal Reference (time points are measured in months)

| Sample Lot | Formulation | Condition | Time Point | Acidic Peaks % Change from Ref Std | Main Peak % Change from Ref Std | Basic Peaks % Change from Ref Std |
|---|---|---|---|---|---|---|
| NB1206p86A | 190 mg/mL SAN-300 30 mM Acetate 220 mM Sorbitol 0.01% PS-80, pH 5.5 | Initial | | 0.0 | −0.4 | 2.3 |
| | | −75° C. | 6M | 1.2 | −1.5 | 5.0 |
| | | | 12M[a] | 3.2 | −1.6 | −1.8 |
| | | 2-8° C. | 1M | 0.3 | 0.0 | −0.8 |
| | | | 3M | 4.5 | −4.3 | 9.5 |
| | | | 6M | 1.7 | −1.0 | −0.4 |
| | | | 9M | −0.1 | 1.3 | −6.3 |
| | | | 12M[a] | −0.1 | 2.8 | −16.0 |
| | | 2-8° C. (Inverted) | 6M | 1.7 | −0.6 | −2.7 |
| | | | 12M[a] | 1.3 | 2.1 | −16.9 |
| | | 30° C./65% RH | 1M | 9.9 | −0.6 | −25.4 |
| | | | 3M | 45.4 | −18.3 | −38.6 |
| | | | 6M | 101.7 | −51.6 | −63.6 |
| | | | 9M | 133.5 | −69.3 | −56.1 |
| | | | 12M[a] | 154.3 | −78.0 | −81.8 |
| | | 40° C./75% RH | 1M | 46.6 | −20.4 | −41.8 |
| | | | 3M | 138.7 | −65.7 | −66.4 |
| | | | 6M | NA | NA | NA |
| NB1206p86C | 120 mg/mL SAN-300 30 mM Acetate 220 mM Sorbitol 0.01% PS-80, pH 5.5 | Initial | | −0.2 | 0.5 | −2.4 |
| | | −75° C. | 6M | 3.0 | −1.7 | −0.6 |
| | | 2-8° C. | 3M | 8.4 | −3.4 | −7.1 |
| | | | 6M | 1.8 | 0.1 | −8.0 |
| | | 2-8° C. (Inverted) | 6M | 2.2 | 0.1 | −9.3 |
| | | 30° C./65% RH | 3M | 47.4 | −17.6 | −48.1 |
| | | | 6M | 104.1 | −51.8 | −71.6 |
| | | 40° C./75% RH | 3M | 138.1 | −65.3 | −66.5 |
| | | | 6M | NA | NA | NA |
| NB1206p86B | 180 mg/mL SAN-300 30 mM Histidine 250 mM Sorbitol | Initial | | 0.6 | −0.1 | −1.9 |
| | | −75° C. | 6M | 4.2 | −2.4 | 1.4 |
| | | | 12M | 3.7 | −0.9 | −6.8 |
| | | 2-8° C. | 1M | 1.9 | 0.2 | −5.7 |

TABLE 30-continued

Summary of CEX Results for SAN-300 Stability Samples: Relative to Internal Reference (time points are measured in months)

| Sample Lot | Formulation | Condition | Time Point | Acidic Peaks % Change from Ref Std | Main Peak % Change from Ref Std | Basic Peaks % Change from Ref Std |
|---|---|---|---|---|---|---|
| | 0.01% PS-20, pH 6.0 | | 3M | 4.3 | 0.7 | −15.5 |
| | | | 6M | 7.6 | −1.7 | −16.9 |
| | | | 9M | 4.5 | 2.3 | −28.8 |
| | | | 12M | 7.4 | 0.8 | −30.9 |
| | | 2-8° C. (Inverted) | 6M | 6.6 | −1.3 | −16.1 |
| | | | 12M | 8.3 | −0.3 | −26.6 |
| | | 30° C./65% RH | 1M | 13.8 | 1.1 | −40.7 |
| | | | 3M | 44.8 | −13.1 | −60.4 |
| | | | 6M | 106.0 | −45.9 | −78.8 |
| | | | 9M | 141.5 | −61.6 | −79.2 |
| | | | 12M | 157.0 | −71.3 | −81.2 |
| | | 40° C./75% RH | 1M | 46.6 | −16.3 | −47.2 |
| | | | 3M | 126.2 | −58.2 | −62.5 |
| | | | 6M | NA | NA | NA |
| NB1206p86D | 120 mg/mL SAN-300 30 mM Histidine 250 mM Sorbitol 0.01% PS-20, pH 6.0 | Initial | | 0.2 | −0.4 | 2.0 |
| | | −75° C. | 6M | −0.3 | 1.2 | −7.8 |
| | | 2-8° C. | 3M | −1.7 | 3.2 | −11.5 |
| | | | 6M | 2.6 | 2.8 | −30.2 |
| | | 2-8° C. (Inverted) | 6M | 0.9 | 3.6 | −29.9 |
| | | 30° C./65% RH | 3M | 41.8 | −12.7 | −54.1 |
| | | | 6M | 106.0 | −44.8 | −86.8 |
| | | 40° C./75% RH | 3M | 127.5 | −56.9 | −72.7 |
| | | | 6M | NA | NA | NA |

[a] Due to a pressure-failure, the final bracketing reference was not run. Values are calculated using a single reference injection.
[b] Due to excessive degradation, samples were not integrated The two data sets were comparable.

Both high-concentration formulations retained their initial charge heterogeneity profile after 12 months storage at −75° C. and 2-8° C. While results for formulations NB1206p86A and NB1206p86B were nearly indistinguishable at intended storage conditions, accelerated and stressed conditions more clearly established that the histidine buffer system led to reduced changes in SAN-300 charge heterogeneity. Both NB1206p86A and NB1206p86B showed similar trends at 30° C. and 40° C., with the histidine formulation consistently retaining more of its initial charge profile. The shift to more acidic variants at elevated temperatures was not found to be concentration-dependent, as low-concentration samples were indistinguishable from associated high-concentration samples.

CONCLUSIONS

Both high-concentration formulations displayed excellent stability for up to 12 months under intended storage conditions (−75° C. and 2-8° C.). Results from SEC, SDS-PAGE and CEX indicate that compared with the acetate formulation, the histidine formulation provides better SAN-300 stability.

Example 13. Exemplary Liquid Formulation

A liquid formulation containing 180 mg/mL of anti-VLA1 monoclonal antibody having a light chain sequence of SEQ ID NO:1 and a heavy chain sequence of SEQ ID NO:2 in 30 mM histidine, 250 mM sorbitol, 0.01% polysorbate 20, pH 6.0, with a final fill volume of 1 mL/vial was produced using methods described in Example 6. The formulation met each of the criteria shown in Table 31. The formulation was packaged for storage at 2-8° C. in a 2 mL USP Type 1 borosilicate glass vial with a 13 mm chlorobutyl based stopper with flourotech coating on plug and B2 coating on the top and an aluminum over seal with flip top cap.

TABLE 31

| Specifications | | |
|---|---|---|
| | Attribute | Criterion |
| General | Appearance (see USP <631>) | Clear to opalescent Slightly yellow to yellow Essentially free from visible particulate matter |
| | pH (see USP <791>) | 5-7 |
| | Particulates (see USP <788>) | ≥10 μm particles: ≤6000 particles per container ≥25 μm particles: ≤600 particles per container |
| | Osmolality (see USP<785>) | 270-380 mOsm/Kg |
| | Protein Concentration (A280) | 165-190 mg/mL |
| Identity[1] | Charge Profile by Imaging Capillary Isoelectric Focusing (icIEF) | pI of the main peak is ±0.1 from that of the reference standard |
| | Potency (ELISA) | Demonstrates Binding to Integrin α1 I domain |
| Biological Potency | Potency (ELISA) | 80%-125% of Reference Standard |
| Purity and impurities | Impurities by Reducing CE-SDS | Total Impurities <15.0% |
| | Impurities by Non-Reducing CE-SDS | Total impurities <15.0% |

TABLE 31-continued

| Specifications | |
|---|---|
| Attribute | Criterion |
| Aggregation by Size Exclusion Chromatography (SEC) | ≤10.0% Total Aggregation |
| Safety Endotoxin Sterility | ≤90.0 EU/mL Complies with USP requirements |

What is claimed is:

1. An aqueous antibody pharmaceutical composition comprising:
   a. 180 mg/mL of the anti-VLA-1 antibody, said antibody having one or both of: a light chain variable region having the amino acid sequence of SEQ ID NO:4 and a heavy chain variable region having the amino acid sequence of SEQ ID NO:5;
   b. 30 mM histidine;
   c. 250 mM sorbitol; and
   d. 0.01% polysorbate 20; and wherein the aqueous antibody pharmaceutical composition has a pH of 6.0, wherein said composition is stable after storage at 2 to 8° C. for at least 3 years, as indicated by the presence of less than 10% total aggregation as assessed by size exclusion chromatography.

2. The aqueous antibody pharmaceutical composition of claim 1, wherein said composition is substantially free of citrate.

3. The aqueous antibody pharmaceutical composition of claim 1, wherein said composition has an osmolality of 270 mOsm/kg to 380 mOsm/kg.

4. The aqueous antibody pharmaceutical composition of claim 1, wherein said composition has a viscosity of less than 15 cP.

5. The aqueous antibody pharmaceutical composition of claim 1, wherein said composition is stable after storage at 2 to 8° C. for at least 3 years, as indicated by the <15% impurities as assessed by reducing capillary electrophoresis sodium dodecyl sulfate (CE-SDS).

6. The aqueous antibody pharmaceutical composition of claim 1, wherein said composition is stable after storage at 2 to 8° C. for at least 3 years, as indicated by less than 5% total aggregation as assessed by size exclusion chromatography.

7. The aqueous antibody pharmaceutical composition of claim 1, wherein said composition is stable after storage at 2 to 8° C. for at least 48 months.

* * * * *

UNITED STATES PATENT AND TRADEMARK OFFICE
CERTIFICATE OF CORRECTION

PATENT NO. : 10,160,808 B2
APPLICATION NO. : 14/379095
DATED : December 25, 2018
INVENTOR(S) : Fowler et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

This patent is subject to a terminal disclaimer.

Signed and Sealed this
Sixteenth Day of June, 2020

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn His Met
            20                  25                  30

Phe Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 2
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

```
<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

-continued

```
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
            435                 440                 445

<210> SEQ ID NO 3
<211> LENGTH: 1179
<212> TYPE: PRT
<213> ORGANISM: Homo sapiens

<400> SEQUENCE: 3

Met Ala Pro Arg Pro Arg Ala Arg Pro Gly Val Ala Val Ala Cys Cys
1               5                  10                  15
Trp Leu Leu Thr Val Val Leu Arg Cys Cys Val Ser Phe Asn Val Asp
                20                  25                  30
Val Lys Asn Ser Met Thr Phe Ser Gly Pro Val Glu Asp Met Phe Gly
            35                  40                  45
Tyr Thr Val Gln Gln Tyr Glu Asn Glu Glu Gly Lys Trp Val Leu Ile
        50                  55                  60
Gly Ser Pro Leu Val Gly Gln Pro Lys Asn Arg Thr Gly Asp Val Tyr
65                  70                  75                  80
Lys Cys Pro Val Gly Arg Gly Glu Ser Leu Pro Cys Val Lys Leu Asp
                85                  90                  95
Leu Pro Val Asn Thr Ser Ile Pro Asn Val Thr Glu Val Lys Glu Asn
                100                 105                 110
Met Thr Phe Gly Ser Thr Leu Val Thr Asn Pro Asn Gly Gly Phe Leu
            115                 120                 125
Ala Cys Gly Pro Leu Tyr Ala Tyr Arg Cys Gly His Leu His Tyr Thr
        130                 135                 140
Thr Gly Ile Cys Ser Asp Val Ser Pro Thr Phe Gln Val Val Asn Ser
145                 150                 155                 160
Ile Ala Pro Val Gln Glu Cys Ser Thr Gln Leu Asp Ile Val Ile Val
                165                 170                 175
Leu Asp Gly Ser Asn Ser Ile Tyr Pro Trp Asp Ser Val Thr Ala Phe
                180                 185                 190
Leu Asn Asp Leu Leu Glu Arg Met Asp Ile Gly Pro Lys Gln Thr Gln
            195                 200                 205
Val Gly Ile Val Gln Tyr Gly Glu Asn Val Thr His Glu Phe Asn Leu
        210                 215                 220
Asn Lys Tyr Ser Ser Thr Glu Glu Val Leu Val Ala Ala Lys Lys Ile
225                 230                 235                 240
Val Gln Arg Gly Gly Arg Gln Thr Met Thr Ala Leu Gly Ile Asp Thr
                245                 250                 255
Ala Arg Lys Glu Ala Phe Thr Glu Ala Arg Gly Ala Arg Arg Gly Val
                260                 265                 270
Lys Lys Val Met Val Ile Val Thr Asp Gly Glu Ser His Asp Asn His
            275                 280                 285
Arg Leu Lys Lys Val Ile Gln Asp Cys Glu Asp Glu Asn Ile Gln Arg
        290                 295                 300
Phe Ser Ile Ala Ile Leu Gly Ser Tyr Asn Arg Gly Asn Leu Ser Thr
305                 310                 315                 320
Glu Lys Phe Val Glu Glu Ile Lys Ser Ile Ala Ser Glu Pro Thr Glu
                325                 330                 335
Lys His Phe Phe Asn Val Ser Asp Glu Leu Ala Leu Val Thr Ile Val
```

```
              340             345             350
Lys Thr Leu Gly Glu Arg Ile Phe Ala Leu Glu Ala Thr Ala Asp Gln
            355             360             365

Ser Ala Ala Ser Phe Glu Met Glu Met Ser Gln Thr Gly Phe Ser Ala
            370             375             380

His Tyr Ser Gln Asp Trp Val Met Leu Gly Ala Val Gly Ala Tyr Asp
385             390             395             400

Trp Asn Gly Thr Val Val Met Gln Lys Ala Ser Gln Ile Ile Ile Pro
                405             410             415

Arg Asn Thr Thr Phe Asn Val Glu Ser Thr Lys Lys Asn Glu Pro Leu
            420             425             430

Ala Ser Tyr Leu Gly Tyr Thr Val Asn Ser Ala Thr Ala Ser Ser Gly
            435             440             445

Asp Val Leu Tyr Ile Ala Gly Gln Pro Arg Tyr Asn His Thr Gly Gln
            450             455             460

Val Ile Ile Tyr Arg Met Glu Asp Gly Asn Ile Lys Ile Leu Gln Thr
465             470             475             480

Leu Ser Gly Glu Gln Ile Gly Ser Tyr Phe Gly Ser Ile Leu Thr Thr
                485             490             495

Thr Asp Ile Asp Lys Asp Ser Asn Thr Asp Ile Leu Leu Val Gly Ala
            500             505             510

Pro Met Tyr Met Gly Thr Glu Lys Glu Glu Gln Gly Lys Val Tyr Val
            515             520             525

Tyr Ala Leu Asn Gln Thr Arg Phe Glu Tyr Gln Met Ser Leu Glu Pro
            530             535             540

Ile Lys Gln Thr Cys Cys Ser Ser Arg Gln His Asn Ser Cys Thr Thr
545             550             555             560

Glu Asn Lys Asn Glu Pro Cys Gly Ala Arg Phe Gly Thr Ala Ile Ala
                565             570             575

Ala Val Lys Asp Leu Asn Leu Asp Gly Phe Asn Asp Ile Val Ile Gly
            580             585             590

Ala Pro Leu Glu Asp Asp His Gly Gly Ala Val Tyr Ile Tyr His Gly
            595             600             605

Ser Gly Lys Thr Ile Arg Lys Glu Tyr Ala Gln Arg Ile Pro Ser Gly
            610             615             620

Gly Asp Gly Lys Thr Leu Lys Phe Phe Gly Gln Ser Ile His Gly Glu
625             630             635             640

Met Asp Leu Asn Gly Asp Gly Leu Thr Asp Val Thr Ile Gly Gly Leu
                645             650             655

Gly Gly Ala Ala Leu Phe Trp Ser Arg Asp Val Ala Val Val Lys Val
            660             665             670

Thr Met Asn Phe Glu Pro Asn Lys Val Asn Ile Gln Lys Lys Asn Cys
            675             680             685

His Met Glu Gly Lys Glu Thr Val Cys Ile Asn Ala Thr Val Cys Phe
690             695             700

Asp Val Lys Leu Lys Ser Lys Glu Asp Thr Ile Tyr Glu Ala Asp Leu
705             710             715             720

Gln Tyr Arg Val Thr Leu Asp Ser Leu Arg Gln Ile Ser Arg Ser Phe
                725             730             735

Phe Ser Gly Thr Gln Glu Arg Lys Val Gln Arg Asn Ile Thr Val Arg
            740             745             750

Lys Ser Glu Cys Thr Lys His Ser Phe Tyr Met Leu Asp Lys His Asp
            755             760             765
```

-continued

Phe Gln Asp Ser Val Arg Ile Thr Leu Asp Phe Asn Leu Thr Asp Pro
    770                 775                 780

Glu Asn Gly Pro Val Leu Asp Asp Ser Leu Pro Asn Ser Val His Glu
785                 790                 795                 800

Tyr Ile Pro Phe Ala Lys Asp Cys Gly Asn Lys Glu Lys Cys Ile Ser
                805                 810                 815

Asp Leu Ser Leu His Val Ala Thr Thr Glu Lys Asp Leu Leu Ile Val
            820                 825                 830

Arg Ser Gln Asn Asp Lys Phe Asn Val Ser Leu Thr Val Lys Asn Thr
        835                 840                 845

Lys Asp Ser Ala Tyr Asn Thr Arg Thr Ile Val His Tyr Ser Pro Asn
    850                 855                 860

Leu Val Phe Ser Gly Ile Glu Ala Ile Gln Lys Asp Ser Cys Glu Ser
865                 870                 875                 880

Asn His Asn Ile Thr Cys Lys Val Gly Tyr Pro Phe Leu Arg Arg Gly
                885                 890                 895

Glu Met Val Thr Phe Lys Ile Leu Phe Gln Phe Asn Thr Ser Tyr Leu
            900                 905                 910

Met Glu Asn Val Thr Ile Tyr Leu Ser Ala Thr Ser Asp Ser Glu Glu
        915                 920                 925

Pro Pro Glu Thr Leu Ser Asp Asn Val Val Asn Ile Ser Ile Pro Val
    930                 935                 940

Lys Tyr Glu Val Gly Leu Gln Phe Tyr Ser Ser Ala Ser Glu Tyr His
945                 950                 955                 960

Ile Ser Ile Ala Ala Asn Glu Thr Val Pro Glu Val Ile Asn Ser Thr
                965                 970                 975

Glu Asp Ile Gly Asn Glu Ile Asn Ile Phe Tyr Leu Ile Arg Lys Ser
            980                 985                 990

Gly Ser Phe Pro Met Pro Glu Leu Lys Leu Ser Ile Ser Phe Pro Asn
        995                 1000                1005

Met Thr Ser Asn Gly Tyr Pro Val Leu Tyr Pro Thr Gly Leu Ser
    1010                1015                1020

Ser Ser Glu Asn Ala Asn Cys Arg Pro His Ile Phe Glu Asp Pro
    1025                1030                1035

Phe Ser Ile Asn Ser Gly Lys Lys Met Thr Thr Ser Thr Asp His
    1040                1045                1050

Leu Lys Arg Gly Thr Ile Leu Asp Cys Asn Thr Cys Lys Phe Ala
    1055                1060                1065

Thr Ile Thr Cys Asn Leu Thr Ser Ser Asp Ile Ser Gln Val Asn
    1070                1075                1080

Val Ser Leu Ile Leu Trp Lys Pro Thr Phe Ile Lys Ser Tyr Phe
    1085                1090                1095

Ser Ser Leu Asn Leu Thr Ile Arg Gly Glu Leu Arg Ser Glu Asn
    1100                1105                1110

Ala Ser Leu Val Leu Ser Ser Asn Gln Lys Arg Glu Leu Ala
    1115                1120                1125

Ile Gln Ile Ser Lys Asp Gly Leu Pro Gly Arg Val Pro Leu Trp
    1130                1135                1140

Val Ile Leu Leu Ser Ala Phe Ala Gly Leu Leu Leu Leu Met Leu
    1145                1150                1155

Leu Ile Leu Ala Leu Trp Lys Ile Gly Phe Phe Lys Arg Pro Leu
    1160                1165                1170

-continued

Lys Lys Lys Met Glu Lys
        1175

<210> SEQ ID NO 4
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 5
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 6
<211> LENGTH: 3540
<212> TYPE: DNA
<213> ORGANISM: Homo sapiens
<220> FEATURE:
<221> NAME/KEY: CDS

<222> LOCATION: (1)..(3537)

<400> SEQUENCE: 6

| | | | | | | | | | | | | | | | | |
|---|---|---|---|---|---|---|---|---|---|---|---|---|---|---|---|---|
| atg | gcc | cct | cgg | ccc | cgc | gcc | cgc | cca | ggg | gtc | gct | gtc | gcc | tgc | tgc | 48 |
| Met | Ala | Pro | Arg | Pro | Arg | Ala | Arg | Pro | Gly | Val | Ala | Val | Ala | Cys | Cys | |
| 1 | | | | 5 | | | | | 10 | | | | | 15 | | |
| tgg | ctc | ctc | act | gtt | gtt | cta | cgc | tgc | tgc | gta | tca | ttc | aat | gtt | gat | 96 |
| Trp | Leu | Leu | Thr | Val | Val | Leu | Arg | Cys | Cys | Val | Ser | Phe | Asn | Val | Asp | |
| | | | 20 | | | | | 25 | | | | | 30 | | | |
| gtg | aaa | aat | tca | atg | act | ttc | agc | ggc | ccg | gtg | gaa | gac | atg | ttt | gga | 144 |
| Val | Lys | Asn | Ser | Met | Thr | Phe | Ser | Gly | Pro | Val | Glu | Asp | Met | Phe | Gly | |
| | | 35 | | | | | 40 | | | | | 45 | | | | |
| tat | act | gtt | caa | caa | tat | gaa | aat | gaa | gaa | gga | aaa | tgg | gtg | ctt | att | 192 |
| Tyr | Thr | Val | Gln | Gln | Tyr | Glu | Asn | Glu | Glu | Gly | Lys | Trp | Val | Leu | Ile | |
| | 50 | | | | | 55 | | | | | 60 | | | | | |
| ggt | tct | ccg | tta | gtt | ggc | caa | ccc | aaa | aac | aga | act | gga | gat | gtc | tat | 240 |
| Gly | Ser | Pro | Leu | Val | Gly | Gln | Pro | Lys | Asn | Arg | Thr | Gly | Asp | Val | Tyr | |
| 65 | | | | | 70 | | | | | 75 | | | | | 80 | |
| aag | tgt | cca | gtt | ggg | aga | ggt | gaa | tca | tta | cct | tgt | gta | aag | ttg | gat | 288 |
| Lys | Cys | Pro | Val | Gly | Arg | Gly | Glu | Ser | Leu | Pro | Cys | Val | Lys | Leu | Asp | |
| | | | | 85 | | | | | 90 | | | | | 95 | | |
| cta | cca | gtt | aat | aca | tca | att | ccc | aat | gtc | aca | gaa | gta | aag | gag | aac | 336 |
| Leu | Pro | Val | Asn | Thr | Ser | Ile | Pro | Asn | Val | Thr | Glu | Val | Lys | Glu | Asn | |
| | | | 100 | | | | | 105 | | | | | 110 | | | |
| atg | aca | ttt | gga | tca | act | tta | gtc | acc | aac | cca | aat | gga | gga | ttt | ctg | 384 |
| Met | Thr | Phe | Gly | Ser | Thr | Leu | Val | Thr | Asn | Pro | Asn | Gly | Gly | Phe | Leu | |
| | | 115 | | | | | 120 | | | | | 125 | | | | |
| gct | tgt | ggg | ccc | tta | tat | gcc | tat | aga | tgt | gga | cat | ttg | cat | tac | aca | 432 |
| Ala | Cys | Gly | Pro | Leu | Tyr | Ala | Tyr | Arg | Cys | Gly | His | Leu | His | Tyr | Thr | |
| | 130 | | | | | 135 | | | | | 140 | | | | | |
| act | gga | atc | tgt | tct | gac | gtc | agc | ccc | aca | ttt | caa | gtc | gtg | aat | tcc | 480 |
| Thr | Gly | Ile | Cys | Ser | Asp | Val | Ser | Pro | Thr | Phe | Gln | Val | Val | Asn | Ser | |
| 145 | | | | | 150 | | | | | 155 | | | | | 160 | |
| att | gcc | cct | gta | caa | gaa | tgc | agc | act | caa | ctg | gac | ata | gtc | ata | gtg | 528 |
| Ile | Ala | Pro | Val | Gln | Glu | Cys | Ser | Thr | Gln | Leu | Asp | Ile | Val | Ile | Val | |
| | | | | 165 | | | | | 170 | | | | | 175 | | |
| ctg | gat | ggt | tcc | aac | agt | att | tac | cca | tgg | gac | agt | gtt | aca | gct | ttt | 576 |
| Leu | Asp | Gly | Ser | Asn | Ser | Ile | Tyr | Pro | Trp | Asp | Ser | Val | Thr | Ala | Phe | |
| | | | 180 | | | | | 185 | | | | | 190 | | | |
| tta | aat | gac | ctt | ctt | gaa | aga | atg | gat | att | ggt | cct | aaa | cag | aca | cag | 624 |
| Leu | Asn | Asp | Leu | Leu | Glu | Arg | Met | Asp | Ile | Gly | Pro | Lys | Gln | Thr | Gln | |
| | | 195 | | | | | 200 | | | | | 205 | | | | |
| gtt | gga | att | gta | cag | tat | gga | gaa | aac | gtg | acc | cat | gag | ttc | aac | ctc | 672 |
| Val | Gly | Ile | Val | Gln | Tyr | Gly | Glu | Asn | Val | Thr | His | Glu | Phe | Asn | Leu | |
| | 210 | | | | | 215 | | | | | 220 | | | | | |
| aat | aag | tat | tct | tcc | acc | gaa | gag | gta | ctt | gtt | gca | gca | aag | aaa | ata | 720 |
| Asn | Lys | Tyr | Ser | Ser | Thr | Glu | Glu | Val | Leu | Val | Ala | Ala | Lys | Lys | Ile | |
| 225 | | | | | 230 | | | | | 235 | | | | | 240 | |
| gtc | cag | aga | ggt | ggc | cgc | cag | act | atg | aca | gct | ctt | gga | ata | gac | aca | 768 |
| Val | Gln | Arg | Gly | Gly | Arg | Gln | Thr | Met | Thr | Ala | Leu | Gly | Ile | Asp | Thr | |
| | | | | 245 | | | | | 250 | | | | | 255 | | |
| gca | aga | aag | gag | gca | ttc | acg | gaa | gcc | cgg | ggt | gcc | cga | aga | gga | gtt | 816 |
| Ala | Arg | Lys | Glu | Ala | Phe | Thr | Glu | Ala | Arg | Gly | Ala | Arg | Arg | Gly | Val | |
| | | | 260 | | | | | 265 | | | | | 270 | | | |
| aaa | aaa | gtc | atg | gtt | att | gtg | aca | gat | gga | gag | tct | cat | gac | aat | cat | 864 |
| Lys | Lys | Val | Met | Val | Ile | Val | Thr | Asp | Gly | Glu | Ser | His | Asp | Asn | His | |
| | | 275 | | | | | 280 | | | | | 285 | | | | |
| cga | ctg | aag | aag | gtc | atc | caa | gac | tgt | gaa | gat | gaa | aac | att | caa | cgg | 912 |
| Arg | Leu | Lys | Lys | Val | Ile | Gln | Asp | Cys | Glu | Asp | Glu | Asn | Ile | Gln | Arg | |
| | 290 | | | | | 295 | | | | | 300 | | | | | |

```
ttt tcc ata gct att ctt ggc agc tat aac cga gga aat tta agc act      960
Phe Ser Ile Ala Ile Leu Gly Ser Tyr Asn Arg Gly Asn Leu Ser Thr
305                 310                 315                 320 gaa aaa ttt gtg gag gaa ata aaa tca att gca agt gaa ccc act gaa     1008
Glu Lys Phe Val Glu Glu Ile Lys Ser Ile Ala Ser Glu Pro Thr Glu
                325                 330                 335 aag cat ttc ttc aat gtc tct gat gaa ttg gct cta gtc acc att gtt     1056
Lys His Phe Phe Asn Val Ser Asp Glu Leu Ala Leu Val Thr Ile Val
            340                 345                 350 aaa act ctg gga gaa aga ata ttt gcc ctg gaa gcc aca gct gac cag     1104
Lys Thr Leu Gly Glu Arg Ile Phe Ala Leu Glu Ala Thr Ala Asp Gln
        355                 360                 365 tca gca gct tca ttt gaa atg gaa atg tct cag act ggc ttc agt gct     1152
Ser Ala Ala Ser Phe Glu Met Glu Met Ser Gln Thr Gly Phe Ser Ala
    370                 375                 380 cat tat tca cag gac tgg gtc atg ctt gga gca gta gga gcc tat gat     1200
His Tyr Ser Gln Asp Trp Val Met Leu Gly Ala Val Gly Ala Tyr Asp
385                 390                 395                 400 tgg aat gga aca gtt gtc atg cag aag gct agt caa atc ata atc cct     1248
Trp Asn Gly Thr Val Val Met Gln Lys Ala Ser Gln Ile Ile Ile Pro
                405                 410                 415 cga aac aca acc ttt aat gtt gag tct acc aaa aag aat gaa ccg ctt     1296
Arg Asn Thr Thr Phe Asn Val Glu Ser Thr Lys Lys Asn Glu Pro Leu
            420                 425                 430 gct tct tat tta ggt tac act gta aac tct gct act gct tct tct gga     1344
Ala Ser Tyr Leu Gly Tyr Thr Val Asn Ser Ala Thr Ala Ser Ser Gly
        435                 440                 445 gat gtg ctc tat att gct gga cag cct cgg tac aat cat aca ggc cag     1392
Asp Val Leu Tyr Ile Ala Gly Gln Pro Arg Tyr Asn His Thr Gly Gln
    450                 455                 460 gtc att atc tac agg atg gaa gat gga aac atc aaa att ctc cag acg     1440
Val Ile Ile Tyr Arg Met Glu Asp Gly Asn Ile Lys Ile Leu Gln Thr
465                 470                 475                 480 ctc agt gga gaa cag att ggt tcc tac ttt ggc agt att tta aca aca     1488
Leu Ser Gly Glu Gln Ile Gly Ser Tyr Phe Gly Ser Ile Leu Thr Thr
                485                 490                 495 act gac att gac aag gat tct aat act gac att ctt cta gtc gga gcc     1536
Thr Asp Ile Asp Lys Asp Ser Asn Thr Asp Ile Leu Leu Val Gly Ala
            500                 505                 510 cct atg tac atg gga aca gag aag gag gag caa gga aaa gtg tat gtg     1584
Pro Met Tyr Met Gly Thr Glu Lys Glu Glu Gln Gly Lys Val Tyr Val
        515                 520                 525 tat gct ctc aat cag aca agg ttt gaa tat caa atg agc ctg gaa cct     1632
Tyr Ala Leu Asn Gln Thr Arg Phe Glu Tyr Gln Met Ser Leu Glu Pro
    530                 535                 540 att aag cag acg tgc tgt tca tct cgg cag cac aat tca tgc aca aca     1680
Ile Lys Gln Thr Cys Cys Ser Ser Arg Gln His Asn Ser Cys Thr Thr
545                 550                 555                 560 gaa aac aaa aat gag cca tgc ggg gct cgt ttt gga act gca att gct     1728
Glu Asn Lys Asn Glu Pro Cys Gly Ala Arg Phe Gly Thr Ala Ile Ala
                565                 570                 575 gct gta aaa gac ctc aat ctt gat gga ttt aat gac atc gtg ata gga     1776
Ala Val Lys Asp Leu Asn Leu Asp Gly Phe Asn Asp Ile Val Ile Gly
            580                 585                 590 gct ccg ctg gaa gat gat cac ggg gga gct gtg tac att tat cat gga     1824
Ala Pro Leu Glu Asp Asp His Gly Gly Ala Val Tyr Ile Tyr His Gly
        595                 600                 605 agt ggc aag act ata agg aaa gag tat gca caa cgt att cca tca ggt     1872
Ser Gly Lys Thr Ile Arg Lys Glu Tyr Ala Gln Arg Ile Pro Ser Gly
```

```
            610                 615                 620
ggg gat ggt aag aca ctg aaa ttt ttt ggc cag tct atc cac gga gaa    1920
Gly Asp Gly Lys Thr Leu Lys Phe Phe Gly Gln Ser Ile His Gly Glu
625                 630                 635                 640 atg gat tta aat ggt gac ggt ctg aca gat gtg act att ggg ggc ctt    1968
Met Asp Leu Asn Gly Asp Gly Leu Thr Asp Val Thr Ile Gly Gly Leu
                645                 650                 655 ggt ggt gct gcc ctc ttc tgg tcc cga gat gtg gcc gta gtt aaa gtg    2016
Gly Gly Ala Ala Leu Phe Trp Ser Arg Asp Val Ala Val Val Lys Val
            660                 665                 670 acc atg aat ttt gag cca aat aaa gtg aat att caa aag aaa aac tgc    2064
Thr Met Asn Phe Glu Pro Asn Lys Val Asn Ile Gln Lys Lys Asn Cys
        675                 680                 685 cat atg gag gga aag gaa aca gta tgc ata aat gct aca gtg tgt ttt    2112
His Met Glu Gly Lys Glu Thr Val Cys Ile Asn Ala Thr Val Cys Phe
    690                 695                 700 gat gtg aaa tta aag tct aaa gaa gac acg att tat gaa gct gat ttg    2160
Asp Val Lys Leu Lys Ser Lys Glu Asp Thr Ile Tyr Glu Ala Asp Leu
705                 710                 715                 720 cag tac cgt gtc acc cta gat tca cta aga caa ata tca cga agt ttt    2208
Gln Tyr Arg Val Thr Leu Asp Ser Leu Arg Gln Ile Ser Arg Ser Phe
                725                 730                 735 ttc tct gga act caa gag aga aag gtt caa agg aac atc aca gtt cga    2256
Phe Ser Gly Thr Gln Glu Arg Lys Val Gln Arg Asn Ile Thr Val Arg
            740                 745                 750 aaa tca gaa tgc act aag cac tcc ttc tac atg ttg gac aag cat gac    2304
Lys Ser Glu Cys Thr Lys His Ser Phe Tyr Met Leu Asp Lys His Asp
        755                 760                 765 ttt cag gac tct gtg aga ata acg ttg gac ttt aat ctt acc gat cca    2352
Phe Gln Asp Ser Val Arg Ile Thr Leu Asp Phe Asn Leu Thr Asp Pro
    770                 775                 780 gaa aat ggg cct gtt ctt gat gat tct cta cca aac tca gta cat gaa    2400
Glu Asn Gly Pro Val Leu Asp Asp Ser Leu Pro Asn Ser Val His Glu
785                 790                 795                 800 tat att ccc ttt gcc aaa gat tgt gga aat aag gaa aaa tgt atc tca    2448
Tyr Ile Pro Phe Ala Lys Asp Cys Gly Asn Lys Glu Lys Cys Ile Ser
                805                 810                 815 gac ctc agc ctg cat gtc gcc acc act gaa aag gac ctg ctg att gtc    2496
Asp Leu Ser Leu His Val Ala Thr Thr Glu Lys Asp Leu Leu Ile Val
            820                 825                 830 cga tcc cag aat gat aag ttc aac gtt agc ctc aca gtc aaa aat aca    2544
Arg Ser Gln Asn Asp Lys Phe Asn Val Ser Leu Thr Val Lys Asn Thr
        835                 840                 845 aag gac agt gcc tat aac acc agg aca ata gtg cat tat tct cca aat    2592
Lys Asp Ser Ala Tyr Asn Thr Arg Thr Ile Val His Tyr Ser Pro Asn
850                 855                 860 cta gtt ttt tca gga att gag gct atc caa aaa gac agt tgt gaa tct    2640
Leu Val Phe Ser Gly Ile Glu Ala Ile Gln Lys Asp Ser Cys Glu Ser
865                 870                 875                 880 aat cat aat atc aca tgt aaa gtt gga tat ccc ttc ctg aga aga gga    2688
Asn His Asn Ile Thr Cys Lys Val Gly Tyr Pro Phe Leu Arg Arg Gly
                885                 890                 895 gag atg gta act ttc aaa ata ttg ttt cag ttt aac aca tcc tat ctc    2736
Glu Met Val Thr Phe Lys Ile Leu Phe Gln Phe Asn Thr Ser Tyr Leu
            900                 905                 910 atg gaa aat gtg acc att tat tta agt gca aca agt gac agc gaa gaa    2784
Met Glu Asn Val Thr Ile Tyr Leu Ser Ala Thr Ser Asp Ser Glu Glu
        915                 920                 925 cct cct gaa acc ctt tct gat aat gta gta aac att tct atc ccg gta    2832
```

```
Pro Pro Glu Thr Leu Ser Asp Asn Val Val Asn Ile Ser Ile Pro Val
    930                 935                 940 aaa tat gaa gtt gga cta cag ttt tac agc tct gca agt gaa tac cac      2880
Lys Tyr Glu Val Gly Leu Gln Phe Tyr Ser Ser Ala Ser Glu Tyr His
945                 950                 955                 960 att tca att gct gcc aat gag aca gtc cct gaa gtt att aat tct act      2928
Ile Ser Ile Ala Ala Asn Glu Thr Val Pro Glu Val Ile Asn Ser Thr
                965                 970                 975 gag gac att gga aat gaa att aat atc ttc tac ttg att aga aaa agt      2976
Glu Asp Ile Gly Asn Glu Ile Asn Ile Phe Tyr Leu Ile Arg Lys Ser
            980                 985                 990 gga tct ttt cca atg cca gag ctt aag ctg tca att tca ttc ccc aat      3024
Gly Ser Phe Pro Met Pro Glu Leu Lys Leu Ser Ile Ser Phe Pro Asn
        995                 1000                1005 atg aca tca aat ggt tac cct gtg ctg tac cca act gga ttg tca           3069
Met Thr Ser Asn Gly Tyr Pro Val Leu Tyr Pro Thr Gly Leu Ser
    1010                1015                1020 tct tct gag aat gca aac tgc aga ccc cat atc ttt gag gat cct           3114
Ser Ser Glu Asn Ala Asn Cys Arg Pro His Ile Phe Glu Asp Pro
    1025                1030                1035 ttc agt atc aac tct gga aag aaa atg act aca tca act gac cat           3159
Phe Ser Ile Asn Ser Gly Lys Lys Met Thr Thr Ser Thr Asp His
    1040                1045                1050 ctc aaa cga ggc aca att ctg gac tgc aat aca tgt aaa ttt gct           3204
Leu Lys Arg Gly Thr Ile Leu Asp Cys Asn Thr Cys Lys Phe Ala
    1055                1060                1065 acc atc aca tgt aat ctc act tct tct gac atc agc caa gtc aat           3249
Thr Ile Thr Cys Asn Leu Thr Ser Ser Asp Ile Ser Gln Val Asn
    1070                1075                1080 gtt tcg ctt atc ttg tgg aaa cca act ttt ata aaa tca tat ttt           3294
Val Ser Leu Ile Leu Trp Lys Pro Thr Phe Ile Lys Ser Tyr Phe
    1085                1090                1095 tcc agc tta aat ctt act ata agg gga gaa ctt cgg agt gaa aat           3339
Ser Ser Leu Asn Leu Thr Ile Arg Gly Glu Leu Arg Ser Glu Asn
    1100                1105                1110 gca tct ctg gtt tta agt agc agc aat caa aaa aga gag ctt gct           3384
Ala Ser Leu Val Leu Ser Ser Ser Asn Gln Lys Arg Glu Leu Ala
    1115                1120                1125 att caa ata tcc aaa gat ggg cta ccg ggc aga gtg cca tta tgg           3429
Ile Gln Ile Ser Lys Asp Gly Leu Pro Gly Arg Val Pro Leu Trp
    1130                1135                1140 gtc atc ctg ctg agt gct ttt gcc gga ttg ttg ctg tta atg ctg           3474
Val Ile Leu Leu Ser Ala Phe Ala Gly Leu Leu Leu Leu Met Leu
    1145                1150                1155 ctc att tta gca ctg tgg aag att gga ttc ttc aaa aga cca ctg           3519
Leu Ile Leu Ala Leu Trp Lys Ile Gly Phe Phe Lys Arg Pro Leu
    1160                1165                1170 aaa aag aaa atg gag aaa tga                                          3540
Lys Lys Lys Met Glu Lys
    1175
```